(12) United States Patent
Dai et al.

(10) Patent No.: US 9,957,263 B2
(45) Date of Patent: May 1, 2018

(54) BROMODOMAIN INHIBITORS

(71) Applicant: AbbVie Inc., Waukegan, IL (US)

(72) Inventors: Yujia Dai, Gurnee, IL (US); Steven D. Fidanze, Grayslake, IL (US); Lisa Hasvold, Grayslake, IL (US); James Holms, Gurnee, IL (US); Dachun Liu, Vernon Hills, IL (US); William McClellan, Waukegan, IL (US); Keith McDaniel, Wauconda, IL (US); Jasmina Marjanovic, Chicago, IL (US); George Sheppard, Wilmette, IL (US); Le Wang, Vernon Hills, IL (US)

(73) Assignee: AbbVie Inc., North Chicago, IL (US)

( * ) Notice: Subject to any disclaimer, the term of this patent is extended or adjusted under 35 U.S.C. 154(b) by 0 days. days.

(21) Appl. No.: 14/392,201

(22) PCT Filed: Jun. 27, 2014

(86) PCT No.: PCT/CN2014/080991
§ 371 (c)(1),
(2) Date: Dec. 23, 2015

(87) PCT Pub. No.: WO2014/206345
PCT Pub. Date: Dec. 31, 2014

(65) Prior Publication Data
US 2016/0272630 A1 Sep. 22, 2016

Related U.S. Application Data

(63) Continuation-in-part of application No. PCT/CN2014/077395, filed on May 13, 2014.

(60) Provisional application No. 61/840,559, filed on Jun. 28, 2013.

(51) Int. Cl.
| | |
|---|---|
| C07D 471/02 | (2006.01) |
| A61K 31/44 | (2006.01) |
| A61K 31/497 | (2006.01) |
| C07D 471/04 | (2006.01) |
| A61K 45/06 | (2006.01) |
| A61K 31/437 | (2006.01) |
| A61K 31/496 | (2006.01) |
| A61K 31/5377 | (2006.01) |
| A61K 31/541 | (2006.01) |
| A61K 31/551 | (2006.01) |
| A61K 31/4545 | (2006.01) |
| A61K 31/506 | (2006.01) |

(52) U.S. Cl.
CPC .......... *C07D 471/04* (2013.01); *A61K 31/437* (2013.01); *A61K 31/4545* (2013.01); *A61K 31/496* (2013.01); *A61K 31/497* (2013.01); *A61K 31/506* (2013.01); *A61K 31/5377* (2013.01); *A61K 31/541* (2013.01); *A61K 31/551* (2013.01); *A61K 45/06* (2013.01)

(58) Field of Classification Search
CPC ... A61K 31/437; A61K 31/496; C07D 471/04
USPC ............................ 514/300, 253.04; 546/113
See application file for complete search history.

(56) References Cited

FOREIGN PATENT DOCUMENTS

| | | |
|---|---|---|
| CN | 103037865 A | 4/2013 |
| EP | 0652218 B1 | 7/2001 |
| JP | H08337583 A | 12/1996 |
| WO | 2006129623 A1 | 12/2006 |
| WO | 2011054848 A1 | 5/2011 |
| WO | 2011143651 A1 | 11/2011 |
| WO | 2013097052 A1 | 7/2013 |
| WO | 2013097601 A1 | 7/2013 |

OTHER PUBLICATIONS

LoRusso "BET inhibitors as Agents for anti-Cancer Therapy," http://tatcongress.org/wp-content/uploads/2016/03/07.2-Patricia-LoRusso.pdf, pp. 1, 10 and 11, 2016.*
Anand P., et al., "BET Bromodomains Mediate Transcriptional Pause Release in Heart Failure," Cell, 2013, vol. 154 (3), pp. 569-582.
Banerjee C., et al., "BET Bromodomain Inhibition as a Novel Strategy for Reactivation of HIV-1," Journal of Leukocyte Biology, 2012, vol. 92 (6), pp. 1147-1154.
Berge S.M., et al., "Pharmaceutical Salts," Journal of Pharmaceutical Sciences, 1977, vol. 66 (1), pp. 1-19.
Dalpiaz., et al., "Synthesis and Evaluation of Novel Pyrrolo[2, 3-D]And 1-28 Thieno[2, 3-D]Pyridazinones as In Vitro a Ntiproliferative Agents," Acta Chimica Slovenica, 2009, vol. 56, pp. 571-575.
Dawson M.A., et al., "Inhibition of BET Recruitment to Chromatin as an Effective Treatment for MLL-fusion Leukaemia," Nature, 2011, vol. 478 (7370), pp. 529-533.
(Continued)

*Primary Examiner* — Shengjun Wang
(74) *Attorney, Agent, or Firm* — Michael S. Montgomery

(57) ABSTRACT

Compounds of formula (I) and pharmaceutically acceptable salts thereof are provided. The compounds are useful as agents in the treatment of diseases and conditions, including inflammatory diseases, cancer, and AIDS. Pharmaceutical compositions comprised of one or more compounds of formula (I) are also provided.

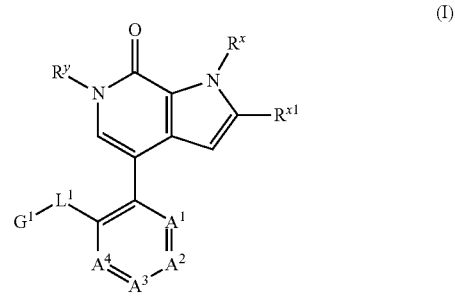

5 Claims, No Drawings

(56) References Cited

OTHER PUBLICATIONS

Delmore J.E., et al., "BET Bromodomain Inhibition as a Therapeutic Strategy to Target c-Myc," Cell, 2011, vol. 146 (6), pp. 904-917.
Denis G.V., "Bromodomain Coactivators in Cancer, Obesity, type 2 Diabetes, and Inflammation," Discovery Medicine, 2010, vol. 10 (55), pp. 489-499.
Eastwood B.J., et al., "The Minimum Significant Ratio: A Statistical Parameter to Characterize the Reproducibility of Potency Estimates from Concentration-Response Assays and Estimation by Replicate-Experiment Studies," Journal of Biomolecular Screening, 2006, vol. 11 (3), pp. 253-261.
Greene T.W., et al., "Protection for the Amino group," Protective Groups in Organic Synthesis, 1999, Third Edition, pp. 494-653.
Huang B., et al., "Brd4 Coactivates Transcriptional Activation of NF-kappaB Via Specific Binding to Acetylated RelA," Molecular and Cellular Biology, 2009, vol. 29 (5), pp. 1375-1387.
Ikeura Y., et al., "Potent NK1 Receptor Antagonists: Synthesis and Antagonistic Activity of Various Heterocycles with an N[3,5-bis(trifluoromethyl)benzyl]-N-methylcarbamoyl Substituent," Chemical and Pharmaceutical Bulletin, 1997, vol. 45 (10), pp. 1642-1652.
International Search Report and Written Opinion for Application No. PCT/CN2014/080991, dated Oct. 9, 2014, 18 pages.
International Search Report and Written Opinion for Application No. PCT/CN2014/077395, dated Aug. 20, 2014, 15 pages.
Jang M.K., et al., "The Bromodomain Protein Brd4 is a Positive Regulatory Component of P-TEFb and Stimulates RNA Polymerase II-dependent Transcription," Molecular Cell, 2005, vol. 19 (4), pp. 523-534.
Leroy G., et al., "The Double Bromodomain Proteins Brd2 and Brd3 Couple Histone Acetylation to Transcription," Molecular Cell, 2008, vol. 30 (1), pp. 51-60.
Liu R., et al., Role of Transcription Factor Acetylation in Diabetic Kidney Disease, Sirt1 and Protein Acetylation in Diabetic Kidney Disease, Diabetes, 2014, 14 pages.
Matzuk M.M., et al., "Small-molecule Inhibition of BRDT for Male Contraception," Cell, 2012, vol. 150 (4), pp. 573-684.
Mertz J.A., et al., "Targeting MYC Dependence in Cancer by Inhibiting BET Bromodomains," Proceedings of the National Academy of Sciences, 2011, vol. 108 (40), pp. 16669-16674.
Miyaura N., et al., "Palladium-Catalyzed Cross-Coupling Reactions of Organoboron Compounds," Chemical Reviews, 1995, vol. 95 (7), pp. 2457-2483.
Nicodeme E., et al., "Suppression of Inflammation by a Synthetic Histone Mimic," Nature, 2010, vol. 468 (7327), pp. 1119-1123.
Prescott, Ed., Methods in Cell Biology, vol. XIV, Academic Press, New York, 1976, pp. 33.
Spiltoir J.I., et al., "BET Acetyl-Lysine Binding Proteins Control Pathological Cardiac Hypertrophy," Journal of Molecular and Cellular Cardiology, 2013, vol. 63, pp. 175-179.
Sutton, V.R. et al., "Bcl-2 Prevents Apoptosis Induced by Perforin and Granzyme B, But Not That Mediated by Whole Cytotoxic Lymphocytes," Journal of Immunology, 1997, vol. 158 (12), pp. 5783-5790.
Suzuki A., et al., "Recent advances in the cross-coupling reactions of organoboron derivatives with organic electrophiles, 1995-1998," Journal of Organometallic Chemistry, 1999, 576 (1-2), 147-168.
Tang X., et al., "Assessment of Brd4 Inhibition in Idiopathic Pulmonary Fibrosis Lung Fibroblasts and in Vivo Models of Lung Fibrosis," American Journal of Pathology, 2013, vol. 183 (2), pp. 470-479.
Yang Z., et al., "Brd4 Recruits P-TEFb to Chromosomes at Late Mitosis to Promote G1 Gene Expression and Cell Cycle Progression," Molecular and Cellular Biology, 2008, vol. 28 (3), pp. 967-976.
Zhang, G., et al., "Down-regulation of NF-κB Transcriptional Activity in HIV-associated Kidney Disease by BRD4 Inhibition," Journal of Biological Chemistry, 2012, vol. 287 (34), pp. 28840-28851.
Zuber J., et al., "RNAi Screen Identifies Brd4 as a Therapeutic Target in Acute Myeloid Leukaemia," Nature, 2011, vol. 478 (7370), pp. 524-528.

\* cited by examiner

BROMODOMAIN INHIBITORS

BACKGROUND

Bromodomains refer to conserved protein structural folds which bind to N-acetylated lysine residues that are found in some proteins. The BET family of bromodomain containing proteins is comprised of four members (BRD2, BRD3, BRD4 and BRDt). Each member of the BET family employs two bromodomains to recognize N-acetylated lysine residues found primarily, but not exclusively, on the amino-terminal tails of histone proteins. These interactions modulate gene expression by recruiting transcription factors to specific genome locations within chromatin. For example, histone-bound BRD4 recruits the transcription factor P-TEFb to promoters, resulting in the expression of a subset of genes involved in cell cycle progression (Yang et al., Mol. Cell. Biol. 28: 967-976 (2008)). BRD2 and BRD3 also function as transcriptional regulators of growth promoting genes (LeRoy et al., Mol. Cell 30: 51-60 (2008)). BET family members were recently established as being important for the maintenance of several cancer types (Zuber et al., Nature 478: 524-528 (2011); Mertz et al; Proc. Nat'l. Acad. Sci. 108: 16669-16674 (2011); Delmore et al., Cell 146: 1-14, (2011); Dawson et al., Nature 478: 529-533 (2011)). BET family members have also been implicated in mediating acute inflammatory responses through the canonical NF-KB pathway (Huang et al., Mol. Cell. Biol. 29: 1375-1387 (2009)) resulting in the upregulation of genes associated with the production of cytokines (Nicodeme et al., Nature 468: 1119-1123, (2010)). Suppression of cytokine induction by BET bromodomain inhibitors has been shown to be an effective approach to treat inflammation-mediated kidney disease in an animal model (Zhang, et al., J. Biol. Chem. 287: 28840-28851 (2012)). BRD2 function has been linked to predisposition for dyslipidemia or improper regulation of adipogenesis, elevated inflammatory profiles and increased susceptibility to autoimmune diseases (Denis, Discovery Medicine 10: 489-499 (2010)). The human immunodeficiency virus utilizes BRD4 to initiate transcription of viral RNA from stably integrated viral DNA (Jang et al., Mol. Cell, 19: 523-534 (2005)). Treatment of db/db mice with a BET specific bromodomain inhibitor has been shown to attenuate proteinuria, thus providing a potential new treatment for diabetic nephropathy (Liu, et al., Diabetes, 2014). BET bromodomain inhibitors have also been shown to reactivate HIV transcription in models of latent T cell infection and latent monocyte infection (Banerjee, et al, J. Leukocyte Biol. doi:10.1189/jlb.0312165). BRDt has an important role in spermatogenesis that is blocked by BET bromodomain inhibitors (Matzuk, et al., Cell 150: 673-684 (2012)). Studies with BET inhibitors have demonstrated proof-of-concept efficacy in animal models of sepsis and endotoxic shock (Nicodeme, et al., Nature 468: 1119-1123 (2010)), insulin resistance and hepatic steatosis (Bradner, et al., *Composition and methods for modulating metabolism.* WO2011/143651A1), idiopathic pulmonary fibrosis (Tang, et l., Am. J. Pathol. 183: 470-479 (2013)) and heart failure (Spiltoir, et al., J. Mol. Cellular Cardiol. 63: 175-179 (2013), Anand, et al., Cell 154: 569-582 (2013)). Thus, compounds that inhibit the binding of BET family bromodomains to their cognate acetylated lysine proteins are being pursued for the treatment of cancer, inflammatory diseases, kidney diseases, diseases involving metabolism or fat accumulation, and some viral infections, as well as for providing a method for male contraception. Accordingly, there is an ongoing medical need to develop new drugs to treat these indications.

SUMMARY

In one aspect the present invention provides for compounds of formula (I) or pharmaceutically acceptable salt thereof,

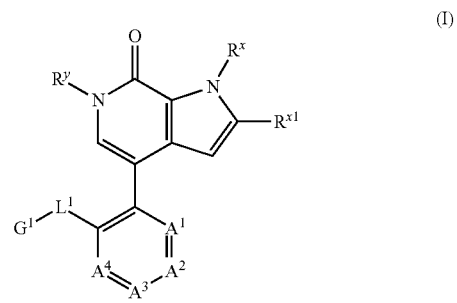

(I)

wherein
$R^x$ is hydrogen or $C_1$-$C_3$ alkyl;
$R^y$ is hydrogen or $C_1$-$C_3$ alkyl;
$A^1$ is N or $CR^1$, $A^2$ is N or $CR^2$, $A^3$ is N or $CR^3$; and $A^4$ is N or $CR^4$; wherein zero, one, two, or three of $A^1$, $A^2$, $A^3$, and $A^4$ are N;
$R^1$ is hydrogen, $C_1$-$C_6$ alkyl, $C_2$-$C_6$ alkenyl, $C_2$-$C_6$ alkynyl, halogen, $C_1$-$C_6$ haloalkyl, CN, or $NO_2$;
$R^2$ is hydrogen, —$S(O)_2R^{2a}$, —$S(O)_2NR^{2b}R^{2c}$, —$N(R^{2b})S(O)_2R^{2a}$, or —($C_1$-$C_6$ alkylenyl)-$S(O)_2R^{2a}$; wherein $R^{2a}$ is $C_1$-$C_6$ alkyl or $C_1$-$C_6$ haloalkyl; and $R^{2b}$ and $R^{2c}$ are each independently hydrogen, $C_1$-$C_6$ alkyl, or $C_1$-$C_6$ haloalkyl;
$L^1$ is O, N(H), or $OCH_2$ wherein the $CH_2$ moiety of $OCH_2$ is attached to $G^1$;
$R^{x1}$, $G^1$, $R^3$, and $R^4$, are selected from (i), (ii), (iii), or (iv);
(i) $R^{x1}$ is —CN, -$G^{x1}$-$G^{x2}$, —($C_1$-$C_6$ alkylenyl)-$G^{x1}$-$G^{x2}$, —$C(O)N(R^{xa})(R^{xb})$, $C_1$-$C_6$ alkyl substituted with one substituent selected from the group consisting of —CN, —$OR^{xb}$, —$SR^{xb}$, —$S(O)R^{xb}$, —$S(O)_2R^{xb}$, —$NR^{xa}R^{xb}$, —$C(O)R^{xb}$, —$C(O)OR^{xb}$, —$C(O)NR^{xa}R^{xb}$, and —$S(O)_2NR^{xa}R^{xb}$; $C_2$-$C_6$ alkenyl, or $C_2$-$C_6$ alkynyl; wherein the $C_2$-$C_6$ alkenyl and $C_2$-$C_6$ alkynyl are each independently substituted with one substituent selected from the group consisting of —CN, —$OR^{xc}$, —$SR^{xc}$, —$S(O)R^{xc}$, —$S(O)_2R^{xc}$, —$NR^{xa}R^{xc}$, —$C(O)R^{xc}$, —$C(O)OR^{xc}$, —$C(O)NR^{xa}R^{xc}$, —$S(O)_2NR^{xa}R^{xc}$, and $G^{x1}$;
$G^1$ is phenyl, $C_3$-$C_6$ cycloalkyl, $C_5$-$C_6$ heteroaryl, or $C_4$-$C_6$ heterocycle; wherein each $G^1$ is independently unsubstituted or substituted with 1, 2, 3, 4, or 5 substituents independently selected from the group consisting of $R^u$ and $R^v$ groups;
$R^3$ is $R^{1a}$, —C(O)OH, —$C(O)NR^{3a}R^{3b}$, —$NR^{3a}R^{3b}$, $G^{3a}$, -$G^{3a}$-$G^{3b}$, —($C_1$-$C_6$ alkylenyl)-$OR^{3a}$, —($C_1$-$C_6$ alkylenyl)-$NR^{3a}R^{3b}$, —($C_1$-$C_6$ alkylenyl)-$G^{3a}$, or —($C_1$-$C_6$ alkylenyl)-$G^{3a}$-$G^{3b}$; and
$R^4$ is $R^{1a}$ or $G^4$;
(ii) $R^{x1}$ is —CN, -$G^{x1}$-$G^{x2}$, —($C_1$-$C_6$ alkylenyl)-$G^{x1}$-$G^{x2}$, —$C(O)N(R^{xa})(R^{xb})$, hydrogen, $C_2$-$C_6$ alkenyl, $C_2$-$C_6$ alkynyl, —$C(O)OR^{ax1}$, —$C(O)NR^{bx1}R^{cx1}$, —$C(O)R^{dx1}$, —$S(O)_2R^{dx1}$, —$S(O)_2NR^{bx1}R^{cx1}$, $G^1$, $C_1$-$C_6$ haloalkyl, or $C_1$-$C_6$ alkyl; wherein the $C_1$-$C_6$ alkyl, $C_2$-$C_6$ alkenyl, and $C_2$-$C_6$ alkynyl are each optionally substituted with one substituent selected from the group consisting of —CN, —$OR^{xc}$, —$SR^{xc}$, —S(O)

$R^{xc}$, —S(O)$_2$R$^{xc}$, —NR$^{xa}$R$^{xc}$, —C(O)R$^{xc}$, —C(O)OR$^{xc}$, —C(O)NR$^{xa}$R$^{xc}$, —S(O)$_2$NR$^{xa}$R$^{xc}$, and G$^{x1}$;

G$^1$ is phenyl, C$_3$-C$_6$ cycloalkyl, C$_5$-C$_6$ heteroaryl, or C$_4$-C$_6$ heterocycle; wherein each G$^1$ is substituted with one R$^u$ group and is optionally further substituted with 1, 2, 3, 4, or 5 R$^v$ groups;

R$^3$ is R$^{1a}$, —C(O)OH, —C(O)NR$^{3a}$R$^{3b}$, —NR$^{3a}$R$^{3b}$, G$^{3a}$, -G$^{3a}$-G$^{3b}$, —(C$_1$-C$_6$ alkylenyl)-OR$^{3a}$, —(C$_1$-C$_6$ alkylenyl)-NR$^{3a}$R$^{3b}$, —(C$_1$-C$_6$ alkylenyl)-G$^{3a}$, or —(C$_1$-C$_6$ alkylenyl)-G$^{3a}$-G$^{3b}$; and R$^4$ is R$^{1a}$ or G$^4$;

(iii) R$^{x1}$ is —CN, -G$^{x1}$-G$^{x2}$, —(C$_1$-C$_6$ alkylenyl)-G$^{x1}$-G$^{x2}$, —C(O)N(R$^{xa}$)(R$^{xb}$), hydrogen, C$_2$-C$_6$ alkenyl, C$_2$-C$_6$ alkynyl, —C(O)OR$^{ax1}$, —C(O)NR$^{bx1}$R$^{cx1}$, —C(O)R$^{dx1}$, —S(O)$_2$R$^{dx1}$, —S(O)$_2$NR$^{bx1}$R$^{cx1}$, G$^{x1}$, C$_1$-C$_6$ haloalkyl, or C$_1$-C$_6$ alkyl; wherein the C$_1$-C$_6$ alkyl, C$_2$-C$_6$ alkenyl, and C$_2$-C$_6$ alkynyl are each optionally substituted with one substituent selected from the group consisting of —CN, —OR$^{xc}$, —SR$^{xc}$, —S(O)R$^{xc}$, —S(O)$_2$R$^{xc}$, —NR$^{xa}$R$^{xc}$, —C(O)R$^{xc}$, —C(O)OR$^{xc}$, —C(O)NR$^{xa}$R$^{xc}$, —S(O)$_2$NR$^{xa}$R$^{xc}$, and G$^{x1}$;

G$^1$ is phenyl, C$_3$-C$_6$ cycloalkyl, C$_5$-C$_6$ heteroaryl, or C$_4$-C$_6$ heterocycle; wherein each G$^1$ is independently unsubstituted or substituted with 1, 2, 3, 4, or 5 substituents independently selected from the group consisting of R$^u$ and R$^v$ groups;

R$^3$ is —C(O)OH, —C(O)NR$^{3a}$R$^{3b}$, —NR$^{3a}$R$^{3b}$, G$^{3a}$, -G$^{3a}$-G$^{3b}$, —(C$_1$-C$_6$ alkylenyl)-OR$^{3a}$, —(C$_1$-C$_6$ alkylenyl)-NR$^{3a}$R$^{3b}$, —(C$_1$-C$_6$ alkylenyl)-G$^{3a}$, or —(C$_1$-C$_6$ alkylenyl)-G$^{3a}$-G$^{3b}$; and R$^4$ is R$^{1a}$ or G$^4$;

(iv) R$^{x1}$ is —CN, -G$^{x1}$-G$^{x2}$, —(C$_1$-C$_6$ alkylenyl)-G$^{x1}$-G$^{x2}$, —C(O)N(R$^{xa}$)(R$^{xb}$), hydrogen, C$_2$-C$_6$ alkenyl, C$_2$-C$_6$ alkynyl, —C(O)OR$^{ax1}$, —C(O)NR$^{bx1}$R$^{cx1}$, —C(O)R$^{dx1}$, —S(O)$_2$R$^{dx1}$, —S(O)$_2$NR$^{bx1}$R$^{cx1}$, G$^{x1}$, C$_1$-C$_6$ haloalkyl, or C$_1$-C$_6$ alkyl; wherein the C$_1$-C$_6$ alkyl, C$_2$-C$_6$ alkenyl, and C$_2$-C$_6$ alkynyl are each optionally substituted with one substituent selected from the group consisting of —CN, —OR$^{xc}$, —SR$^{xc}$, —S(O)R$^{xc}$, —S(O)$_2$R$^{xc}$, —NR$^{xa}$R$^{xc}$, —C(O)R$^{xc}$, —C(O)OR$^{xc}$, —C(O)NR$^{xa}$R$^{xc}$, —S(O)$_2$NR$^{xa}$R$^{xc}$, and G$^{x1}$;

G$^1$ is phenyl, C$_3$-C$_6$ cycloalkyl, C$_5$-C$_6$ heteroaryl, or C$_4$-C$_6$ heterocycle; wherein each G$^1$ is independently unsubstituted or substituted with 1, 2, 3, 4, or 5 substituents independently selected from the group consisting of R$^u$ and R$^v$ groups;

R$^3$ is R$^{1a}$, —C(O)OH, —C(O)NR$^{3a}$R$^{3b}$, —NR$^{3a}$R$^{3b}$, G$^{3a}$, -G$^{3a}$-G$^{3b}$, —(C$_1$-C$_6$ alkylenyl)-OR$^{3a}$, —(C$_1$-C$_6$ alkylenyl)-NR$^{3a}$R$^{3b}$, —(C$_1$-C$_6$ alkylenyl)-G$^{3a}$, or —(C$_1$-C$_6$ alkylenyl)-G$^{3a}$-G$^{3b}$; and R$^4$ is G$^4$;

R$^{xa}$, at each occurrence, is independently hydrogen, C$_1$-C$_6$ alkyl, or C$_1$-C$_6$ haloalkyl;

R$^{xb}$, at each occurrence, is independently C$_1$-C$_6$ alkyl substituted with one substituent selected from the group consisting of —CN, —OR$^{ax1}$, —SR$^{ax1}$, —S(O)R$^{dx1}$, —S(O)$_2$R$^{dx1}$, —NR$^{bx1}$R$^{cx1}$, —C(O)R$^{ax1}$, —C(O)OR$^{ax1}$, —C(O)NR$^{bx1}$ R$^{cx1}$, and —S(O)$_2$NR$^{bx1}$R$^{cx1}$;

R$^{xc}$, at each occurrence, is independently hydrogen, C$_1$-C$_6$ alkyl, C$_1$-C$_6$ haloalkyl, G$^a$, —(C$_1$-C$_6$ alkylenyl)-G$^a$, or R$^{xb}$;

R$^{ax1}$, R$^{bx1}$, and R$^{cx1}$, at each occurrence, are each independently hydrogen, C$_1$-C$_6$ alkyl, C$_1$-C$_6$ haloalkyl, G$^a$, or —(C$_1$-C$_6$ alkylenyl)-G$^a$;

R$^{dx1}$, at each occurrence, is independently C$_1$-C$_6$ alkyl, C$_1$-C$_6$ haloalkyl, G$^a$, or —(C$_1$-C$_6$ alkylenyl)-G$^a$;

R$^{1a}$, at each occurrence, is independently hydrogen, C$_1$-C$_6$ alkyl, C$_2$-C$_6$ alkenyl, C$_2$-C$_6$ alkynyl, halogen, C$_1$-C$_6$ haloalkyl, CN, or NO$_2$;

R$^{3a}$ and R$^{3b}$, at each occurrence, are each independently hydrogen, C$_1$-C$_6$ alkyl, C$_1$-C$_6$ haloalkyl, G$^{3a}$, -G$^{3a}$-G$^{3b}$, —(C$_1$-C$_6$ alkylenyl)-G$^{3a}$, —(C$_1$-C$_6$ alkylenyl)-G$^{3a}$-G$^{3b}$, or C$_1$-C$_6$ alkyl substituted with one substituents selected from the group consisting of —CN, —OR$^h$, —SR$^h$, —S(O)R$^i$, —S(O)$_2$R$^h$, —NR$^j$R$^k$, —C(O)R$^h$, —C(O)OR$^h$, —C(O)NR$^j$R$^k$, and —S(O)$_2$NR$^j$R$^k$;

G$^4$, at each occurrence, is independently phenyl, C$_3$-C$_6$ cycloalkyl, C$_5$-C$_6$ heteroaryl, or C$_4$-C$_6$ heterocycle; each of which is optionally substituted with 1, 2, 3, 4, or 5 substituents independently selected from the group consisting of C$_1$-C$_6$ alkyl, NO$_2$, halogen, C$_1$-C$_6$ haloalkyl, —CN, oxo, —OR$^h$, —SR$^h$, —S(O)$_2$R$^h$, and —NR$^j$R$^k$;

R$^u$, at each occurrence, is independently —(C$_1$-C$_6$ alkylenyl)-G$^u$, —(C$_2$-C$_6$ alkynylene)-G$^u$, —(C$_1$-C$_6$ alkylenyl)-SR$^h$, —C(O)—Z$^1$, —C(O)—NZ$^1$Z$^2$, —S(O)$_2$—Z$^1$, —N(Z$^2$)Z$^1$, or —N(Z$^2$)S(O)$_2$—Z$^1$; wherein Z$^1$ is G$^u$, —(C$_1$-C$_6$ alkylenyl)-G$^u$, —(C$_2$-C$_6$ alkenylene)-G$^u$, —(C$_1$-C$_6$ alkylenyl)-CN, —(C$_1$-C$_6$ alkylenyl)-SR$^h$, —(C$_1$-C$_6$ alkylenyl)-OR$^h$, —(C$_1$-C$_6$ alkylenyl)-NR$^j$R$^k$, or —(C$_1$-C$_6$ alkylenyl)-C$_1$-C$_4$ alkoxy-C$_1$-C$_4$ alkoxy, and Z$^2$ is hydrogen, C$_1$-C$_6$ alkyl, or C$_1$-C$_6$ haloalkyl;

G$^u$, at each occurrence, is independently aryl, heteroaryl, heterocycle, cycloalkyl, or cycloalkenyl, wherein each G$^u$ is independently unsubstituted or substituted with 1, 2, 3, 4, or 5 substituents independently selected from the group consisting of C$_1$-C$_6$ alkyl, C$_2$-C$_6$ alkenyl, C$_2$-C$_6$ alkynyl, halogen, C$_1$-C$_6$ haloalkyl, —CN, oxo, NO$_2$, —OR$^h$, —O—(C$_2$-C$_6$ alkylenyl)-NR$^j$R$^k$, —OC(O)R$^i$, —OC(O)NR$^j$R$^k$, —O—(C$_1$-C$_6$ alkylenyl)-NR$^j$R$^k$, —SR$^h$, —S(O)$_2$R$^h$, —S(O)$_2$NR$^j$R$^k$, —C(O)R$^h$, —C(O)OR$^h$, —C(O)NR$^j$R$^k$, —NR$^j$R$^k$, —N(R$^h$)C(O)R$^i$, —N(R$^h$)S(O)$_2$R$^i$, —N(R$^h$)C(O)O(R$^i$), —N(R$^h$)C(O)NR$^j$R$^k$, G$^{ua}$, —(C$_1$-C$_6$ alkylenyl)-OR$^h$, —(C$_1$-C$_6$ alkylenyl)-OC(O)R$^i$, —(C$_1$-C$_6$ alkylenyl)-OC(O)NR$^j$R$^k$, —(C$_1$-C$_6$ alkylenyl)-SR$^h$, —(C$_1$-C$_6$ alkylenyl)-S(O)$_2$R$^h$, —(C$_1$-C$_6$ alkylenyl)-S(O)$_2$NR$^j$R$^k$, —(C$_1$-C$_6$ alkylenyl)-C(O)R$^h$, —(C$_1$-C$_6$ alkylenyl)-C(O)OR$^h$, —(C$_1$-C$_6$ alkylenyl)-C(O)NR$^j$R$^k$, —(C$_1$-C$_6$ alkylenyl)-NR$^j$R$^k$, —(C$_1$-C$_6$ alkylenyl)-N(R$^h$)C(O)R$^i$, —(C$_1$-C$_6$ alkylenyl)-N(R$^h$)S(O)$_2$R$^1$, —(C$_1$-C$_6$ alkylenyl)-N(R$^h$)C(O)O(R$^i$), —(C$_1$-C$_6$ alkylenyl)-N(R$^h$)C(O)NR$^j$R$^k$, —(C$_1$-C$_6$ alkylenyl)-CN, and —(C$_1$-C$_6$ alkylenyl)-G$^{ua}$;

G$^a$ G$^{x1}$, G$^{x2}$, G$^{3a}$, G$^{3b}$, and G$^{ua}$, at each occurrence, are each independently aryl, heteroaryl, heterocycle, cycloalkyl, or cycloalkenyl, each of which is optionally substituted with 1, 2, 3, 4, or 5 R$^z$ groups;

R$^z$ and R$^v$, at each occurrence, are each independently C$_1$-C$_6$ alkyl, C$_2$-C$_6$ alkenyl, C$_2$-C$_6$ alkynyl, halogen, C$_1$-C$_6$ haloalkyl, —CN, oxo, NO$_2$, —OR$^h$, —OC(O)R$^i$, —OC(O)NR$_j$R$^k$, —SR$^h$, —S(O)$_2$R$^h$, —S(O)$_2$NR$^j$R$^k$, —C(O)R$^h$, —C(O)OR$^h$, —C(O)NR$^j$R$^k$, —N(R$^h$)C(O)R$^i$, —N(R$^h$)S(O)$_2$R$^i$, —N(R$^h$)C(O)O (R$^i$), —N(R$^h$)C(O)NR$^j$R$^k$, —(C$_1$-C$_6$ alkylenyl)-OR$^h$, —(C$_1$-C$_6$ alkylenyl)-OC(O)R$^i$, —(C$_1$-C$_6$ alkylenyl)-OC(O)NR$^j$R$^k$, —(C$_1$-C$_6$ alkylenyl)-SR$^h$, —(C$_1$-C$_6$ alkylenyl)-S(O)$_2$R$^h$, —(C$_1$-C$_6$ alkylenyl)-S(O)$_2$NR$^j$R$^k$, —(C$_1$-C$_6$ alkylenyl)-C(O)R$^h$, —(C$_1$-C$_6$ alkylenyl)-C(O)OR$^h$, —(C$_1$-C$_6$ alkylenyl)-C(O)NR$^j$R$^k$, —(C$_1$-C$_6$ alkylenyl)-NR$^j$R$^k$, —(C$_1$-C$_6$ alkylenyl)-N(R$^h$)C(O)R$^i$, —(C$_1$-C$_6$ alkylenyl)-N(R$^h$)S(O)$_2$R$^i$, —(C$_1$-C$_6$ alkylenyl)-N(R$^h$)C(O)O(R$^i$), —(C$_1$-C$_6$ alkylenyl)-N(R$^h$)C(O)NR$^j$R$^k$, or —(C$_1$-C$_6$ alkylenyl)-CN;

$R^h$, $R^j$, $R^k$, at each occurrence, are each independently hydrogen, $C_1$-$C_6$ alkyl, or $C_1$-$C_6$ haloalkyl; and $R^i$, at each occurrence, is independently $C_1$-$C_6$ alkyl or $C_1$-$C_6$ haloalkyl.

In another aspect, the present invention provides for methods for treating or preventing disorders that are ameliorated by inhibition of BET. Such methods comprise of administering to the subject a therapeutically effective amount of a compound of formula (I), or a pharmaceutically acceptable salt thereof, alone, or in combination with a pharmaceutically acceptable carrier.

Some of the methods are directed to treating or preventing an inflammatory disease or cancer or AIDS.

In another aspect, the present invention relates to methods of treating cancer in a subject comprising administering a therapeutically effective amount of a compound of formula (I) or a pharmaceutically acceptable salt thereof, to a subject in need thereof. In certain embodiments, the cancer is selected from the group consisting of: acoustic neuroma, acute leukemia, acute lymphocytic leukemia, acute myelocytic leukemia (monocytic, myeloblastic, adenocarcinoma, angiosarcoma, astrocytoma, myelomonocytic and promyelocytic), acute t-cell leukemia, basal cell carcinoma, bile duct carcinoma, bladder cancer, brain cancer, breast cancer, bronchogenic carcinoma, cervical cancer, chondrosarcoma, chordoma, choriocarcinoma, chronic leukemia, chronic lymphocytic leukemia, chronic myelocytic (granulocytic) leukemia, chronic myelogenous leukemia, colon cancer, colorectal cancer, craniopharyngioma, cystadenocarcinoma, diffuse large B-cell lymphoma, dysproliferative changes (dysplasias and metaplasias), embryonal carcinoma, endometrial cancer, endotheliosarcoma, ependymoma, epithelial carcinoma, erythroleukemia, esophageal cancer, estrogen-receptor positive breast cancer, essential thrombocythemia, Ewing's tumor, fibrosarcoma, follicular lymphoma, germ cell testicular cancer, glioma, glioblastoma, gliosarcoma, heavy chain disease, hemangioblastoma, hepatoma, hepatocellular cancer, hormone insensitive prostate cancer, leiomyosarcoma, leukemia, liposarcoma, lung cancer, lymphagioendotheliosarcoma, lymphangiosarcoma, lymphoblastic leukemia, lymphoma (Hodgkin's and non-Hodgkin's), malignancies and hyperproliferative disorders of the bladder, breast, colon, lung, ovaries, pancreas, prostate, skin and uterus, lymphoid malignancies of T-cell or B-cell origin, leukemia, lymphoma, medullary carcinoma, medulloblastoma, melanoma, meningioma, mesothelioma, multiple myeloma, myelogenous leukemia, myeloma, myxosarcoma, neuroblastoma, NUT midline carcinoma (NMC), non-small cell lung cancer, oligodendroglioma, oral cancer, osteogenic sarcoma, ovarian cancer, pancreatic cancer, papillary adenocarcinomas, papillary carcinoma, pinealoma, polycythemia vera, prostate cancer, rectal cancer, renal cell carcinoma, retinoblastoma, rhabdomyosarcoma, sarcoma, sebaceous gland carcinoma, seminoma, skin cancer, small cell lung carcinoma, solid tumors (carcinomas and sarcomas), small cell lung cancer, stomach cancer, squamous cell carcinoma, synovioma, sweat gland carcinoma, thyroid cancer, Waldenstrom's macroglobulinemia, testicular tumors, uterine cancer and Wilms' tumor. In certain embodiments, the methods further comprise administering a therapeutically effective amount of at least one additional therapeutic agent. In certain embodiments, the additional therapeutic agent is selected from the group consisting of cytarabine, bortezomib, and 5-azacitidine.

In another aspect, the present invention relates to methods of treating a disease or condition in a subject comprising administering a therapeutically effective amount of a compound of formula (I) or a pharmaceutically acceptable salt thereof, to a subject in need thereof, wherein said disease or condition is selected from the group consisting of: Addison's disease, acute gout, ankylosing spondylitis, asthma, atherosclerosis, Behcet's disease, bullous skin diseases, cardiac myopathy, cardiac hypertrophy, chronic obstructive pulmonary disease (COPD), Crohn's disease, dermatitis, eczema, giant cell arteritis, glomerulonephritis, heart failure, hepatitis, hypophysitis, inflammatory bowel disease, Kawasaki disease, lupus nephritis, multiple sclerosis, myocarditis, myositis, nephritis, organ transplant rejection, osteoarthritis, pancreatitis, pericarditis, Polyarteritis nodosa, pneumonitis, primary biliary cirrhosis, psoriasis, psoriatic arthritis, rheumatoid arthritis, scleritis, sclerosing cholangitis, sepsis, systemic lupus erythematosus, Takayasu's Arteritis, toxic shock, thyroiditis, type I diabetes, ulcerative colitis, uveitis, vitiligo, vasculitis, and Wegener's granulomatosis. In certain embodiments, the methods further comprise administering a therapeutically effective amount of at least one additional therapeutic agent.

In another aspect, the present invention relates to methods of treating a chronic kidney disease or condition in a subject comprising administering a therapeutically effective amount of a compound of formula (I) or a pharmaceutically acceptable salt thereof, to a subject in need thereof, wherein said disease or condition is selected from the group consisting of: diabetic nephropathy, hypertensive nephropathy, HIV-associated nephropathy, glomerulonephritis, lupus nephritis, IgA nephropathy, focal segmental glomerulosclerosis, membranous glomerulonephritis, minimal change disease, polycystic kidney disease and tubular interstitial nephritis. In certain embodiments, the methods further comprise administering a therapeutically effective amount of at least one additional therapeutic agent.

In another aspect, the present invention relates to methods of treating an acute kidney injury or disease or condition in a subject comprising administering a therapeutically effective amount of a compound of formula (I) or a pharmaceutically acceptable salt thereof, to a subject in need thereof, wherein said acute kidney injury or disease or condition is selected from the group consisting of: ischemia-reperfusion induced, cardiac and major surgery induced, percutaneous coronary intervention induced, radio-contrast agent induced, sepsis induced, pneumonia induced, and drug toxicity induced. In certain embodiments, the methods further comprise administering a therapeutically effective amount of at least one additional therapeutic agent.

In another aspect, the present invention relates to methods of treating AIDS in a subject comprising administering a therapeutically effective amount of a compound of formula (I) or a pharmaceutically acceptable salt thereof, to a subject in need thereof. In certain embodiments, the methods further comprise administering a therapeutically effective amount of at least one additional therapeutic agent.

In another aspect, the present invention relates to methods of treating obesity, dyslipidemia, hypercholesterolemia, Alzheimer's disease, metabolic syndrome, hepatic steatosis, type II diabetes, insulin resistance, diabetic retinopathy or diabetic neuropathy in a subject comprising administering a therapeutically effective amount of a compound of formula (I) or a pharmaceutically acceptable salt thereof, to a subject in need thereof. In certain embodiments, the methods further comprise administering a therapeutically effective amount of at least one additional therapeutic agent.

In another aspect, the present invention relates to methods of preventing conception by inhibiting spermatogenesis in a subject comprising administering a therapeutically effective amount of a compound of formula (I) or a pharmaceutically acceptable salt thereof, to a subject in need thereof. In certain embodiments, the methods further comprise administering a therapeutically effective amount of at least one additional therapeutic agent.

A further aspect of the invention provides the use of a compound of formula (I), alone or in combination with at least one additional therapeutic agent, in the manufacture of a medicament for treating or preventing conditions and disorders disclosed herein, and with or without a pharmaceutically acceptable carrier.

Pharmaceutical compositions comprising a compound of formula (I), or a pharmaceutically acceptable salt, alone or in combination with at least one additional therapeutic agent, are also provided.

DETAILED DESCRIPTION

Disclosed herein are compounds of formula (I)

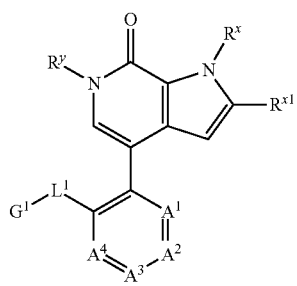

(I)

wherein $R^x$, $R^y$, $R^{x1}$, $A^1$, $A^2$, $A^3$, $A^4$, $L^1$ and $G^1$ are defined above in the Summary of the Invention and below in the Detailed Description. Further, compositions comprising such compounds and methods for treating conditions and disorders using such compounds and compositions are also disclosed.

Compounds disclosed herein may contain one or more variable(s) that occur more than one time in any substituent or in the formulae herein. Definition of a variable on each occurrence is independent of its definition at another occurrence. Further, combinations of sub stituents are permissible only if such combinations result in stable compounds. Stable compounds are compounds, which can be isolated from a reaction mixture.

Definitions

It is noted that, as used in this specification and the intended claims, the singular form "a," "an," and "the" include plural referents unless the context clearly dictates otherwise. Thus, for example, reference to "a compound" includes a single compound as well as one or more of the same or different compounds, reference to "optionally a pharmaceutically acceptable carrier" refers to a single optional pharmaceutically acceptable carrier as well as one or more pharmaceutically acceptable carriers, and the like.

As used in the specification and the appended claims, unless specified to the contrary, the following terms have the meaning indicated: The term "alkenyl" as used herein, means a straight or branched hydrocarbon chain containing from 2 to 10 carbons and containing at least one carbon-carbon double bond. The term "$C_2$-$C_6$ alkenyl" means an alkenyl group containing 2-6 carbon atoms. Non-limiting examples of alkenyl include buta-1,3-dienyl, ethenyl, 2-propenyl, 2-methyl-2-propenyl, 3-butenyl, 4-pentenyl, and 5-hexenyl.

The term "$C_2$-$C_6$ alkenylene" means a divalent group derived from a straight or branched chain hydrocarbon of 2 to 6 carbon atoms and contains at least one carbon-carbon double bond. Representative examples of $C_2$-$C_6$ alkenylene include, but are not limited to, —CH═CH— and —CH$_2$CH═CH—.

The term "alkyl" as used herein, means a saturated, straight or branched hydrocarbon chain radical. In some instances, the number of carbon atoms in an alkyl moiety is indicated by the prefix "$C_x$-$C_y$", wherein x is the minimum and y is the maximum number of carbon atoms in the substituent. Thus, for example, "$C_1$-$C_6$ alkyl" refers to an alkyl substituent containing from 1 to 6 carbon atoms and "$C_1$-$C_3$ alkyl" refers to an alkyl substituent containing from 1 to 3 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 1-methylbutyl, 2-methylbutyl, 3-methylbutyl, 3,3-dimethylbutyl, 1,1-dimethylpropyl, 1,2-dimethylpropyl, 2,2-dimethylpropyl, 1-methylpropyl, 2-methylpropyl, 1-ethylpropyl, 1,2,2-trimethylpropyl, 3-methylhexyl, 2,2-dimethylpentyl, 2,3-dimethylpentyl, n-heptyl, n-octyl, n-nonyl, and n-decyl.

The term "alkylene" or "alkylenyl" means a divalent radical derived from a straight or branched, saturated hydrocarbon chain, for example, of 1 to 10 carbon atoms or of 1 to 6 carbon atoms ($C_1$-$C_6$ alkylenyl) or of 1 to 4 carbon atoms or of 1 to 3 carbon atoms ($C_1$-$C_3$ alkylenyl) or of 2 to 6 carbon atoms ($C_2$-$C_6$ alkylenyl). Examples of alkylene and alkylenyl include, but are not limited to, —CH$_2$—, —CH$_2$CH$_2$—, —C(CH$_3$)$_2$)—CH$_2$CH$_2$CH$_2$—, —CH$_2$CH$_2$CH$_2$CH$_2$—, and —CH$_2$CH(CH$_3$)CH$_2$—.

The term "$C_2$-$C_6$ alkynyl" as used herein, means a straight or branched chain hydrocarbon radical containing from 2 to 6 carbon atoms and containing at least one carbon-carbon triple bond. Representative examples of $C_2$-$C_6$ alkynyl include, but are not limited, to acetylenyl, 1-propynyl, 2-propynyl, 3-butynyl, 2-pentynyl, and 1-butynyl.

The term "$C_2$-$C_6$ alkynylene" means a divalent group derived from a straight or branched chain hydrocarbon of from 2 to 6 carbon atoms containing at least one triple bond. Representative examples of alkynylene include, but are not limited to —CH(CH$_3$)CH$_2$C≡C—, —CCCH$_2$—, and —C≡CCH(CH$_3$)CH$_2$—.

The term "$C_1$-$C_4$ alkoxy" as used herein, means a $C_1$-$C_4$ alkyl group, as defined herein, appended to the parent molecular moiety through an oxygen atom. Representative examples of $C_1$-$C_4$ alkoxy include, but are not limited to, methoxy, ethoxy, propoxy, 2-propoxy, and butoxy.

The term "aryl" as used herein, means phenyl or a bicyclic aryl. The bicyclic aryl is naphthyl, or a phenyl fused to a monocyclic cycloalkyl, or a phenyl fused to a monocyclic cycloalkenyl. Non-limiting examples of the aryl groups include dihydroindenyl, indenyl, naphthyl, dihydronaphthalenyl, and tetrahydronaphthalenyl. The bicyclic aryls are attached to the parent molecular moiety through any carbon atom contained within the bicyclic ring systems.

The term "cycloalkyl" as used herein, refers to a radical that is a monocyclic cyclic alkyl, a bicyclic cycloalkyl, or a spiro cycloalkyl. The monocyclic cycloalkyl is a carbocyclic ring system containing three to eight carbon atoms, zero heteroatoms and zero double bonds. Examples of monocyclic ring systems include cyclopropyl, cyclobutyl, cyclopentyl, cyclohexyl, cycloheptyl, and cyclooctyl. The bicyclic cycloalkyl is a monocyclic cycloalkyl fused to a monocyclic cycloalkyl ring. The monocyclic and the bicyclic cycloalkyl groups may contain one or two alkylene bridges, each consisting of one, two, three, or four carbon atoms in length, and each bridge links two non-adjacent carbon atoms of the ring system. Non-limiting examples of bicyclic ring systems include bicyclo[3.1.1]heptane, bicyclo[2.2.1]heptane, bicyclo[2.2.2]octane, bicyclo[3.2.2]nonane, bicyclo[3.3.1] nonane, and bicyclo[4.2.1]nonane, tricyclo[3.3.1.0$^{3,7}$] nonane (octahydro-2,5-methanopentalene or noradamantane), and tricyclo[3.3.1.1$^{3,7}$]decane (adamantane). A spiro cycloalkyl is a monocyclic cycloalkyl wherein two substituents on the same carbon atom of the monocyclic cycloalkyl ring together with said carbon atom form a second monocyclic cycloalkyl ring. The monocyclic, the bicyclic, and the spiro cycloalkyl groups are attached to the parent molecular moiety through any substitutable atom contained within the ring system.

The term "$C_3$-$C_6$ cycloalkyl" as used herein, means cyclopropyl, cyclobutyl, cyclopentyl, and cyclohexyl.

The term "cycloalkenyl" as used herein, refers to a monocyclic or a bicyclic hydrocarbon ring radical. The monocyclic cycloalkenyl has four-, five-, six-, seven- or eight carbon atoms and zero heteroatoms. The four-membered ring systems have one double bond, the five- or six-membered ring systems have one or two double bonds, and the seven- or eight-membered ring systems have one, two, or three double bonds. Representative examples of monocyclic cycloalkenyl groups include, but are not limited to, cyclobutenyl, cyclopentenyl, cyclohexenyl, cycloheptenyl, and cyclooctenyl. The bicyclic cycloalkenyl is a monocyclic cycloalkenyl fused to a monocyclic cycloalkyl group, or a monocyclic cycloalkenyl fused to a monocyclic cycloalkenyl group. The monocyclic or bicyclic cycloalkenyl ring may contain one or two alkylene bridges, each consisting of one, two, or three carbon atoms, and each linking two non-adjacent carbon atoms of the ring system. Representative examples of the bicyclic cycloalkenyl groups include, but are not limited to, 4,5,6,7-tetrahydro-3aH-indene, octahydronaphthalenyl, and 1,6-dihydro-pentalene. The monocyclic and bicyclic cycloalkenyls can be attached to the parent molecular moiety through any substitutable atom contained within the ring systems.

The term "$C_5$-$C_8$ cycloalkenyl" as used herein, means a cyclohexenyl, cyclohexadienyl, cyclopentenyl, cycloheptenyl, and cyclooctenyl. The $C_5$-$C_8$ cycloalkenyls can be attached to the parent molecular moiety through any substitutable atom contained within the ring systems.

The term "halo" or "halogen" as used herein, means Cl, Br, I, and F.

The term "haloalkyl" as used herein, means an alkyl group, as defined herein, in which one, two, three, four, five or six hydrogen atoms are replaced by halogen. The term "$C_1$-$C_6$ haloalkyl" means a $C_1$-$C_6$ alkyl group, as defined herein, in which one, two, three, four, five or six hydrogen atoms are replaced by halogen. The term "$C_1$-$C_3$ haloalkyl" means a $C_1$-$C_3$ alkyl group, as defined herein, in which one, two, or three hydrogen atoms are replaced by halogen. Representative examples of haloalkyl include, but are not limited to, chloromethyl, 2-fluoroethyl, 2,2-difluoroethyl, 2,2,2-trifluoroethyl, trifluoromethyl, difluoromethyl, pentafluoroethyl, 2-chloro-3-fluoropentyl, trifluorobutyl, and trifluoropropyl.

The term "heterocycle" or "heterocyclic" as used herein, means a radical of a monocyclic heterocycle, a bicyclic heterocycle, and a spiro heterocycle. A monocyclic heterocycle is a three-, four-, five-, six-, seven-, or eight-membered carbocyclic ring also containing at least one heteroatom independently selected from the group consisting of O, N, and S. A three- or four-membered ring contains zero or one double bond, and one heteroatom selected from the group consisting of O, N, and S. When two O atoms or one O atom and one S atom are present in a heterocyclic ring, then the two O atoms or one O atom and one S atom are not bonded directly to each other. A five-membered ring contains zero or one double bond and one, two, or three heteroatoms selected from the group consisting of O, N, and S. Examples of five-membered heterocyclic rings include those containing in the ring: 1 O; 1 S; 1 N; 2 N; 3 N; 1 S and 1 N; 1 S, and 2 N; 1 O and 1 N; or 1 O and 2 N. Examples of 5-membered heterocyclic groups include tetrahydrofuranyl, dihydrofuranyl, tetrahydrothienyl, dihydrothienyl, imidazolidinyl, oxazolidinyl, imidazolinyl, isoxazolidinyl, pyrrolidinyl, 2-pyrrolinyl, and 3-pyrrolinyl. A six-membered ring contains zero, one, or two double bonds and one, two, or three heteroatoms selected from the group consisting of O, N, and S. Examples of six-membered heterocyclic rings include those containing in the ring: 1 O; 2 O; 1 S; 2 S; 1 N; 2 N; 3 N; 1 S, 1 O, and 1 N; 1 S and 1 N; 1 S and 2 N; 1 S and 1 O; 1 S and 2 O; 1 Q and 1 N; and 1 O and 2 N. Examples of 6-membered heterocyclic groups include tetrahydropyranyl, dihydropyranyl, dioxanyl, 1,3-dioxolanyl, 1,4-dithianyl, hexahydropyrimidine, morpholinyl, piperazinyl, piperidinyl, 2H-pyranyl, 4H-pyranyl, pyrazolidinyl, pyrazolinyl, 1,2,3,6-tetrahydropyridinyl, tetrahydrothiopyranyl, 1,1-dioxo-hexahydro-1-thiopyranyl, 1,1-dioxo-1λ$^6$-thiomorpholinyl, thiomorpholinyl, thioxanyl, and trithianyl. Seven- and eight-membered rings contains zero, one, two, or three double bonds and one, two, or three heteroatoms selected from the group consisting of O, N, and S. Representative examples of monocyclic heterocycles include, but are not limited to, azetidinyl, azepanyl, aziridinyl, diazepanyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, oxetanyl, piperazinyl, piperidinyl, pyranyl, pyrazolinyl, pyrazolidinyl, pyrrolinyl, pyrrolidinyl, tetrahydrofuranyl, tetrahydropyridinyl, tetrahydropyranyl, tetrahydrothienyl, thiadiazolinyl, thiadiazolidinyl, thiazolinyl, thiazolidinyl, thiomorpholinyl, thiopyranyl, and trithianyl. The bicyclic heterocycle is a monocyclic heterocycle fused to a phenyl group, or a monocyclic heterocycle fused to a monocyclic cycloalkyl, or a monocyclic heterocycle fused to a monocyclic cycloalkenyl, or a monocyclic heterocycle fused to a monocyclic heterocycle. Representative examples of bicyclic heterocycles include, but are not limited to, benzopyranyl, benzothiopyranyl, 2,3-dihydrobenzofuranyl, 2,3-dihydrobenzothienyl, 2,3-dihydro-1H-indolyl, 3,4-dihydroisoquinolin-2(1H)-yl, 2,3,4, 6-tetrahydro-1H-pyrido[1,2-a]pyrazin-2-yl, hexahydropyrano[3,4-b][1,4]oxazin-1(5H)-yl. The monocyclic heterocycle and the bicyclic heterocycle may contain one or two alkylene bridges or an alkenylene bridge, or mixture thereof, each consisting of no more than four carbon atoms and each linking two non adjacent atoms of the ring system. Examples of such bridged heterocycle include, but are not limited to, azabicyclo[2.2.1]heptyl (including 2-azabicyclo [2.2.1]hept-2-yl), azabicyclo[3.2.1]oct-8-yl, octahydro-2,5-epoxypentalene, hexahydro-2H-2,5-methanocyclopenta[b] furan, hexahydro-1H-1,4-methanocyclopenta[c]furan, aza-admantane (1-azatricyclo[3.3.1.1$^{3,7}$]decane), and oxa-adamantane (2-oxatricyclo[3.3.1.1$^{3,7}$]decane). A spiro heterocycle is a monocyclic heterocycle wherein two substituents on the same carbon atom of the monocyclic heterocycle ring together with said carbon atom form a second ring system selected from a monocyclic cycloalkyl, a bicyclic cycloalkyl, a monocyclic heterocycle, or a bicyclic heterocycle. Examples of spiro heterocycle include, but not limited to, 6-azaspiro[2.5]oct-6-yl, 1'H, 4H-spiro[1,3-benzodioxine-2,4'-piperidin]-1'-yl, 1'H, spiro[2-benzofuran-1,4'-piperidin]-1'-yl, and 1,4-dioxa-8-azaspiro[4.5]dec-8-yl. The monocyclic, the bicyclic, and the spiro heterocycles can be unsubstituted or substituted. The monocyclic, the bicyclic and the spiro heterocycles are connected to the parent molecular moiety through any carbon atom or any nitrogen atom contained within the ring systems.

The nitrogen and sulfur heteroatoms in the heterocycle rings may optionally be oxidized (e.g. 1,1-dioxidotetrahydrothienyl, 1,1-dioxido-1,2-thiazolidinyl, 1,1-dioxidothiomorpholinyl)) and the nitrogen atoms may optionally be quarternized.

The term "$C_3$-$C_7$ heterocycle" or "$C_3$-$C_7$ heterocyclic" as used herein, means a 3, 4, 5, 6 or 7 membered monocyclic heterocycle as defined herein above.

The term "$C_4$-$C_6$ heterocycle" or "$C_4$-$C_6$ heterocyclic" as used herein, means a 4, 5, or 6 membered monocyclic heterocycle as defined herein above. Examples of $C_4$-$C_6$ heterocycle include azetidinyl, pyrrolidinyl, 1,2-thiazolidinyl, tetrahydrofuranyl, tetrahydropyranyl, piperazinyl, piperidinyl, pyridin-1(2H)-yl, thiomorpholinyl, and morpholinyl.

The term "heteroaryl" as used herein, means a monocyclic heteroaryl and a bicyclic heteroaryl. The monocyclic heteroaryl is a five- or six-membered ring. The five-membered ring contains two double bonds. The five membered ring may contain one heteroatom selected from O or S; or one, two, three, or four nitrogen atoms and optionally one oxygen or one sulfur atom. The six-membered ring contains three double bonds and one, two, three or four nitrogen atoms. Representative examples of monocyclic heteroaryl include, but are not limited to, furanyl, imidazolyl, isoxazolyl, isothiazolyl, oxadiazolyl, 1,3-oxazolyl, pyridinyl, pyridazinyl, pyrimidinyl, pyrazinyl, pyrazolyl, pyrrolyl, tetrazolyl, thiadiazolyl, 1,3-thiazolyl, thienyl, triazolyl, and triazinyl. The bicyclic heteroaryl consists of a monocyclic heteroaryl fused to a phenyl, or a monocyclic heteroaryl fused to a monocyclic cycloalkyl, or a monocyclic heteroaryl fused to a monocyclic cycloalkenyl, or a monocyclic heteroaryl fused to a monocyclic heteroaryl, or a monocyclic heteroaryl fused to a monocyclic heterocycle. Representative examples of bicyclic heteroaryl groups include, but are not limited to, benzofuranyl, benzothienyl, benzoxazolyl, benzimidazolyl, benzoxadiazolyl, phthalazinyl, 2,6-dihydropyrrolo[3,4-c]pyrazol-5(4H)-yl, 6,7-dihydro-pyrazolo[1,5-a]pyrazin-5(4H)-yl, 6,7-dihydro-1,3-benzothiazolyl, imidazo[1,2-a]pyridinyl, indazolyl, indolyl, isoindolyl, isoquinolinyl, naphthyridinyl, pyridoimidazolyl, quinolinyl, 2,4,6,7-tetrahydro-5H-pyrazolo[4,3-c]pyridin-5-yl, thiazolo[5,4-b]pyridin-2-yl, thiazolo[5,4-d]pyrimidin-2-yl, and 5,6,7,8-tetrahydroquinolin-5-yl. The monocyclic and bicyclic heteroaryl groups are connected to the parent molecular moiety through any substitutable carbon atom or any substitutable nitrogen atom contained within the ring systems. The nitrogen atom in the heteroaryl rings may optionally be oxidized and may optionally be quarternized.

The term "$C_5$-$C_6$ heteroaryl" as used herein, means a 5- or 6-membered monocyclic heteroaryl ring as described above. Examples of $C_5$-$C_6$ heteroaryl include furanyl, thienyl, pyrazolyl, imidazolyl, 1,2,4-oxadiazolyl, 1,2,4-triazolyl, 1,3-thiazolyl, pyridinyl, pyrimidinyl, and pyrazinyl.

The term "heteroatom" as used herein, means a nitrogen, oxygen, and sulfur.

The term "oxo" as used herein, means a =O group.

If a moiety is described as "substituted", a non-hydrogen radical is in the place of hydrogen radical of any substitutable atom of the moiety. Thus, for example, a substituted heterocycle moiety is a heterocycle moiety in which at least one non-hydrogen radical is in the place of a hydrogen radical on the heterocycle. It should be recognized that if there are more than one substitution on a moiety, each non-hydrogen radical may be identical or different (unless otherwise stated).

If a moiety is described as being "optionally substituted," the moiety may be either (1) not substituted or (2) substituted. If a moiety is described as being optionally substituted with up to a particular number of non-hydrogen radicals, that moiety may be either (1) not substituted; or (2) substituted by up to that particular number of non-hydrogen radicals or by up to the maximum number of substitutable positions on the moiety, whichever is less. Thus, for example, if a moiety is described as a heteroaryl optionally substituted with up to 3 non-hydrogen radicals, then any heteroaryl with less than 3 substitutable positions would be optionally substituted by up to only as many non-hydrogen radicals as the heteroaryl has substitutable positions. To illustrate, tetrazolyl (which has only one substitutable position) would be optionally substituted with up to one non-hydrogen radical. To illustrate further, if an amino nitrogen is described as being optionally substituted with up to 2 non-hydrogen radicals, then a primary amino nitrogen will be optionally substituted with up to 2 non-hydrogen radicals, whereas a secondary amino nitrogen will be optionally substituted with up to only 1 non-hydrogen radical.

The terms "treat", "treating", and "treatment" refer to a method of alleviating or abrogating a disease and/or its attendant symptoms.

The terms "prevent", "preventing", and "prevention" refer to a method of preventing the onset of a disease and/or its attendant symptoms or barring a subject from acquiring a disease. As used herein, "prevent", "preventing" and "prevention" also include delaying the onset of a disease and/or its attendant symptoms and reducing a subject's risk of acquiring a disease.

The phrase "therapeutically effective amount" means an amount of a compound, or a pharmaceutically acceptable salt thereof, sufficient to prevent the development of or to alleviate to some extent one or more of the symptoms of the condition or disorder being treated when administered alone or in conjunction with another therapeutic agent or treatment in a particular subject or subject population. For example in a human or other mammal, a therapeutically effective amount can be determined experimentally in a laboratory or clinical setting, or may be the amount required by the guidelines of the United States Food and Drug Administration, or equivalent foreign agency, for the particular disease and subject being treated.

The term "subject" is defined herein to refer to animals such as mammals, including, but not limited to, primates (e.g., humans), cows, sheep, goats, horses, dogs, cats, rabbits, rats, mice and the like. In preferred embodiments, the subject is a human.

Compounds

Compounds of the invention have the general formula (I) as described above.

Particular values of variable groups in compounds of formula (I) are as follows. Such values may be used where appropriate with any of the other values, definitions, claims or embodiments defined hereinbefore or hereinafter.

In certain embodiments of formula (I), $R^x$ is hydrogen or $C_1$-$C_3$ alkyl.

In certain embodiments, $R^x$ is hydrogen.

In certain embodiments, $R^x$ is $C_1$-$C_3$ alkyl. In some such embodiments, $R^x$ is methyl.

In certain embodiments of formula (I), $R^y$ is hydrogen or $C_1$-$C_3$ alkyl.

In certain embodiments, $R^y$ is $C_1$-$C_3$ alkyl. In some such embodiments, $R^y$ is methyl.

In certain embodiments, $R^y$ is hydrogen.

In certain embodiments of formula (I), $A^1$ is N or $CR^1$, $A^2$ is N or $CR^2$, $A^3$ is N or $CR^3$; and $A^4$ is N or $CR^4$; wherein zero, one, two, or three of $A^1$, $A^2$, $A^3$, and $A^4$ are N.

In certain embodiments, $A^1$ is $CR^1$, $A^2$ is $CR^2$, $A^3$ is $CR^3$; and $A^4$ is $CR^4$.

In certain embodiments, one of $A^1$, $A^2$, $A^3$, and $A^4$ is N.

In certain embodiments of formula (I), $R^1$ is hydrogen, $C_1$-$C_6$ alkyl, $C_2$-$C_6$ alkenyl, $C_2$-$C_6$ alkynyl, halogen, $C_1$-$C_6$ haloalkyl, CN, or $NO_2$.

In certain embodiments, $R^1$ is hydrogen.

In certain embodiments of formula (I), $R^2$ is hydrogen, —S(O)$_2R^{2a}$, —S(O)$_2NR^{2b}R^{2c}$, —N($R^{2b}$)S(O)$_2$$R^{2a}$, or —($C_1$-$C_6$ alkylenyl)-S(O)$_2$$R^{2a}$; wherein $R^{2a}$ is $C_1$-$C_6$ alkyl or $C_1$-$C_6$ haloalkyl; and $R^{2b}$ and $R^{2c}$ are each independently hydrogen, $C_1$-$C_6$ alkyl, or $C_1$-$C_6$ haloalkyl.

In certain embodiments, $R^2$ is hydrogen, —S(O)$_2R^{2a}$, —S(O)$_2NR^{2b}R^{2c}$, —N($R^{2b}$)S(O)$_2$$R^{2a}$, or —($C_1$-$C_3$ alkylenyl)-S(O)$_2$$R^{2a}$. In some such embodiments, $R^{2a}$ is $C_1$-$C_3$ alkyl; and $R^{2b}$ and $R^{2c}$ are each independently hydrogen or $C_1$-$C_3$ alkyl.

In certain embodiments, $R^2$ is hydrogen, —S(O)$_2R^{2a}$, or —N($R^{2b}$)S(O)$_2$$R^{2a}$. In some such embodiments, $R^{2a}$ is $C_1$-$C_3$ alkyl; and $R^{2b}$ is hydrogen.

In certain embodiments of formula (I), $L^1$ is O, N(H), or $OCH_2$ wherein the $CH_2$ moiety of $OCH_2$ is attached to $G^1$.

In certain embodiments, $L^1$ is O or $OCH_2$.

In certain embodiments, $L^1$ is O.

In certain embodiments, $L^1$ is $OCH_2$.

In certain embodiments, $L^1$ is N(H).

In certain embodiments of formula (I), $R^{x1}$, $G^1$, $R^3$, and $R^4$, are selected from (i), (ii), (iii), or (iv).

In certain embodiments, $R^{x1}$, $G^1$, $R^3$, and $R^4$, are selected from (i).

In certain embodiments, $R^{x1}$, $G^1$, $R^3$, and $R^4$, are selected from (i) wherein $R^{x1}$ is $G^{x2}$, —($C_1$-$C_6$ alkylenyl)-$G^{x1}$-$G^{x2}$, —C(O)N($R^{xa}$)($R^{xb}$), $C_2$-$C_6$ alkenyl, or $C_2$-$C_6$ alkynyl; wherein the $C_2$-$C_6$ alkenyl and $C_2$-$C_6$ alkynyl are each independently substituted with one substituent selected from the group consisting of —CN, —OR$^{xc}$, —SR$^{xc}$, —S(O)R$^{xc}$, —S(O)$_2R^{xc}$, —NR$^{xa}R^{xc}$, —C(O)R$^{xc}$, —C(O)OR$^{xc}$, —C(O)NR$^{xa}R^{xc}$, —S(O)$_2$NR$^{xa}R^{xc}$, and $G^{x1}$.

In certain embodiments, $R^{x1}$, $G^1$, $R^3$, and $R^4$, are selected from (i) wherein $R^{x1}$ is —($C_1$-$C_6$ alkylenyl)-$G^{x1}$-$G^{x2}$, $C_2$-$C_6$ alkenyl, or $C_2$-$C_6$ alkynyl; wherein the $C_2$-$C_6$ alkenyl and $C_2$-$C_6$ alkynyl are each independently substituted with one substituent selected from the group consisting of —CN, —OR$^{xc}$, —SR$^{xc}$, —S(O)R$^{xc}$, —S(O)$_2R^{xc}$, —NR$^{xa}R^{xc}$, —C(O)R$^{xc}$, —C(O)OR$^{xc}$, —C(O)NR$^{xa}R^{xc}$, —S(O)$_2$NR$^{xa}R^{xc}$, and $G^{x1}$.

In certain embodiments, $R^{x1}$, $G^1$, $R^3$, and $R^4$, are selected from (i) wherein $R^{x1}$ is —($C_1$-$C_6$ alkylenyl)-$G^{x1}$-$G^{x2}$. In some such embodiments, $G^{x1}$ is optionally substituted $C_4$-$C_6$ heterocycle. In some such embodiments, $G^{x1}$ is azetidinyl, pyrrolidinyl, piperazinyl, 1,4-diazepanyl, morpholinyl, or piperidinyl; each of which is optionally substituted. In some such embodiments, $G^{x1}$ is optionally substituted piperazinyl. In some such embodiments, $G^{x2}$ is phenyl, $C_3$-$C_6$ cycloalkyl, $C_5$-$C_6$ heteroaryl, or $C_4$-$C_6$ heterocycle, each of which is optionally substituted.

In certain embodiments, $R^{x1}$, $G^1$, $R^3$, and $R^4$, are selected from (i) wherein $R^{x1}$ is -$G^{x1}$-$G^{x2}$. In some such embodiments, $G^{x1}$ is optionally substituted $C_5$-$C_6$ heteroaryl. In some such embodiments, $G^{x1}$ is pyrazolyl, 1,2,4-oxadiazolyl, or pyridinyl; each of which is optionally substituted. In some such embodiments, $G^{x2}$ is phenyl, $C_5$-$C_6$ heteroaryl, $C_4$-$C_6$ heterocycle, or $C_3$-$C_6$ cycloalkyl; each of which is optionally substituted. In some such embodiments, $G^{x2}$ is phenyl, thiazolyl, pyridinyl, pyrazinyl, cyclopropyl, cyclohexyl, piperidinyl, tetrahydropyranyl, or morpholinyl; each of which is optionally substituted.

In certain embodiments, $R^{x1}$, $G^1$, $R^3$, and $R^4$, are selected from (i) wherein $R^{x1}$ is —C(O)N($R^{xa}$)($R^{xb}$). In some such embodiments, $R^{xa}$ hydrogen or $C_1$-$C_3$ alkyl. In some such embodiments, $R^{xa}$ is hydrogen. In some such embodiments, $R^{xb}$ is $C_1$-$C_6$ alkyl substituted with one substituent selected from the group consisting of —CN, —NR$^{bx1}R_{cx1}$, —C(O)R$^{ax1}$, and —C(O)NR$^{bx1}R^{cx1}$. In some such embodiments, $R^{bx1}$ is hydrogen or $C_1$-$C_6$ alkyl, and $R^{cx1}$ is hydrogen, $C_1$-$C_6$ alkyl, or $G^a$. In some such embodiments, $R^{bx1}$ is hydrogen or $C_1$-$C_6$ alkyl, and $R^{cx1}$ is hydrogen, $C_1$-$C_6$ alkyl, or optionally substituted $C_3$-$C_6$ cycloalkyl. In some such embodiments, $R^{bx1}$ and $R^{cx1}$ are each independently hydrogen or $C_1$-$C_6$ alkyl. In some such embodiments, $R^{ax1}$ is optionally substituted $C_4$-$C_6$ heterocycle.

In certain embodiments, $R^{x1}$, $G^1$, $R^3$, and $R^4$, are selected from (i) wherein $R^{x1}$ is $C_2$-$C_6$ alkenyl, wherein the $C_2$-$C_6$ alkenyl is substituted with one substituent selected from the group consisting of —CN, —OR$^{xc}$, —SR$^{xc}$, —S(O)R$^{xc}$, —S(O)$_2R^{xc}$, —NR$^{xa}R^{xc}$, —C(O)R$^{xc}$, —C(O)OR$^{xc}$, —C(O)NR$^{xa}R^{xc}$, —S(O)$_2$NR$^{xa}R^{xc}$, and $G^{x1}$. In some such embodiments, the $C_2$-$C_6$ alkenyl is substituted with one —C(O)NR$^{xa}R^{xc}$ group. In some such embodiments, the $C_2$-$C_6$ alkenyl is substituted with one —NR$^{xa}R^{xc}$ group. In some such embodiments, $R^{xa}$ and $R^{xc}$ are each independently hydrogen or $C_1$-$C_6$ alkyl.

In certain embodiments, $R^{x1}$, $G^1$, $R^3$, and $R^4$, are selected from (i) wherein $R^{x1}$ is $C_2$-$C_6$ alkynyl substituted with one substituent selected from the group consisting of —NR$^{xa}R^{xc}$ and —OR$^{xc}$ group. In some such embodiments, $R^{xa}$ and $R^{xc}$ are each independently hydrogen or $C_1$-$C_6$ alkyl.

In certain embodiments, $R^{x1}$, $G^1$, $R^3$, and $R^4$, are selected from (i) wherein $R^{x1}$ is $G^{x1}$-$G^{x2}$, $C_2$-$C_6$ alkynyl substituted with one —OR$^{xc}$ group, or $C_2$-$C_6$ alkenyl substituted with one —C(O)NR$^{xa}R^{xc}$ group. In some such embodiments, $G^{x1}$ is optionally substituted $C_5$-$C_6$ heteroaryl. In some such embodiments, $G^{x1}$ is pyrazolyl, 1,2,4-oxadiazolyl, or pyridinyl; each of which is optionally substituted. In some such embodiments, $G^{x2}$ is phenyl, $C_5$-$C_6$ heteroaryl, $C_4$-$C_6$ heterocycle, or $C_3$-$C_6$ cycloalkyl; each of which is optionally substituted. In some such embodiments, $G^{x2}$ is phenyl, thiazolyl, pyridinyl, pyrazinyl, cyclopropyl, cyclohexyl, piperidinyl, tetrahydropyranyl, or morpholinyl; each of which is optionally substituted. In some such embodiments, $R^{xa}$ and $R^{xc}$ are each independently hydrogen or $C_1$-$C_6$ alkyl.

In certain embodiments, $R^{x1}$, $G^1$, $R^3$, and $R^4$, are selected from (i) wherein $G^1$ is phenyl, $C_3$-$C_6$ cycloalkyl, or $C_4$-$C_6$ heterocycle, each of which is optionally substituted with 1, 2, 3, 4, or 5 $R^v$ groups. In some such embodiments, each $R^v$ is independently $C_1$-$C_6$ alkyl, halogen, $C_1$-$C_6$ haloalkyl, —CN, —OR$^h$, or NR$^jR^k$.

In certain embodiments, $R^{x1}$, $G^1$, $R^3$, and $R^4$, are selected from (i) wherein $G^1$ is phenyl or $C_3$-$C_6$ cycloalkyl, each of which is optionally substituted with 1, 2, 3, 4, or 5 $R^v$ groups. In some such embodiments, each $R^v$ is independently $C_1$-$C_3$ alkyl, halogen, or $C_1$-$C_3$ haloalkyl.

In certain embodiments, $R^{x1}$, $G^1$, $R^3$, and $R^4$, are selected from (i) wherein $G^1$ is phenyl or cyclopropyl, each of which is optionally substituted with 1, 2, 3, 4, or 5 $R^v$ groups. In some such embodiments, each $R^v$ is independently $C_1$-$C_3$ alkyl, halogen, or $C_1$-$C_3$ haloalkyl. In some such embodiments, each $G^1$ is optionally substituted with 1 or 2 halogens. In some such embodiments, the $G^1$ group is substituted. In some such embodiments, the halogen is fluorine.

In certain embodiments, $R^{x1}$, $G^1$, $R^3$, and $R^4$, are selected from (i) wherein $G^1$ is cyclopropyl which is optionally substituted with 1 or 2 halogens. In some such embodiments, the halogen is fluorine.

In certain embodiments, $R^{x1}$, $G^1$, $R^3$, and $R^4$, are selected from (i) wherein $G^1$ is phenyl substituted with 1 or 2 $R^v$ groups. In some such embodiments, each $R^v$ is independently $C_1$-$C_3$ alkyl or halogen.

In certain embodiments, $R^{x1}$, $G^1$, $R^3$, and $R^4$, are selected from (i) wherein $G^1$ is phenyl substituted with 1 or 2 halogens. In some such embodiments, the halogen is fluorine.

In certain embodiments, $R^{x1}$, $G^1$, $R^3$, and $R^4$, are selected from (i) wherein $G^1$ is cyclohexyl which is optionally substituted with 1, 2, 3, 4, or 5 $R^v$ groups. In some such embodiments, each $R^v$ is independently $C_1$-$C_3$ alkyl, halogen, or $C_1$-$C_3$ haloalkyl. In some such embodiments, $G^1$ is unsubstituted cyclohexyl.

In certain embodiments, $R^{x1}$, $G^1$, $R^3$, and $R^4$, are selected from (i) wherein $R^3$ is $R^{1a}$.

In some such embodiments, $R^3$ is $R^{1a}$, and $R^{1a}$ is hydrogen.

In certain embodiments, $R^{x1}$, $G^1$, $R^3$, and $R^4$, are selected from (i) wherein $R^4$ is $R^{1a}$. In some such embodiments, $R^4$ is $R^{1a}$, and $R^{1a}$ is hydrogen.

In certain embodiments, $R^{x1}$, $G^1$, $R^3$, and $R^4$, are selected from (ii).

In certain embodiments, $R^{x1}$, $G^1$, $R^3$, and $R^4$, are selected from (ii) wherein $R^{x1}$ is hydrogen or —C(O)NR$^{bx1}$R$^{cx1}$.

In certain embodiments, $R^{x1}$, $G^1$, $R^3$, K and $R^4$, are selected from (ii) wherein $R^{x1}$ is hydrogen.

In certain embodiments, $R^{x1}$, $G^1$, $R^3$, and $R^4$, are selected from (ii) wherein $R^{x1}$ is —C(O)NR$^{bx1}$R$^{cx1}$. In some such embodiments, R$^{bx1}$ and R$^{cx1}$ are each independently hydrogen or $C_1$-$C_6$ alkyl.

In certain embodiments, $R^{x1}$, $G^1$, $R^3$, and $R^4$, are selected from (ii) wherein $G^1$ is phenyl, $C_3$-$C_6$ cycloalkyl, or $C_4$-$C_6$ heterocycle, wherein each $G^1$ is substituted with one $R^u$ group and is optionally further substituted with 1, 2, or 3 $R^v$ groups. In some such embodiments, each $R^v$ is independently $C_1$-$C_3$ alkyl, halogen, $C_1$-$C_3$ haloalkyl, —CN, or —OR$^h$. In some such embodiments, each $R^v$ is independently $C_1$-$C_3$ alkyl, halogen, or $C_1$-$C_3$ haloalkyl. In some such embodiments, $R^v$ is halogen. In some such embodiments, $R^v$ is Cl. In some such embodiments, $R^v$ is $C_1$-$C_3$ alkyl.

In certain embodiments, $R^{x1}$, $G^1$, $R^3$, and $R^4$, are selected from (ii) wherein $G^1$ is phenyl, cyclohexyl, or piperidinyl, wherein each $G^1$ is substituted with one $R^u$ group and is optionally further substituted with 1, 2, or 3 $R^v$ groups. In some such embodiments, each $R^v$ is independently $C_1$-$C_3$ alkyl, halogen, $C_1$-$C_3$ haloalkyl, —CN, or —OR$^h$. In some such embodiments, each $R^v$ is independently $C_1$-$C_3$ alkyl, halogen, or $C_1$-$C_3$ haloalkyl. In some such embodiments, $R^v$ is halogen. In some such embodiments, $R^v$ is Cl. In some embodiments, $R^v$ is $C_1$-$C_3$ alkyl.

In certain embodiments, $R^{x1}$, $G^1$, $R^3$, and $R^4$, are selected from (ii) wherein $G^1$ is phenyl or $C_3$-$C_6$ cycloalkyl, wherein each $G^1$ is substituted with one $R^u$ group and is optionally further substituted with 1, 2, or 3 $R^v$ groups. In some such embodiments, each $R^v$ is independently $C_1$-$C_3$ alkyl, halogen, $C_1$-$C_3$ haloalkyl, —CN, or —OR$^h$. In some such embodiments, each $R^v$ is independently $C_1$-$C_3$ alkyl, halogen, or $C_1$-$C_3$ haloalkyl. In some such embodiments, $R^v$ is halogen. In some such embodiments, $R^v$ is Cl. In some embodiments, $R^v$ is $C_1$-$C_3$ alkyl.

$R^u$ is as described in the Summary and embodiments herein below.

In certain embodiments, $R^u$ is —($C_1$-$C_6$ alkylenyl)-$G^u$. In certain embodiments, $R^u$ is —($C_1$-$C_6$ alkylenyl)-$G^u$, and $G^u$ is phenyl, $C_3$-$C_6$ cycloalkyl, $C_5$-$C_6$ heteroaryl, or $C_4$-$C_6$ heterocycle, each of which is optionally substituted. In certain embodiments, $R^u$ is —($C_1$-$C_6$ alkylenyl)-$G^u$, and $G^u$ is phenyl, $C_5$-$C_6$ heteroaryl, or $C_4$-$C_6$ heterocycle, each of which is optionally substituted. In certain embodiments, $R^u$ is —($C_1$-$C_6$ alkylenyl)-$G^u$, and $G^u$ is phenyl, cyclopentyl, thienyl, imidazolyl, pyrazolyl, azetidinyl, pyrrolidinyl, 1,2-thiazolidinyl, piperidinyl, pyridin-1(2H)-yl, or morpholinyl, each of which is optionally substituted. In certain embodiments, $R^u$ is —($C_1$-$C_6$ alkylenyl)-$G^u$, and $G^u$ is phenyl, thienyl, imidazolyl, pyrazolyl, azetidinyl, pyrrolidinyl, 1,2-thiazolidinyl, piperidinyl, pyridin-1(2H)-yl, or morpholinyl, each of which is optionally substituted. In certain embodiments, $R^u$ is —($C_1$-$C_6$ alkylenyl)-$G^u$, and $G^u$ is phenyl, thienyl, or morpholinyl, each of which is optionally substituted. In certain embodiments, $R^u$ is —($C_1$-$C_6$ alkylenyl)-$G^u$, and $G^u$ is optionally substituted phenyl.

In certain embodiments, $R^u$ is —($C_2$-$C_6$ alkynylene)-$G^u$. In certain embodiments, $R^u$ is —($C_2$-$C_6$ alkynylene)-$G^u$, and $G^u$ is optionally substituted $C_4$-$C_6$ heterocycle. In certain embodiments, $R^u$ is —($C_2$-$C_6$ alkynylene)-$G^u$, and $G^u$ is optionally substituted morpholinyl.

In certain embodiments, $R^u$ is —($C_1$-$C_6$ alkylenyl)-SR$^h$.

In certain embodiments, $R^u$ is —C(O)—$Z^1$.

In certain embodiments, $R^u$ is —C(O)—$Z^1$ wherein $Z^1$ is $G^u$, —($C_1$-$C_6$ alkylenyl)-$G^u$, —($C_1$-$C_6$ alkylenyl)-SR$^h$, —($C_1$-$C_6$ alkylenyl)-OR$^h$, —($C_1$-$C_6$ alkylenyl)-NR$^j$R$^k$, or —($C_1$-$C_6$ alkylenyl)-$C_1$-$C_4$ alkoxy-$C_1$-$C_4$ alkoxy. In some such embodiments, $G^u$ is phenyl, naphthyl, $C_3$-$C_6$ cycloalkyl, or $C_4$-$C_6$ heterocycle, each of which is optionally substituted.

In certain embodiments, $R^u$ is —C(O)—NZ$^1$Z$^2$.

In certain embodiments, $R^u$ is —C(O)—NZ$^1$Z$^2$ wherein $Z^1$ is $G^u$, —($C_1$-$C_6$ alkylenyl)-$G^u$, —($C_1$-$C_6$ alkylenyl)-CN, or —($C_1$-$C_6$ alkylenyl)-NR$^j$R$^k$, and $Z^2$ is hydrogen or $C_1$-$C_3$ alkyl. In some such embodiments, $G^u$ is phenyl, naphthyl, $C_3$-$C_6$ cycloalkyl, or $C_4$-$C_6$ heterocycle, each of which is optionally substituted.

In certain embodiments, $R^u$ is —S(O)$_2$—$Z^1$.

In certain embodiments, $R^u$ is —S(O)$_2$—$Z^1$ wherein $Z^1$ is $G^u$, —($C_1$-$C_6$ alkylenyl)-$G^u$, or —($C_2$-$C_6$ alkenylene)-$G^u$. In some such embodiments, $G^u$ is phenyl, naphthyl, $C_3$-$C_6$ cycloalkyl, $C_5$-$C_6$ heteroaryl, or $C_4$-$C_6$ heterocycle, each of which is optionally substituted.

In certain embodiments, $R^u$ is —N(Z$^2$)Z$^1$.

In certain embodiments, $R^u$ is —N(Z$^2$)Z$^1$ wherein $Z^1$ is —($C_1$-$C_6$ alkylenyl)-$G^u$, —($C_1$-$C_6$ alkylenyl)-SR$^h$, or —($C_1$-$C_6$ alkylenyl)-OR$^h$, and $Z^2$ is hydrogen or $C_1$-$C_3$ alkyl. In some such embodiments, $G^u$ is phenyl, naphthyl, $C_3$-$C_6$ cycloalkyl, $C_5$-$C_6$ heteroaryl, or $C_4$-$C_6$ heterocycle, each of which is optionally substituted.

In certain embodiments, $R^u$ is —N(Z$^2$)Z$^1$ wherein $Z^1$ is —($C_1$-$C_6$ alkylenyl)-$G^u$, and $Z^2$ is hydrogen or $C_1$-$C_3$ alkyl. In some such embodiments, $G^u$ is phenyl or naphthyl, each of which is optionally substituted.

In certain embodiments, $R^u$ is —N(Z$^2$)S(O)$_2$—$Z^1$.

In certain embodiments, $R^u$ is $-N(Z^2)S(O)_2-Z^1$, wherein $Z^1$ is $G^u$ or $-(C_1-C_6$ alkylenyl)-$G^u$, and $Z^2$ is hydrogen or $C_1-C_3$ alkyl. In some such embodiments, $G^u$ is phenyl, naphthyl, $C_3-C_6$ cycloalkyl, $C_5-C_6$ heteroaryl, or $C_4-C_6$ heterocycle, each of which is optionally substituted.

In certain embodiments, $R^u$ is $-N(Z^2)S(O)_2-Z^1$, wherein $Z^1$ is $G^u$ and $Z^2$ is hydrogen. In some such embodiments, $G^u$ is optionally substituted $C_3-C_6$ cycloalkyl. In some such embodiments, $G^u$ is optionally substituted cyclopropyl. In some such embodiments, the optional substituents are $C_1-C_3$ alkyl, halogen, and $C_1-C_3$ haloalkyl.

In certain embodiments, $R^u$ is $-(C_1-C_6$ alkylenyl)-$G^u$, $-N(Z^2)Z^1$, or $-N(Z^2)S(O)_2-Z^1$.

In certain embodiments, $R^u$ is $-(C_1-C_6$ alkylenyl)-$G^u$ and $G^u$ is phenyl, $C_5-C_6$ heteroaryl, or $C_4-C_6$ heterocycle, each of which is optionally substituted; or $R^u$ is $-N(Z^2)S(O)_2-Z^1$, wherein $Z^1$ is $G^u$, and $Z^2$ is hydrogen; or $R^u$ is $-N(Z^2)Z^1$ wherein $Z^1$ is $-(C_1-C_6$ alkylenyl)-$G^u$, and $Z^2$ is hydrogen or $C_1-C_3$ alkyl.

In certain embodiments, $R^u$ is $-(C_1-C_6$ alkylenyl)-$G^u$ and $G^u$ is optionally substituted phenyl; or $R^u$ is $-N(Z^2)S(O)_2-Z^1$, wherein $Z^1$ is $G^u$ and $G^u$ is optionally substituted $C_3-C_6$ cycloalkyl, and $Z^2$ is hydrogen; or $R^u$ is $-N(Z^2)Z^1$ wherein $Z^1$ is $-(C_1-C_6$ alkylenyl)-$G^u$ wherein $G^u$ is phenyl or naphthyl, each of which is optionally substituted, and $Z^2$ is hydrogen or $C_1-C_3$ alkyl.

In certain embodiments, $R^{x1}$, $G^1$, $R^3$, and $R^4$, are selected from (ii) wherein $R^3$ is $R^{1a}$. In some such embodiments, $R^3$ is $R^{1a}$, and $R^{1a}$ is hydrogen.

In certain embodiments, $R^{x1}$, $G^1$, $R^3$, and $R^4$, are selected from (ii) wherein $R^4$ is $R^{1a}$. In some such embodiments, $R^4$ is $R^{1a}$, and $R^{1a}$ is hydrogen.

In certain embodiments, $R^{x1}$, $G^1$, $R^3$, and $R^4$, are selected from (iii).

In certain embodiments, $R^{x1}$, $G^1$, $R^3$, and $R^4$, are selected from (iii) wherein $R^{x1}$ is hydrogen or $-C(O)NR^{bx1}R^{cx1}$.

In certain embodiments, $R^{x1}$, $G^1$, $R^3$, and $R^4$, are selected from (iii) wherein $R^{x1}$ is hydrogen.

In certain embodiments, $R^{x1}$, $G^1$, $R^3$, and $R^4$, are selected from (iii) wherein $R^{x1}$ is $-C(O)NR^{bx1}R^{cx1}$. In some such embodiments, $R^{bx1}$ and $R^{cx1}$ are each independently hydrogen or $C_1-C_6$ alkyl.

In certain embodiments, $R^{x1}$, $G^1$, $R^3$, and $R^4$, are selected from (iii) wherein $G^1$ is phenyl, $C_3-C_6$ cycloalkyl, or $C_4-C_6$ heterocycle, each of which is optionally substituted with 1, 2, 3, 4, or 5 $R^v$ groups. In some such embodiments, each $R^v$ is independently $C_1-C_6$ alkyl, halogen, $C_1-C_6$ haloalkyl, $-CN$, $-OR^h$, or $NR^jR^k$.

In certain embodiments, $R^{x1}$, $G^1$, $R^3$, and $R^4$, are selected from (iii) wherein $G^1$ is phenyl or $C_3-C_6$ cycloalkyl, each of which is optionally substituted with 1, 2, 3, 4, or 5 $R^v$ groups. In some such embodiments, each $R^v$ is independently $C_1-C_3$ alkyl, halogen, or $C_1-C_3$ haloalkyl.

In certain embodiments, $R^{x1}$, $G^1$, $R^3$, and $R^4$, are selected from (iii) wherein $G^1$ is phenyl or cyclopropyl, each of which is optionally substituted with 1, 2, 3, 4, or 5 $R^v$ groups. In some such embodiments, each $R^v$ is independently $C_1-C_3$ alkyl, halogen, or $C_1-C_3$ haloalkyl. In some such embodiments, each $G^1$ is optionally substituted with 1 or 2 halogens. In some such embodiments, the $G^1$ group is substituted. In some such embodiments, the halogen is fluorine.

In certain embodiments, $R^{x1}$, $G^1$, $R^3$, and $R^4$, are selected from (iii) wherein $G^1$ is cyclopropyl which is optionally substituted with 1 or 2 halogens. In some such embodiments, the halogen is fluorine.

In certain embodiments, $R^{x1}$, $G^1$, $R^3$, and $R^4$, are selected from (iii) wherein $G^1$ is phenyl substituted with 1 or 2 $R^v$ groups. In some such embodiments, each $R^v$ is independently $C_1-C_3$ alkyl or halogen.

In certain embodiments, $R^{x1}$, $G^1$, $R^3$, and $R^4$, are selected from (iii) wherein $G^1$ is phenyl substituted with 1 or 2 halogens. In some such embodiments, the halogen is fluorine.

In certain embodiments, $R^{x1}$, $G^1$, $R^3$, and $R^4$, are selected from (iii) wherein $R^3$ is $-C(O)OH$, $-C(O)NR^{3a}R^{3b}$, $G^{3a}$, $-(C_1-C_6$ alkylenyl)-$OR^{3a}$, $-(C_1-C_6$ alkylenyl)-$NR^{3a}R^{3b}$, $-(C_1-C_6$ alkylenyl)-$G^{3a}$, or $-(C_1-C_6$ alkylenyl)-$G^{3a}$-$G^{3b}$. In some such embodiments, $G^{3a}$ and $G^{3b}$ are each independently phenyl, $C_3-C_6$ cycloalkyl, $C_5-C_6$ heteroaryl, or $C_4-C_6$ heterocycle, each of which is optionally substituted.

In certain embodiments, $R^{x1}$, $G^1$, $R^3$, and $R^4$, are selected from (iii) wherein $R^3$ is $-C(O)OH$, $-C(O)NR^{3a}R^{3b}$, or $-(C_1-C_6$ alkylenyl)-$G^{3a}$. In some such embodiments, $G^{3a}$ is optionally substituted $C_4-C_6$ heterocycle. In some such embodiments, $G^{3a}$ is piperidinyl or morpholinyl, each of which is optionally substituted.

In certain embodiments, $R^{x1}$, $G^1$, $R^3$, and $R^4$, are selected from (iii) wherein $R^3$ is $-C(O)OH$.

In certain embodiments, $R^{x1}$, $G^1$, $R^3$, and $R^4$, are selected from (iii) wherein $R^3$ is $-C(O)NR^{3a}R^{3b}$.

In certain embodiments, $R^{x1}$, $G^1$, $R^3$, and $R^4$, are selected from (iii) wherein $R^3$ is $-C(O)NR^{3a}R^{3b}$. In some such embodiments, $R^{3a}$ is hydrogen, $C_1-C_3$ alkyl, $(C_1-C_6$ alkylenyl)-$G^{3a}$, or $C_1-C_6$ alkyl substituted with one substituent selected from the group consisting of $-CN$, $-NR^jR^k$, $-C(O)NR^jR^k$ and $-C(O)OR^h$, and $R^{3b}$ is hydrogen, $C_1-C_6$ alkyl, $G^{3a}$, or $-(C_1-C_6$ alkylenyl)-$G^{3a}$. In some such embodiments, $R^{3a}$ is hydrogen, $C_1-C_3$ alkyl, $-(C_1-C_6$ alkylenyl)-$G^{3a}$, or $C_1-C_6$ alkyl substituted with one substituent selected from the group consisting of $-C(O)NR^jR^k$ and $-C(O)OR^h$, and $R^{3b}$ is hydrogen, $C_1-C_3$ alkyl, $G^{3a}$, or $-(C_1-C_6$ alkylenyl)-$G^{3a}$. In some such embodiments, $G^{3a}$ is phenyl, $C_3-C_6$ cycloalkyl, $C_5-C_6$ heteroaryl, or $C_4-C_6$ heterocycle, each of which is optionally substituted. In some such embodiments, $G^{3a}$ is phenyl, $C_3-C_6$ cycloalkyl, or $C_4-C_6$ heterocycle, each of which is optionally substituted. In some such embodiments, $G^{3a}$ is phenyl, pyridinyl, pyrimidinyl, thiomorpholinyl, morpholinyl, piperidinyl, pyrrolidinyl, tetrahydropyranyl, cyclopentyl, or cyclohexyl, each of which is optionally substituted.

In certain embodiments, $R^{x1}$, $G^1$, $R^3$, and $R^4$, are selected from (iii) wherein $R^3$ is $-C(O)NR^{3a}R^{3b}$, wherein $R^{3a}$ is hydrogen or $C_1-C_3$ alkyl, and $R^{3b}$ is hydrogen, $C_1-C_3$ alkyl, or $G^{3a}$. In some such embodiments, $G^{3a}$ is phenyl, $C_3-C_6$ cycloalkyl, $C_5-C_6$ heteroaryl, or $C_4-C_6$ heterocycle, each of which is optionally substituted. In some such embodiments, $G^{3a}$ is $C_3-C_6$ cycloalkyl or $C_4-C_6$ heterocycle, each of which is optionally substituted. In some such embodiments, $G^{3a}$ is optionally substituted tetrahydropyranyl or optionally substituted cyclopentyl.

In certain embodiments, $R^{x1}$, $G^1$, $R^3$, and $R^4$, are selected from (iii) wherein $R^3$ is $G^{3a}$. In some such embodiments, $G^{3a}$ is phenyl, $C_3-C_6$ cycloalkyl, $C_5-C_6$ heteroaryl, or $C_4-C_6$ heterocycle, each of which is optionally substituted. In some such embodiments, $G^{3a}$ is optionally substituted $C_5-C_6$ heteroaryl. In some such embodiments, $G^{3a}$ is optionally substituted pyrazolyl. In some such embodiments, $G^{3a}$ is optionally substituted with 1 or 2 substituents independently selected from the group consisting of $C_1-C_3$ alkyl, $C_1-C_3$ haloalkyl, or halogen.

In certain embodiments, $R^{x1}$, $G^1$, $R^3$, and $R^4$, are selected from (iii) wherein $R^3$ is $-(C_1-C_6$ alkylenyl)-$OR^{3a}$. In some such embodiments, $R^{3a}$ is hydrogen, $C_1-C_6$ alkyl, or $C_1-C_6$ haloalkyl. In some such embodiments, $R^{3a}$ is hydrogen or $C_1$-$C_3$ alkyl. In some such embodiments, $R^{3a}$ is hydrogen.

In certain embodiments, $R^{x1}$, $G^1$, $R^3$, and $R^4$, are selected from (iii) wherein $R^3$ is —($C_1$-$C_6$ alkylenyl)-$NR^{3a}R^{3b}$. In some such embodiments, $R^{3a}$ is hydrogen or $C_1$-$C_3$ alkyl, and $R^{3b}$ is hydrogen, $C_1$-$C_3$ alkyl, $G^{3a}$, or $C_2$-$C_6$ alkyl substituted with one $OR^h$ group. In some such embodiments, $G^{3a}$ is phenyl, $C_3$-$C_6$ cycloalkyl, $C_5$-$C_6$ heteroaryl, or $C_4$-$C_6$ heterocycle, each of which is optionally substituted. In some such embodiments, $G^{3a}$ is optionally substituted $C_3$-$C_6$ cycloalkyl. In some such embodiments, $G^{3a}$ is optionally substituted cyclopentyl.

In certain embodiments, $R^{x1}$, $G^1$, $R^3$, and $R^4$, are selected from (iii) wherein $R^3$ is —($C_1$-$C_6$ alkylenyl)-$G^{3a}$. In some such embodiments, $G^{3a}$ is phenyl, $C_3$-$C_6$ cycloalkyl, $C_5$-$C_6$ heteroaryl, or $C_4$-$C_6$ heterocycle, each of which is optionally substituted. In some such embodiments, $G^{3a}$ is optionally substituted $C_4$-$C_6$ heterocycle. In some such embodiments, $G^{3a}$ is morpholinyl, piperidinyl, or piperazinyl, each of which is optionally substituted.

In certain embodiments, $R^{x1}$, $G^1$, $R^3$, and $R^4$, are selected from (iii) wherein $R^3$ is —($C_1$-$C_6$ alkylenyl)-$G^{3a}$-$G^{3b}$. In some such embodiments, $G^{3a}$ and $G^{3b}$ are each independently phenyl, $C_3$-$C_6$ cycloalkyl, $C_5$-$C_6$ heteroaryl, or $C_4$-$C_6$ heterocycle, each of which is optionally substituted. In some such embodiments, $G^{3a}$ is optionally substituted $C_4$-$C_6$ heterocycle. In some such embodiments, $G^{3a}$ is optionally substituted pyrrolidinyl.

In certain embodiments, $R^{x1}$, $G^1$, $R^3$, and $R^4$, are selected from (iii) wherein $R^4$ is $R^{1a}$. In some such embodiments, $R^4$ is $R^{1a}$, and $R^{1a}$ is hydrogen.

In certain embodiments, $R^{x1}$, $G^1$, $R^3$, and $R^4$, are selected from (iv).

In certain embodiments, $R^{x1}$, $G^1$, $R^3$, and $R^4$, are selected from (iv) wherein $R^{x1}$ is hydrogen.

In certain embodiments, $R^{x1}$, $G^1$, $R^3$, and $R^4$, are selected from (iv) wherein $G^1$ is phenyl, $C_3$-$C_6$ cycloalkyl, or $C_4$-$C_6$ heterocycle, each of which is optionally substituted with 1, 2, 3, 4, or 5 $R^v$ groups. In some such embodiments, each $R^v$ is independently $C_1$-$C_6$ alkyl, halogen, $C_1$-$C_6$ haloalkyl, —CN, —$OR^h$, or $NR^jR^k$.

In certain embodiments, $R^{x1}$, $G^1$, $R^3$, and $R^4$, are selected from (iv) wherein $G^1$ is phenyl or $C_3$-$C_6$ cycloalkyl, each of which is optionally substituted with 1, 2, 3, 4, or 5 $R^v$ groups. In some such embodiments, each $R^v$ is independently $C_1$-$C_3$ alkyl, halogen, or $C_1$-$C_3$ haloalkyl.

In certain embodiments, $R^{x1}$, $G^1$, $R^3$, and $R^4$, are selected from (iv) wherein $G^1$ is phenyl or cyclopropyl, each of which is optionally substituted with 1, 2, 3, 4, or 5 $R^v$ groups. In some such embodiments, each $R^v$ is independently $C_1$-$C_3$ alkyl, halogen, or $C_1$-$C_3$ haloalkyl. In some such embodiments, each $G^1$ is optionally substituted with 1 or 2 halogens. In some such embodiments, the $G^1$ group is substituted. In some such embodiments, the halogen is fluorine.

In certain embodiments, $R^{x1}$, $G^1$, $R^3$, and $R^4$, are selected from (iv) wherein $G^1$ is cyclopropyl which is optionally substituted with 1 or 2 halogens. In some such embodiments, the halogen is fluorine.

In certain embodiments, $R^{x1}$, $G^1$, $R^3$, and $R^4$, are selected from (iv) wherein $G^1$ is phenyl substituted with 1 or 2 halogens. In some such embodiments, the halogen is fluorine.

In certain embodiments, $R^{x1}$, $G^1$, $R^3$, and $R^4$, are selected from (iv) wherein $R^3$ is $R^{1a}$. In some such embodiments, $R^3$ is $R^{1a}$, and $R^{1a}$ is hydrogen.

In certain embodiments, $R^{x1}$, $G^1$, $R^3$, and $R^4$, are selected from (iv) wherein $R^4$ is $G^4$. In some such embodiments, $G^4$ is optionally substituted $C_3$-$C_6$ cycloalkyl. In some such embodiments, $G^4$ is optionally substituted cyclopropyl. In some such embodiments, $G^4$ is unsubstituted cyclopropyl.

Various embodiments of substituents $R^x$, $R^y$, $R^{x1}$, $L^1$, $G^1$, $A^1$, $A^2$, $A^3$, and $A^4$ have been discussed above. These substituents embodiments can be combined to form various embodiments of compounds of formula (I). All embodiments of compounds of formula (I), formed by combining the substituent embodiments discussed above are within the scope of Applicant's invention, and some illustrative embodiments of the compounds of formula (I) are provided below.

In one embodiment, the invention is directed to compounds of formula (I), wherein $R^x$ is hydrogen, and $R^y$ is $C_1$-$C_3$ alkyl.

In one embodiment, the invention is directed to compounds of formula (I), wherein $R^x$ is hydrogen, $R^y$ is $C_1$-$C_3$ alkyl, $A^1$ is $CR^1$, $A^2$ is $CR^2$, $A^3$ is $CR^3$; and $A^4$ is $CR^4$.

In one embodiment, the invention is directed to compounds of formula (I), wherein $R^x$ is hydrogen, $R^y$ is $C_1$-$C_3$ alkyl, and one of $A^1$, $A^2$, $A^3$, and $A^4$ is N.

In one embodiment, the invention is directed to compounds of formula (I), wherein $R^x$ is hydrogen, $R^y$ is $C_1$-$C_3$ alkyl, $R^2$ is hydrogen, —$S(O)_2R^{2a}$, or —$N(R^{2b})S(O)_2R^{2a}$; $R^{2a}$ is $C_1$-$C_3$ alkyl; and $R^{2b}$ is hydrogen.

In one embodiment, the invention is directed to compounds of formula (I), wherein $R^x$ is hydrogen, $R^y$ is methyl, $A^1$ is $CR^1$, $A^2$ is $CR^2$, $A^3$ is $CR^3$; and $A^4$ is $CR^4$, $R^1$ is hydrogen, and $R^{x1}$, $G^1$, $R^3$, and $R^4$, are selected from (i).

In one embodiment, the invention is directed to compounds of formula (I), wherein $R^x$ is hydrogen, $R^y$ is methyl, $A^1$ is $CR^1$, $A^2$ is $CR^2$, $A^3$ is $CR^3$; and $A^4$ is $CR^4$, $R^1$ is hydrogen, $R^{x1}$, $G^1$, $R^3$, and $R^4$, are selected from (i) wherein $R^3$ is $R^{1a}$; $R^4$ is $R^{1a}$; and $G^1$ is phenyl, $C_3$-$C_6$ cycloalkyl, or $C_4$-$C_6$ heterocycle, each of which is optionally substituted with 1, 2, 3, 4, or 5 $R^v$ groups.

In one embodiment, the invention is directed to compounds of formula (I), wherein $R^x$ is hydrogen, $R^y$ is methyl, $A^1$ is $CR^1$, $A^2$ is $CR^2$, $A^3$ is $CR^3$; and $A^4$ is $CR^4$, $R^1$ is hydrogen, $R^{x1}$, $G^1$, $R^3$, and $R^4$, are selected from (i) wherein $R^3$ is $R^{1a}$; $R^4$ is $R^{1a}$; $R^{1a}$ is hydrogen; and $G^1$ is phenyl or $C_3$-$C_6$ cycloalkyl, each of which is optionally substituted with 1, 2, 3, 4, or 5 $R^v$ groups.

In one embodiment, the invention is directed to compounds of formula (I), wherein $R^x$ is hydrogen, $R^y$ is methyl, $A^1$ is $CR^1$, $A^2$ is $CR^2$, $A^3$ is $CR^3$; and $A^4$ is $CR^4$, $R^1$ is hydrogen, $R^{x1}$, $G^1$, $R^3$, and $R^4$, are selected from (i) wherein $R^3$ is $R^{1a}$; $R^4$ is $R^{1a}$; $R^{1a}$ is hydrogen; $G^1$ is phenyl or $C_3$-$C_6$ cycloalkyl, each of which is optionally substituted with 1, 2, 3, 4, or 5 $R^v$ groups; and $R^{x1}$ is -$G^{x1}$-$G^{x2}$, —($C_1$-$C_1$-$C_6$ alkylenyl)-$G^{x1}$-$G^{x2}$, —$C(O)N(R^{xa})(R^{xb})$, $C_2$-$C_6$ alkenyl, or $C_2$-$C_6$ alkynyl; wherein the $C_2$-$C_6$ alkenyl and $C_2$-$C_6$ alkynyl are each independently substituted with one substituent selected from the group consisting of —CN, —$OR^{xc}$, —$SR^{xc}$, —$S(O)R^{xc}$, —$S(O)_2R^{xc}$, —$NR^{xa}R^{xc}$, —$C(O)R^{xc}$, —$C(O)OR^{xc}$, —$C(O)NR^{xa}R^{xc}$, —$S(O)_2NR^{xa}R^{xc}$, and $G^{x1}$.

In one embodiment, the invention is directed to compounds of formula (I), wherein $R^x$ is hydrogen, $R^y$ is methyl, $A^1$ is $CR^1$, $A^2$ is $CR^2$, $A^3$ is $CR^3$; and $A^4$ is $CR^4$, $R^1$ is hydrogen, $R^{x1}$, $G^1$, $R^3$, and $R^4$, are selected from (i) wherein $R^3$ is $R^{1a}$; $R^4$ is $R^{1a}$; $R^{1a}$ is hydrogen; $G^1$ is phenyl or $C_3$-$C_6$ cycloalkyl, each of which is optionally substituted with 1, 2, 3, 4, or 5 $R^v$ groups; $R^{x1}$ is -$G^{x1}$-$G^{x2}$, —($C_1$-$C_6$ alkylenyl)-$G^{x1}$-$G^{x2}$, —$C(O)N(R^{xa})(R^{xb})$, $C_2$-$C_6$ alkenyl, or $C_2$-$C_6$ alkynyl; wherein the $C_2$-$C_6$ alkenyl and $C_2$-$C_6$ alkynyl are each independently substituted with one substituent selected from the group consisting of —CN, —$OR^{xc}$, —$SR^{xc}$, —$S(O)R^{xc}$, —S(O)$_2$R$^{xc}$, —NR$^{xa}$R$^{xc}$, —C(O)R$^{xc}$, —C(O)OR$^{xc}$, —C(O)NR$^{xa}$R$^{xc}$, —S(O)$_2$NR$^{xa}$R$^{xc}$, and G$^{x1}$; and R$^2$ is hydrogen, —S(O)$_2$R$^{2a}$, or —N(R$^{2b}$)S(O)$_2$R$^{2a}$.

In one embodiment, the invention is directed to compounds of formula (I), wherein R$^x$ is hydrogen, R$^y$ is methyl, A$^1$ is CR$^1$, A$^2$ is CR$^2$, A$^3$ is CR$^3$; and A$^4$ is CR$^4$, R$^1$ is hydrogen, R$^{x1}$, G$^1$, R$^3$, and R$^4$, are selected from (i) wherein R$^3$ is R$^{1a}$; R$^4$ is R$^{1a}$; R$^{1a}$ is hydrogen; G$^1$ is phenyl or C$_3$-C$_6$ cycloalkyl, each of which is optionally substituted with 1, 2, 3, 4, or 5 R$^v$ groups; R$^{x1}$ is —(C$_1$-C$_6$ alkylenyl)-G$^{x1}$-G$^{x2}$ wherein G$^{x1}$ is optionally substituted C$_4$-C$_6$ heterocycle, and G$^{x2}$ is phenyl, C$_3$-C$_6$ cycloalkyl, C$_5$-C$_6$ heteroaryl, or C$_4$-C$_6$ heterocycle, each of which is optionally substituted; and R$^2$ is hydrogen, —S(O)$_2$R$^{2a}$, or —N(R$^{2b}$)S(O)$_2$R$^{2a}$. In some such embodiments, G$^{x2}$ is optionally substituted phenyl. In some such embodiments, R$^{2b}$ is hydrogen and R$^{2a}$ is C$_1$-C$_3$ alkyl.

In one embodiment, the invention is directed to compounds of formula (I), wherein R$^x$ is hydrogen, R$^y$ is methyl, A$^1$ is CR$^1$, A$^2$ is CR$^2$, A$^3$ is CR$^3$; and A$^4$ is CR$^4$, R$^1$ is hydrogen, R$^{x1}$, G$^1$, R$^3$, and R$^4$, are selected from (i) wherein R$^3$ is R$^{1a}$; R$^4$ is R$^{1a}$; R$^{1a}$ is hydrogen; G$^1$ is phenyl or C$_3$-C$_6$ cycloalkyl, each of which is optionally substituted with 1, 2, 3, 4, or 5 R$^v$ groups; R$^{x1}$ is -G$^{x1}$-G$^{x2}$, C$_2$-C$_6$ alkynyl substituted with one —OR$^{xc}$ group, or C$_2$-C$_6$ alkenyl substituted with one —C(O)NR$^{xa}$R$^{xc}$ group; and R$^2$ is hydrogen, —S(O)$_2$R$^{2a}$, or —N(R$^{2b}$)S(O)$_2$R$^{2a}$. In some such embodiments, R$^{xa}$ and R$^{xc}$ are each independently hydrogen or C$_1$-C$_6$ alkyl.

In one embodiment, the invention is directed to compounds of formula (I), wherein R$^x$ is hydrogen, R$^y$ is methyl, A$^1$ is CR$^1$, A$^2$ is CR$^2$, A$^3$ is CR$^3$; and A$^4$ is CR$^4$, R$^1$ is hydrogen, and R$^{x1}$, G$^1$, R$^3$, and R$^4$, are selected from (ii).

In one embodiment, the invention is directed to compounds of formula (I), wherein R$^x$ is hydrogen, R$^y$ is methyl, A$^1$ is CR$^1$, A$^2$ is CR$^2$, A$^3$ is CR$^3$; and A$^4$ is CR$^4$, R$^1$ is hydrogen, R$^{x1}$, G$^1$, R$^3$, and R$^4$, are selected from (ii) wherein R$^{x1}$ is hydrogen or —C(O)N(R$^{bx1}$)(R$^{cx1}$), R$^3$ is R$^{1a}$; R$^4$ is R$^{1a}$; and G$^1$ is phenyl, C$_3$-C$_6$ cycloalkyl, or C$_4$-C$_6$ heterocycle, wherein each G$^1$ is substituted with one R$^u$ group and is optionally further substituted with 1, 2, or 3 R$^v$ groups.

In one embodiment, the invention is directed to compounds of formula (I), wherein R$^x$ is hydrogen, R$^y$ is methyl, A$^1$ is CR$^1$, A$^2$ is CR$^2$, A$^3$ is CR$^3$; and A$^4$ is CR$^4$, R$^1$ is hydrogen, R$^{x1}$, G$^1$, R$^3$, and R$^4$, are selected from (ii) wherein R$^{x1}$ is hydrogen or —C(O)N(R$^{bx1}$)(R$^{cx1}$), R$^3$ is R$^{1a}$; R$^4$ is R$^{1a}$; R$^{1a}$ is hydrogen; G$^1$ is phenyl, C$_3$-C$_6$ cycloalkyl, or C$_4$-C$_6$ heterocycle, wherein each G$^1$ is substituted with one R$^u$ group and is optionally further substituted with 1, 2, or 3 R$^v$ groups; and R$^2$ is hydrogen, —S(O)$_2$R$^{2a}$, or —N(R$^{2b}$)S(O)$_2$R$^{2a}$.

In one embodiment, the invention is directed to compounds of formula (I), wherein R$^x$ is hydrogen, R$^y$ is methyl, A$^1$ is CR$^1$, A$^2$ is CR$^2$, A$^3$ is CR$^3$; and A$^4$ is CR$^4$, R$^1$ is hydrogen, R$^{x1}$, G$^1$, R$^3$, and R$^4$, are selected from (ii) wherein R$^{x1}$ is hydrogen or —C(O)N(R$^{bx1}$)(R$^{cx1}$); R$^3$ is R$^{1a}$; R$^4$ is R$^{1a}$; R$^{1a}$ is hydrogen; G$^1$ is phenyl or C$_3$-C$_6$ cycloalkyl, wherein each G$^1$ is substituted with one R$^u$ group and is optionally further substituted with 1, 2, or 3 R$^v$ groups; R$^2$ is hydrogen, —S(O)$_2$R$^{2a}$, or —N(R$^{2b}$)S(O)$_2$R$^{2a}$; and R$^u$ is —(C$_1$-C$_6$ alkylenyl)-G$^u$, —N(Z$^2$)Z$^1$, or —N(Z$^2$)S(O)$_2$—Z$^1$. In some such embodiments, R$^{bx1}$ and R$^{cx1}$ are each independently hydrogen or C$_1$-C$_6$ alkyl.

In one embodiment, the invention is directed to compounds of formula (I), wherein R$^x$ is hydrogen, R$^y$ is methyl, A$^1$ is CR$^1$, A$^2$ is CR$^2$, A$^3$ is CR$^3$; and A$^4$ is CR$^4$, R$^1$ is hydrogen, and R$^{x1}$, G$^1$, R$^3$, and R$^4$, are selected from (iii).

In one embodiment, the invention is directed to compounds of formula (I), wherein R$^x$ is hydrogen, R$^y$ is methyl, A$^1$ is CR$^1$, A$^2$ is CR$^2$, A$^3$ is CR$^3$; and A$^4$ is CR$^4$, R$^1$ is hydrogen, R$^{x1}$, G$^1$, R$^3$, and R$^4$, are selected from (iii) wherein R$^{x1}$ is hydrogen or —C(O)NR$^{bx1}$R$^{cx1}$; R$^4$ is R$^{1a}$; and G$^1$ is phenyl, C$_3$-C$_6$ cycloalkyl, or C$_4$-C$_6$ heterocycle, each of which is optionally substituted with 1, 2, 3, 4, or 5 R$^v$ groups.

In one embodiment, the invention is directed to compounds of formula (I), wherein R$^x$ is hydrogen, R$^y$ is methyl, A$^1$ is CR$^1$, A$^2$ is CR$^2$, A$^3$ is CR$^3$; and A$^4$ is CR$^4$, R$^1$ is hydrogen, R$^{x1}$, G$^1$, R$^3$, and R$^4$, are selected from (iii) wherein R$^{x1}$ is hydrogen or —C(O)NR$^{bx1}$R$^{cx1}$; R$^4$ is R$^{1a}$; R$^{1a}$ is hydrogen; and G$^1$ is phenyl or C$_3$-C$_6$ cycloalkyl, each of which is optionally substituted with 1, 2, 3, 4, or 5 R$^v$ groups.

In one embodiment, the invention is directed to compounds of formula (I), wherein R$^x$ is hydrogen, R$^y$ is methyl, A$^1$ is CR$^1$, A$^2$ is CR$^2$, A$^3$ is CR$^3$; and A$^4$ is CR$^4$, R$^1$ is hydrogen, R$^{x1}$, G$^1$, R$^3$, and R$^4$, are selected from (iii) wherein R$^{x1}$ is hydrogen or —C(O)NR$^{bx1}$R$^{cx1}$; R$^4$ is R$^{1a}$; R$^{1a}$ is hydrogen; G$^1$ is phenyl or C$_3$-C$_6$ cycloalkyl, each of which is optionally substituted with 1, 2, 3, 4, or 5 R$^v$ groups; and R$^3$ is —C(O)OH, —C(O)NR$^{3a}$R$^{3b}$, G$^{3a}$, —(C$_1$-C$_6$ alkylenyl)-OR$^{3a}$, —(C$_1$-C$_6$ alkylenyl)-NR$^{3a}$R$^{3b}$, —(C$_1$-C$_6$ alkylenyl)-G$^{3a}$, or —(C$_1$-C$_6$ alkylenyl)-G$^{3a}$-G$^{3b}$.

In one embodiment, the invention is directed to compounds of formula (I), wherein R$^x$ is hydrogen, R$^y$ is methyl, A$^1$ is CR$^1$, A$^2$ is CR$^2$, A$^3$ is CR$^3$; and A$^4$ is CR$^4$, R$^1$ is hydrogen, R$^{x1}$, G$^1$, R$^3$, and R$^4$, are selected from (iii) wherein R$^{x1}$ is hydrogen or —C(O)NR$^{bx1}$R$^{cx1}$; R$^4$ is R$^{1a}$, R$^{1a}$ is hydrogen; G$^1$ is phenyl or C$_3$-C$_6$ cycloalkyl, each of which is optionally substituted with 1, 2, 3, 4, or 5 R$^v$ groups; R$^3$ is —C(O)OH, —C(O)NR$^{3a}$R$^{3b}$, G$^{3a}$, —(C$_1$-C$_6$ alkylenyl)-OR$^{3a}$, —(C$_1$-C$_6$ alkylenyl)-NR$^{3a}$R$^{3b}$, —(C$_1$-C$_6$ alkylenyl)-G$^{3a}$, or —(C$_1$-C$_6$ alkylenyl)-G$^{3a}$-G$^{3b}$; and R$^2$ is hydrogen, —S(O)$_2$R$^{2a}$, or —N(R$^{2b}$)S(O)$_2$R$^{2a}$.

In one embodiment, the invention is directed to compounds of formula (I), wherein R$^x$ is hydrogen, R$^y$ is methyl, A$^1$ is CR$^1$, A$^2$ is CR$^2$, A$^3$ is CR$^3$; and A$^4$ is CR$^4$, R$^1$ is hydrogen, R$^{x1}$, G$^1$, R$^3$, and R$^4$, are selected from (iii) wherein R$^{x1}$ is hydrogen or —C(O)NR$^{bx1}$R$^{cx1}$; R$^4$ is R$^{1a}$, R$^{1a}$ is hydrogen; G$^1$ is phenyl which is optionally substituted with 1, 2, 3, 4, or 5 R$^v$ groups; R$^3$ is —C(O)OH, —C(O)NR$^{3a}$R$^{3b}$, or —(C$_1$-C$_6$ alkylenyl)-G$^{3a}$; and R$^2$ is hydrogen, —S(O)$_2$R$^{2a}$, or —N(R$^{2b}$)S(O)$_2$R$^{2a}$. In some such embodiments, R$^3$ is —(C$_1$-C$_6$ alkylenyl)-G$^{3a}$ wherein G$^{3a}$ is optionally substituted C$_4$-C$_6$ heterocycle. In some such embodiments, R$^3$ is —(C$_1$-C$_6$ alkylenyl)-G$^{3a}$ wherein G$^{3a}$ is piperidinyl or morpholinyl, each of which is optionally substituted. In some such embodiments, R$^3$ is —C(O)NR$^{3a}$R$^{3b}$. In some such embodiments, R$^{bx1}$ and R$^{cx1}$ are each independently hydrogen or C$_1$-C$_6$ alkyl. In some such embodiments, R$^2$ is hydrogen.

In one embodiment, the invention is directed to compounds of formula (I), wherein R$^x$ is hydrogen, R$^y$ is methyl, A$^1$ is CR$^1$, A$^2$ is CR$^2$, A$^3$ is CR$^3$; and A$^4$ is CR$^4$, R$^1$ is hydrogen, and R$^{x1}$, G$^1$, R$^3$, and R$^4$, are selected from (iv).

In one embodiment, the invention is directed to compounds of formula (I), wherein $R^x$ is hydrogen, $R^y$ is methyl, $A^1$ is $CR^1$, $A^2$ is $CR^2$, $A^3$ is $CR^3$; and $A^4$ is $CR^4$, $R^1$ is hydrogen, and $R^{x1}$, $G^1$, $R^3$, and $R^4$, are selected from (iv) wherein $R^{x1}$ is hydrogen; $R^3$ is $R^{1a}$; and $G^1$ is phenyl, $C_3$-$C_6$ cycloalkyl, or $C_4$-$C_6$ heterocycle, each of which is optionally substituted with 1, 2, 3, 4, or 5 $R^v$ groups.

In one embodiment, the invention is directed to compounds of formula (I), wherein $R^x$ is hydrogen, $R^y$ is methyl, $A^1$ is $CR^1$, $A^2$ is $CR^2$, $A^3$ is $CR^3$; and $A^4$ is $CR^4$, $R^1$ is hydrogen, and $R^{x1}$, $G^1$, $R^3$, and $R^4$, are selected from (iv) wherein $R^{x1}$ is hydrogen; $R^3$ is $R^{1a}$; $R^{1a}$ is hydrogen; and $G^1$ is phenyl or $C_3$-$C_6$ cycloalkyl, each of which is optionally substituted with 1, 2, 3, 4, or 5 $R^v$ groups.

In one embodiment, the invention is directed to compounds of formula (I), wherein $R^x$ is hydrogen, $R^y$ is methyl, $A^1$ is $CR^1$, $A^2$ is $CR^2$, $A^3$ is $CR^3$; and $A^4$ is $CR^4$, $R^1$ is hydrogen, and $R^{x1}$, $G^1$, $R^3$, and $R^4$, are selected from (iv) wherein $R^{x1}$ is hydrogen; $R^3$ is $R^{1a}$; $R^{1a}$ is hydrogen; $G^1$ is phenyl or $C_3$-$C_6$ cycloalkyl, each of which is optionally substituted with 1, 2, 3, 4, or 5 $R^v$ groups, and $R^4$ is optionally substituted $C_3$-$C_6$ cycloalkyl.

In one embodiment, the invention is directed to compounds of formula (I), wherein $R^x$ is hydrogen, $R^y$ is methyl, $A^1$ is $CR^1$, $A^2$ is $CR^2$, $A^3$ is $CR^3$; and $A^4$ is $CR^4$, $R^1$ is hydrogen, and $R^{x1}$, $G^1$, $R^3$, and $R^4$, are selected from (iv) wherein $R^{x1}$ is hydrogen; $R^3$ is $R^{1a}$; $R^{1a}$ is hydrogen; $G^1$ is phenyl or $C_3$-$C_6$ cycloalkyl, each of which is optionally substituted with 1, 2, 3, 4, or 5 $R^v$ groups, $R^4$ is optionally substituted cyclopropyl, and $R^2$ is hydrogen, —$S(O)_2R^{2a}$, or —$N(R^{2b})S(O)_2R^{2a}$.

Compounds of formula (I) may contain one or more asymmetrically substituted atoms. Compounds of formula (I) may also exist as individual stereoisomers (including enantiomers and diastereomers) and mixtures thereof. Individual stereoisomers of compounds of formula (I) may be prepared synthetically from commercially available starting materials that contain asymmetric or chiral centers or by preparation of racemic mixtures followed by resolution of the individual stereoisomer using methods that are known to those of ordinary skill in the art. Examples of resolution are, for example, (i) attachment of a mixture of enantiomers to a chiral auxiliary, separation of the resulting mixture of diastereomers by recrystallization or chromatography, followed by liberation of the optically pure product; or (ii) separation of the mixture of enantiomers or diastereomers on chiral chromatographic columns.

Compounds of formula (I) may also include the various geometric isomers and mixtures thereof resulting from the disposition of substituents around a carbon-carbon double bond, a carbon-nitrogen double bond, a cycloalkyl group, or a heterocycle group. Substituents around a carbon-carbon double bond or a carbon-nitrogen double bond are designated as being of Z or E configuration and substituents around a cycloalkyl or heterocycle are designated as being of cis or trans configuration.

Within the present invention it is to be understood that compounds disclosed herein may exhibit the phenomenon of tautomerism and all tautomeric isomers are included in the scope of the invention.

Thus, the formula drawings within this specification can represent only one of the possible tautomeric, geometric, or stereoisomeric forms. It is to be understood that the invention encompasses any tautomeric, geometric, or stereoisomeric form, and mixtures thereof, and is not to be limited merely to any one tautomeric, geometric, or stereoisomeric form utilized within the formula drawings.

Exemplary compounds of formula (I) include, but are not limited to:

4-[2-(cyclopropylmethoxy)-4-(3-methyl-1H-pyrazol-5-yl)phenyl]-6-methyl-1,6-dihydro-7H-pyrrolo[2,3-c]pyridin-7-one;

N-[4-(2,4-difluorophenoxy)-2-[(dimethylamino)methyl]-5-(6-methyl-7-oxo-6,7-dihydro-1H-pyrrolo[2,3-c]pyridin-4-yl)phenyl]ethanesulfonamide;

N-[4-(2,4-difluorophenoxy)-5-(6-methyl-7-oxo-6,7-dihydro-1H-pyrrolo[2,3-c]pyridin-4-yl)-2-(piperidin-1-ylmethyl)phenyl]ethanesulfonamide;

N-[4-(2,4-difluorophenoxy)-5-(6-methyl-7-oxo-6,7-dihydro-1H-pyrrolo[2,3-c]pyridin-4-yl)-2-(morpholin-4-ylmethyl)phenyl]ethanesulfonamide;

N-{4-(2,4-difluorophenoxy)-5-(6-methyl-7-oxo-6,7-dihydro-1H-pyrrolo[2,3-c]pyridin-4-yl)-2-[(4-methylpiperazin-1-yl)methyl]phenyl}ethanesulfonamide;

N-[4-(2,4-difluorophenoxy)-2-(hydroxymethyl)-5-(6-methyl-7-oxo-6,7-dihydro-1H-pyrrolo[2,3-c]pyridin-4-yl)phenyl]ethanesulfonamide;

N-{2-[(cyclopentylamino)methyl]-4-(2,4-difluorophenoxy)-5-(6-methyl-7-oxo-6,7-dihydro-1H-pyrrolo[2,3-c]pyridin-4-yl)phenyl}ethanesulfonamide;

5-(2,4-difluorophenoxy)-2-[(ethylsulfonyl)amino]-4-(6-methyl-7-oxo-6,7-dihydro-1H-pyrrolo[2,3-c]pyridin-4-yl)benzamide;

N-cyclopentyl-5-(2,4-difluorophenoxy)-2-[(ethylsulfonyl)amino]-4-(6-methyl-7-oxo-6,7-dihydro-1H-pyrrolo[2,3-c]pyridin-4-yl)benzamide;

5-(2,4-difluorophenoxy)-2-[(ethylsulfonyl)amino]-N,N-dimethyl-4-(6-methyl-7-oxo-6,7-dihydro-1H-pyrrolo[2,3-c]pyridin-4-yl)benzamide;

5-(2,4-difluorophenoxy)-2-[(ethylsulfonyl)amino]-4-(6-methyl-7-oxo-6,7-dihydro-1H-pyrrolo[2,3-c]pyridin-4-yl)benzoic acid;

5-(2,4-difluorophenoxy)-2-[(ethylsulfonyl)amino]-4-(6-methyl-7-oxo-6,7-dihydro-1H-pyrrolo[2,3-c]pyridin-4-yl)-N-(tetrahydro-2H-pyran-4-yl)benzamide;

N-[4-(2,4-difluorophenoxy)-2-{[(2-hydroxyethyl)amino]methyl}-5-(6-methyl-7-oxo-6,7-dihydro-1H-pyrrolo[2,3-c]pyridin-4-yl)phenyl]ethanesulfonamide;

N-{4-(2,4-difluorophenoxy)-5-(6-methyl-7-oxo-6,7-dihydro-1H-pyrrolo[2,3-c]pyridin-4-yl)-2-[(2-phenylpyrrolidin-1-yl)methyl]phenyl}ethanesulfonamide;

N-[3-cyclopropyl-4-(2,4-difluorophenoxy)-5-(6-methyl-7-oxo-6,7-dihydro-1H-pyrrolo[2,3-c]pyridin-4-yl)phenyl]ethanesulfonamide;

4-{2-[(2,2-difluorocyclopropyl)methoxy]-5-(ethylsulfonyl)phenyl}-6-methyl-2-{[4-(pyridin-4-yl)piperazin-1-yl]methyl}-1,6-dihydro-7H-pyrrolo[2,3-c]pyridin-7-one;

4-{2-[(2,2-difluorocyclopropyl)methoxy]-5-(ethylsulfonyl)phenyl}-6-methyl-2-{[4-(1,3-thiazol-2-yl)piperazin-1-yl]methyl}-1,6-dihydro-7H-pyrrolo[2,3-c]pyridin-7-one;

4-{2-[(2,2-difluorocyclopropyl)methoxy]-5-(ethylsulfonyl)phenyl}-6-methyl-2-{[4-(pyrazin-2-yl)piperazin-1-yl]methyl}-1,6-dihydro-7H-pyrrolo[2,3-c]pyridin-7-one;

4-{2-[(2,2-difluorocyclopropyl)methoxy]-5-(ethylsulfonyl)phenyl}-6-methyl-2-{[4-(pyrimidin-2-yl)piperazin-1-yl]methyl}-1, 6-dihydro-7H-pyrrolo[2,3-c]pyridin-7-one;

4-{2-[(2,2-difluorocyclopropyl)methoxy]-5-(ethylsulfonyl)phenyl}-6-methyl-2-{[4-(pyridin-3-yl)piperazin-1-yl]methyl}-1,6-dihydro-7H-pyrrolo[2,3-c]pyridin-7-one;

N-cyclopropyl-3-[2-(6-methyl-7-oxo-6,7-dihydro-1H-pyrrolo[2,3-c]pyridin-4-yl)-4-(methylsulfonyl)phenoxy]benzamide;

6-methyl-4-[2-{3-[(4-methylpiperazin-1-yl)carbonyl]phenoxy}-5-(methylsulfonyl)phenyl]-1,6-dihydro-7H-pyrrolo[2,3-c]pyridin-7-one;

4-{2-[3-({4-[2-(1H-imidazol-1-yl)ethyl]piperazin-1-yl}carbonyl)phenoxy]-5-(methylsulfonyl)phenyl}-6-methyl-1,6-dihydro-7H-pyrrolo[2,3-c]pyridin-7-one;

6-methyl-4-[5-(methylsulfonyl)-2-(3-{[4-(pyrrolidin-1-yl)piperidin-1-yl]carbonyl}phenoxy)phenyl]-1,6-dihydro-7H-pyrrolo[2,3-c]pyridin-7-one;

N-cyclohexyl-3-[2-(6-methyl-7-oxo-6,7-dihydro-1H-pyrrolo[2,3-c]pyridin-4-yl)-4-(methylsulfonyl)phenoxy]benzamide;

4-[2-(3-{[4-(2-hydroxyethyl)piperazin-1-yl]carbonyl}phenoxy)-5-(methylsulfonyl)phenyl]-6-methyl-1,6-dihydro-7H-pyrrolo[2,3-c]pyridin-7-one;

3-[2-(6-methyl-7-oxo-6,7-dihydro-1H-pyrrolo[2,3-c]pyridin-4-yl)-4-(methylsulfonyl)phenoxy]-N-[3-(2-oxopyrrolidin-1-yl)propyl]benzamide;

4-[2-{3-[(4-cyclopentylpiperazin-1-yl)carbonyl]phenoxy}-5-(methylsulfonyl)phenyl]-6-methyl-1, 6-dihydro-7H-pyrrolo[2,3-c]pyridin-7-one;

4-{2-[3-({4-[2-(dimethylamino)ethyl]piperazin-1-yl}carbonyl)phenoxy]-5-(methylsulfonyl)phenyl}-6-methyl-1,6-dihydro-7H-pyrrolo[2,3-c]pyridin-7-one;

4-[2-{3-[(4-acetylpiperazin-1-yl)carbonyl]phenoxy}-5-(methylsulfonyl)phenyl]-6-methyl-1,6-dihydro-7H-pyrrolo[2,3-c]pyridin-7-one;

6-methyl-4-[5-(methylsulfonyl)-2-(3-{[4-(trifluoromethyl)piperidin-1-yl]carbonyl}phenoxy)phenyl]-1,6-dihydro-7H-pyrrolo[2,3-c]pyridin-7-one;

N-(cyanomethyl)-N-methyl-3-[2-(6-methyl-7-oxo-6,7-dihydro-1H-pyrrolo[2,3-c]pyridin-4-yl)-4-(methylsulfonyl)phenoxy]benzamide;

N-[2-(dimethyl amino)ethyl]-3-[2-(6-methyl-7-oxo-6,7-dihydro-1H-pyrrolo[2,3-c]pyridin-4-yl)-4-(methylsulfonyl)phenoxy]benzamide;

3-[2-(6-methyl-7-oxo-6,7-dihydro-1H-pyrrolo[2,3-c]pyridin-4-yl)-4-(methylsulfonyl)phenoxy]-N-[(2R)-tetrahydrofuran-2-ylmethyl]benzamide;

3-[2-(6-methyl-7-oxo-6,7-dihydro-1H-pyrrolo[2,3-c]pyridin-4-yl)-4-(methylsulfonyl)phenoxy]-N-[2-(pyrrolidin-1-yl)ethyl]benzamide;

N-(3,5-difluorobenzyl)-3-[2-(6-methyl-7-oxo-6,7-dihydro-1H-pyrrolo[2,3-c]pyridin-4-yl)-4-(methylsulfonyl)phenoxy]benzamide;

N-(2,4-difluorobenzyl)-3-[2-(6-methyl-7-oxo-6,7-dihydro-1H-pyrrolo[2,3-c]pyridin-4-yl)-4-(methylsulfonyl)phenoxy]benzamide;

N-{3-[2-(6-methyl-7-oxo-6,7-dihydro-1H-pyrrolo[2,3-c]pyridin-4-yl)-4-(methylsulfonyl)phenoxy]phenyl}-1-phenylmethanesulfonamide;

4-methoxy-N-{3-[2-(6-methyl-7-oxo-6,7-dihydro-1H-pyrrolo[2,3-c]pyridin-4-yl)-4-(methylsulfonyl)phenoxy]phenyl}benzenesulfonamide;

3-fluoro-N-{3-[2-(6-methyl-7-oxo-6,7-dihydro-1H-pyrrolo[2,3-c]pyridin-4-yl)-4-(methylsulfonyl)phenoxy]phenyl}benzenesulfonamide;

4-fluoro-N-{3-[2-(6-methyl-7-oxo-6,7-dihydro-1H-pyrrolo[2,3-c]pyridin-4-yl)-4-(methylsulfonyl)phenoxy]phenyl}benzenesulfonamide;

3-methoxy-N-{3-[2-(6-methyl-7-oxo-6,7-dihydro-1H-pyrrolo[2,3-c]pyridin-4-yl)-4-(methylsulfonyl)phenoxy]phenyl}benzenesulfonamide;

N-{3-[2-(6-methyl-7-oxo-6,7-dihydro-1H-pyrrolo[2,3-c]pyridin-4-yl)-4-(methylsulfonyl)phenoxy]phenyl}-4-nitrobenzenesulfonamide;

4-acetyl-N-{3-[2-(6-methyl-7-oxo-6,7-dihydro-1H-pyrrolo[2,3-c]pyridin-4-yl)-4-(methylsulfonyl)phenoxy]phenyl}benzenesulfonamide;

5-(dimethylamino)-N-{3-[2-(6-methyl-7-oxo-6,7-dihydro-1H-pyrrolo[2,3-c]pyridin-4-yl)-4-(methylsulfonyl)phenoxy]phenyl}naphthalene-1-sulfonamide;

N-{3-[2-(6-methyl-7-oxo-6,7-dihydro-1H-pyrrolo[2,3-c]pyridin-4-yl)-4-(methylsulfonyl)phenoxy]phenyl}-4-(propan-2-yl)benzenesulfonamide;

2,4-difluoro-N-{3-[2-(6-methyl-7-oxo-6,7-dihydro-1H-pyrrolo[2,3-c]pyridin-4-yl)-4-(methylsulfonyl)phenoxy]phenyl}benzenesulfonamide;

3-(difluoromethoxy)-N-{3-[2-(6-methyl-7-oxo-6,7-dihydro-1H-pyrrolo[2,3-c]pyridin-4-yl)-4-(methylsulfonyl)phenoxy]phenyl}benzenesulfonamide;

N-{3-[2-(6-methyl-7-oxo-6,7-dihydro-1H-pyrrolo[2,3-c]pyridin-4-yl)-4-(methylsulfonyl)phenoxy]phenyl}cyclopropanesulfonamide;

3-methyl-N-{3-[2-(6-methyl-7-oxo-6,7-dihydro-1H-pyrrolo[2,3-c]pyridin-4-yl)-4-(methylsulfonyl)phenoxy]phenyl}benzenesulfonamide;

N-{3-[2-(6-methyl-7-oxo-6,7-dihydro-1H-pyrrolo[2,3-c]pyridin-4-yl)-4-(methylsulfonyl)phenoxy]phenyl}-3-nitrobenzenesulfonamide;

4-fluoro-2-methyl-N-{3-[2-(6-methyl-7-oxo-6,7-dihydro-1H-pyrrolo[2,3-c]pyridin-4-yl)-4-(methylsulfonyl)phenoxy]phenyl}benzenesulfonamide;

3,4-dimethoxy-N-{3-[2-(6-methyl-7-oxo-6,7-dihydro-1H-pyrrolo[2,3-c]pyridin-4-yl)-4-(methylsulfonyl)phenoxy]phenyl}benzenesulfonamide;

N-{3-[2-(6-methyl-7-oxo-6,7-dihydro-1H-pyrrolo[2,3-c]pyridin-4-yl)-4-(methylsulfonyl)phenoxy]phenyl}-4-(methylsulfonyl)benzenesulfonamide;

2-cyano-N-{3-[2-(6-methyl-7-oxo-6,7-dihydro-1H-pyrrolo[2,3-c]pyridin-4-yl)-4-(methylsulfonyl)phenoxy]phenyl}benzenesulfonamide;

4-cyano-N-{3-[2-(6-methyl-7-oxo-6,7-dihydro-1H-pyrrolo[2,3-c]pyridin-4-yl)-4-(methylsulfonyl)phenoxy]phenyl}benzenesulfonamide;

3-cyano-N-{3-[2-(6-methyl-7-oxo-6,7-dihydro-1H-pyrrolo[2,3-c]pyridin-4-yl)-4-(methylsulfonyl)phenoxy]phenyl}benzenesulfonamide;

2-chloro-4-fluoro-N-{3-[2-(6-methyl-7-oxo-6,7-dihydro-1H-pyrrolo[2,3-c]pyridin-4-yl)-4-(methylsulfonyl)phenoxy]phenyl}benzenesulfonamide;

1-methyl-N-{3-[2-(6-methyl-7-oxo-6,7-dihydro-1H-pyrrolo[2,3-c]pyridin-4-yl)-4-(methylsulfonyl)phenoxy]phenyl}-1H-imidazole-4-sulfonamide;

3-[({3-[2-(6-methyl-7-oxo-6,7-dihydro-1H-pyrrolo[2,3-c]pyridin-4-yl)-4-(methylsulfonyl)phenoxy]phenyl}amino)methyl]benzonitrile;

4-[({3-[2-(6-methyl-7-oxo-6,7-dihydro-1H-pyrrolo[2,3-c]pyridin-4-yl)-4-(methylsulfonyl)phenoxy]phenyl}amino)methyl]benzonitrile;

4-[2-{3-[(4-fluorobenzyl)amino]phenoxy}-5-(methylsulfonyl)phenyl]-6-methyl-1,6-dihydro-7H-pyrrolo[2,3-c]pyridin-7-one;

4-{2-[(2,2-difluorocyclopropyl)methoxy]-5-(ethylsulfonyl)phenyl}-2-[3-(dimethylamino)prop-1-yn-1-yl]-6-methyl-1,6-dihydro-7H-pyrrolo[2,3-c]pyridin-7-one;

4-[2-{3-[(2-methoxyethyl)amino]phenoxy}-5-(methylsulfonyl)phenyl]-6-methyl-1,6-dihydro-7H-pyrrolo[2,3-c]pyridin-7-one;

6-methyl-4-[5-(methylsulfonyl)-2-{3-[(tetrahydrofuran-2-ylmethyl)amino]phenoxy}phenyl]-1,6-dihydro-7H-pyrrolo[2,3-c]pyridin-7-one;

4-[2-{3-[(3-methoxybenzyl)amino]phenoxy}-5-(methylsulfonyl)phenyl]-6-methyl-1,6-dihydro-7H-pyrrolo[2,3-c]pyridin-7-one;

4-[2-{3-[(2-fluorobenzyl)amino]phenoxy}-5-(methylsulfonyl)phenyl]-6-methyl-1,6-dihydro-7H-pyrrolo[2,3-c]pyridin-7-one;

4-[2-{3-[(3-fluorobenzyl)amino]phenoxy}-5-(methylsulfonyl)phenyl]-6-methyl-1,6-dihydro-7H-pyrrolo[2,3-c]pyridin-7-one;

6-methyl-4-[5-(methylsulfonyl)-2-(3-{[3-(trifluoromethoxy)benzyl]amino}phenoxy)phenyl]-1,6-dihydro-7H-pyrrolo[2,3-c]pyridin-7-one;

4-[2-{3-[(2,4-dimethylbenzyl)amino]phenoxy}-5-(methylsulfonyl)phenyl]-6-methyl-1,6-dihydro-7H-pyrrolo[2,3-c]pyridin-7-one;

2-[({3-[2-(6-methyl-7-oxo-6,7-dihydro-1H-pyrrolo[2,3-c]pyridin-4-yl)-4-(methylsulfonyl)phenoxy]phenyl}amino)methyl]benzonitrile;

4-[2-{3-[(2-chloro-4-fluorobenzyl)amino]phenoxy}-5-(methylsulfonyl)phenyl]-6-methyl-1,6-dihydro-7H-pyrrolo[2,3-c]pyridin-7-one;

4-[2-{3-[(3,5-difluorobenzyl)amino]phenoxy}-5-(methylsulfonyl)phenyl]-6-methyl-1,6-dihydro-7H-pyrrolo[2,3-c]pyridin-7-one;

4-{2-[3-({4-[3-(dimethylamino)propoxy]benzyl}amino)phenoxy]-5-(methylsulfonyl)phenyl}-6-methyl-1,6-dihydro-7H-pyrrolo[2,3-c]pyridin-7-one;

4-[2-(3-{[3-(dimethylamino)benzyl]amino}phenoxy)-5-(methylsulfonyl)phenyl]-6-methyl-1,6-dihydro-7H-pyrrolo[2,3-c]pyridin-7-one;

4-[2-{3-[(2,3-dihydro-1,4-benzodioxin-6-ylmethyl)amino]phenoxy}-5-(methylsulfonyl)phenyl]-6-methyl-1,6-dihydro-7H-pyrrolo[2,3-c]pyridin-7-one;

6-methyl-4-[5-(methylsulfonyl)-2-{3-[(tetrahydrofuran-3-ylmethyl)amino]phenoxy}phenyl]-1,6-dihydro-7H-pyrrolo[2,3-c]pyridin-7-one;

N-{4-[({3-[2-(6-methyl-7-oxo-6,7-dihydro-1H-pyrrolo[2,3-c]pyridin-4-yl)-4-(methylsulfonyl)phenoxy]phenyl}amino)methyl]phenyl}acetamide;

4-[2-{3-[(4-methoxybenzyl)amino]phenoxy}-5-(methylsulfonyl)phenyl]-6-methyl-1,6-dihydro-7H-pyrrolo[2,3-c]pyridin-7-one;

4-[2-{3-[(cyclopropylmethyl)amino]phenoxy}-5-(methylsulfonyl)phenyl]-6-methyl-1,6-dihydro-7H-pyrrolo[2,3-c]pyridin-7-one;

4-[2-{3-[(2-cyclopentylethyl)amino]phenoxy}-5-(methylsulfonyl)phenyl]-6-methyl-1,6-dihydro-7H-pyrrolo[2,3-c]pyridin-7-one;

4-[2-{4-chloro-2-[3-(morpholin-4-yl)prop-1-yn-1-yl]phenoxy}-5-(ethylsulfonyl)phenyl]-6-methyl-1,6-dihydro-7H-pyrrolo[2,3-c]pyridin-7-one;

4-[2-{4-chloro-2-[3-(morpholin-4-yl)propyl]phenoxy}-5-(ethylsulfonyl)phenyl]-6-methyl-1,6-dihydro-7H-pyrrolo[2,3-c]pyridin-7-one;

6-methyl-4-[5-(methylsulfonyl)-2-{[1-(phenyl sulfonyl)piperidin-4-yl]amino}phenyl]-1,6-dihydro-7H-pyrrolo[2,3-c]pyridin-7-one;

4-[2-({1-[(dimethylamino)acetyl]piperidin-4-yl}amino)-5-(methylsulfonyl)phenyl]-6-methyl-1,6-dihydro-7H-pyrrolo[2,3-c]pyridin-7-one;

6-methyl-4-[2-({1-[3-(methyl sulfanyl)propyl]piperidin-4-yl}amino)-5-(methylsulfonyl)phenyl]-1,6-dihydro-7H-pyrrolo[2,3-c]pyridin-7-one;

N-{4-[(4-{[2-(6-methyl-7-oxo-6,7-dihydro-1H-pyrrolo[2,3-c]pyridin-4-yl)-4-(methylsulfonyl)phenyl]amino}piperidin-1-yl)methyl]phenyl}acetamide;

6-methyl-4-[5-(methylsulfonyl)-2-{[1-(3,4,5-trimethoxybenzyl)piperidin-4-yl]amino}phenyl]-1,6-dihydro-7H-pyrrolo[2,3-c]pyridin-7-one;

6-methyl-4-[5-(methylsulfonyl)-2-{[1-(thiophen-2-ylmethyl)piperidin-4-yl]amino}phenyl]-1,6-dihydro-7H-pyrrolo[2,3-c]pyridin-7-one;

4-{2-[(1-{4-[3-(dimethylamino)propoxy]benzyl}piperidin-4-yl)amino]-5-(methylsulfonyl)phenyl}-6-methyl-1,6-dihydro-7H-pyrrolo[2,3-c]pyridin-7-one;

6-methyl-4-[2-({1-[(methyl sulfanyl)acetyl]piperidin-4-yl}amino)-5-(methylsulfonyl)phenyl]-1,6-dihydro-7H-pyrrolo[2,3-c]pyridin-7-one;

6-methyl-4-[5-(methylsulfonyl)-2-({1-[3-(2,3,4-trimethoxyphenyl)propanoyl]piperidin-4-yl}amino)phenyl]-1,6-dihydro-7H-pyrrolo[2,3-c]pyridin-7-one;

1-[(4-{[2-(6-methyl-7-oxo-6,7-dihydro-1H-pyrrolo[2,3-c]pyridin-4-yl)-4-(methylsulfonyl)phenyl]amino}piperidin-1-yl)carbonyl]cyclopropanecarboxamide;

4-[2-({1-[(4-methoxycyclohexyl)carbonyl]piperidin-4-yl}amino)-5-(methylsulfonyl)phenyl]-6-methyl-1,6-dihydro-7H-pyrrolo[2,3-c]pyridin-7-one;

4-[2-{[1-(methoxyacetyl)piperidin-4-yl]amino}-5-(methylsulfonyl)phenyl]-6-methyl-1,6-dihydro-7H-pyrrolo[2,3-c]pyridin-7-one;

6-methyl-4-[2-({1-[(4-methylpiperazin-1-yl)acetyl]piperidin-4-yl}amino)-5-(methylsulfonyl)phenyl]-1,6-dihydro-7H-pyrrol o[2,3-c]pyridin-7-one;

6-methyl-4-[5-(methylsulfonyl)-2-{[1-(pyrrolidin-1-ylacetyl)piperidin-4-yl]amino}phenyl]-1,6-dihydro-7H-pyrrolo[2,3-c]pyridin-7-one;

4-[2-({1-[(2-methoxyethoxy)acetyl]piperidin-4-yl}amino)-5-(methylsulfonyl)phenyl]-6-methyl-1,6-dihydro-7H-pyrrol o[2,3-c]pyridin-7-one;

6-methyl-4-[5-(methylsulfonyl)-2-({1-[3-(morpholin-4-yl)propanoyl]piperidin-4-yl}amino)phenyl]-1,6-dihydro-7H-pyrrolo[2,3-c]pyridin-7-one; 6-methyl-4-[2-({1-[(4-methylphenyl)acetyl]piperidin-4-yl}amino)-5-(methylsulfonyl)phenyl]-1,6-dihydro-7H-pyrrol o[2,3-c]pyridin-7-one;

4-[2-{[1-(benzyl sulfonyl)piperidin-4-yl]amino}-5-(methylsulfonyl)phenyl]-6-methyl-1,6-dihydro-7H-pyrrol o[2,3-c]pyridin-7-one;

6-methyl-4-{5-(methylsulfonyl)-2-[(1-{[(E)-2-phenylethenyl]sulfonyl}piperidin-4-yl)amino]phenyl}-1,6-dihydro-7H-pyrrolo[2,3-c]pyridin-7-one;

N-{4-[(4-{[2-(6-methyl-7-oxo-6,7-dihydro-1H-pyrrolo[2,3-c]pyridin-4-yl)-4-(methylsulfonyl)phenyl]amino}piperidin-1-yl)sulfonyl]phenyl}acetamide;

4-[2-({1-[(4-methoxyphenyl)sulfonyl]piperidin-4-yl}amino)-5-(methylsulfonyl)phenyl]-6-methyl-1,6-dihydro-7H-pyrrol o[2,3-c]pyridin-7-one;

3-[(4-{[2-(6-methyl-7-oxo-6,7-dihydro-1H-pyrrolo[2,3-c]pyridin-4-yl)-4-(methylsulfonyl)phenyl]amino}piperidin-1-yl)sulfonyl]benzonitrile;

6-methyl-4-[5-(methylsulfonyl)-2-{[1-(thiophen-2-yl sulfonyl)piperidin-4-yl]amino}phenyl]-1,6-dihydro-7H-pyrrolo[2,3-c]pyridin-7-one;

6-methyl-4-[5-(methylsulfonyl)-2-({trans-4-[(thiophen-2-ylmethyl)amino]cyclohexyl}amino)phenyl]-1,6-dihydro-7H-pyrrolo[2,3-c]pyridin-7-one;

N-(4-{[((trans-4-{[2-(6-methyl-7-oxo-6,7-dihydro-1H-pyrrolo[2,3-c]pyridin-4-yl)-4-(methylsulfonyl)phenyl]amino}cyclohexyl)amino]methyl}phenyl)acetamide;

4-[2-({trans-4-[(2,4-difluorobenzyl)amino]cyclohexyl}amino)-5-(methylsulfonyl)phenyl]-6-methyl-1,6-dihydro-7H-pyrrolo[2,3-c]pyridin-7-one;

6-methyl-4-[5-(methylsulfonyl)-2-({trans-4-[(naphthalen-2-ylmethyl)amino]cyclohexyl}amino)phenyl]-1,6-dihydro-7H-pyrrolo[2,3-c]pyridin-7-one;

4-[2-({trans-4-[(2-methoxyethyl)amino]cyclohexyl}amino)-5-(methylsulfonyl)phenyl]-6-methyl-1,6-dihydro-7H-pyrrolo[2,3-c]pyridin-7-one;

6-methyl-4-{2-[(trans-4-{[3-(methyl sulfanyl)propyl]amino}cyclohexyl)amino]-5-(methylsulfonyl)phenyl}-1,6-dihydro-7H-pyrrolo[2,3-c]pyridin-7-one;

4-[2-({trans-4-[(4-chlorobenzyl)amino]cyclohexyl}amino)-5-(methylsulfonyl)phenyl]-6-methyl-1,6-dihydro-7H-pyrrolo[2,3-c]pyridin-7-one, 4-[2-(2,4-difluorophenoxy)-5-(methylsulfonyl)phenyl]-6-methyl-2-{[4-(1,3-thiazol-2-yl)piperazin-1-yl]methyl}-1,6-dihydro-7H-pyrrolo[2,3-c]pyridin-7-one;

2-[(4-cyclopropylpiperazin-1-yl)methyl]-4-[2-(2,4-difluorophenoxy)-5-(methylsulfonyl)phenyl]-6-methyl-1,6-dihydro-7H-pyrrolo[2,3-c]pyridin-7-one;

4-[2-(2,4-difluorophenoxy)-5-(methylsulfonyl)phenyl]-6-methyl-2-{[4-(tetrahydro-2H-pyran-4-yl)piperazin-1-yl]methyl}-1,6-dihydro-7H-pyrrolo[2,3-c]pyridin-7-one;

4-[2-(2,4-difluorophenoxy)-5-(ethylsulfonyl)phenyl]-6-methyl-2-(1-phenyl-1H-pyrazol-5-yl)-1,6-dihydro-7H-pyrrolo[2,3-c]pyridin-7-one;

4-[2-(2,4-difluorophenoxy)-5-(ethylsulfonyl)phenyl]-6-methyl-2-[2-(morpholin-4-yl)pyridin-3-yl]-1,6-dihydro-7H-pyrrolo[2,3-c]pyridin-7-one;

4-[2-{2-[(cyclopropylmethyl)amino]-6-methylphenoxy}-5-(ethylsulfonyl)phenyl]-N-ethyl-6-methyl-7-oxo-6,7-dihydro-1H-pyrrolo[2,3-c]pyridine-2-carboxamide;

4-[2-(2-chloro-6-methylphenoxy)-5-(ethylsulfonyl)phenyl]-N-(cyanomethyl)-6-methyl-7-oxo-6,7-dihydro-1H-pyrrolo[2,3-c]pyridine-2-carboxamide;

4-[2-(2-chloro-6-methylphenoxy)-5-(ethylsulfonyl)phenyl]-6-methyl-N-[1-(methyl amino)-1-oxopropan-2-yl]-7-oxo-6,7-dihydro-1H-pyrrolo[2,3-c]pyridine-2-carboxamide;

4-[2-(2-chloro-6-methylphenoxy)-5-(ethylsulfonyl)phenyl]-6-methyl-7-oxo-N-[2-oxo-2-(piperidin-1-yl)ethyl]-6,7-dihydro-1H-pyrrolo[2,3-c]pyridine-2-carboxamide;

4-[2-(2-chloro-6-methylphenoxy)-5-(ethylsulfonyl)phenyl]-N-(2-cyanoethyl)-6-methyl-7-oxo-6,7-dihydro-1H-pyrrolo[2,3-c]pyridine-2-carboxamide;

4-[2-(2-chloro-6-methylphenoxy)-5-(ethylsulfonyl)phenyl]-6-methyl-N-[2-(methyl amino)-2-oxoethyl]-7-oxo-6,7-dihydro-1H-pyrrolo[2,3-c]pyridine-2-carboxamide;

4-[2-(2,4-difluorophenoxy)-5-(methylsulfonyl)phenyl]-6-methyl-2-{[4-(1-methylpiperidin-4-yl)piperazin-1-yl]methyl}-1,6-dihydro-7H-pyrrolo[2,3-c]pyridin-7-one;

4-[2-(2,4-difluorophenoxy)-5-(methylsulfonyl)phenyl]-6-methyl-2-{[4-(pyridin-2-yl)-1,4-diazepan-1-yl]methyl}-1,6-dihydro-7H-pyrrolo[2,3-c]pyridin-7-one;

4-[2-(2,4-difluorophenoxy)-5-(methylsulfonyl)phenyl]-2-{[3-(furan-2-yl)morpholin-4-yl]methyl}-6-methyl-1,6-dihydro-7H-pyrrolo[2,3-c]pyridin-7-one;

4-[2-(2,4-difluorophenoxy)-5-(methylsulfonyl)phenyl]-2-{[4-(3,5-dimethyl-4H-1,2,4-triazol-4-yl)piperidin-1-yl]methyl}-6-methyl-1,6-dihydro-7H-pyrrolo[2,3-c]pyridin-7-one;

4-[2-(2,4-difluorophenoxy)-5-(methylsulfonyl)phenyl]-2-{[3-(3,5-dimethyl-1H-pyrazol-1-yl)azetidin-1-yl]methyl}-6-methyl-1,6-dihydro-7H-pyrrolo[2,3-c]pyridin-7-one;

4-[2-(2,4-difluorophenoxy)-5-(methylsulfonyl)phenyl]-6-methyl-2-{[4-(morpholin-4-yl)piperidin-1-yl]methyl}-1,6-dihydro-7H-pyrrolo[2,3-c]pyridin-7-one;

4-[2-(2,4-difluorophenoxy)-5-(methylsulfonyl)phenyl]-6-methyl-2-{[2-(3-methyl-1,2,4-oxadiazol-5-yl)pyrrolidin-1-yl]methyl}-1,6-dihydro-7H-pyrrolo[2,3-c]pyridin-7-one;

4-[2-(2,4-difluorophenoxy)-5-(methylsulfonyl)phenyl]-6-methyl-2-{[4-(pyridin-2-yl)piperazin-1-yl]methyl}-1,6-dihydro-7H-pyrrolo[2,3-c]pyridin-7-one;

N-ethyl-4-[5-(ethylsulfonyl)-2-{2-methyl-6-[(tetrahydrofuran-3-ylmethyl)amino]phenoxy}phenyl]-6-methyl-7-oxo-6,7-dihydro-1H-pyrrolo[2,3-c]pyridine-2-carboxamide;

(2E)-3-{4-[2-(2,6-dimethylphenoxy)-5-(ethylsulfonyl)phenyl]-6-methyl-7-oxo-6,7-dihydro-1H-pyrrolo[2,3-c]pyridin-2-yl}-N-ethylprop-2-enamide;

2-(3-cyclopropyl-1,2,4-oxadiazol-5-yl)-4-[2-(2,6-dimethylphenoxy)-5-(methylsulfonyl)phenyl]-6-methyl-1,6-dihydro-7H-pyrrolo[2,3-c]pyridin-7-one;

2-(3-cyclohexyl-1,2,4-oxadiazol-5-yl)-4-[2-(2,6-dimethylphenoxy)-5-(methylsulfonyl)phenyl]-6-methyl-1,6-dihydro-7H-pyrrolo[2,3-c]pyridin-7-one;

4-[2-(2,6-dimethylphenoxy)-5-(methylsulfonyl)phenyl]-6-methyl-2-(3 oxadiazol-5-yl)-1,6-dihydro-7H-pyrrolo[2,3-c]pyridin-7-one;

4-[2-(2,6-dimethylphenoxy)-5-(methylsulfonyl)phenyl]-6-methyl-2-[3-(pyridin-3-yl)-1,2,4-oxadiazol-5-yl]-1,6-dihydro-7H-pyrrolo[2,3-c]pyridin-7-one;

4-[2-(2,6-dimethylphenoxy)-5-(methylsulfonyl)phenyl]-6-methyl-2-[3-(pyridin-2-yl)-1,2,4-oxadiazol-5-yl]-1,6-dihydro-7H-pyrrolo[2,3-c]pyridin-7-one;

4-[2-(2,6-dimethylphenoxy)-5-(methylsulfonyl)phenyl]-6-methyl-2-[3-(pyrazin-2-yl)-1,2,4-oxadiazol-5-yl]-1,6-dihydro-7H-pyrrolo[2,3-c]pyridin-7-one;

4-[2-(2,6-dimethylphenoxy)-5-(methylsulfonyl)phenyl]-6-methyl-2-[3-(tetrahydro-2H-pyran-4-yl)-1,2,4-oxadiazol-5-yl]-1,6-dihydro-7H-pyrrolo[2,3-c]pyridin-7-one;

4-[2-(2,6-dimethylphenoxy)-5-(methylsulfonyl)phenyl]-6-methyl-2-[3-(1,3-thiazol-4-yl)-1,2,4-oxadiazol-5-yl]-1,6-dihydro-7H-pyrrolo[2,3-c]pyridin-7-one;

N-[2-(diethylamino)-2-methylpropyl]-4-[2-(2,6-dimethylphenoxy)-5-(methylsulfonyl)phenyl]-6-methyl-7-oxo-6,7-dihydro-1H-pyrrolo[2,3-c]pyridine-2-carboxamide;

N-[4-(diethylamino)butyl]-4-[2-(2,6-dimethylphenoxy)-5-(methylsulfonyl)phenyl]-6-methyl-7-oxo-6,7-dihydro-1H-pyrrolo[2,3-c]pyridine-2-carboxamide;

N-ethyl-4-{5-(ethylsulfonyl)-2-[2-methyl-6-(1H-pyrazol-1-ylmethyl)phenoxy]phenyl}-6-methyl-7-oxo-6,7-dihydro-1H-pyrrolo[2,3-c]pyridine-2-carboxamide;

N-ethyl-4-{5-(ethylsulfonyl)-2-[2-methyl-6-(morpholin-4-ylmethyl)phenoxy]phenyl}-6-methyl-7-oxo-6,7-dihydro-1H-pyrrolo[2,3-c]pyridine-2-carboxamide;

N-ethyl-4-{5-(ethylsulfonyl)-2-[2-methyl-6-(piperidin-1-ylmethyl)phenoxy]phenyl}-6-methyl-7-oxo-6,7-dihydro-1H-pyrrolo[2,3-c]pyridine-2-carboxamide;
N-ethyl-4-{5-(ethylsulfonyl)-2-[2-methyl-6-(2-phenylethyl)phenoxy]phenyl}-6-methyl-7-oxo-6,7-dihydro-1H-pyrrolo[2,3-c]pyridine-2-carboxamide;
4-[2-(cyclohexyloxy)-5-(ethylsulfonyl)phenyl]-6-methyl-2-[1-(piperidin-4-yl)-1H-pyrazol-4-yl]-1, 6-dihydro-7H-pyrrolo[2,3-c]pyridin-7-one;
N-ethyl-4-{5-(ethylsulfonyl)-2-[2-(1H-imidazol-1-ylmethyl)-6-methylphenoxy]phenyl}-6-methyl-7-oxo-6,7-dihydro-1H-pyrrolo[2,3-c]pyridine-2-carboxamide;
N-ethyl-4-[5-(ethylsulfonyl)-2-{2-methyl-6-[(2-oxopyrrolidin-1-yl)methyl]phenoxy}phenyl]-6-methyl-7-oxo-6,7-dihydro-1H-pyrrolo[2,3-c]pyridine-2-carboxamide;
4-[2-{2-[(1,1-dioxido-1,2-thiazolidin-2-yl)methyl]-6-methylphenoxy}-5-(ethylsulfonyl)phenyl]-N-ethyl-6-methyl-7-oxo-6,7-dihydro-1H-pyrrolo[2,3-c]pyridine-2-carboxamide;
4-[2-(2,6-dimethylphenoxy)-4-{[2-(methylamino)-2-oxoethyl](pyridin-2-ylmethyl)carbamoyl}phenyl]-N-ethyl-6-methyl-7-oxo-6,7-dihydro-1H-pyrrolo[2,3-c]pyridine-2-carboxamide;
4-[2-(2,6-dimethylphenoxy)-4-{methyl[1-(propanoyloxy)piperidin-4-yl]carbamoyl}phenyl]-N-ethyl-6-methyl-7-oxo-6,7-dihydro-1H-pyrrolo[2,3-c]pyridine-2-carboxamide;
1-({4-[2-(2,4-difluorophenoxy)-5-(methylsulfonyl)phenyl]-6-methyl-7-oxo-6,7-dihydro-1H-pyrrolo[2,3-c]pyridin-2-yl}methyl)-N,N-dimethyl-4-(2-oxopyrrolidin-1-yl)piperidine-4-carboxamide;
4-[2-(2,4-difluorophenoxy)-5-(methylsulfonyl)phenyl]-6-methyl-2-{[3-(1H-1,2,4-triazol-1-yl)azetidin-1-yl]methyl}-1,6-dihydro-7H-pyrrolo[2,3-c]pyridin-7-one;
N-ethyl-4-[5-(ethylsulfonyl)-2-{2-methyl-6-[(2-oxoazetidin-1-yl)methyl]phenoxy}phenyl]-6-methyl-7-oxo-6,7-dihydro-1H-pyrrolo[2,3-c]pyridine-2-carboxamide;
N-ethyl-4-[5-(ethylsulfonyl)-2-{2-methyl-6-[(2-oxopyridin-1(2H)-yl)methyl]phenoxy}phenyl]-6-methyl-7-oxo-6,7-dihydro-1H-pyrrolo[2,3-c]pyridine-2-carboxamide;
3-[({4-[2-(2,4-difluorophenoxy)-5-(methylsulfonyl)phenyl]-6-methyl-7-oxo-6,7-dihydro-1H-pyrrolo[2,3-c]pyridin-2-yl}methyl)amino]propanamide;
methyl 3-[{3-(2, 6-dimethylphenoxy)-4-[2-(ethylcarbamoyl)-6-methyl-7-oxo-6,7-dihydro-1H-pyrrolo[2,3-c]pyridin-4-yl]benzoyl}(phenyl)amino]propanoate;
4-[4-{benzyl[3-(morpholin-4-yl)propyl]carbamoyl}-2-(2,6-dimethylphenoxy)phenyl]-N-ethyl-6-methyl-7-oxo-6,7-dihydro-1H-pyrrolo[2,3-c]pyridine-2-carboxamide;
4-[4-{(3,4-dichlorophenyl)[2-(thiomorpholin-4-yl)ethyl]carbamoyl}-2-(2,6-dimethylphenoxy)phenyl]-N-ethyl-6-methyl-7-oxo-6,7-dihydro-1H-pyrrolo[2,3-c]pyridine-2-carboxamide;
N-{4-(2,4-difluorophenoxy)-3-[2-(3-methoxyprop-1-yn-1-yl)-6-methyl-7-oxo-6,7-dihydro-1H-pyrrolo[2,3-c]pyridin-4-yl]phenyl}ethanesulfonamide;
4-{2-[2-(2-cyclopentylethyl)-6-methylphenoxy]-5-(ethylsulfonyl)phenyl}-N-ethyl-6-methyl-7-oxo-6,7-dihydro-1H-pyrrolo[2,3-c]pyridine-2-carboxamide;
4-[2-(2,6-dimethylphenoxy)-4-{(1-phenylpropan-2-yl)[3-(pyrrolidin-1-yl)propyl]carbamoyl}phenyl]-N-ethyl-6-methyl-7-oxo-6,7-dihydro-1H-pyrrolo[2,3-c]pyridine-2-carboxamide;
4-{4-[(cyanomethyl)(1-phenylpropan-2-yl)carbamoyl]-2-(2,6-dimethylphenoxy)phenyl}-N-ethyl-6-methyl-7-oxo-6,7-dihydro-1H-pyrrolo[2,3-c]pyridine-2-carboxamide;
4-{4-[(cyanomethyl)(2-phenylpropyl)carbamoyl]-2-(2,6-dimethylphenoxy)phenyl}-N-ethyl-6-methyl-7-oxo-6,7-dihydro-1H-pyrrolo[2,3-c]pyridine-2-carboxamide;
4-{4-[(3-chlorophenyl)(cyanomethyl)carbamoyl]-2-(2,6-dimethylphenoxy)phenyl}-N-ethyl-6-methyl-7-oxo-6,7-dihydro-1H-pyrrolo[2,3-c]pyridine-2-carboxamide;
4-{4-[(4-chlorophenyl)(cyanomethyl)carbamoyl]-2-(2,6-dimethylphenoxy)phenyl}-N-ethyl-6-methyl-7-oxo-6,7-dihydro-1H-pyrrolo[2,3-c]pyridine-2-carboxamide;
4-[4-{[2-(diethylamino)ethyl](2-methylphenyl)carbamoyl}-2-(2,6-dimethylphenoxy)phenyl]-N-ethyl-6-methyl-7-oxo-6,7-dihydro-1H-pyrrolo[2,3-c]pyridine-2-carboxamide;
4-[4-{(cyanomethyl)[3-(trifluoromethyl)phenyl]carbamoyl}dimethylphenoxy)phenyl]-N-ethyl-6-methyl-7-oxo-6,7-dihydro-1H-pyrrolo[2,3-c]pyridine-2-carboxamide;
4-[4-{cyclohexyl[3-(dimethylamino)propyl]carbamoyl}-2-(2,6-dimethylphenoxy)phenyl]-N-ethyl-6-methyl-7-oxo-6,7-dihydro-1H-pyrrolo[2,3-c]pyridine-2-carboxamide;
4-{4-[benzyl(4-chlorobenzyl)carbamoyl]-2-(2,6-dimethylphenoxy)phenyl}-N-ethyl-6-methyl-7-oxo-6,7-dihydro-1H-pyrrolo[2,3-c]pyridine-2-carboxamide;
4-[4-{[2-(dimethylamino)ethyl](pyrimidin-2-yl)carbamoyl}-2-(2,6-dimethylphenoxy)phenyl]-N-ethyl-6-methyl-7-oxo-6,7-dihydro-1H-pyrrolo[2,3-c]pyridine-2-carboxamide;
4-{4-[(3-chlorophenyl)(2-cyanoethyl)carbamoyl]-2-(2,6-dimethylphenoxy)phenyl}-N-ethyl-6-methyl-7-oxo-6,7-dihydro-1H-pyrrolo[2,3-c]pyridine-2-carboxamide;
4-{4-[(2-cyanoethyl)(cyclohexyl)carbamoyl]-2-(2,6-dimethylphenoxy)phenyl}-N-ethyl-6-methyl-7-oxo-6,7-dihydro-1H-pyrrolo[2,3-c]pyridine-2-carboxamide;
4-{4-[(cyanomethyl)(phenyl)carbamoyl]-2-(2,6-dimethylphenoxy)phenyl}-N-ethyl-6-methyl-7-oxo-6,7-dihydro-1H-pyrrolo[2,3-c]pyridine-2-carboxamide;
4-[4-{[2-(diethylamino)ethyl](2-methoxyphenyl)carbamoyl}-2-(2, 6-dimethylphenoxy)phenyl]-N-ethyl-6-methyl-7-oxo-6,7-dihydro-1H-pyrrolo[2,3-c]pyridine-2-carboxamide;
4-[4-{[2-(dimethylamino)ethyl](phenyl)carbamoyl}-2-(2, 6-dimethylphenoxy)phenyl]-N-ethyl-6-methyl-7-oxo-6,7-dihydro-1H-pyrrolo[2,3-c]pyridine-2-carboxamide;
ethyl 4-[{3-(2,6-dimethylphenoxy)-4-[2-(ethylcarbamoyl)-6-methyl-7-oxo-6,7-dihydro-1H-pyrrolo[2,3-c]pyridin-4-yl]benzoyl}(phenyl)amino]butanoate;
4-[4-{[2-(dimethylamino)ethyl](pyridin-2-yl)carbamoyl}-2-(2,6-dimethylphenoxy)phenyl]-N-ethyl-6-methyl-7-oxo-6,7-dihydro-1H-pyrrolo[2,3-c]pyridine-2-carboxamide;
4-[4-{[2-(diethylamino)ethyl](phenyl)carbamoyl}-2-(2, 6-dimethylphenoxy)phenyl]-N-ethyl-6-methyl-7-oxo-6,7-dihydro-1H-pyrrolo[2,3-c]pyridine-2-carboxamide;

4-{4-[(cyanomethyl)(4-methoxyphenyl)carbamoyl]-2-(2,6-dimethylphenoxy)phenyl}-N-ethyl-6-methyl-7-oxo-6,7-dihydro-1H-pyrrolo[2,3-c]pyridine-2-carboxamide;

4-{4-[butyl(2-cyanoethyl)carbamoyl]-2-(2, 6-dimethylphenoxy)phenyl}-N-ethyl-6-methyl-7-oxo-6,7-dihydro-1H-pyrrolo[2,3-c]pyridine-2-carboxamide;

4-[4-{[2-(dimethylamino)ethyl](2-fluoropyridin-4-yl)carbamoyl}-2-(2, 6-dimethylphenoxy)phenyl]-N-ethyl-6-methyl-7-oxo-6,7-dihydro-1H-pyrrolo[2,3-c]pyridine-2-carboxamide;

4-{4-[cyclohexyl(phenyl)carbamoyl]-2-(2,6-dimethylphenoxy)phenyl}-N-ethyl-6-methyl-7-oxo-6,7-dihydro-1H-pyrrolo[2,3-c]pyridine-2-carboxamide;

N-{3-[cyclohexyl(methyl)amino]propyl}-4-[2-(2, 6-dimethylphenoxy)-5-(methylsulfonyl)phenyl]-6-methyl-7-oxo-6,7-dihydro-1H-pyrrolo[2,3-c]pyridine-2-carboxamide; and 4-[2-(2,4-difluorophenoxy)-5-(methylsulfonyl)phenyl]-6-methyl-2-[(4-methyl-2-phenylpiperazin-1-yl)methyl]-1,6-dihydro-7H-pyrrolo[2,3-c]pyridin-7-one;

or a pharmaceutically acceptable salt thereof.

Compounds of formula (I) may be used in the form of pharmaceutically acceptable salts. The phrase "pharmaceutically acceptable salt" means those salts which are, within the scope of sound medical judgement, suitable for use in contact with the tissues of humans and lower animals without undue toxicity, irritation, allergic response and the like and are commensurate with a reasonable benefit/risk ratio.

Pharmaceutically acceptable salts have been described in S. M. Berge et al. J. Pharmaceutical Sciences, 1977, 66: 1-19.

Compounds of formula (I) may contain either a basic or an acidic functionality, or both, and can be converted to a pharmaceutically acceptable salt, when desired, by using a suitable acid or base. The salts may be prepared in situ during the final isolation and purification of the compounds of the invention.

Examples of acid addition salts include, but are not limited to acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, fumarate, hydrochloride, hydrobromide, hydroiodide, 2-hydroxyethansulfonate (isothionate), lactate, malate, maleate, methanesulfonate, nicotinate, 2-naphthalenesulfonate, oxalate, palmitoate, pectinate, persulfate, 3-phenylpropionate, picrate, pivalate, propionate, succinate, tartrate, thiocyanate, phosphate, glutamate, bicarbonate, p-toluenesulfonate and undecanoate. Also, the basic nitrogen-containing groups can be quaternized with such agents as lower alkyl halides such as, but not limited to, methyl, ethyl, propyl, and butyl chlorides, bromides and iodides; dialkyl sulfates like dimethyl, diethyl, dibutyl and diamyl sulfates; long chain halides such as, but not limited to, decyl, lauryl, myristyl and stearyl chlorides, bromides and iodides; arylalkyl halides like benzyl and phenethyl bromides and others. Water or oil-soluble or dispersible products are thereby obtained. Examples of acids which may be employed to form pharmaceutically acceptable acid addition salts include such inorganic acids as hydrochloric acid, hydrobromic acid, sulfuric acid, and phosphoric acid and such organic acids as acetic acid, fumaric acid, maleic acid, 4-methylbenzenesulfonic acid, succinic acid and citric acid.

Basic addition salts may be prepared in situ during the final isolation and purification of compounds of this invention by reacting a carboxylic acid-containing moiety with a suitable base such as, but not limited to, the hydroxide, carbonate or bicarbonate of a pharmaceutically acceptable metal cation or with ammonia or an organic primary, secondary or tertiary amine. Pharmaceutically acceptable salts include, but are not limited to, cations based on alkali metals or alkaline earth metals such as, but not limited to, lithium, sodium, potassium, calcium, magnesium and aluminum salts and the like and nontoxic quaternary ammonia and amine cations including ammonium, tetramethylammonium, tetraethylammonium, methylamine, dimethylamine, trimethylamine, triethylamine, diethylamine, ethylamine and the like. Other examples of organic amines useful for the formation of base addition salts include ethylenediamine, ethanolamine, diethanolamine, piperidine, piperazine and the like.

The term "pharmaceutically acceptable prodrug" or "prodrug" as used herein, represents those prodrugs of the compounds of the present invention which are, within the scope of sound medical judgement, suitable for use in contact with the tissues of humans and lower animals without undue toxicity, irritation, allergic response, and the like, commensurate with a reasonable benefit/risk ratio, and effective for their intended use.

The present invention contemplates compounds of formula (I) formed by synthetic means or formed by in vivo biotransformation of a prodrug.

Compounds described herein can exist in unsolvated as well as solvated forms, including hydrated forms, such as hemi-hydrates. In general, the solvated forms, with pharmaceutically acceptable solvents such as water and ethanol among others are equivalent to the unsolvated forms for the purposes of the invention.

General Synthesis

The compounds described herein, including compounds of general formula (I) and specific examples, can be prepared by methodologies known in the art, for example, through the reaction schemes depicted in schemes 1-4. The variables $A^1$, $A^3$, $A^3$, $A^4$, $R^x$, $R^y$, $R^{x1}$, $L^1$, $G^1$, $R^{xa}$, $R^{xb}$, $R^{xc}$, $R^{bx1}$, $R^{cx1}$, $G^{x1}$, and $G^{x2}$ used in the following schemes have the meanings as set forth in the summary and detailed description sections, unless otherwise noted. PG denotes a protecting group such as, for example, benzyl or tosyl group. Suitable protecting groups and the methods for protecting and deprotecting different substituents using such suitable protecting groups are well known to those skilled in the art; examples of which can be found in T. Greene and P. Wuts, Protecting Groups in Organic Synthesis ($3^{rd}$ ed.), John Wiley & Sons, NY (1999), which is incorporated herein by reference in its entirety.

Abbreviations used in the descriptions of the schemes and the specific examples have the following meanings: DIPEA for diisopropylethylamine, DMA for N,N-dimethylacetamide, DMSO for dimethyl sulfoxide, dppf for 1,1'-bis(diphenylphosphino)ferrocene, HATU for 0-(7-azabenzotriazol-1-yl)-N,N,N',N'-tetramethyluronium hexafluorophosphate; HPLC for High Performance Liquid chromatography, Prep HPLC for Preparative High Performance Liquid chromatography, MeOH for methanol, $Pd_2(dba)_3$ for tris(dibenzylideneacetone)dipalladium(O), $PdCl_2(PPh_3)_2$ for bis(triphenylphosphine)palladium(II) dichloride, TFA for trifluoroacetic acid, THF for tetrahydrofuran, and tosyl for toluenesulfonyl.

Scheme 1

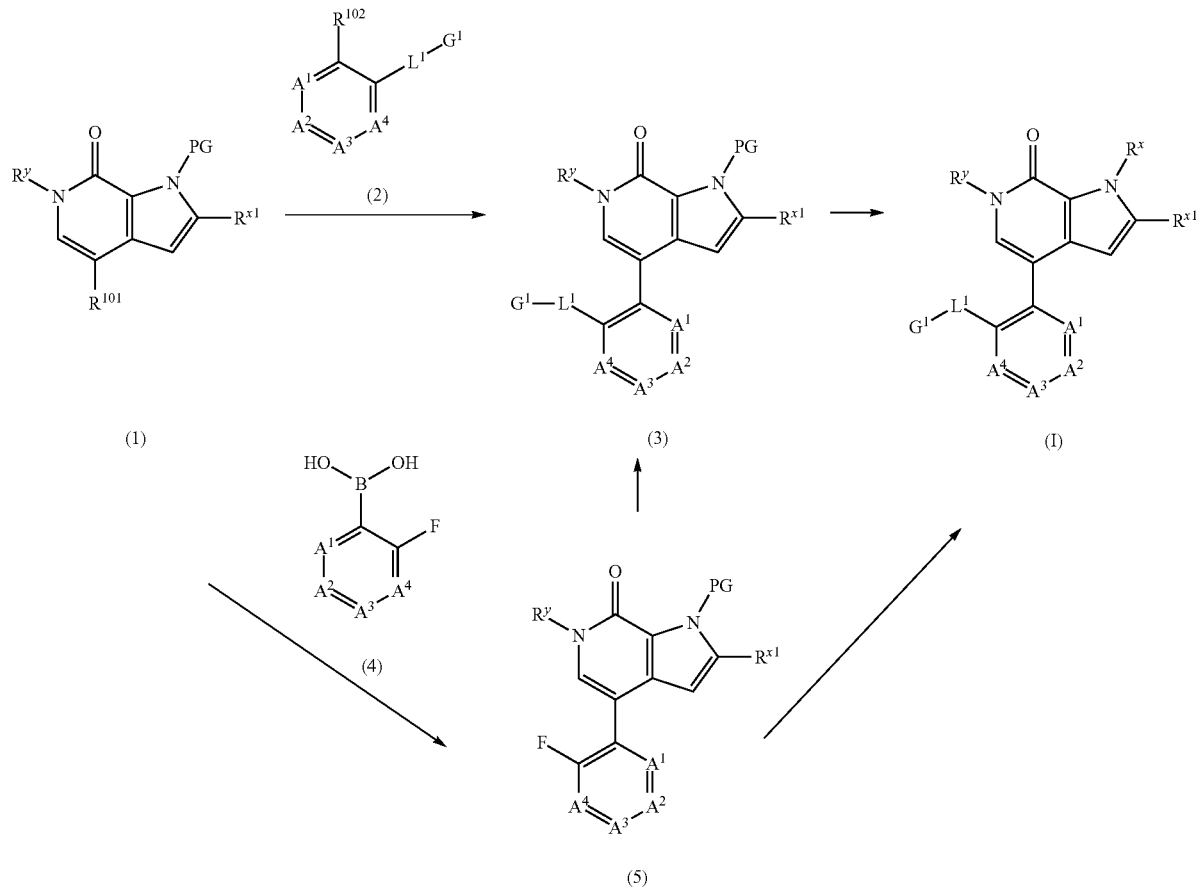

Compounds of general formula (I) may be prepared (a) by treating an aryl halide, an aryl mesylate, or an aryl triflate with an aryl boronic acid or derivatives thereof (e.g. boronic esters) under Suzuki coupling condition (N. Miyama and A. Suzuki, Chem. Rev. 1995, 95:2457-2483, J. Organomet. Chem. 1999, 576:147-148), and (b) removal of the protecting group (PG), as illustrated in Scheme 1. Thus coupling of compounds of formula (1) wherein $R^{101}$ is Br, Cl, mesylate, or triflate with compounds of formula (2) wherein $R^{102}$ is boronic acid or derivatives thereof (e.g. boronic esters), or coupling of (1) wherein $R^{101}$ is boronic acid or derivatives thereof (e.g. boronic esters) with compounds (2) wherein $R^{102}$ is Br, Cl, mesylate, or triflate, provides intermediates of formula (3). Generally, the coupling reaction is effected in the presence of a palladium catalyst and a base, and optionally in the presence of a ligand, and in a suitable solvent at elevated temperature (for example, at a temperature ranging from about 80° C. to about 150° C.). The reaction may be facilitated by microwave irradiation. Examples of the palladium catalyst include, but are not limited to, tetrakis (triphenylphosphine)palladium(O), tris(dibenzylideneacetone)dipalladium(O), and palladium(II)acetate. Examples of suitable bases that may be employed include, but are not limited to, carbonates or phosphates of sodium, potassium, and cesium; and cesium fluoride. Examples of suitable ligands include, but are not limited to, 1,3,5,7-tetramethyl-6-phenyl-2,4,8-trioxa-6-phosphaadamantane, 2-dicyclohexylphosphino-2',4',6'-triisopropylbiphenyl (X-phos), and 1,1'-bis(diphenylphosphanyl) ferrocene. Non-limiting examples of suitable solvent include methanol, dimethoxyethane, N,N-dimethylformamide, dimethylsulfoxide, dioxane, tetrahydrofuran, and water, or a mixture thereof.

Alternatively, treatment of formula (1) wherein $R^{101}$ is Br, Cl, or triflate with boronic acid of formula (4), followed by displacement of the fluoride atom in (4) with an appropriate alcohol or amine of formula $G^1$-$L^1$-H wherein $L^1$ is O or NH, provides compounds of formula (3) or formula (I) wherein $R^x$ is hydrogen.

Displacement of the fluorine with an alcohol or amine may be achieved in a solvent such as, but not limited to, dimethylsulfoxide, dimethylformamide, dioxane, or tetrahydrofuran, and in the presence of a base such as, but not limited to, cesium carbonate, potassium carbonate, or sodium hydride and at a temperature from about 40° C. to about 120° C.

The protecting group (PG) may be removed in situ during the displacement reaction or the coupling conditions described above.

Alternatively, removal of the protecting group (PG) to afford compounds of general formula (I) wherein $R^x$ is hydrogen may be accomplished using reaction conditions known generally to one skilled in the art, or modifications thereof. For example, the tosyl protecting group may be removed in the presence of a base such as, but not limited to, cesium carbonate, sodium hydroxide, or sodium hydride. The reaction is generally performed in the presence of a suitable solvent such as, but not limited to, dimethylsulfoxide, methanol, or tetrahydrofuran, and at a temperature of about 40° C. to about 120° C. The benzyl protecting group may be removed by hydrogenation in the presence of a catalyst such as, but not limited to, palladium on carbon and under hydrogen atmosphere. The reaction is typically performed in the presence of a solvent such as, but not limited to, methanol or ethyl acetate, and at about room temperature.

Removal of the (trimethylsilyl)ethoxy)methyl protecting group may be achieved by treatment with a base such as, but not limited to, cesium carbonate or sodium hydride, or with a fluoride reagent such as, but not limited to, TBAF (tetrabutylammonium fluoride). The reaction is generally performed in the presence of a suitable solvent such as, but not limited to, dimethylsulfoxide, ethanol, or tetrahydrofuran, and at a temperature of about 40° C. to about 120° C. Removal of the (trimethylsilyl)ethoxy)methyl protecting group may also be achieved by treatment with an mild acid such as but not limited to, aqueous hydrochloric acid. The reaction is generally performed in the presence of a suitable solvent such as, but not limited to, ethanol, or methanol, and at a temperature of about 25° C. to about 80° C.

catalyst such as, but not limited to, Raney-Nickel and under hydrogen atmosphere (about 30 psi) and in a solvent such as, but not limited to, ethyl acetate, at about room temperature generally affords compounds of formula (8). Protection of the nitrogen atom with protecting group such as, but not limited to, benzyl, tosyl, and (trimethylsilyl)ethoxy)methyl group can be derived from reaction with an appropriate halide in the presence of a strong base such as, for example, sodium hydride, to provide compounds of formula (9).

Treatment of (9) with an acid such as, for example, hydrochloric acid or hydrobromic acid and in a solvent such as, for example, dioxane or water, at about 40° C. to about 100° C., provides compounds of formula (10).

Alkylation of (10) with a halide or mesylate, in the presence of a base such as, for example, sodium hydride, cesium carbonate, or potassium carbonate, and in a solvent such as, for example, dimethylformamide or dimethylsulfoxide at a temperature of about 0° C. to about 50° C. provides compounds of formula (11).

Treatment of the compounds of formula (11) with 4,4,4',4',5,5,5',5'-octamethyl-2,2'-bi(1,3,2-dioxaborolane) affords compounds of formula (12). In general, the conversion may

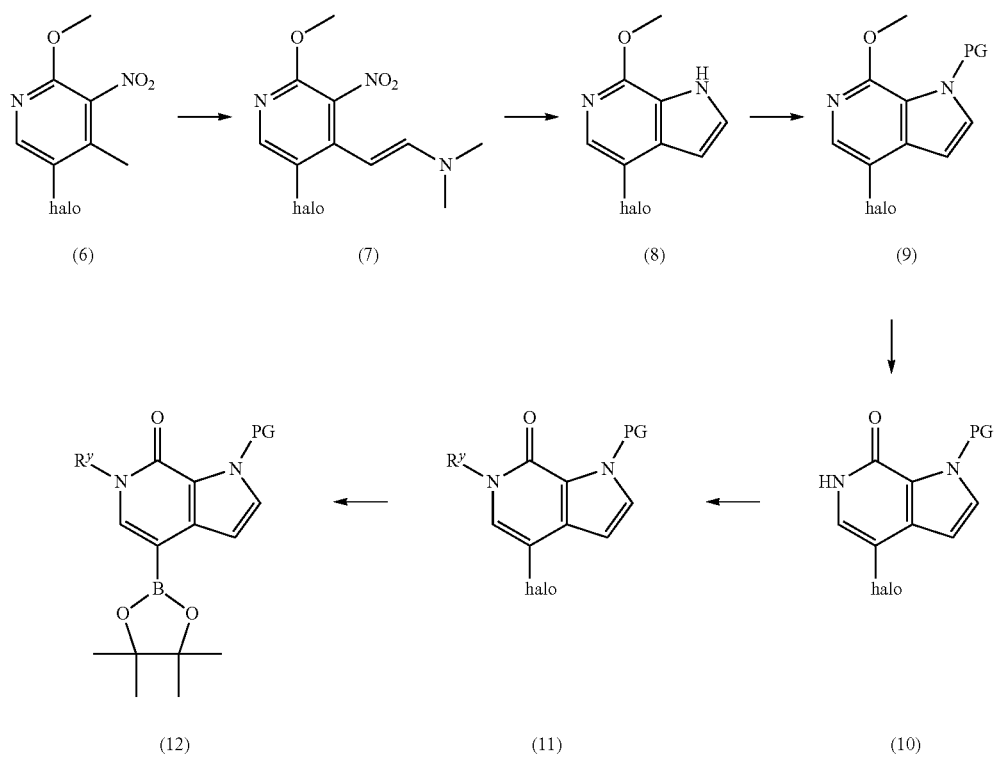

Scheme 2

Compounds of formula (1) wherein $R^{x1}$ is hydrogen may be prepared by general synthetic methods as shown in Scheme 2.

Treatment of compounds of formula (6) wherein halo is Br, Cl, or I, with 1,1-dimethoxy-N,N-dimethylmethanamine at elevated temperature (e.g. about 60° C. to about 100° C.), in the absence or presence of a base, and in a solvent such as, but not limited to, N,N-dimethylformamide, provides compounds of formula (7). Examples of suitable bases include, but are not limited to, lithium or sodium methanolate. Catalytic hydrogenation of (7) in the presence of a be facilitated by a palladium catalyst such as, for example, tetrakis(triphenylphosphine)palladium(0), tris(dibenzylideneacetone)dipalladium(0), or palladium(II)acetate, an optional ligand such as, but not limited to, 2-dicyclohexylphosphino-2',4',6'-triisopropylbiphenyl, 2-dicyclohexylphosphino-2',4',6'-triisopropylbiphenyl (X-phos), or 1,1'-bis(diphenylphosphanyl) ferrocene, and a base such as, but not limited to, carbonates, acetates, or phosphates. of sodium, potassium, or cesium; and cesium fluoride. Non-limiting examples of suitable solvents include methanol, dimethoxyethane, N,N-dimethylformamide, dimethylsulfoxide, dioxane, tetrahydrofuran, and water, or a mixture thereof

Scheme 3

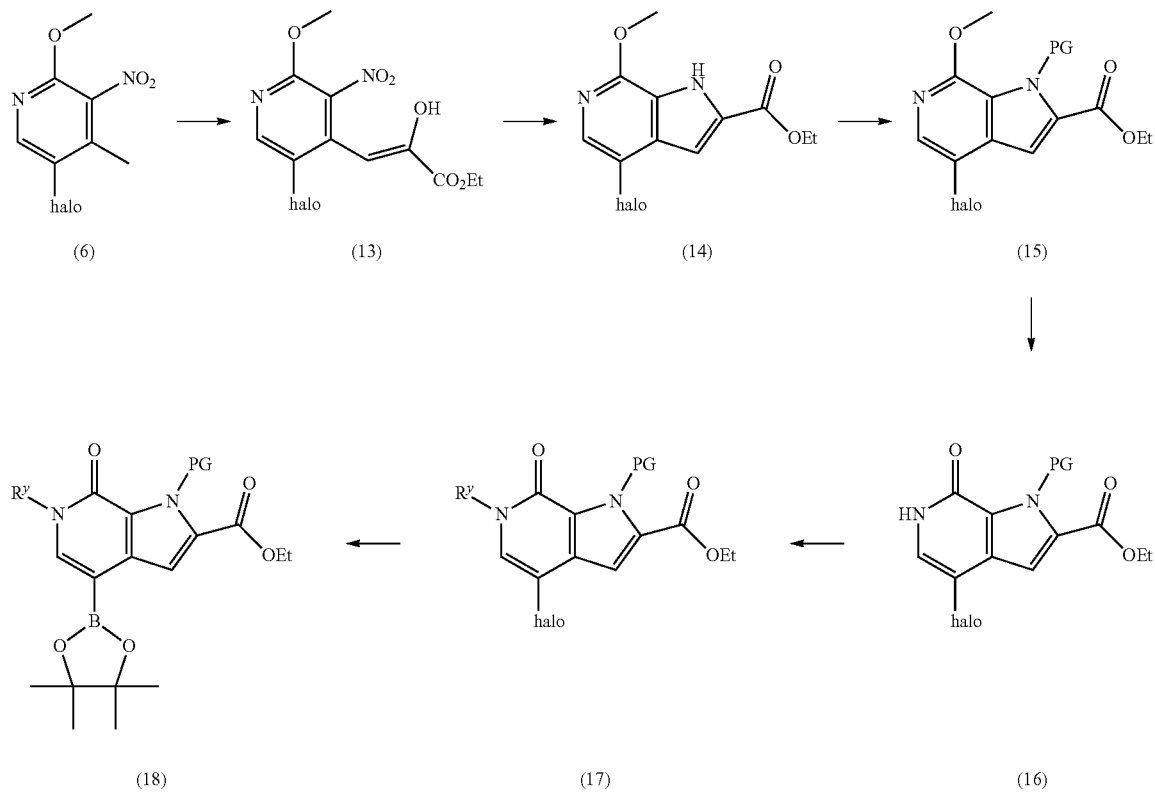

Scheme 3 demonstrates a general approach to the preparation of compounds of formula (1) wherein $R^{101}$ is boronic acid derivative, and $R^{x1}$ is —COOEt.

An ester of formula (14) may be obtained from (a) treatment of (6) with diethyl oxalate in the presence of a base such as, but not limited to, potassium ethoxide or sodium ethoxide, in a solvent such as, but not limited to, ethanol, dioxane, or diethyl ether, and at a temperature of about 40° C. to about 80° C.; and (b) cyclization of the resulting intermediates (13) in the presence of iron and in ethanol and acetic acid, at a temperature of about 80° C. to about 100° C. Conversion of (14) to (18) may be achieved by employing reaction conditions discussed in Scheme 2.

Scheme 4 illustrates a general approach to the preparation of compounds of formula (I) wherein $R^{x1}$ is -$G^{x1}$-$G^{x2}$, —C(O)N($R^{xa}$)($R^{xb}$) or $C_1$ alkyl substituted with one —NR$^{xa}$R$^{xb}$ group.

Scheme 4

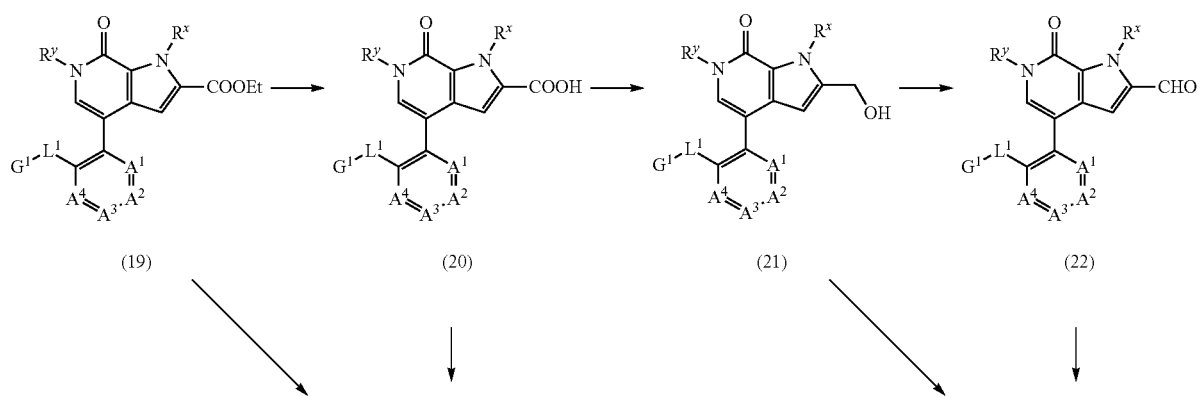

-continued

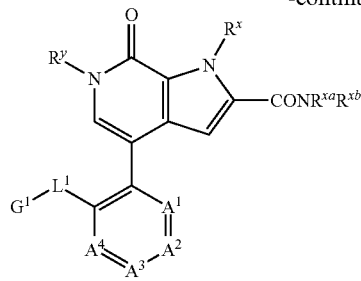

(24)

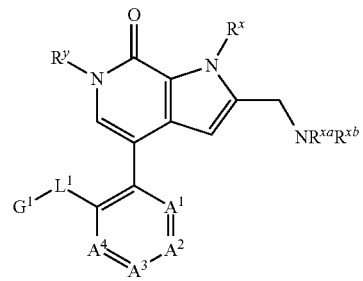

(23)

Palladium coupling of compounds (18) with compounds (2) wherein $R^{102}$ is Br, Cl, mesylate, or triflate, followed by removal of the protecting group (either in situ or treatment with a base) using reaction conditions described in Scheme 2, provides compounds (19). Hydrolysis of the esters (19) affords the corresponding acids (20) which may be coupled with an appropriate amines of formula $NH(R^{xa})(R^{xb})$ to provide the amides (24). Amides (24) may also be prepared directly from the reaction of the esters (19) with an amines of formula $NH(R^{xa})(R^{xb})$. Reduction of the acids (20) followed by oxidation provides the aldehydes (22). Reductive amination of (22) provides amines of formula (23). Amines (23) may also be obtained from direct displacement of the alcohols (22) by amines of formula $NH(R^{xa})(R^{xb})$.

Compounds of general formula (I) wherein $R^{x1}$ is —C(O)$NR^{bx1}R^{cx1}$ or $C_1$ alkyl substituted with one —$NR^{xa}R^{xc}$ group may be prepared similarly.

Optimum reaction conditions and reaction times for each individual step may vary depending on the particular reactants employed and substituents present in the reactants used. Unless otherwise specified, solvents, temperatures and other reaction conditions may be readily selected by one of ordinary skill in the art. Specific procedures are provided in the Synthetic Examples section. Reactions may be further processed in the conventional manner, e.g. by eliminating the solvent from the residue and further purified according to methodologies generally known in the art such as, but not limited to, crystallization, distillation, extraction, trituration and chromatography. Unless otherwise described, the starting materials and reagents are either commercially available or may be prepared by one skilled in the art from commercially available materials using methods described in the chemical literature.

Routine experimentations, including appropriate manipulation of the reaction conditions, reagents and sequence of the synthetic route, protection of any chemical functionality that can not be compatible with the reaction conditions, and deprotection at a suitable point in the reaction sequence of the method are included in the scope of the invention. Suitable protecting groups and the methods for protecting and deprotecting different substituents using such suitable protecting groups are well known to those skilled in the art; examples of which can be found in T. Greene and P. Wuts, Protecting Groups in Organic Synthesis ($3^{rd}$ ed.), John Wiley & Sons, NY (1999), which is incorporated herein by reference in its entirety. Synthesis of the compounds of the invention can be accomplished by methods analogous to those described in the synthetic schemes described hereinabove and in specific examples.

Starting materials, if not commercially available, can be prepared by procedures selected from standard organic chemical techniques, techniques that are analogous to the synthesis of known, structurally similar compounds, or techniques that are analogous to the above described schemes or the procedures described in the synthetic examples section.

When an optically active form of a compound is required, it can be obtained by carrying out one of the procedures described herein using an optically active starting material (prepared, for example, by asymmetric induction of a suitable reaction step), or by resolution of a mixture of the stereoisomers of the compound or intermediates using a standard procedure (such as chromatographic separation, recrystallization or enzymatic resolution).

Similarly, when a pure geometric isomer of a compound is required, it can be prepared by carrying out one of the above procedures using a pure geometric isomer as a starting material, or by resolution of a mixture of the geometric isomers of the compound or intermediates using a standard procedure such as chromatographic separation.

Pharmaceutical Compositions

This invention also provides for pharmaceutical compositions comprising a therapeutically effective amount of a compound of formula (I), or a pharmaceutically acceptable salt thereof together with a pharmaceutically acceptable carrier, diluent, or excipient therefor. The phrase "pharmaceutical composition" refers to a composition suitable for administration in medical or veterinary use.

The pharmaceutical compositions that comprise a compound of formula (I), alone or in combination with a second therapeutic agent, may be administered to the subjects orally, rectally, parenterally, intracisternally, intravaginally, intraperitoneally, topically (as by powders, ointments or drops), bucally or as an oral or nasal spray. The term "parenterally" as used herein, refers to modes of administration which include intravenous, intramuscular, intraperitoneal, intrasternal, subcutaneous and intraarticular injection and infusion.

The term "pharmaceutically acceptable carrier" as used herein, means a non-toxic, inert solid, semi-solid or liquid filler, diluent, encapsulating material or formulation auxiliary of any type. Some examples of materials which can serve as pharmaceutically acceptable carriers are sugars such as, but not limited to, lactose, glucose and sucrose; starches such as, but not limited to, corn starch and potato starch; cellulose and its derivatives such as, but not limited to, sodium carboxymethyl cellulose, ethyl cellulose and cellulose acetate; powdered tragacanth; malt; gelatin; talc; excipients such as, but not limited to, cocoa butter and suppository waxes; oils such as, but not limited to, peanut oil, cottonseed oil, safflower oil, sesame oil, olive oil, corn oil and soybean oil; glycols; such a propylene glycol; esters such as, but not limited to, ethyl oleate and ethyl laurate; agar; buffering agents such as, but not limited to, magnesium hydroxide and aluminum hydroxide; alginic acid; pyrogen-free water; isotonic saline; Ringer's solution; ethyl alcohol, and phosphate buffer solutions, as well as other non-toxic compatible lubricants such as, but not limited to, sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Pharmaceutical compositions for parenteral injection comprise pharmaceutically acceptable sterile aqueous or nonaqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), vegetable oils (such as olive oil), injectable organic esters (such as ethyl oleate) and suitable mixtures thereof. Proper fluidity can be maintained, for example, by the use of coating materials such as lecithin, by the maintenance of the required particle size in the case of dispersions and by the use of surfactants.

These compositions may also contain adjuvants such as preservatives, wetting agents, emulsifying agents and dispersing agents. Prevention of the action of microorganisms can be ensured by the inclusion of various antibacterial and antifungal agents, for example, paraben, chlorobutanol, phenol sorbic acid and the like. It may also be desirable to include isotonic agents such as sugars, sodium chloride and the like. Prolonged absorption of the injectable pharmaceutical form can be brought about by the inclusion of agents, which delay absorption such as aluminum monostearate and gelatin.

In some cases, in order to prolong the effect of the drug, it is desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally-administered drug form may be accomplished by dissolving or suspending the drug in an oil vehicle.

Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions which are compatible with body tissues.

The injectable formulations can be sterilized, for example, by filtration through a bacterial-retaining filter or by incorporating sterilizing agents in the form of sterile solid compositions which can be dissolved or dispersed in sterile water or other sterile injectable medium just prior to use.

Solid dosage forms for oral administration include capsules, tablets, pills, powders and granules. In certain embodiments, solid dosage forms may contain from 1% to 95% (w/w) of a compound of formula (I). In certain embodiments, the compound of formula (I) may be present in the solid dosage form in a range of from 5% to 70% (w/w). In such solid dosage forms, the active compound may be mixed with at least one inert, pharmaceutically acceptable excipient or carrier, such as sodium citrate or dicalcium phosphate and/or a) fillers or extenders such as starches, lactose, sucrose, glucose, mannitol and silicic acid; b) binders such as carboxymethylcellulose, alginates, gelatin, polyvinylpyrrolidone, sucrose and acacia; c) humectants such as glycerol; d) disintegrating agents such as agar-agar, calcium carbonate, potato or tapioca starch, alginic acid, certain silicates and sodium carbonate; e) solution retarding agents such as paraffin; f) absorption accelerators such as quaternary ammonium compounds; g) wetting agents such as cetyl alcohol and glycerol monostearate; h) absorbents such as kaolin and bentonite clay and i) lubricants such as talc, calcium stearate, magnesium stearate, solid polyethylene glycols, sodium lauryl sulfate and mixtures thereof. In the case of capsules, tablets and pills, the dosage form may also comprise buffering agents.

The pharmaceutical composition may be a unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampules. Also, the unit dosage form can be a capsule, tablet, cachet, or lozenge itself, or it can be the appropriate number of any of these in packaged form. The quantity of active component in a unit dose preparation may be varied or adjusted from 0.1 mg to 1000 mg, from 1 mg to 100 mg, or from 1% to 95% (w/w) of a unit dose, according to the particular application and the potency of the active component. The composition can, if desired, also contain other compatible therapeutic agents.

The dose to be administered to a subject may be determined by the efficacy of the particular compound employed and the condition of the subject, as well as the body weight or surface area of the subject to be treated. The size of the dose also will be determined by the existence, nature, and extent of any adverse side-effects that accompany the administration of a particular compound in a particular subject. In determining the effective amount of the compound to be administered in the treatment or prophylaxis of the disorder being treated, the physician can evaluate factors such as the circulating plasma levels of the compound, compound toxicities, and/or the progression of the disease, etc. In general, the dose equivalent of a compound is from about 1 µg/kg to 100 mg/kg for a typical subject.

For administration, compounds of the formula (I) may be administered at a rate determined by factors that can include, but are not limited to, the $LD_{50}$ of the compound, the pharmacokinetic profile of the compound, contraindicated drugs, and the side-effects of the compound at various concentrations, as applied to the mass and overall health of the subject. Administration can be accomplished via single or divided doses.

The compounds utilized in the pharmaceutical method of the invention can be administered at the initial dosage of about 0.001 mg/kg to about 100 mg/kg daily. In certain embodiments, the daily dose range is from about 0.1 mg/kg to about 10 mg/kg. The dosages, however, may be varied depending upon the requirements of the subject, the severity of the condition being treated, and the compound being employed. Determination of the proper dosage for a particular situation is within the skill of the practitioner. Treatment may be initiated with smaller dosages, which are less than the optimum dose of the compound. Thereafter, the dosage is increased by small increments until the optimum effect under circumstances is reached. For convenience, the total daily dosage may be divided and administered in portions during the day, if desired.

Solid compositions of a similar type may also be employed as fillers in soft and hard-filled gelatin capsules using such carriers as lactose or milk sugar as well as high molecular weight polyethylene glycols and the like.

The solid dosage forms of tablets, dragees, capsules, pills and granules can be prepared with coatings and shells such as enteric coatings and other coatings well-known in the pharmaceutical formulating art. They may optionally contain opacifying agents and may also be of a composition such that they release the active ingredient(s) only, or preferentially, in a certain part of the intestinal tract, optionally, in a delayed manner. Examples of embedding compositions which can be used include polymeric substances and waxes.

The active compounds can also be in micro-encapsulated form, if appropriate, with one or more of the above-mentioned carriers.

Liquid dosage forms for oral administration include pharmaceutically acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor and sesame oils), glycerol, tetrahydrofurfuryl alcohol, polyethylene glycols and fatty acid esters of sorbitan and mixtures thereof.

Besides inert diluents, the oral compositions may also include adjuvants such as wetting agents, emulsifying and suspending agents, sweetening, flavoring and perfuming agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar, tragacanth and mixtures thereof.

Compositions for rectal or vaginal administration are preferably suppositories which can be prepared by mixing the compounds of this invention with suitable non-irritating carriers or carriers such as cocoa butter, polyethylene glycol or a suppository wax which are solid at room temperature but liquid at body temperature and therefore melt in the rectum or vaginal cavity and release the active compound.

Compounds of formula (I) may also be administered in the form of liposomes. Liposomes generally may be derived from phospholipids or other lipid substances. Liposomes are formed by mono- or multi-lamellar hydrated liquid crystals which are dispersed in an aqueous medium. Any non-toxic, physiologically acceptable and metabolizable lipid capable of forming liposomes can be used. The present compositions in liposome form may contain, in addition to a compound of formula (I), stabilizers, preservatives, excipients and the like. Examples of lipids include, but are not limited to, natural and synthetic phospholipids and phosphatidyl cholines (lecithins), used separately or together.

Methods to form liposomes have been described, see example, Prescott, Ed., Methods in Cell Biology, Volume XIV, Academic Press, New York, N.Y. (1976), p. 33 et seq.

Dosage forms for topical administration of a compound described herein include powders, sprays, ointments and inhalants. The active compound may be mixed under sterile conditions with a pharmaceutically acceptable carrier and any needed preservatives, buffers or propellants which may be required. Opthalmic formulations, eye ointments, powders and solutions are also contemplated as being within the scope of this invention.

Methods of Use

The compounds of formula (I), or pharmaceutically acceptable salts thereof, and pharmaceutical compositions comprising a compound of formula (I), or a pharmaceutically acceptable salt thereof, can be administered to a subject suffering from a bromodomain-mediated disorder or condition. The term "administering" refers to the method of contacting a compound with a subject. Thus, the compounds of formula (I) may be administered by injection, that is, intravenously, intramuscularly, intracutaneously, subcutaneously, intraduodenally, parentally, or intraperitoneally. Also, the compounds described herein can be administered by inhalation, for example, intranasally. Additionally, the compounds of formula (I) may be administered transdermally, topically, via implantation, transdermally, topically, and via implantation. In certain embodiments, the compounds of the formula (I) may be delivered orally. The compounds can also be delivered rectally, bucally, intravaginally, ocularly, or by insufflation. Bromodomain-mediated disorders and conditions can be treated prophylactically, acutely, and chronically using compounds of formula (I), depending on the nature of the disorder or condition. Typically, the host or subject in each of these methods is human, although other mammals can also benefit from the administration of a compound of formula (I).

A "bromodomain-mediated disorder or condition" is characterized by the participation of one or more bromodomains (e.g., BRD4) in the inception, manifestation of one or more symptoms or disease markers, severity, or progression of a disorder or condition. Accordingly, compounds of formula (I) may be used to treat cancer, including, but not limited to acoustic neuroma, acute leukemia, acute lymphocytic leukemia, acute myelocytic leukemia (monocytic, myeloblastic, adenocarcinoma, angiosarcoma, astrocytoma, myelomonocytic and promyelocytic), acute t-cell leukemia, basal cell carcinoma, bile duct carcinoma, bladder cancer, brain cancer, breast cancer, bronchogenic carcinoma, cervical cancer, chondrosarcoma, chordoma, choriocarcinoma, chronic leukemia, chronic lymphocytic leukemia, chronic myelocytic (granulocytic) leukemia, chronic myelogenous leukemia, colon cancer, colorectal cancer, craniopharyngioma, cystadenocarcinoma, diffuse large B-cell lymphoma, dysproliferative changes (dysplasias and metaplasias), embryonal carcinoma, endometrial cancer, endotheliosarcoma, ependymoma, epithelial carcinoma, erythroleukemia, esophageal cancer, estrogen-receptor positive breast cancer, essential thrombocythemia, Ewing's tumor, fibrosarcoma, follicular lymphoma, germ cell testicular cancer, glioma, glioblastoma, gliosarcoma, heavy chain disease, hemangioblastoma, hepatoma, hepatocellular cancer, hormone insensitive prostate cancer, leiomyosarcoma, leukemia, liposarcoma, lung cancer, lymphagioendotheliosarcoma, lymphangiosarcoma, lymphoblastic leukemia, lymphoma (Hodgkin's and non-Hodgkin's), malignancies and hyperproliferative disorders of the bladder, breast, colon, lung, ovaries, pancreas, prostate, skin and uterus, lymphoid malignancies of T-cell or B-cell origin, leukemia, lymphoma, medullary carcinoma, medulloblastoma, melanoma, meningioma, mesothelioma, multiple myeloma, myelogenous leukemia, myeloma, myxosarcoma, neuroblastoma, NUT midline carcinoma (NMC), non-small cell lung cancer, oligodendroglioma, oral cancer, osteogenic sarcoma, ovarian cancer, pancreatic cancer, papillary adenocarcinomas, papillary carcinoma, pinealoma, polycythemia vera, prostate cancer, rectal cancer, renal cell carcinoma, retinoblastoma, rhabdomyosarcoma, sarcoma, sebaceous gland carcinoma, seminoma, skin cancer, small cell lung carcinoma, solid tumors (carcinomas and sarcomas), small cell lung cancer, stomach cancer, squamous cell carcinoma, synovioma, sweat gland carcinoma, thyroid cancer, Waldenstrom's macroglobulinemia, testicular tumors, uterine cancer and Wilms' tumor.

Further, compounds of formula (I) may be used to treat inflammatory diseases, inflammatory conditions, and autoimmune diseases, including, but not limited to: Addison's disease, acute gout, ankylosing spondylitis, asthma, atherosclerosis, Behcet's disease, bullous skin diseases, chronic obstructive pulmonary disease (COPD), Crohn's disease, dermatitis, eczema, giant cell arteritis, glomerulonephritis, hepatitis, hypophysitis, inflammatory bowel disease, Kawasaki disease, lupus nephritis, multiple sclerosis, myocarditis, myositis, nephritis, organ transplant rejection, osteoarthritis, pancreatitis, pericarditis, Polyarteritis nodosa, pneumonitis, primary biliary cirrhosis, psoriasis, psoriatic arthritis, rheumatoid arthritis, scleritis, sclerosing cholangitis, sepsis, systemic lupus erythematosus, Takayasu's Arteritis, toxic shock, thyroiditis, type I diabetes, ulcerative colitis, uveitis, vitiligo, vasculitis, and Wegener's granulomatosis.

Compounds of formula (I), or pharmaceutically acceptable salts thereof, may be used to treat AIDS.

The compounds of formula (I) may be co-administered to a subject. The term "co-administered" means the administration of two or more different therapeutic agents or treatments (e.g., radiation treatment) that are administered to a subject by combination in the same pharmaceutical composition or separate pharmaceutical compositions. Thus co-administration involves administration at the same time of a single pharmaceutical composition comprising two or more therapeutic agents or administration of two or more different compositions to the same subject at the same or different times.

The compounds of the invention can be co-administered with a therapeutically effective amount of one or more agents to treat a cancer, where examples of the agents include, such as radiation, alkylating agents, angiogenesis inhibitors, antibodies, antimetabolites, antimitotics, antiproliferatives, antivirals, aurora kinase inhibitors, apoptosis promoters (for example, Bcl-xL, Bcl-w and Bfl-1) inhibitors, activators of death receptor pathway, Bcr-Abl kinase inhibitors, BiTE (Bi-Specific T cell Engager) antibodies, antibody drug conjugates, biologic response modifiers, cyclin-dependent kinase inhibitors, cell cycle inhibitors, cyclooxygenase-2 inhibitors, DVDs (dual variable domain antibodies), leukemia viral oncogene homolog (ErbB2) receptor inhibitors, growth factor inhibitors, heat shock protein (HSP)-90 inhibitors, histone deacetylase (HDAC) inhibitors, hormonal therapies, immunologicals, inhibitors of inhibitors of apoptosis proteins (IAPB), intercalating antibiotics, kinase inhibitors, kinesin inhibitors, Jak2 inhibitors, mammalian target of rapamycin inhibitors, microRNA's, mitogen-activated extracellular signal-regulated kinase inhibitors, multivalent binding proteins, non-steroidal anti-inflammatory drugs (NSAIDs), poly ADP (adenosine diphosphate)-ribose polymerase (PARP) inhibitors, platinum chemotherapeutics, polo-like kinase (Plk) inhibitors, phosphoinositide-3 kinase (bromodomain) inhibitors, proteosome inhibitors, purine analogs, pyrimidine analogs, receptor tyrosine kinase inhibitors, etinoids/deltoids plant alkaloids, small inhibitory ribonucleic acids (siRNAs), topoisomerase inhibitors, ubiquitin ligase inhibitors, and the like, and in combination with one or more of these agents.

BiTE antibodies are bi-specific antibodies that direct T-cells to attack cancer cells by simultaneously binding the two cells. The T-cell then attacks the target cancer cell. Examples of BiTE antibodies include adecatumumab (Micromet MT201), blinatumomab (Micromet MT103) and the like. Without being limited by theory, one of the mechanisms by which T-cells elicit apoptosis of the target cancer cell is by exocytosis of cytolytic granule components, which include perforin and granzyme B. In this regard, Bcl-2 has been shown to attenuate the induction of apoptosis by both perforin and granzyme B. These data suggest that inhibition of Bcl-2 could enhance the cytotoxic effects elicited by T-cells when targeted to cancer cells (V. R. Sutton, D. L. Vaux and J. A. Trapani, *J. of Immunology* 1997, 158 (12), 5783).

SiRNAs are molecules having endogenous RNA bases or chemically modified nucleotides. The modifications do not abolish cellular activity, but rather impart increased stability and/or increased cellular potency. Examples of chemical modifications include phosphorothioate groups, 2'-deoxynucleotide, 2'-OCH$_3$-containing ribonucleotides, 2'-F-ribonucleotides, 2'-methoxyethyl ribonucleotides, combinations thereof and the like. The siRNA can have varying lengths (e.g., 10-200 bps) and structures (e.g., hairpins, single/double strands, bulges, nicks/gaps, mismatches) and are processed in cells to provide active gene silencing. A double-stranded siRNA (dsRNA) can have the same number of nucleotides on each strand (blunt ends) or asymmetric ends (overhangs). The overhang of 1-2 nucleotides can be present on the sense and/or the antisense strand, as well as present on the 5'- and/or the 3'-ends of a given strand.

Multivalent binding proteins are binding proteins comprising two or more antigen binding sites. Multivalent binding proteins are engineered to have the three or more antigen binding sites and are generally not naturally occurring antibodies. The term "multispecific binding protein" means a binding protein capable of binding two or more related or unrelated targets. Dual variable domain (DVD) binding proteins are tetravalent or multivalent binding proteins binding proteins comprising two or more antigen binding sites. Such DVDs may be monospecific (i.e., capable of binding one antigen) or multispecific (i.e., capable of binding two or more antigens). DVD binding proteins comprising two heavy chain DVD polypeptides and two light chain DVD polypeptides are referred to as DVD Ig's. Each half of a DVD Ig comprises a heavy chain DVD polypeptide, a light chain DVD polypeptide, and two antigen binding sites. Each binding site comprises a heavy chain variable domain and a light chain variable domain with a total of 6 CDRs involved in antigen binding per antigen binding site. Multispecific DVDs include DVD binding proteins that bind DLL4 and VEGF, or C-met and EFGR or ErbB3 and EGFR.

Alkylating agents include altretamine, AMD-473, AP-5280, apaziquone, bendamustine, brostallicin, busulfan, carboquone, carmustine (BCNU), chlorambucil, CLORETAZINE® (laromustine, VNP 40101M), cyclophosphamide, decarbazine, estramustine, fotemustine, glufosfamide, ifosfamide, KW-2170, lomustine (CCNU), mafosfamide, melphalan, mitobronitol, mitolactol, nimustine, nitrogen mustard N-oxide, ranimustine, temozolomide, thiotepa, TREANDA® (bendamustine), treosulfan, rofosfamide and the like.

Angiogenesis inhibitors include endothelial-specific receptor tyrosine kinase (Tie-2) inhibitors, epidermal growth factor receptor (EGFR) inhibitors, insulin growth factor-2 receptor (IGFR-2) inhibitors, matrix metalloproteinase-2 (MMP-2) inhibitors, matrix metalloproteinase-9 (MMP-9) inhibitors, platelet-derived growth factor receptor (PDGFR) inhibitors, thrombospondin analogs, vascular endothelial growth factor receptor tyrosine kinase (VEGFR) inhibitors and the like.

Antimetabolites include ALIMTA® (pemetrexed disodium, LY231514, MTA), 5-azacitidine, XELODA® (capecitabine), carmofur, LEUSTAT® (cladribine), clofarabine, cytarabine, cytarabine ocfosfate, cytosine arabinoside, decitabine, deferoxamine, doxifluridine, eflornithine, EICAR (5-ethynyl-1-β-D-ribofuranosylimidazole-4-carboxamide), enocitabine, ethnylcytidine, fludarabine, 5-fluorouracil alone or in combination with leucovorin, GEMZAR® (gemcitabine), hydroxyurea, ALKERAN® (melphalan), mercaptopurine, 6-mercaptopurine riboside, methotrexate, mycophenolic acid, nelarabine, nolatrexed, ocfosfate, pelitrexol, pentostatin, raltitrexed, Ribavirin, triapine, trimetrexate, S-1, tiazofurin, tegafur, TS-1, vidarabine, UFT and the like.

Antivirals include ritonavir, hydroxychloroquine and the like.

Aurora kinase inhibitors include ABT-348, AZD-1152, MLN-8054, VX-680, Aurora A-specific kinase inhibitors, Aurora B-specific kinase inhibitors and pan-Aurora kinase inhibitors and the like.

Bcl-2 protein inhibitors include ABT-199, AT-101 ((−) gossypol), GENASENSE® (G3139 or oblimersen (Bcl-2-targeting antisense oligonucleotide)), IPI-194, IPI-565, N-(4-(4-((4'-chloro(1,1'-biphenyl)-2-yl)methyl)piperazin-1-yl)benzoyl)-4-(((1R)-3-(dimethylamino)-1-((phenylsulfanyl)methyl)propyl)amino)-3-nitrobenzenesulfonamide) (ABT-737), N-(4-(4-((2-(4-chlorophenyl)-5,5-dimethyl-1-cyclohex-1-en-1-yl)methyl)piperazin-1-yl)benzoyl)-4-(((1R)-3-(morpholin-4-yl)-1-((phenylsulfanyl)methyl)propyl)amino)-3-((trifluoromethyl)sulfonyl) benzenesulfonamide (ABT-263), GX-070 (obatoclax) and the like.

Bcr-Abl kinase inhibitors include DASATINIB® (BMS-354825), GLEEVEC® (imatinib) and the like.

CDK inhibitors include AZD-5438, BMI-1040, BMS-032, BMS-387, CVT-2584, flavopyridol, GPC-286199, MCS-5A, PD0332991, PHA-690509, seliciclib (CYC-202, R-roscovitine), ZK-304709 and the like.

COX-2 inhibitors include ABT-963, ARCOXIA® (etoricoxib), BEXTRA® (valdecoxib), BMS347070, CELEBREX® (celecoxib), COX-189 (lumiracoxib), CT-3, DERAIVIAXX® (deracoxib), JTE-522, 4-methyl-2-(3,4-dimethylphenyl)-1-(4-sulfamoylphenyl-1H-pyrrole), MK-663 (etoricoxib), NS-398, parecoxib, RS-57067, SC-58125, SD-8381, SVT-2016, S-2474, T-614, VIOXX® (rofecoxib) and the like.

EGFR inhibitors include EGFR antibodies, ABX-EGF, anti-EGFR immunoliposomes, EGF-vaccine, EMD-7200, ERBITUX® (cetuximab), HR3, IgA antibodies, IRESSA® (gefitinib), TARCEVA® (erlotinib or OSI-774), TP-38, EGFR fusion protein, TYKERB® (lapatinib) and the like.

ErbB2 receptor inhibitors include CP-724-714, CI-1033 (canertinib), HERCEPTIN® (trastuzumab), TYKERB® (lapatinib), OMNITARG® (2C4, petuzumab), TAK-165, GW-572016 (ionafarnib), GW-282974, EKB-569, PI-166, dHER2 (HER2 vaccine), APC-8024 (HER-2 vaccine), anti-HER/2neu bispecific antibody, B7.her2IgG3, AS HER2 trifunctional bispecfic antibodies, mAB AR-209, mAB 2B-1 and the like.

Histone deacetylase inhibitors include depsipeptide, LAQ-824, MS-275, trapoxin, suberoylanilide hydroxamic acid (SAHA), TSA, valproic acid and the like.

HSP-90 inhibitors include 17-AAG-nab, 17-AAG, CNF-101, CNF-1010, CNF-2024, 17-DMAG, geldanamycin, IPI-504, KOS-953, MYCOGRAB® (human recombinant antibody to HSP-90), NCS-683664, PU24FCl, PU-3, radicicol, SNX-2112, STA-9090 VER49009 and the like.

Inhibitors of inhibitors of apoptosis proteins include HGS 1029, GDC-0145, GDC-0152, LCL-161, LBW-242 and the like.

Antibody drug conjugates include anti-CD22-MC-MMAF, anti-CD22-MC-MMAE, anti-CD22-MCC-DM1, CR-011-vcMMAE, PSMA-ADC, MEDI-547, SGN-19Am SGN-35, SGN-75 and the like Activators of death receptor pathway include TRAIL, antibodies or other agents that target TRAIL or death receptors (e.g., DR4 and DR5) such as Apomab, conatumumab, ETR2-ST01, GDC0145, (lexatumumab), HGS-1029, LBY-135, PRO-1762 and trastuzumab.

Kinesin inhibitors include Eg5 inhibitors such as AZD4877, ARRY-520; CENPE inhibitors such as GSK923295A and the like.

JAK-2 inhibitors include CEP-701 (lesaurtinib), XL019 and INCB018424 and the like.

MEK inhibitors include ARRY-142886, ARRY-438162 PD-325901, PD-98059 and the like.

mTOR inhibitors include AP-23573, CCI-779, everolimus, RAD-001, rapamycin, temsirolimus, ATP-competitive TORC1/TORC2 inhibitors, including PI-103, PP242, PP30, Torin 1 and the like.

Non-steroidal anti-inflammatory drugs include AIVIIGESIC® (salsalate), DOLOBID® (diflunisal), MOTRIN® (ibuprofen), ORUDIS® (ketoprofen), RELAFEN® (nabumetone), FELDENE® (piroxicam), ibuprofen cream, ALEVE® (naproxen) and NAPROSYN® (naproxen), VOLTAREN® (diclofenac), INDOCIN® (indomethacin), CLINORIL® (sulindac), TOLECTIN® (tolmetin), LODINE® (etodolac), TORADOL® (ketorolac), DAYPRO® (oxaprozin) and the like.

PDGFR inhibitors include C-451, CP-673, CP-868596 and the like.

Platinum chemotherapeutics include cisplatin, ELOXATIN® (oxaliplatin) eptaplatin, lobaplatin, nedaplatin, PARAPLATIN® (carboplatin), satraplatin, picoplatin and the like.

Polo-like kinase inhibitors include BI-2536 and the like.

Phosphoinositide-3 kinase (PI3K) inhibitors include wortmannin, LY294002, XL-147, CAL-120, ONC-21, AEZS-127, ETP-45658, PX-866, GDC-0941, BGT226, BEZ235, XL765 and the like.

Thrombospondin analogs include ABT-510, ABT-567, ABT-898, TSP-1 and the like.

VEGFR inhibitors include AVASTIN® (bevacizumab), ABT-869, AEE-788, ANGIOZYME™ (a ribozyme that inhibits angiogenesis (Ribozyme Pharmaceuticals (Boulder, Colo.) and Chiron, (Emeryville, Calif.)), axitinib (AG-13736), AZD-2171, CP-547,632, IM-862, MACUGEN (pegaptamib), NEXAVAR® (sorafenib, BAY43-9006), pazopanib (GW-786034), vatalanib (PTK-787, ZK-222584), SUTENT® (sunitinib, SU-11248), VEGF trap, ZACTIMA™ (vandetanib, ZD-6474), GA101, ofatumumab, ABT-806 (mAb-806), ErbB3 specific antibodies, BSG2 specific antibodies, DLL4 specific antibodies and C-met specific antibodies, and the like.

Antibiotics include intercalating antibiotics aclarubicin, actinomycin D, amrubicin, annamycin, adriamycin, BLENOXANE® (bleomycin), daunorubicin, CAELYX® or MYOCET® (liposomal doxorubicin), elsamitrucin, epirubicin, glarbuicin, ZAVEDOS® (idarubicin), mitomycin C, nemorubicin, neocarzinostatin, peplomycin, pirarubicin, rebeccamycin, stimalamer, streptozocin, VALSTAR® (valrubicin), zinostatin and the like.

Topoisomerase inhibitors include aclarubicin, 9-aminocamptothecin, amonafide, amsacrine, becatecarin, belotecan, BN-80915, CAMPTOSAR® (irinotecan hydrochloride), camptothecin, CARDIOXANE® (dexrazoxine), diflomotecan, edotecarin, ELLENCE® or PHARMORUBICIN® (epirubicin), etoposide, exatecan, 10-hydroxycamptothecin, gimatecan, lurtotecan, mitoxantrone, orathecin, pirarbucin, pixantrone, rubitecan, sobuzoxane, SN-38, tafluposide, topotecan and the like.

Antibodies include AVASTIN® (bevacizumab), CD40-specific antibodies, chTNT-1/B, denosumab, ERBITUX® (cetuximab), HUMAX-CD4® (zanolimumab), IGF1R-specific antibodies, lintuzumab, PANOREX® (edrecolomab), RENCAREX® (WX G250), RITUXAN® (rituximab), ticilimumab, trastuzimab, CD20 antibodies types I and II and the like.

Hormonal therapies include ARIMIDEX® (anastrozole), AROMASIN® (exemestane), arzoxifene, CASODEX® (bicalutamide), CETROTIDE® (cetrorelix), degarelix, deslorelin, DESOPAN® (trilostane), dexamethasone, DROGENIL® (flutamide), EVISTA® (raloxifene), AFEMA™ (fadrozole), FARESTON® (toremifene), FASLODEX® (fulvestrant), FEMARA® (letrozole), formestane, glucocorticoids, HECTOROL® (doxercalciferol), RENAGEL® (sevelamer carbonate), lasofoxifene, leuprolide acetate, MEGACE® (megesterol), MIFEPREX® (mifepristone), NILANDRON™ (nilutamide), NOLVADEX® (tamoxifen citrate), PLENAXIS™ (abarelix), prednisone, PROPECIA® (finasteride), rilostane, SUPREFACT® (buserelin), TRELSTAR® (luteinizing hormone releasing hormone (LHRH)), VANTAS® (Histrelin implant), VETORYL® (trilostane or modrastane), ZOLADEX® (fosrelin, goserelin) and the like.

Deltoids and retinoids include seocalcitol (EB1089, CB1093), lexacalcitrol (KH1060), fenretinide, PANRETIN® (aliretinoin), ATRAGEN® (liposomal tretinoin), TARGRETIN® (bexarotene), LGD-1550 and the like.

PARP inhibitors include ABT-888 (veliparib), olaparib, KU-59436, AZD-2281, AG-014699, BSI-201, BGP-15, INO-1001, ONO-2231 and the like.

Plant alkaloids include, but are not limited to, vincristine, vinblastine, vindesine, vinorelbine and the like.

Proteasome inhibitors include VELCADE® (bortezomib), MG132, NPI-0052, PR-171 and the like.

Examples of immunologicals include interferons and other immune-enhancing agents. Interferons include interferon alpha, interferon alpha-2a, interferon alpha-2b, interferon beta, interferon gamma-1a, ACTIMMUNE® (interferon gamma-1b) or interferon gamma-nl, combinations thereof and the like. Other agents include ALFAFERONE®, (IFN-α), BAM-002 (oxidized glutathione), BEROMUN® (tasonermin), BEXXAR® (tositumomab), CAMPATH® (alemtuzumab), CTLA4 (cytotoxic lymphocyte antigen 4), decarbazine, denileukin, epratuzumab, GRANOCYTE® (lenograstim), lentinan, leukocyte alpha interferon, imiquimod, MDX-010 (anti-CTLA-4), melanoma vaccine, mitumomab, molgramostim, MYLOTARG™ (gemtuzumab ozogamicin), NEUPOGEN® (filgrastim), OncoVAC-CL, OVAREX® (oregovomab), pemtumomab (Y-muHMFG1), PROVENGE® (sipuleucel-T), sargaramostim, sizofilan, teceleukin, THERACYS® (Bacillus Calmette-Guerin), ubenimex, VIRULIZIN® (immunotherapeutic, Lorus Pharmaceuticals), Z-100 (Specific Substance of Maruyama (SSM)), WF-10 (Tetrachlorodecaoxide (TCDO)), PROLEUKIN® (aldesleukin), ZADAXIN® (thymalfasin), ZENAPAX® (daclizumab), ZEVALIN® (90Y-Ibritumomab tiuxetan) and the like.

Biological response modifiers are agents that modify defense mechanisms of living organisms or biological responses, such as survival, growth or differentiation of tissue cells to direct them to have anti-tumor activity and include krestin, lentinan, sizofiran, picibanil PF-3512676 (CpG-8954), ubenimex and the like.

Pyrimidine analogs include cytarabine (ara C or Arabinoside C), cytosine arabinoside, doxifluridine, FLUDARA® (fludarabine), 5-FU (5-fluorouracil), floxuridine, GEMZAR® (gemcitabine), TOMUDEX® (ratitrexed), TROXATYL™ (triacetyluridine troxacitabine) and the like.

Purine analogs include LANVIS® (thioguanine) and PURI-NETHOL® (mercaptopurine).

Antimitotic agents include batabulin, epothilone D (KOS-862), N-(2-((4-hydroxyphenyl)amino)pyridin-3-yl)-4-methoxybenzenesulfonamide, ixabepilone (BMS 247550), paclitaxel, TAXOTERE® (docetaxel), PNU100940 (109881), patupilone, XRP-9881 (larotaxel), vinflunine, ZK-EPO (synthetic epothilone) and the like.

Ubiquitin ligase inhibitors include MDM2 inhibitors, such as nutlins, NEDD8 inhibitors such as MLN4924 and the like.

Compounds of this invention can also be used as radiosensitizers that enhance the efficacy of radiotherapy. Examples of radiotherapy include external beam radiotherapy, teletherapy, brachytherapy and sealed, unsealed source radiotherapy and the like.

Additionally, compounds having formula (I) may be combined with other chemotherapeutic agents such as ABRAXANE™ (ABI-007), ABT-100 (farnesyl transferase inhibitor), ADVEXIN®(Ad5CMV-p53 vaccine), ALTOCOR® or MEVACOR® (lovastatin), AMPLIGEN® (poly I:poly C12U, a synthetic RNA), APTOSYN® (exisulind), AREDIA® (pamidronic acid), arglabin, L-asparaginase, atamestane (1-methyl-3,17-dione-androsta-1,4-diene), AVAGE® (tazarotene), AVE-8062 (combreastatin derivative) BEC2 (mitumomab), cachectin or cachexin (tumor necrosis factor), canvaxin (vaccine), CEAVAC® (cancer vaccine), CELEUK® (celmoleukin), CEPLENE® (histamine dihydrochloride), CERVARIX® (human papillomavirus vaccine), CHOP® (C: CYTOXAN® (cyclophosphamide); H: ADRIAMYCIN® (hydroxydoxorubicin); O: Vincristine (ONCOVIN®); P: prednisone), CYPAT™ (cyproterone acetate), combrestatin A4P, DAB(389)EGF (catalytic and translocation domains of diphtheria toxin fused via a His-Ala linker to human epidermal growth factor) or TransMID-107R™ (diphtheria toxins), dacarbazine, dactinomycin, 5,6-dimethylxanthenone-4-acetic acid (DMXAA), eniluracil, EVIZON™ (squalamine lactate), DIMERICINE® (T4N5 liposome lotion), discodermolide, DX-8951f (exatecan mesylate), enzastaurin, EP0906 (epithilone B), GARDASIL® (quadrivalent human papillomavirus (Types 6, 11, 16, 18) recombinant vaccine), GASTRIMMUNE®, GENASENSE®, GMK (ganglioside conjugate vaccine), GVAX® (prostate cancer vaccine), halofuginone, histerelin, hydroxycarbamide, ibandronic acid, IGN-101, IL-13-PE38, IL-13-

PE38QQR (cintredekin besudotox), IL-13-pseudomonas exotoxin, interferon-α, interferon-γ, JUNOVAN™ or MEPACT™ (mifamurtide), lonafarnib, 5,10-methylenetetrahydrofolate, miltefosine (hexadecylphosphocholine), NEOVASTATAAE-941), NEUTREXIN® (trimetrexate glucuronate), NIPENT® (pentostatin), ONCONASE® (a ribonuclease enzyme), ONCOPHAGE® (melanoma vaccine treatment), ONCOVAX® (IL-2 Vaccine), ORATHECIN™ (rubitecan), OSIDEM® (antibody-based cell drug), OVAREX® MAb (murine monoclonal antibody), paclitaxel, PANDIMEX™ (aglycone saponins from ginseng comprising 20(S)protopanaxadiol (aPPD) and 20(S)protopanaxatriol (aPPT)), panitumumab, PANVAC-VF (investigational cancer vaccine), pegaspargase, PEG Interferon A, phenoxodiol, procarbazine, rebimastat, REMOVAB® (catumaxomab), REVLIMID® (lenalidomide), RSR13 (efaproxiral), SOMATULINE® LA (lanreotide), SORIATANE® (acitretin), staurosporine (Streptomyces staurospores), talabostat (PT100), TARGRETIN® (bexarotene), TAXOPREXIN® (DHA-paclitaxel), TELCYTA® (canfosfamide, TLK286), temilifene, TEMODAR® (temozolomide), tesmilifene, thalidomide, THERATOPE® (STn-KLH), thymitaq (2-amino-3,4-dihydro-6-methyl-4-oxo-5-(4-pyridylthio)quinazoline dihydrochloride), TNFERADE™ (adenovector: DNA carrier containing the gene for tumor necrosis factor-α), TRACLEER® or ZAVESCA® (bosentan), tretinoin (Retin-A), tetrandrine, TRISENOX® (arsenic trioxide), VIRULIZIN®, ukrain (derivative of alkaloids from the greater celandine plant), vitaxin (anti-alphavbeta3 antibody), XCYTRIN® (motexafin gadolinium), XINLAY™ (atrasentan), XYOTAX™ (paclitaxel poliglumex), YONDELIS® (trabectedin), ZD-6126, ZINECARD® (dexrazoxane), ZOMETA® (zolendronic acid), zorubicin and the like.

The compounds of the invention can also be co-administered with a therapeutically effective amount of one or more agents to treat an inflammatory disease or condition, or autoimmune disease, where examples of the agents include, such as methotrexate, 6-mercaptopurine, azathioprine sulphasalazine, mesalazine, olsalazine chloroquinine/hydroxychloroquine, pencillamine, aurothiomalate (intramuscular and oral), azathioprine, cochicine, corticosteroids (oral, inhaled and local injection), beta-2 adrenoreceptor agonists (salbutamol, terbutaline, salmeteral), xanthines (theophylline, aminophylline), cromoglycate, nedocromil, ketotifen, ipratropium and oxitropium, cyclosporin, FK506, rapamycin, mycophenolate mofetil, leflunomide, NSAIDs, for example, ibuprofen, corticosteroids such as prednisolone, phosphodiesterase inhibitors, adensosine agonists, antithrombotic agents, complement inhibitors, adrenergic agents, agents which interfere with signalling by proinflammatory cytokines such as TNFα or IL-1 (e.g., NIK, IKK, p38 or MAP kinase inhibitors), IL-1β converting enzyme inhibitors, T-cell signalling inhibitors such as kinase inhibitors, metalloproteinase inhibitors, sulfasalazine, 6-mercaptopurines, angiotensin converting enzyme inhibitors, soluble cytokine receptors and derivatives thereof (e.g. soluble p55 or p75 TNF receptors and the derivatives p75TNFRIgG (etanercept) and p55TNFRIgG (Lenercept), sIL-1RI, sIL-1RII, sIL-6R), antiinflammatory cytokines (e.g. IL-4, IL-10, IL-11, IL-13 and TGFβ), celecoxib, folic acid, hydroxychloroquine sulfate, rofecoxib, etanercept, infliximab, naproxen, valdecoxib, sulfasalazine, methylprednisolone, meloxicam, methylprednisolone acetate, gold sodium thiomalate, aspirin, triamcinolone acetonide, propoxyphene napsylate/apap, folate, nabumetone, diclofenac, piroxicam, etodolac, diclofenac sodium, oxaprozin, oxycodone HCl, hydrocodone bitartrate/apap, diclofenac sodium/misoprostol, fentanyl, anakinra, tramadol HCl, salsalate, sulindac, cyanocobalamin/fa/pyridoxine, acetaminophen, alendronate sodium, prednisolone, morphine sulfate, lidocaine hydrochloride, indomethacin, glucosamine sulf/chondroitin, amitriptyline HCl, sulfadiazine, oxycodone HCl/acetaminophen, olopatadine HCl misoprostol, naproxen sodium, omeprazole, cyclophosphamide, rituximab, IL-1 TRAP, MRA, CTLA4-IG, IL-18 BP, anti-IL-12, Anti-IL15, BIRB-796, SC10-469, VX-702, AMG-548, VX-740, Roflumilast, IC-485, CDC-801, S1P1 agonists (such as FTY720), PKC family inhibitors (such as Ruboxistaurin or AEB-071) and Mesopram. In certain embodiments, combinations include methotrexate or leflunomide and in moderate or severe rheumatoid arthritis cases, cyclosporine and anti-TNF antibodies as noted above.

Non-limiting examples of therapeutic agents for inflammatory bowel disease with which a compound of formula (I) of the invention may be co-administered include the following: budenoside; epidermal growth factor; corticosteroids; cyclosporin, sulfasalazine; aminosalicylates; 6-mercaptopurine; azathioprine; metronidazole; lipoxygenase inhibitors; mesalamine; olsalazine; balsalazide; antioxidants; thromboxane inhibitors; IL-1 receptor antagonists; anti-IL-1β monoclonal antibodies; anti-IL-6 monoclonal antibodies; growth factors; elastase inhibitors; pyridinyl-imidazole compounds; antibodies to or antagonists of other human cytokines or growth factors, for example, TNF, LT, IL-1, IL-2, IL-6, IL-7, IL-8, IL-12, IL-15, IL-16, IL-23, EMAP-II, GM-CSF, FGF, and PDGF; cell surface molecules such as CD2, CD3, CD4, CD8, CD25, CD28, CD30, CD40, CD45, CD69, CD90 or their ligands; methotrexate; cyclosporine; FK506; rapamycin; mycophenolate mofetil; leflunomide; NSAIDs, for example, ibuprofen; corticosteroids such as prednisolone; phosphodiesterase inhibitors; adenosine agonists; antithrombotic agents; complement inhibitors; adrenergic agents; agents which interfere with signalling by proinflammatory cytokines such as TNFα or IL-1 (e.g. NIK, IKK, or MAP kinase inhibitors); IL-1β converting enzyme inhibitors; TNFα converting enzyme inhibitors; T-cell signalling inhibitors such as kinase inhibitors; metalloproteinase inhibitors; sulfasalazine; azathioprine; 6-mercaptopurines; angiotensin converting enzyme inhibitors; soluble cytokine receptors and derivatives thereof (e.g. soluble p55 or p75 TNF receptors, sIL-1RI, sIL-1RII, sIL-6R) and antiinflammatory cytokines (e.g. IL-4, IL-10, IL-11, IL-13 and TGFβ). Preferred examples of therapeutic agents for Crohn's disease with which a compound of formula (I) may be combined include the following: TNF antagonists, for example, anti-TNF antibodies, D2E7 (adalimumab), CA2 (infliximab), CDP 571, TNFR-Ig constructs, (p75TNFRIgG (etanercept) and p55TNFRIgG (LENERCEPT™) inhibitors and PDE4 inhibitors. A compound of formula (I) may be combined with corticosteroids, for example, budenoside and dexamethasone; sulfasalazine, 5-aminosalicylic acid; olsalazine; and agents which interfere with synthesis or action of proinflammatory cytokines such as IL-1, for example, IL-1β converting enzyme inhibitors and IL-1ra; T cell signaling inhibitors, for example, tyrosine kinase inhibitors; 6-mercaptopurine; IL-11; mesalamine; prednisone; azathioprine; mercaptopurine; infliximab; methylprednisolone sodium succinate; diphenoxylate/atrop sulfate; loperamide hydrochloride; methotrexate; omeprazole; folate; ciprofloxacin/dextrose-water; hydrocodone bitartrate/apap; tetracycline hydrochloride; fluocinonide; metronidazole; thimerosal/boric acid; cholestyramine/sucrose; ciprofloxacin hydrochloride; hyoscyamine sulfate; meperidine hydrochloride; midazolam hydrochloride; oxycodone HCl/acetaminophen; promethazine hydrochloride; sodium phosphate; sulfamethoxazole/trimethoprim; celecoxib; polycarbophil; propoxyphene napsylate; hydrocortisone; multivitamins; balsalazide disodium; codeine phosphate/apap; colesevelam HCl; cyanocobalamin; folic acid; levofloxacin; methylprednisolone; natalizumab and interferon-gamma.

Non-limiting examples of therapeutic agents for multiple sclerosis with which a compound of formula (I) may be co-administered include the following: corticosteroids; prednisolone; methylprednisolone; azathioprine; cyclophosphamide; cyclosporine; methotrexate; 4-aminopyridine; tizanidine; interferon-β1a (AVONEX®; Biogen); interferon-β1b (BETASERON®; Chiron/Berlex); interferon α-n3) (Interferon Sciences/Fujimoto), interferon-α (Alfa Wassermann/J&J), interferon β1A-IF (Serono/Inhale Therapeutics), Peginterferon α 2b (Enzon/Schering-Plough), Copolymer 1 (Cop-1; COPAXONE®; Teva Pharmaceutical Industries, Inc.); hyperbaric oxygen; intravenous immunoglobulin; cladribine; antibodies to or antagonists of other human cytokines or growth factors and their receptors, for example, TNF, LT, IL-1, IL-2, IL-6, IL-7, IL-8, IL-12, IL-23, IL-15, IL-16, EMAP-II, GM-CSF, FGF, and PDGF. A compound of formula (I) cmay be combined with antibodies to cell surface molecules such as CD2, CD3, CD4, CD8, CD19, CD20, CD25, CD28, CD30, CD40, CD45, CD69, CD80, CD86, CD90 or their ligands. A compound of formula (I) may also be combined with agents such as methotrexate, cyclosporine, FK506, rapamycin, mycophenolate mofetil, leflunomide, an S1P1 agonist, NSAIDs, for example, ibuprofen, corticosteroids such as prednisolone, phosphodiesterase inhibitors, adensosine agonists, antithrombotic agents, complement inhibitors, adrenergic agents, agents which interfere with signalling by proinflammatory cytokines such as TNFα or IL-1 (e.g., NIK, IKK, p38 or MAP kinase inhibitors), IL-1β converting enzyme inhibitors, TACE inhibitors, T-cell signaling inhibitors such as kinase inhibitors, metalloproteinase inhibitors, sulfasalazine, azathioprine, 6-mercaptopurines, angiotensin converting enzyme inhibitors, soluble cytokine receptors and derivatives thereof (e.g. soluble p55 or p75 TNF receptors, sIL-1RI, sIL-1RII, sIL-6R) and antiinflammatory cytokines (e.g. IL-4, IL-10, IL-13 and TGFβ).

A compound of formula (I) may also be co-administered with agents, such as alemtuzumab, dronabinol, daclizumab, mitoxantrone, xaliproden hydrochloride, fampridine, glatiramer acetate, natalizumab, sinnabidol, α-immunokine NNSO3, ABR-215062, AnergiX.MS, chemokine receptor antagonists, BBR-2778, calagualine, CPI-1189, LEM (liposome encapsulated mitoxantrone), THC.CBD (cannabinoid agonist), MBP-8298, mesopram (PDE4 inhibitor), MNA-715, anti-IL-6 receptor antibody, neurovax, pirfenidone allotrap 1258 (RDP-1258), sTNF-R1, talampanel, teriflunomide, TGF-beta2, tiplimotide, VLA-4 antagonists (for example, TR-14035, VLA4 Ultrahaler, Antegran-ELAN/Biogen), interferon gamma antagonists and IL-4 agonists.

Non-limiting examples of therapeutic agents for ankylosing spondylitis with which a compound of formula (I) may be co-administered include the following: ibuprofen, diclofenac, misoprostol, naproxen, meloxicam, indomethacin, diclofenac, celecoxib, rofecoxib, sulfasalazine, methotrexate, azathioprine, minocyclin, prednisone, and anti-TNF antibodies, D2E7 (HUMIRA®), CA2 (infliximab), CDP 571, TNFR-Ig constructs, (p75TNFRIgG (ENBREL®) and p55TNFRIgG (LENERCEPT®).

Non-limiting examples of therapeutic agents for asthma with which a compound of formula (I) may be co-administered include the following: albuterol, salmeterol/fluticasone, montelukast sodium, fluticasone propionate, budesonide, prednisone, salmeterol xinafoate, levalbuterol HCl, albuterol sulfate/ipratropium, prednisolone sodium phosphate, triamcinolone acetonide, beclomethasone dipropionate, ipratropium bromide, azithromycin, pirbuterol acetate, prednisolone, theophylline anhydrous, methylprednisolone sodium succinate, clarithromycin, zafirlukast, formoterol fumarate, influenza virus vaccine, amoxicillin trihydrate, flunisolide, allergy injection, cromolyn sodium, fexofenadine hydrochloride, flunisolide/menthol, amoxicillin/clavulanate, levofloxacin, inhaler assist device, guaifenesin, dexamethasone sodium phosphate, moxifloxacin HCl, doxycycline hyclate, guaifenesin/d-methorphan, p-ephedrine/cod/chlorphenir, gatifloxacin, cetirizine hydrochloride, mometasone furoate, salmeterol xinafoate, benzonatate, cephalexin, pe/hydrocodone/chlorphenir, cetirizine HCl/pseudoephed, phenylephrine/cod/promethazine, codeine/promethazine, cefprozil, dexamethasone, guaifenesin/pseudoephedrine, chlorpheniramine/hydrocodone, nedocromil sodium, terbutaline sulfate, epinephrine, methylprednisolone, anti-IL-13 antibody, and metaproterenol sulfate.

Non-limiting examples of therapeutic agents for COPD with which a compound of formula (I) may be co-administered include the following: albuterol sulfate/ipratropium, ipratropium bromide, salmeterol/fluticasone, albuterol, salmeterol xinafoate, fluticasone propionate, prednisone, theophylline anhydrous, methylprednisolone sodium succinate, montelukast sodium, budesonide, formoterol fumarate, triamcinolone acetonide, levofloxacin, guaifenesin, azithromycin, beclomethasone dipropionate, levalbuterol HCl, flunisolide, ceftriaxone sodium, amoxicillin trihydrate, gatifloxacin, zafirlukast, amoxicillin/clavulanate, flunisolide/menthol, chlorpheniramine/hydrocodone, metaproterenol sulfate, methylprednisolone, mometasone furoate, p-ephedrine/cod/chlorphenir, pirbuterol acetate, p-ephedrine/loratadine, terbutaline sulfate, tiotropium bromide, (R,R)-formoterol, TgAAT, cilomilast and roflumilast.

Non-limiting examples of therapeutic agents for psoriasis with which a compound of formula (I) may be co-administered include the following: calcipotriene, clobetasol propionate, triamcinolone acetonide, halobetasol propionate, tazarotene, methotrexate, fluocinonide, betamethasone diprop augmented, fluocinolone acetonide, acitretin, tar shampoo, betamethasone valerate, mometasone furoate, ketoconazole, pramoxine/fluocinolone, hydrocortisone valerate, flurandrenolide, urea, betamethasone, clobetasol propionate/emoll, fluticasone propionate, azithromycin, hydrocortisone, moisturizing formula, folic acid, desonide, pimecrolimus, coal tar, diflorasone diacetate, etanercept folate, lactic acid, methoxsalen, hc/bismuth subgal/znox/resor, methylprednisolone acetate, prednisone, sunscreen, halcinonide, salicylic acid, anthralin, clocortolone pivalate, coal extract, coal tar/salicylic acid, coal tar/salicylic acid/sulfur, desoximetasone, diazepam, emollient, fluocinonide/emollient, mineral oil/castor oil/na lact, mineral oil/peanut oil, petroleum/isopropyl myristate, psoralen, salicylic acid, soap/tribromsalan, thimerosal/boric acid, celecoxib, infliximab, cyclosporine, alefacept, efalizumab, tacrolimus, pimecrolimus, PUVA, UVB, sulfasalazine, ABT-874 and ustekinamab.

Non-limiting examples of therapeutic agents for psoriatic arthritis with which a compound of formula (I) may be co-administered include the following: methotrexate, etanercept, rofecoxib, celecoxib, folic acid, sulfasalazine, naproxen, leflunomide, methylprednisolone acetate, indomethacin, hydroxychloroquine sulfate, prednisone, sulindac, betamethasone diprop augmented, infliximab, methotrexate, folate, triamcinolone acetonide, diclofenac, dimethylsulfoxide, piroxicam, diclofenac sodium, ketoprofen, meloxicam, methylprednisolone, nabumetone, tolmetin sodium, calcipotriene, cyclosporine, diclofenac sodium/misoprostol, fluocinonide, glucosamine sulfate, gold sodium thiomalate, hydrocodone bitartrate/apap, ibuprofen, risedronate sodium, sulfadiazine, thioguanine, valdecoxib, alefacept, D2E7 (adalimumab), and efalizumab.

Preferred examples of therapeutic agents for SLE (Lupus) with which a compound of formula (I) may be co-administered include the following: NSAIDS, for example, diclofenac, naproxen, ibuprofen, piroxicam, indomethacin; COX2 inhibitors, for example, celecoxib, rofecoxib, valdecoxib; anti-malarials, for example, hydroxychloroquine; steroids, for example, prednisone, prednisolone, budenoside, dexamethasone; cytotoxics, for example, azathioprine, cyclophosphamide, mycophenolate mofetil, methotrexate; inhibitors of PDE4 or purine synthesis inhibitor, for example Cellcept®. A compound of formula (I) may also be combined with agents such as sulfasalazine, 5-aminosalicylic acid, olsalazine, Imuran® and agents which interfere with synthesis, production or action of proinflammatory cytokines such as IL-1, for example, caspase inhibitors like IL-1β converting enzyme inhibitors and IL-1ra. A compound of formula (I) may also be used with T cell signaling inhibitors, for example, tyrosine kinase inhibitors; or molecules that target T cell activation molecules, for example, CTLA-4-IgG or anti-B7 family antibodies, anti-PD-1 family antibodies. A compound of formula (I) may be combined with IL-11 or anti-cytokine antibodies, for example, fonotolizumab (anti-IFNg antibody), or anti-receptor receptor antibodies, for example, anti-IL-6 receptor antibody and antibodies to B-cell surface molecules. A compound of formula (I) may also be used with LW 394 (abetimus), agents that deplete or inactivate B-cells, for example, Rituximab (anti-CD20 antibody), lymphostat-B (anti-BlyS antibody), TNF antagonists, for example, anti-TNF antibodies, D2E7 (adalimumab), CA2 (infliximab), CDP 571, TNFR-Ig constructs, (p75TNFRIgG (etanercept) and p55TNFRIgG (LENERCEPT™).

The compounds of the invention can also be co-administered with a therapeutically effective amount of one or more agents used in the prevention or treatment of AIDS, where examples of the agents include, HIV reverse transcriptase inhibitors, HIV protease inhibitors, immunomodulators, and other retroviral drugs. Examples of reverse transcriptase inhibitors include, but are not limited to, abacavir, adefovir, didanosine, dipivoxil delavirdine, efavirenz, lamivudine, nevirapine, stavudine zalcitabine, and zidovudine. Examples of protease inhibitors include, but are not limited to, amprenavir, indinavir, lopinavir, nelfinavir, ritonavir, and saquinavir.

The following Examples may be used for illustrative purposes and should not be deemed to narrow the scope of the invention.

EXAMPLES

Example 1

4-[2-(cyclopropylmethoxy)-4-(3-methyl-1H-pyrazol-5-yl)phenyl]-6-methyl-1,6-dihydro-7H-pyrrolo[2,3-c]pyridin-7-one

Example 1a (E)-2-(5-bromo-2-methoxy-3-nitropyridin-4-yl)-N,N-dimethylethenamine 5-Bromo-2-methoxy-4-methyl-3-nitropyridine (15.0 g, 60.7 mmol) was dissolved in dimethylformamide (300 mL), and lithium methanolate (6.07 mL, 6.07 mmol, 1 M) was added. The reaction mixture was heated at 100° C. To this mixture was added 1,1-dimethoxy-N,N-dimethylmethanamine (64.5 mL, 486 mmol) over 10 minutes. The reaction mixture was stirred at 95° C. for 16 hours. The reaction mixture was cooled to ambient temperature and water was added carefully (300 mL, exothermic). The resulting precipitate was collected by vacuum filtration, washed with water, and dried to provide the title compound (13.9 g, 45.9 mmol, 76% yield).

Example 1b 4-bromo-7-methoxy-1H-pyrrolo[2,3-c]pyridine

Example 1a (13.9 g, 45.8 mmol) and ethyl acetate (150 mL) were added to Ra—Ni 2800 (pre-washed with ethanol), water slurry (6.9 g, 118 mmol) in a stainless steel pressure bottle and stirred for 30 minutes at 30 psi of $H_2$ and ambient temperature. The reaction mixture was filtered, and concentrated. The residue was triturated with dichloromethane, and the solid filtered to provide the title compound (5.82 g). The mother liquor was concentrated and the residue triturated again with dichloromethane and filtered to provide an additional 1.63 g of the title compound. Total yield=7.45 g, 72% yield

Example 1c 4-bromo-7-methoxy-1-tosyl-1H-pyrrolo[2,3-c]pyridine

A solution of Example 1b (7.42 g, 32.7 mmol) in dimethylformamide (235 mL) was stirred at ambient temperature. To this solution was added sodium hydride (1.18 g, 1.96 g of 60% dispersion in oil, 49.0 mmol), and the reaction mixture was stirred for 10 minutes. P-toluenesulfonyl chloride (9.35 g, 49.0 mmol) was then added portion-wise, and the mixture was stirred at ambient temperature under nitrogen for 16 hours. The reaction mixture was quenched carefully with water and the resulting beige solid collected by vacuum filtration on a Buchner funnel, and washed with water. The solid was collected and dried in a vacuum oven at 50° C. to provide 12.4 g (100%) of the title compound.

Example 1d 4-bromo-1-tosyl-1H-pyrrolo[2,3-c]pyridin-7(6H)-one

A solution of Example 1c (12.4 g, 32.6 mmol) in dioxane (140 mL) was stirred at ambient temperature. To this solution was added 4M HCl in dioxane (140 mL). The reaction mixture was stirred at 40° C. for 16 hours. The reaction mixture was cooled to ambient temperature and concentrated. The residue was triturated with diethylether, filtered, and rinsed with additional diethylether and dried to provide the title compound (11.23 g, 30.6 mmol, 94% yield) as a beige solid.

Example 1e 4-bromo-6-methyl-1-tosyl-1H-pyrrolo[2,3-c]pyridin-7(6H)-one

Sodium hydride (0.875 g, 36.5 mmol, 1.46 g of a 60% in oil dispersion) was added to a stirring solution of Example 1d (11.2 g, 30.4 mmol) in dimethylformamide (217 mL) under nitrogen. After 30 minutes, iodomethane (2.27 mL, 36.5 mmol) was added and the solution was stirred at ambient temperature for 3 hours. Upon addition of water (250 mL) a precipitate formed. The precipitate was collected by vacuum filtration, rinsed with water (50 mL) and dried in a vacuum oven at 55° C. overnight to provide 11.2 g of the title compound (96%).

Example 1f 6-methyl-4-(4,4,5,5-tetramethyl-1,3,2-dioxaborolan-2-yl)-1-tosyl-1H-pyrrolo[2,3-c]pyridin-7(6H)-one Example 1e (6.55 g, 17.2 mmol), 4,4,4',4',5,5,5',5'-octamethyl-2,2'-bi(1,3,2-dioxaborolane) (8.73 g, 34.4 mmol), potassium acetate (3.71 g, 37.8 mmol), tris(dibenzylideneacetone)dipalladium(O) (0.393 g, 0.430 mmol) and 2-dicyclohexylphosphino-2',4',6'-triisopropylbiphenyl (X-PHOS, 0.819 g, 1.72 mmol) were combined and sparged with argon for 1 hour with stirring. Dioxane (86 mL) was sparged with nitrogen for 1 hour, and transferred via cannula under nitrogen to the solid components. The mixture was heated under argon at 80° C. for 5 hours. The reaction mixture was cooled to ambient temperature, partitioned between ethyl acetate and water, and filtered through Celite. The ethyl acetate layer was washed twice with saturated aqueous sodium chloride, dried (anhydrous sodium sulfate), filtered, and concentrated. The residue was purified by chromatography (silica gel, 25-80% ethyl acetate in hexane). The resulting material from chromatography was triturated with a minimal amount of hexanes (30 mL) and the particulate solid was collected by filtration, rinsed with a minimal amount of hexanes and dried to constant mass to afford the title compound (5.4 g, 73%).

Example 1g 1-(4-bromo-3-(cyclopropylmethoxy)phenyl)ethanone 1-(4-bromo-3-hydroxyphenyl)ethanone (2.04 g, 9.50 mmol), (bromomethyl)cyclopropane (1.01 mL, 10.5 mmol) and potassium carbonate (1.58 g, 11.4 mmol) were combined in dimethylsulfoxide (10 mL). The reaction mixture was heated at 50° C. for 3 hours. The reaction mixture was partitioned with ethyl acetate and water. The organic layer was washed with saturated aqueous sodium chloride, dried with anhydrous sodium sulfate, filtered, and concentrated. The residue was purified by flash chromatography (silica gel, 10-20% ethyl acetate in heptanes) to provide the title compound (2.05 g, 80%).

Example 1h (Z)-1-(4-bromo-3-(cyclopropylmethoxy)phenyl)-3-hydroxybut-2-en-1-one

Example 1g (1.66 g, 6.17 mmol), sodium ethoxide (0.504 g, 7.40 mmol) and anhydrous ethyl acetate (2.42 mL, 24.7 mmol) were combined and stirred at ambient temperature for 18 hours. To this reaction mixture was added sodium ethoxide (0.840 mg, 1.23 mmol) again and the mixture was stirred at ambient temperature for an additional 4 hours. The reaction mixture was partitioned with ethyl acetate and 1M HCl. The organic layer was washed with saturated aqueous sodium chloride, dried with anhydrous sodium sulfate, filtered, and concentrated. The residue was purified by flash chromatography (silica gel, 0-10% ethyl acetate in heptanes) to provide the title compound (1.57 g, 82%).

Example 1i 5-(4-bromo-3-(cyclopropylmethoxy)phenyl)-3-methyl-1H-pyrazole

Example 1h (1.50 g, 4.82 mmol) and hydrazine (0.159 mL, 5.06 mmol) were combined in ethanol (20 mL). The reaction mixture was stirred at ambient temperature for 1 hour and concentrated to provide the title compound (1.48 g, 100%).

Example 1j

4-[2-(cyclopropylmethoxy)-4-(3-methyl-1H-pyrazol-5-yl)phenyl]-6-methyl-1,6-dihydro-7H-pyrrolo[2,3-c]pyridin-7-one Example 1f (70.0 mg, 0.163 mmol), Example 1i (50.2 mg, 0.163 mmol), cesium fluoride (74.5 mg, 0.490 mmol) and tetrakis(triphenylphosphine)palladium(O) (9.4 mg, 8.1 µmol) were combined in a mixture of dimethoxyethane (2 mL) and methanol (1 mL). The reaction mixture was purged with nitrogen for 15 minutes and heated in a microwave reactor at 130° C. for 80 minutes. The reaction mixture was partitioned with ethyl acetate and water. The organic layer was washed with saturated aqueous sodium chloride, dried with anhydrous sodium sulfate, treated with 3-mercaptopropyl functionalized silica gel, filtered, and concentrated. The residue was purified by flash chromatography (silica gel, 2-6% methanol in dichloromethane) to provide the title compound (34 mg, 56%). $^1$H NMR (300 MHz, DMSO-$d_6$) δ 12.53 (s, 1 H) 11.93 (s, 1 H) 7.08-7.57 (m, 5 H) 6.49 (s, 1 H) 5.98-6.29 (m, 1H) 3.90 (d, J=6.44 Hz, 2 H) 3.56 (s, 3 H) 2.28 (s, 3 H) 1.02-1.15 (m, 1 H) 0.41-0.53 (m, 2H) 0.18-0.31 (m, 2 H). MS (ESI+) m/z 375 (M+H)$^+$.

Example 2

N-[4-(2,4-difluorophenoxy)-2-[(dimethylamino)methyl]-5-(6-methyl-7-oxo-6,7-dihydro-1H-pyrrolo[2,3-c]pyridin-4-yl)phenyl]ethanesulfonamide Example 2a 4-bromo-5-(2,4-difluorophenoxy)-2-nitrobenzoic acid A mixture of 4-bromo-5-fluoro-2-nitrobenzoic acid (3.5 g, 13.3 mmol), 2,4-difluorophenol (1.5 mL, 15.70 mmol), cesium carbonate (9.5 g, 29.2 mmol) and dimethylsulfoxide (28 mL) was heated at 110° C. for 1 hour. After cooling to ambient temperature, water (100 mL) was added. The solution was acidified with 1N HCl (60 mL) and was extracted with ethyl acetate. The ethyl acetate layer was washed with water, saturated aqueous sodium chloride, dried (anhydrous magnesium sulfate), filtered, and concentrated to provide the title compound (4.73 g, 12.64 mmol, 95% yield)

Example 2b methyl 4-bromo-5-(2,4-difluorophenoxy)-2-nitrobenzoate

Oxalyl dichloride (1.1 mL, 13.00 mmol) was added dropwise to a 0° C. suspension of Example 2a (4.3 g, 11.49 mmol) and dichloromethane (50 mL). 3 drops of dimethylformamide were added and the reaction mixture was stirred at ambient temperature for 2 hours. After cooling to 0° C., methanol (9.5 mL, 235 mmol) was added dropwise. The solution was stirred for 15 minutes at 0° C. and for 2.5 hours at ambient temperature The solution was diluted with dichloromethane and was washed with water, saturated aqueous sodium bicarbonate solution, dried (anhydrous sodium sulfate), filtered, and concentrated to provide the title compound (4.3 g, 11.08 mmol, 96% yield).

Example 2c methyl 2-amino-4-bromo-5-(2,4-difluorophenoxy)benzoate

A solution of Example 2b (150 mg, 0.386 mmol), iron powder (108 mg, 1.934 mmol), ammonia hydrochloride (20.67 mg, 0.386 mmol), ethanol (11 mL), tetrahydrofuran (4.4 mL), and water (2.2 mL) was stirred at 85° C. for 3 hours. The reaction mixture was cooled briefly, and filtered through Celite. The filter pad was rinsed well with tetrahydrofuran. The filtrate was diluted with ethyl acetate and was washed with water, saturated aqueous sodium chloride, dried (anhydrous magnesium sulfate), filtered, and concentrated to provide the title compound (140 mg, 0.391 mmol, 101% yield).

Example 2d 4-bromo-5-(2,4-difluorophenoxy)-2-(ethylsulfonamido)benzoic acid

Ethanesulfonyl chloride (3.3 mL, 34.8 mmol) was added dropwise to a 0° C. solution of Example 2c (4.1 g, 11.45 mmol), triethylamine (6.38 mL, 45.8 mmol) and dichloromethane (115 mL). The reaction mixture was stirred at ambient temperature for 18 hours. The reaction mixture was concentrated to dryness. To the residue was added 100 mL dioxane and 40 mL 10% NaOH. This solution was stirred at 95° C. for 2 hours. After cooling to ambient temperature, saturated aqueous NH$_4$Cl solution was added and the solution was extracted with ethyl acetate. The organic layer was washed with water and saturated aqueous sodium chloride sequentially, dried (anhydrous magnesium sulfate), filtered, and concentrated to afford 4.5 g of brown foam. The crude product was triturated with 150 mL hexanes/25 mL Et$_2$O, filtered and dried (in-vacuo) to provide the title compound (4.3 g, 9.86 mmol, 86% yield).

Example 2e

N-(5-bromo-4-(2,4-difluorophenoxy)-2-(hydroxymethyl)phenyl)ethanesulfonamide

Borane tetrahydrofuran complex (1M solution. 20 mL, 20.00 mmol) was added to a solution of Example 2d (4.4 g, 10.09 mmol) and tetrahydrofuran (100 mL). The reaction mixture was stirred at reflux for 5 hours. After cooling to ambient temperature, methanol (25 mL) was added slowly and the solution was concentrated to dryness. 50 mL Methanolic HCl was added to the residue and the solution was stirred at reflux for 45 minutes. After cooling to ambient temperature the solution was concentrated to dryness. Toluene (50 mL) and methanol (50 mL) were added and then concentrated. The residue was dried (in-vacuo) to afford 4.5 g of brown glass. The crude product was absorbed onto silica gel and was flash chromatographed (Biotage 340g KP Snap Cartridge, eluting with dichloromethane containing a gradient with methanol, 0% to 5%) to provide the title compound (3.52 g, 8.34 mmol, 83% yield).

Example 2f

N-(5-bromo-4-(2,4-difluorophenoxy)-2-formylphenyl)ethanesulfonamide

Manganese(IV) oxide (1.5 g, 17.25 mmol) was added portionwise to a ambient temperature solution of Example 2e (0.566 g, 1.340 mmol) and dichloromethane (23 mL). The reaction mixture was stirred at ambient temperature for 3 hours. An additional portion of MnO$_2$ (310 mg, 3.57 mmol) was added and the reaction mixture was stirred at ambient temperature for another 4 hours. The reaction mixture was filtered through Celite and the filter pad was washed with tetrahydrofuran. The combined filtrate was concentrated to provide the title compound (0.51 g, 1.214 mmol, 91% yield).

Example 2g

N-(4-(2,4-difluorophenoxy)-2-formyl-5-(6-methyl-7-oxo-6,7-dihydro-1H-pyrrolo[2,3-c]pyridin-4-yl)phenyl)ethanesulfonamide Using the procedure described for Example 1j and substituting Example 2f for Example 1i provided the title compound.

Example 2h

N-[4-(2,4-difluorophenoxy)-2-[(dimethylamino)methyl]-5-(6-methyl-7-oxo-6,7-dihydro-1H-pyrrolo[2,3-c]pyridin-4-yl)phenyl]ethanesulfonamide Dimethylamine (2M solution in methanol, 0.086 mL, 0.172 mmol) was added to a mixture of Example 2g (150 mg, 0.308 mmol) and 1,2-dichloroethane (1.5 mL). 2 Drops of acetic acid were added (pH 5) and the suspension was stirred at ambient temperature for 2 hours. Sodium triacetoxyhydroborate (65 mg, 0.308 mmol) was added portionwise and the reaction mixture was stirred at ambient temperature for 24 hours. The reaction mixture was diluted with dichloromethane and was washed with saturated aqueous sodium bicarbonate solution and saturated aqueous sodium chloride sequentially, dried (anhydrous sodium sulfate), filtered, and concentrated to afford 130 mg orange foam. The crude product was purified by preparative HPLC on a Phenomenex Luna C8(2) 5 μm 100 Å AXIA column (30 mm×75 mm). A gradient of acetonitrile (A) and 10 mM ammonium acetate in water (B) was used, at a flow rate of 50 mL/minutes (0-0.5 minutes 10% A, 0.5-7.0 minutes linear gradient 10-95% A, 7.0-10.0 minutes 95% A, 10.0-12.0 minutes linear gradient 95-10% A). Samples were injected in 1.5 mL DMSO:methanol (1:1). A custom purification system was used, consisting of the following modules: Waters LC4000 preparative pump; Waters 996 diodearray detector; Waters 717+ autosampler; Waters SAT/IN module, Alltech Varex III evaporative light-scattering detector; Gilson 506C interface box; and two Gilson FC204 fraction collectors. The system was controlled using Waters Millennium32 software, automated using an Abbott developed Visual Basic application for fraction collector control and fraction tracking. Fractions were collected based upon UV signal threshold and selected fractions subsequently analyzed by flow injection analysis mass spectrometry using positive APCI ionization on a Finnigan LCQ using 70:30 methanol:10 mM NH$_4$OH(aq) at a flow rate of 0.8 mL/minutes. Loop-injection mass spectra were acquired using a Finnigan LCQ running LCQ Navigator 1.2 software and a Gilson 215 liquid handler for fraction injection controlled by an Abbott developed Visual Basic application. Purification as described provided the title compound (34 mg, 0.066 mmol, 21% yield). $^1$H NMR (300 MHz, DMSO-d$_6$) δ 12.03 (s, 1H), 7.49 (s, 1H), 7.42-7.30 (m, 2H), 7.28 (t, J=2.7 Hz, 1H), 7.15-7.04 (m, 1H), 7.00 (ddd, J=10.7, 6.1, 2.1 Hz, 1H), 6.87 (s, 1H), 6.30-6.21 (m, 1H), 3.54 (d, J=8.7 Hz, 6H), 3.21 (dd, J=14.7, 7.3 Hz, 2H), 2.20 (s, 6H), 1.25 (t, J=7.3 Hz, 3H). MS (ESI+) m/z 516.9 (M+H)$^+$.

Example 3

N-[4-(2,4-difluorophenoxy)-5-(6-methyl-7-oxo-6,7-dihydro-1H-pyrrolo[2,3-c]pyridin-4-yl)-2-(piperidin-1-ylmethyl)phenyl]ethanesulfonamide Example 3 was prepared according to the procedure used for the preparation of Example 2h, substituting piperidine for dimethylamine and was purified by preparative HPLC on a Phenomenex Luna C8(2) 5 μm 100 Å AXIA column (30 mm×75 mm). A gradient of acetonitrile (A) and 0.1% trifluoroacetic acid in water (B) was used, at a flow rate of 50 mL/min (0-0.5 min 10% A, 0.5-7.0 min linear gradient 10-95% A, 7.0-10.0 min 95% A, 10.0-12.0 min linear gradient 95-10% A). Samples were injected in 1.5 mL DMSO:methanol (1:1). A custom purification system was used, consisting of the following modules: Waters LC4000 preparative pump; Waters 996 diode-array detector; Waters 717+ autosampler; Waters SAT/IN module, Alltech Varex III evaporative light-scattering detector; Gilson 506C interface box; and two Gilson FC204 fraction collectors. The system was controlled using Waters Millennium32 software, automated using an Abbott developed Visual Basic application for fraction collector control and fraction tracking. Fractions were collected based upon UV signal threshold and selected fractions subsequently analyzed by flow injection analysis mass spectrometry using positive APCI ionization on a Finnigan LCQ using 70:30 MeOH:10 mM NH$_4$OH(aq) at a flow rate of 0.8 mL/min. Loop-injection mass spectra were acquired using a Finnigan LCQ running LCQ Navigator 1.2 software and a Gilson 215 liquid handler for fraction injection controlled by an Abbott developed Visual Basic application. to provide the TFA salt of the title compound. $^1$H NMR (300 MHz, DMSO-d$_6$) δ 12.10 (s, 1H), 9.40 (s, 1H), 8.98 (s, 1H), 7.51 (s, 1H), 7.44 (ddd, J=11.5, 8.8, 3.0 Hz, 1H), 7.35 (s, 1H), 7.31 (t, J=2.8 Hz, 1H), 7.28-7.19 (m, 2H), 7.07 (dd, J=11.8, 5.4 Hz, 1H), 6.30 (dd, J=2.6, 2.1 Hz, 1H), 4.41 (d, J=5.3 Hz, 2H), 3.55 (s, 3H), 3.30 (s, 2H), 3.21 (q, J=7.3 Hz, 2H), 2.95 (d, J=11.6 Hz, 2H), 1.83 (d, J=14.5 Hz, 2H), 1.75-1.51 (m, 3H), 1.41 (d, J=11.5 Hz, 2H), 1.28 (t, J=7.3 Hz, 3H). MS (ESI+) m/z 557.0 [M+H]$^+$.

Example 4

N-[4-(2,4-difluorophenoxy)-5-(6-methyl-7-oxo-6,7-dihydro-1H-pyrrolo[2,3-c]pyridin-4-yl)-2-(morpholin-4-ylmethyl)phenyl]ethanesulfonamide Example 4 was prepared according to the procedure used for the preparation of Example 2h, substituting morpholine for dimethylamine and was purified according to the procedure described in Example 3 to provide the TFA salt of the title compound. $^1$H NMR (500 MHz, DMSO-d$_6$) δ 12.09 (s, 1H), 9.58 (d, J=150.2 Hz, 1H), 7.53 (s, 1H), 7.42 (ddd, J=11.5, 8.8, 3.0 Hz, 1H), 7.34 (s, 1H), 7.30 (t, J=2.8 Hz, 1H), 7.21 (td, J=9.4, 5.8 Hz, 2H), 7.08-7.00 (m, 1H), 6.29 (t, J=2.4 Hz, 1H), 4.41 (s, 2H), 3.93 (s, 3H), 3.42 (dd, J=13.6, 10.2 Hz, 3H), 3.21 (q, J=7.3 Hz, 3H), 3.18-3.01 (m, 2H), 1.27 (t, J=7.3 Hz, 3H), 0.43-0.42 (m, 1H), 0.41-0.40 (m, 1H). MS (ESI+) m/z 559.0 (M+H)$^+$.

Example 5

N-{4-(2,4-difluorophenoxy)-5-(6-methyl-7-oxo-6,7-dihydro-1H-pyrrolo[2,3-c]pyridin-4-yl)-2-[(4-methylpiperazin-1-yl)methyl]phenyl}ethanesulfonamide Example 5 was prepared according to the procedure used for the preparation of Example 2h, substituting 4-methylpiperazine for dimethylamine, and purified according to the procedure described in Example 3, to provide the title compound to provide the TFA salt of the title compound. $^1$H NMR (400 MHz, DMSO-d$_6$) δ 12.04 (s, 1H), 9.20 (s, 2H), 7.46 (s, 1H), 7.38 (ddd, J=11.5, 8.8, 3.0 Hz, 1H), 7.28 (dd, J=5.1, 2.1 Hz, 2H), 7.10 (td, J=9.2, 5.6 Hz, 1H), 7.04-6.92 (m, 2H), 6.33-6.22 (m, 1H), 3.70 (d, J=14.3 Hz, 2H), 3.52 (s, 3H), 3.40 (s, 2H), 3.20 (q, J=7.3 Hz, 2H), 2.94 (s, 4H), 2.79 (s, 3H), 2.37 (s, 2H), 1.26 (t, J=7.3 Hz, 3H). MS (ESI+) m/z 572.0 (M+H)$^+$.

Example 6

N-[4-(2,4-difluorophenoxy)-2-(hydroxymethyl)-5-(6-methyl-7-oxo-6,7-dihydro-1H-pyrrolo[2,3-c]pyridin-4-yl)phenyl]ethanesulfonamide Example 6 was prepared according to the procedure used for the preparation of Example 1j, substituting Example 2e for Example 1i. $^1$H NMR (300 MHz, DMSO-d$_6$) δ 12.07 (s, 1H), 9.05 (s, 1H), 7.44 (ddd, J=11.5, 8.8, 3.0 Hz, 1H), 7.35 (s, 1H), 7.33 (s, 1H), 7.29 (t, J=2.8 Hz, 1H), 7.21 (td, J=9.2, 5.7 Hz, 1H), 7.07 (tdd, J=9.3, 3.0, 1.5 Hz, 1H), 6.94 (s, 1H), 6.32-6.24 (m, 1H), 5.32 (s, 1H), 4.60 (s, 2H), 3.55 (s, 3H), 3.18-3.05 (m, 2H), 1.34-1.15 (m, 3H). MS (ESI+) m/z 490.1 (M+H)$^+$.

Example 7

N-{2-[(cyclopentylamino)methyl]-4-(2,4-difluorophenoxy)-5-(6-methyl-7-oxo-6,7-dihydro-1H-pyrrolo[2,3-c]pyridin-4-yl)phenyl}ethanesulfonamide Example 7 was prepared according to the procedure used for the preparation of Example 2h, substituting cyclopentanamine for dimethylamine. $^1$H NMR (300 MHz, DMSO-d$_6$) δ 12.11 (s, 1H), 9.41 (s, 1H), 8.61 (s, 2H), 7.52-7.40 (m, 2H), 7.32 (dd, J=6.1, 3.4 Hz, 2H), 7.25-7.13 (m, 2H), 7.09 (dd, J=12.4, 6.1 Hz, 1H), 6.25 (t, J=2.3 Hz, 1H), 4.25 (s, 2H), 3.55 (s, 3H), 3.20 (q, J=7.3 Hz, 3H), 1.98 (d, J=8.4 Hz, 2H), 1.77-1.42 (m, 6H), 1.37-1.21 (m, 3H). MS (ESI+) m/z 556.9 (M+H)$^+$.

Example 8

5-(2,4-difluorophenoxy)-2-[(ethylsulfonyl)amino]-4-(6-methyl-7-oxo-6,7-dihydro-1H-pyrrolo[2,3-c]pyridin-4-yl)benzamide

Example 8a 4-bromo-5-(2,4-difluorophenoxy)-2-(ethyl sulfonamido)benzamide

Oxalyl dichloride (0.046 mL, 0.544 mmol) was added dropwise to a suspension of Example 2d (214 mg, 0.491 mmol) and dichloromethane (2.2 mL). 1 Drop of dimethylformamide was added and the reaction mixture was stirred at ambient temperature for 2 hours. Solvent was evaporated and the residue was dried (in-vacuo). The acid chloride was suspended in tetrahydrofuran (1.0 mL) and was cooled to 0° C. as ammonium hydroxide (0.65 mL, 4.67 mmol) was added dropwise. The reaction mixture was stirred at ambient temperature for 2 hours. The reaction mixture was diluted with ethyl acetate and was washed with water, saturated aqueous sodium chloride, dried (anhydrous magnesium sulfate), filtered, and concentrated to afford 150 mg brown oil. The crude product was absorbed onto silica gel and was flash chromatographed (Biotage 25g HP Snap Cartridge, eluting with dichloromethane, containing a gradient with methanol, 1% to 8%) to provide the title compound (0.76 g, 0.404 mmol, 82% yield).

Example 8b 5-(2,4-difluorophenoxy)-2-[(ethylsulfonyl)amino]-4-(6-methyl-7-oxo-6,7-dihydro-1H-pyrrolo[2,3-c]pyridin-4-yl)benzamide Using the procedure described for Example 1j and substituting Example 8a for Example 1i provided the title compound. $^1$H NMR (300 MHz, DMSO-$d_6$) δ 12.12 (s, 1H), 11.60 (s, 1H), 8.46 (s, 1H), 7.96 (s, 1H), 7.74 (s, 1H), 7.60 (s, 1H), 7.43-7.38 (m, 1H), 7.38-7.28 (m, 2H), 7.08-7.00 (m, 1H), 7.00-6.90 (m, 1H), 6.52-6.03 (m, 1H), 3.53 (s, 3H), 3.30-3.17 (m, 2H), 1.20 (t, J=7.3 Hz, 3H). MS (ESI+) m/z 503.1 (M+H)$^+$.

Example 9

N-cyclopentyl-5-(2,4-difluorophenoxy)-2-[(ethylsulfonyl)amino]-4-(6-methyl-7-oxo-6,7-dihydro-1H-pyrrolo[2,3-c]pyridin-4-yl)benzamide

Example 9a 4-bromo-N-cyclopentyl-5-(2,4-difluorophenoxy)-2-(ethylsulfonamido)benzamide N1-((ethylimino)methylene)-N3,N3-dimethylpropane-1,3-diamine hydrochloride (95 mg, 0.496 mmol) and N-ethyl-N-isopropylpropan-2-amine (180 μL, 1.031 mmol) were added to a solution of Example 2d (180 mg, 0.413 mmol), cyclopentanamine (41 μL, 0.415 mmol), 1H-benzo[d][1,2,3]triazol-1-ol hydrate (75 mg, 0.490 mmol) and dimethylformamide (4 mL). The reaction mixture was stirred for 18 hours at ambient temperature Solvent was evaporated and the residue was dissolved in dichloromethane, washed with water, saturated aqueous sodium chloride, dried (anhydrous magnesium sulfate), filtered, and concentrated to afford 210 mg brown foam. The crude product was purified by preparative HPLC on a Phenomenex Luna C8(2) 5 μm 100 Å AXIA column (30 mm×75 mm). A gradient of acetonitrile (A) and 0.1% trifluoroacetic acid in water (B) was used, at a flow rate of 50 mL/minutes (0-0.5 minutes 10% A, 0.5-7.0 minutes linear gradient 10-95% A, 7.0-10.0 minutes 95% A, 10.0-12.0 minutes linear gradient 95-10% A). Samples were injected in 1.5 mL DMSO:methanol (1:1). A custom purification system was used, consisting of the following modules: Waters LC4000 preparative pump; Waters 996 diode-array detector; Waters 717+ autosampler; Waters SAT/IN module, Alltech Varex III evaporative light-scattering detector; Gilson 506C interface box; and two Gilson FC204 fraction collectors. The system was controlled using Waters Millennium32 software, automated using an Abbott developed Visual Basic application for fraction collector control and fraction tracking. Fractions were collected based upon UV signal threshold and selected fractions subsequently analyzed by flow injection analysis mass spectrometry using positive APCI ionization on a Finnigan LCQ using 70:30 methanol: 10 mM NH$_4$OH(aq) at a flow rate of 0.8 mL/minutes. Loop-injection mass spectra were acquired using a Finnigan LCQ running LCQ Navigator 1.2 software and a Gilson 215 liquid handler for fraction injection controlled by an Abbott developed Visual Basic application to provide the title compound (97 mg, 0.193 mmol, 46.7% yield)

Example 9b

N-cyclopentyl-5-(2,4-difluorophenoxy)-2-[(ethylsulfonyl)amino]-4-(6-methyl-7-oxo-6,7-dihydro-1H-pyrrolo[2,3-c]pyridin-4-yl)benzamide Using the procedure described for Example 1j and substituting Example 9a for Example 1i provided the title compound. $^1$H NMR (300 MHz, DMSO-$d_6$) δ 12.11 (s, 1H), 11.04 (s, 1H), 8.70 (d, J=7.1 Hz, 1H), 7.71 (s, 1H), 7.65 (s, 1H), 7.41-7.24 (m, 3H), 6.94-6.80 (m, 2H), 6.32-6.19 (m, 1H), 4.21 (dd, J=13.7, 7.0 Hz, 1H), 3.51 (s, 3H), 3.24 (q, J=7.1 Hz, 2H), 1.98-1.80 (m, 2H), 1.67 (s, 2H), 1.54 (d, J=9.2 Hz, 4H), 1.20 (t, J=7.3 Hz, 3H). MS (ESI+) m/z 571.2 (M+H)$^+$.

Example 10

5-(2,4-difluorophenoxy)-2-[(ethylsulfonyl)amino]-N,N-dimethyl-4-(6-methyl-7-oxo-6,7-dihydro-1H-pyrrolo[2,3-c]pyridin-4-yl)benzamide

Example 10a 4-bromo-5-(2,4-difluorophenoxy)-2-(ethylsulfonamido)-N,N-dimethylbenzamide Using the procedure described for Example 9a and substituting dimethylamine for cyclopentanamine provided the title compound.

Example 10b 5-(2,4-difluorophenoxy)-2-[(ethylsulfonyl)amino]-N,N-dimethyl-4-(6-methyl-7-oxo-6,7-dihydro-1H-pyrrolo[2,3-c]pyridin-4-yl)benzamide Using the procedure described for Example 1j and substituting Example 10a for Example 1i provided the title compound. $^1$H NMR (400 MHz, DMSO-$d_6$) δ 12.07 (s, 1H), 9.19 (s, 1H), 7.53 (s, 1H), 7.45-7.35 (m, 2H), 7.31 (t, J=2.8 Hz, 1H), 7.27-7.11 (m, 1H), 7.04 (ddd, J=9.3, 2.9, 1.5 Hz, 1H), 6.75 (s, 1H), 6.37-6.31 (m, 1H), 3.55 (s, 3H), 3.12 (q, J=7.3 Hz, 2H), 2.93 (s, 3H), 2.80 (d, J=9.8 Hz, 3H), 1.22 (t, J=7.3 Hz, 3H). MS (ESI+) m/z 531.1 (M+H)$^+$.

Example 11

5-(2,4-difluorophenoxy)-2-[(ethylsulfonyl)amino]-4-(6-methyl-7-oxo-6,7-dihydro-1H-pyrrolo[2,3-c]pyridin-4-yl)benzoic acid Using the procedure described for Example 1j and substituting Example 2d for Example 1i provided the title compound. $^1$H NMR (300 MHz, DMSO-d$_6$) δ 12.16-12.07 (m, 1H), 10.71-10.52 (m, 1H), 7.76 (s, 1H), 7.49-7.38 (m, 3H), 7.32 (t, J=2.8 Hz, 1H), 7.23 (td, J=9.2, 5.5 Hz, 1H), 7.11-7.00 (m, 1H), 6.32 (t, J=2.3 Hz, 1H), 3.56 (s, 3H), 1.21 (t, J=7.3 Hz, 3H). MS (ESI+) m/z 504.1 (M+H)$^+$.

Example 12

5-(2,4-difluorophenoxy)-2-[(ethylsulfonyl)amino]-4-(6-methyl-7-oxo-6,7-dihydro-1H-pyrrolo[2,3-c]pyridin-4-yl)-N-(tetrahydro-2H-pyran-4-yl)benzamide

Example 12a 4-bromo-5-(2,4-difluorophenoxy)-2-(ethylsulfonamido)-N-(tetrahydro-2H-pyran-4-yl)benzamide Using the procedure described for Example 9a and substituting tetrahydro-2H-pyran-4-amine (CAS 38041-19-9) for cyclopentanamine provided the title compound.

Example 12b 5-(2,4-difluorophenoxy)-2-[(ethylsulfonyl)amino]-4-(6-methyl-7-oxo-6,7-dihydro-1H-pyrrolo[2,3-c]pyridin-4-yl)-N-(tetrahydro-2H-pyran-4-yl)benzamide Using the procedure described for Example 1j and substituting Example 12a for Example 1i provided the title compound. $^1$H NMR (300 MHz, DMSO-d$_6$) δ 12.08 (s, 1H), 10.93 (s, 1H), 8.68 (d, J=7.6 Hz, 1H), 7.71 (d, J=6.5 Hz, 1H), 7.61 (d, J=14.0 Hz, 1H), 7.36 (s, 1H), 7.33-7.24 (m, 2H), 6.94-6.81 (m, 2H), 6.26 (dt, J=20.8, 10.4 Hz, 1H), 4.03 (dt, J=11.4, 4.7 Hz, 1H), 3.87 (d, J=9.9 Hz, 2H), 3.49 (d, J=9.1 Hz, 3H), 3.39 (dd, J=7.6, 5.6 Hz, 2H), 3.23 (dd, J=8.9, 5.7 Hz, 2H), 1.76 (d, J=12.4 Hz, 2H), 1.64-1.46 (m, 2H), 1.21 (t, J=7.3 Hz, 3H). MS (ESI+) m/z 587.5 (M+H)$^+$.

Example 13

N-[4-(2,4-difluorophenoxy)-2-{[(2-hydroxyethyl)amino]methyl}-5-(6-methyl-7-oxo-6,7-dihydro-1H-pyrrolo[2,3-c]pyridin-4-yl)phenyl]ethanesulfonamide Example 13 was prepared according to the procedure used for the preparation of Example 2h, substituting 2-aminoethanol for dimethylamine. $^1$H NMR (400 MHz, DMSO-d$_6$) δ 12.02 (s, 1H), 7.46 (s, 1H), 7.36 (ddd, J=11.4, 8.9, 2.9 Hz, 1H), 7.28 (d, J=4.4 Hz, 2H), 7.10-6.94 (m, 2H), 6.90 (s, 1H), 6.26 (s, 1H), 3.87 (s, 2H), 3.55-3.48 (m, 3H), 3.49-3.43 (m, 4H), 3.15 (dd, J=14.6, 7.3 Hz, 2H), 2.59 (t, J=5.6 Hz, 2H), 1.24 (t, J=7.3 Hz, 3H). MS (ESI+) m/z 532.9 (M+H)$^+$.

Example 14

N-{4-(2,4-difluorophenoxy)-5-(6-methyl-7-oxo-6,7-dihydro-1H-pyrrolo[2,3-c]pyridin-4-yl)-2-[(2-phenylpyrrolidin-1-yl)methyl]phenyl}ethanesulfonamide

Example 14a

N-(5-bromo-4-(2,4-difluorophenoxy)-2-((2-phenylpyrrolidin-1-yl)methyl)phenyl)ethanesulfonamide Example 14a was prepared according to the procedure used for the preparation of Example 2h, substituting Example 2f for Example 2g and substituting 2-phenylpyrrolidine for dimethylamine.

Example 14b

N-{4-(2,4-difluorophenoxy)-5-(6-methyl-7-oxo-6,7-dihydro-1H-pyrrolo[2,3-c]pyridin-4-yl)-2-[(2-phenylpyrrolidin-1-yl)methyl]phenyl}ethanesulfonamide Using the procedure described for Example 1j and substituting Example 14a for Example 1i provided the title compound. $^1$H NMR (400 MHz, DMSO-d$_6$) δ 12.03 (s, 1H), 7.58 (d, J=10.0 Hz, 1H), 7.48-7.38 (m, 2H), 7.37-7.14 (m, 7H), 7.06 (dt, J=32.8, 15.9 Hz, 2H), 6.92 (s, 1H), 6.22 (d, J=20.1 Hz, 1H), 3.66 (d, J=14.3 Hz, 1H), 3.52 (s, 4H), 2.92 (dtd, J=28.7, 14.3, 7.1 Hz, 3H), 2.34-2.08 (m, 2H), 1.77 (dd, J=28.3, 17.5 Hz, 4H), 1.07 (t, J=7.2 Hz, 3H). MS (ESI+) m/z 617.2 (M+H)$^+$.

Example 15

N-[3-cyclopropyl-4-(2,4-difluorophenoxy)-5-(6-methyl-7-oxo-6,7-dihydro-1H-pyrrolo[2,3-c]pyridin-4-yl)phenyl]ethanesulfonamide

Example 15a 1,3-dibromo-2-(2,4-difluorophenoxy)-5-nitrobenzene

A solution of 1,3-dibromo-2-fluoro-5-nitrobenzene (2.38 g, 7.80 mmol), 2,4-difluorophenol (1.025 g, 7.80 mmol) and potassium carbonate (2.70 g, 19.51 mmol) in dimethylformamide (20 mL) was stirred at 75° C. for 3 hours. The reaction mixture was cooled to ambient temperature and partitioned between ethyl acetate and dilute sodium chloride solution. The ethyl acetate layer was dried with anhydrous magnesium sulfate, filtered, and concentrated. The residue was recrystallized from diethylether and heptane, filtered, and dried in a vacuum oven at 50° C. to provide 3.02 g (95%) of the title compound.

Example 15b 1-bromo-3-cyclopropyl-2-(2,4-difluorophenoxy)-5-nitrobenzene

Example 15a (3.61 g, 8.83 mmol), cyclopropylboronic acid (0.76 g, 8.83 mmol), and cesium carbonate (8.63 g, 26.5 mmol) were combined and sparged with argon for 10 minutes. Dioxane (50 mL) and water (10 mL) were added and argon was bubbled through the mixture for 15 minutes. To the resulting mixture was added bis(triphenylphosphine) palladium(II) chloride (0.434 g, 0.618 mmol), and the reaction mixture was stirred under argon at 105° C. for 5 hours. To the cooled reaction mixture was added dilute ammonium chloride solution and the mixture was extracted twice with ethyl acetate. The combined organic layers were dried with anhydrous magnesium sulfate, filtered, and concentrated. The residue was purified twice by chromatography (silica gel, 4-6% dichloromethane in heptane) to afford 0.55 g (17%) of the title compound.

Example 15c 3-bromo-5-cyclopropyl-4-(2,4-difluorophenoxy) aniline

A solution of Example 15b (0.467 g, 1.262 mmol) and ammonium chloride (0.675 g, 12.6 mmol) in ethanol (25 mL), tetrahydrofuran (10 mL) and water (5 mL) was stirred at 0° C. Powdered zinc (1.237 g, 18.92 mmol) was added and the mixture was stirred at 0° C. for 15 minutes and then allowed to warm slowly to ambient temperature and stirred for 3 hours. The reaction mixture was filtered through Celite and rinsed with water and dichloromethane. The organic phase was separated, dried with anhydrous magnesium sulfate, filtered, and concentrated to afford 0.40 g (93%) of the title compound.

Example 15d

N-(3-bromo-5-cyclopropyl-4-(2,4-difluorophenoxy) phenyl)ethanesulfonamide

A solution of Example 15c (0.40 g, 1.18 mmol) and triethylamine (0.66 mL, 4.70 mmol) in dichloromethane (140 mL) was stirred at 0° C. To this solution was added ethanesulfonyl chloride (0.34 mL, 3.53 mmol). The reaction mixture was allowed to warm to ambient temperature and stirred for 3 hours. The reaction mixture was concentrated to provide a crude crystalline solid. The resulting solid residue was dissolved in dioxane (16 mL) and stirred at ambient temperature. A 10% sodium hydroxide solution (8.0 mL) was added and the mixture was stirred at 95° C. for 1 hour. The reaction mixture was cooled to ambient temperature and dilute ammonium chloride solution added until pH was about 7. The mixture was extracted twice with ethyl acetate, dried with anhydrous magnesium sulfate, filtered, and concentrated. The residue was purified by chromatography (silica gel, 20% heptane in dichloromethane) to provide 0.48 g (94%) of the title compound.

Example 15e

N-[3-cyclopropyl-4-(2,4-difluorophenoxy)-5-(6-methyl-7-oxo-6,7-dihydro-1H-pyrrolo[2,3-c]pyridin-4-yl)phenyl]ethanesulfonamide Example 15d (0.438 g, 1.013 mmol), Example 1f (0.456 g, 1.064 mmol), tetrakis(triphenylphosphine)palladium (0) (0.117 g, 0.101 mmol), and cesium fluoride (0.462 g, 3.040 mmol) were combined and sparged with argon for 10 minutes. Dimethoxyethane (10 mL) and methanol (5 mL) were added and argon was bubbled through the mixture for 15 minutes. The reaction mixture was stirred at 120° C. for 50 minutes. To the cooled reaction mixture was added 5N sodium hydroxide aqueous solution (4 mL) and the mixture was stirred for 2 hours at ambient temperature. To the resulting mixture was added dilute ammonium chloride solution and extracted twice with ethyl acetate. The combined organic layers were dried with anhydrous magnesium sulfate, filtered, and concentrated. The residue was purified by chromatography (silica gel, 33% heptane in ethyl acetate) to provide 0.33 g (65%) of the title compound. $^1$H NMR (400 MHz, DMSO-$d_6$) δ 11.99 (s, 1H), 9.79 (s, 1H), 7.29-7.22 (m, 3H), 7.21-7.13 (m, 1H), 6.84 (d, J=2.6 Hz, 1H), 6.76-6.67 (m, 1H), 6.51-6.40 (m, 1H), 6.17 (t, J=2.3 Hz, 1H), 3.46 (s, 3H), 3.13 (q, J=7.3 Hz, 2H), 1.99-1.88 (m, 1H), 1.23 (t, J=7.3 Hz, 3H), 0.93-0.83 (m, 2H), 0.66-0.57 (m, 2H). MS (ESI+) m/z 500.1 (M+H)$^+$.

Example 16

4-{2-[(2,2-difluorocyclopropyl)methoxy]-5-(ethylsulfonyl)phenyl}-6-methyl-2-{[4-(pyridin-4-yl)piperazin-1-yl]methyl}-1,6-dihydro-7H-pyrrolo[2,3-c] pyridin-7-one Example 16a (Z)-ethyl 3-(5-bromo-2-methoxy-3-nitropyridin-4-yl)-2-hydroxyacrylate To a solution of ethanol (15 mL) and ether (150 mL) were added 5-bromo-2-methoxy-4-methyl-3-nitropyridine (14.8 g, 60 mmol), diethyl oxalate (13.2 g, 90 mmol), and potassium ethoxide (6.06 g, 72 mmol). The reaction mixture was heated at 45° C. for 24 hours. During this period, the flask was shaken by hand several times. After cooling to ambient temperature, the reaction mixture was partitioned between water and ethyl acetate. The aqueous layer was extracted with additional ethyl acetate three times. The combined organic layers were washed with saturated aqueous sodium chloride, dried over anhydrous magnesium sulfate, filtered, and concentrated. The residue was purified by flash chromatography (silica gel, 10-20% ethyl acetate in hexanes) to provide 9.5 g of the title compound (yield 46%).

Example 16b ethyl 4-bromo-7-methoxy-1H-pyrrolo[2,3-c]pyridine-2-carboxylate

A mixture Example 16a (9.5 g, 27.4 mmol) and iron powder (7.64 g, 137 mmol) in ethanol (60 mL) and acetic acid (60 mL) was heated at 100° C. for 1 hour. The resulting solid was filtered off, and then washed with additional ethyl acetate. The solvents were removed under reduced pressure to 20% of original volume, and the mixture was partitioned between water and ethyl acetate. The aqueous layer was extracted with additional ethyl acetate several times. The combined organic layers were washed with saturated aqueous sodium chloride, dried over anhydrous magnesium sulfate, filtered, and concentrated. The residue was purified by flash chromatography (silica gel, 20-40% ethyl acetate in hexanes) to afford 6.05 g of the title compound.

Example 16c ethyl 1-benzyl-4-bromo-7-methoxy-1H-pyrrolo[2,3-c]pyridine-2-carboxylate Example 16b (0.88 g, 2.94 mmol) in dimethylformamide (15 mL) was treated with 60% sodium hydride (0.106 g, 4.41 mmol, 0.177 g of a 60% in oil dispersion). The solution was stirred at ambient temperature for 10 minutes. To this solution was added benzyl bromide (0.59 g, 3.45 mmol). The reaction mixture was stirred for another 2 hours and then was partitioned between water and ethyl acetate. The aqueous layer was extracted with additional ethyl acetate twice. The combined organic layers were washed with saturated aqueous sodium chloride, dried over anhydrous magnesium sulfate, filtered, and concentrated. The residue was purified by flash chromatography (silica gel, 20-40% ethyl acetate in hexanes) to afford 1.07 g of the title compound.

Example 16d ethyl 1-benzyl-4-bromo-7-oxo-6,7-dihydro-1H-pyrrolo[2,3-c]pyridine-2-carboxylate Example 16d was prepared according to the procedure used for the preparation of Example 1d, substituting Example 16c for Example 1c.

Example 16e

Example 16e was prepared according to the procedure used for the preparation of Example 1e, substituting Example 16d for Example 1d.

Example 16f ethyl 1-benzyl-6-methyl-7-oxo-4-(4,4,5,5-tetramethyl-1,3,2-dioxaborolan-2-yl)-6,7-dihydro-1H-pyrrolo[2,3-c]pyridine-2-carboxylate A mixture of Example 16e (2 g, 5.14 mmol), bis(pinacolato)diboron (2.61 g, 10.3 mmol), potassium acetate (1.11 g, 11.3 mmol), tris(dibenzylideneacetone)dipalladium(0) (0.235 g, 0.257 mmol), and 2-dicyclohexylphosphino-2',4',6'-triisopropylbiphenyl (0.245 g, 0.514 mmol) in dioxane (50 mL) was stirred at 90° C. for 16 hour under an argon atmosphere. The mixture was filtered through Celite, washed with ethyl acetate several times and concentrated. The residue was purified by flash chromatography (silica gel, 50-75% ethyl acetate/petroleum ether gradient) to afford the title compound (1.15 g, 40% yield).

Example 16g ethyl(4-fluorophenyl)sulfane

Triethylamine (5.44 mL, 39 mmol) was added to a solution of 4-fluorobenzenethiol (5 g, 39 mmol) and iodoethane (3.78 mL, 46.8 mmol) in tetrahydrofuran (50 mL). The resulting mixture was stirred at ambient temperature for 2 hours and then filtered. The filtrate was concentrated and then triturated with hexane, and the resulting solid was dried under vacuum to afford the title compound (4.8 g, 76%).

Example 16h 1-(ethylsulfonyl)-4-fluorobenzene

Example 16g (5 g, 32 mmol) in dichloromethane (200 mL) was treated with 3-chloroperoxybenzoic acid (14.3 g, 70.4 mmol) and stirred at ambient temperature for 6 hours. The solid formed during the reaction mixture was removed by filtration and washed with additional dichloromethane. The combined filtrate was washed with 10% aqueous sodium hydroxide solution (50 mL, twice) and saturated aqueous sodium bicarbonate solution, dried over anhydrous sodium sulfate, filtered, and concentrated. The residue was purified by flash chromatography (silica gel, 15% ethyl acetate in petroleum ether) to afford the title compound (4.6 g, 76%).

Example 16i 2-bromo-4-(ethylsulfonyl)-1-fluorobenzene

Example 16h (1 g, 5.31 mmol) in concentrated $H_2SO_4$ (6 mL) was treated with N-bromosuccinimide (1.040 g, 5.84 mmol). The reaction mixture was stirred at ambient temperature for 6 hours, and then was stirred at 50° C. for 12 hours. The reaction mixture was poured into ice-water. The resulting solid was collected by filtration. The solid was washed with cold water three times, and dried in a vacuum oven overnight. It was then purified by flash chromatography (silica gel, 10:1 to 4:1 petroleum ether/ethyl acetate gradient) to afford the title compound (1.1 g, 4.12 mmol, 78% yield).

Example 16j ethyl 1-benzyl-4-(5-(ethylsulfonyl)-2-fluorophenyl)-6-methyl-7-oxo-6,7-dihydro-1H-pyrrolo[2,3-c]pyridine-2-carboxylate A mixture of Example 16f (1.53 g, 3.51 mmol), Example 16i (1.030 g, 3.86 mmol), 1,3,5,7-tetramethyl-6-phenyl-2,4,8-trioxa-6-phosphaadamantane (0.103 g, 0.351 mmol), $Pd_2$(dba)$_3$ (0.080 g, 0.088 mmol) and $K_3PO_4$ (1.861 g, 8.77 mmol) was sparged with argon for 30 minutes. A mixture of dioxane (20 mL) and water (5 mL) was also sparged with nitrogen for 30 minutes and transferred by syringe into the reaction vessel under argon. The reaction mixture was stirred at 60° C. for 16 hours, cooled to ambient temperature, and partitioned between ethyl acetate and water. The organic layer was extracted with additional ethyl acetate twice. The combined organic layers were washed with saturated aqueous sodium chloride, dried over anhydrous sodium sulfate, filtered, and concentrated. Purification by flash chromatography (silica gel, petroleum ether/ethyl acetate gradient, 5/1 to 2/1) afforded the title compound (1.92 g, 2.46 mmol, 70% yield).

Example 16k ethyl 4-(5-(ethylsulfonyl)-2-fluorophenyl)-6-methyl-7-oxo-6,7-dihydro-1H-pyrrolo[2,3-c]pyridine-2-carboxylate A mixture of Example 16j (3.56 g, 7.17 mmol), anisole (1.566 mL, 14.34 mmol) and $H_2SO_4$ (3.5 mL, 65.7 mmol) in trifluoroacetic acid (70 mL, 909 mmol) was heated at 90° C. for 4 hours. Excess trifluoroacetic acid was removed under reduced pressure, and the residue was partitioned between water (10 mL) and ethyl acetate (40 mL). The organic layer was separated, and the aqueous layer was extracted with additional ethyl acetate twice (80 mL). The combined organic layers were washed with saturated aqueous sodium bicarbonate (20 mL), followed by saturated aqueous sodium chloride (20 mL), dried over anhydrous magnesium sulfate, filtered, and concentrated. The crude residue was treated

Example 16l ethyl 4-(2-((2,2-difluorocyclopropyl)methoxy)-5-(ethylsulfonyl)phenyl)-6-methyl-7-oxo-6,7-dihydro-1H-pyrrolo[2,3-c]pyridine-2-carboxylate A solution of Example 16k (0.8 g, 1.968 mmol) and (2,2-difluorocyclopropyl)methanol (0.426 g, 3.94 mmol) in dimethylsulfoxide (10 mL) was treated with $Cs_2CO_3$ (0.962 g, 2.95 mmol). The reaction mixture was heated at 110° C. for 5 days. During the 5 days, three additional batches of (2,2-difluorocyclopropyl)methanol (0.426 g, 3.94 mmol) were added into the reaction mixture. The reaction mixture was cooled to ambient temperature and poured into ethyl acetate (100 mL) and water (100 mL). The aqueous layer was extracted with ethyl acetate (100 mL, twice). The combined organic layers were dried over anhydrous sodium sulfate, filtered, and concentrated to give the title compound (0.9 g, 1.820 mmol, 92% yield) which was used in the next step without additional purification.

Example 16m 4-(2-((2,2-difluorocyclopropyl)methoxy)-5-(ethylsulfonyl)phenyl)-2-(hydroxymethyl)-6-methyl-1H-pyrrolo[2,3-c]pyridin-7(6H)-one Example 16l (1.8 g, 3.64 mmol) in tetrahydrofuran (20 mL) at 0° C. was treated with $LiAlH_4$ (1 M in tetrahydrofuran) (3.64 mL, 3.64 mmol) dropwise. The reaction mixture was stirred at 0° C. for 2 hours. The reaction mixture was poured into ethyl acetate (100 mL) and water (80 mL) and the mixture was filtered through Celite. The organic layer was separated and the aqueous layer was extracted with ethyl acetate (50 mL, twice). The combined organic layers were dried over anhydrous sodium sulfate, filtered, and concentrated. The crude was purified by flash chromatography (silica gel, ethyl acetate to 30/1 dichlormethane/methanol gradient) to provide the title compound (0.6 g, 1.074 mmol, 29.5% yield).

Example 16n 4-(2-((2,2-difluorocyclopropyl)methoxy)-5-(ethylsulfonyl)phenyl)-6-methyl-7-oxo-6,7-dihydro-1H-pyrrolo[2,3-c]pyridine-2-carbaldehyde To the solution of Example 16m (0.5 g, 1.105 mmol) in dichloromethane (20 mL) at 0° C. was added Dess-Martin Periodinane (0.937 g, 2.210 mmol) and the mixture was stirred at 0° C. for 30 minutes. Then the reaction temperature was allowed to warm to ambient temperature. After 3 hours a solution of $Na_2S_2O_3$ in saturated aqueous $NaHCO_3$ (5 mL) was added to the reaction mixture. The mixture was stirred for 15 minutes and extracted with ethyl acetate. The organic layer was dried over anhydrous magnesium sulfate, filtered, and concentrated to give the title compound (0.6 g, 0.759 mmol, 68.7% yield).

Example 16o

4-{2-[(2,2-difluorocyclopropyl)methoxy]-5-(ethylsulfonyl)phenyl}-6-methyl-2-{[4-(pyridin-4-yl)piperazin-1-yl]methyl}-1,6-dihydro-7H-pyrrolo[2,3-c]pyridin-7-one To a solution of Example 16n (0.10 g, 0.22 mmol) and 1-(pyridin-4-yl)piperazine (0.072 g, 0.44 mmol) in methanol (6 mL) was added zinc chloride (0.030 g, 0.22 mmol) at ambient temperature. The reaction mixture was stirred for 1 hour, followed by the addition of $NaCNBH_4$ (0.028 g, 0.444 mmol), and the reaction mixture was stirred at 25° C. overnight. The reaction mixture was concentrated and the crude material was purified by reverse phase Prep HPLC (C18, 20-50% acetonitrile in 0.01 N $NH_4CO_3$/water) to give the title compound (31 mg, 0.050 mmol, 22.34% yield). $^1$H NMR (400 MHz, DMSO-$d_6$) δ 11.99 (s, 1H), 8.13 (s, 2H), 7.98-7.71 (m, 2H), 7.46-7.30 (m, 2H), 6.76 (d, J=5.6 Hz, 2H), 6.05 (d, J=1.6 Hz, 1H), 4.30-4.16 (m, 2H), 3.64 (s, 2H), 3.57 (s, 3H), 3.33-3.20 (m, 6H), 2.51-2.48 (m, 4H), 2.19-2.04 (m, 1H), 1.68-1.63 (m, 1H), 1.55-1.38 (m, 1H), 1.13 (t, J=7.3 Hz, 3H). MS (ESI+) m/z 598.2 (M+H)$^+$.

Example 17

4-{2-[(2,2-difluorocyclopropyl)methoxy]-5-(ethylsulfonyl)phenyl}-6-methyl-2-{[4-(1,3-thiazol-2-yl)piperazin-1-yl]methyl}-1,6-dihydro-7H-pyrrolo[2,3-c]pyridin-7-one Example 17 was prepared according to the procedure used for the preparation of Example 16o, substituting 2-(piperazin-1-yl)thiazole for 1-(pyridin-4-yl)piperazine. $^1$H NMR (400 MHz, DMSO-$d_6$) δ 11.98 (s, 1H), 7.88-7.77 (m, 2H), 7.41-7.33 (m, 2H), 7.13 (d, J=3.6 Hz, 1H), 6.82 (d, J=3.6 Hz, 1H), 6.05 (s, 1H), 4.30-4.14 (m, 2H), 3.64 (s, 2H), 3.56 (s, 3H), 3.35 (s, 4H), 3.28 (q, J=7.3 Hz, 2H), 2.46 (s, 4H), 2.18-2.08 (m, 1H), 1.71-1.59 (m, 1H), 1.53-1.41 (m, 1H), 1.12 (t, J=7.3 Hz, 3H). MS (ESI+) m/z 604.3 (M+H)$^+$.

Example 18

4-{2-[(2,2-difluorocyclopropyl)methoxy]-5-(ethylsulfonyl)phenyl}-6-methyl-2-{[4-(pyrazin-2-yl)piperazin-1-yl]methyl}-1,6-dihydro-7H-pyrrolo[2,3-c]pyridin-7-one Example 18 was prepared according to the procedure used for the preparation of Example 16o, substituting 2-(piperazin-1-yl)pyrazine for 1-(pyridin-4-yl)piperazine. $^1$H NMR (400 MHz, DMSO-$d_6$) δ 11.98 (s, 1H), 8.27 (s, 1H), 8.05 (s, 1H), 7.88-7.77 (m, 3H), 7.42-7.32 (m, 2H), 6.05 (s, 1H), 4.31-4.14 (m, 2H), 3.64 (s, 2H), 3.56 (s, 3H), 3.54-3.44 (m, 4H), 3.29 (q, J=7.4 Hz, 2H), 2.48-2.44 (m, 4H), 2.20-2.05 (m, 1H), 1.71-1.57 (m, 1H), 1.51-1.39 (m, 1H), 1.12 (t, J=7.3 Hz, 3H). MS (ESI+) m/z 599.3 (M+H)$^+$.

Example 19

4-{2-[(2,2-difluorocyclopropyl)methoxy]-5-(ethylsulfonyl)phenyl}-6-methyl-2-{[4-(pyrimidin-2-yl)piperazin-1-yl]methyl)}-1,6-dihydro-7H-pyrrolo[2,3-c]pyridin-7-one Example 19 was prepared according to the procedure used for the preparation of Example 16o, substituting 2-(piperazin-1-yl)pyrimidine for 1-(pyridin-4-yl)piperazine. $^1$H NMR (400 MHz, DMSO-$d_6$) δ 11.98 (s, 1H), 8.32 (d, J=4.7 Hz, 2H), 7.87-7.78 (m, 2H), 7.41-7.32 (m, 2H), 6.59 (t, J=4.7 Hz, 1H), 6.04 (s, 1H), 4.30-4.15 (m, 2H), 3.73-3.64 (m, 4H), 3.62 (s, 2H), 3.56 (s, 3H), 3.28 (q, J=7.3 Hz, 2H), 2.45-2.37 (m, 4H), 2.20-2.05 (m, 1H), 1.73-1.56 (m, 1H), 1.53-1.40 (m, 1H), 1.13 (t, J=7.3 Hz, 3H). MS (ESI+) m/z 599.3 (M+H)$^+$.

Example 20

4-{2-[(2,2-difluorocyclopropyl)methoxy]-5-(ethylsulfonyl)phenyl}-6-methyl-2-{[4-(pyridin-3-yl)piperazin-1-yl]methyl}-1,6-dihydro-7H-pyrrolo[2,3-c]pyridin-7-one Example 20 was prepared according to the procedure used for the preparation of Example 16o, substituting 1-(pyridin-3-yl)piperazine for 1-(pyridin-4-yl)piperazine. $^1$H NMR (400 MHz, CD$_3$OD) δ 8.19 (d, J=2.8 Hz, 1H), 7.94 (d, J=3.5 Hz, 1H), 7.91-7.89 (m, 2H), 7.39-7.36 (m, 1H), 7.34-7.31 (m, 2H), 7.27-7.23 (m, 1H), 6.18 (s, 1H), 4.31-4.29 (m, 1H), 4.15-4.10 (m, 1H), 3.74 (s, 2H), 3.68 (s, 3H), 3.28-3.19 (m, 6H), 2.67-2.64 (m, 4H), 2.03-2.01 (m, 1H), 1.60-1.46 (m, 1H), 1.28-1.26 (m, 1H), 1.24 (t, J=7.4 Hz, 3H). MS (ESI+) m/z 598.3 (M+H)$^+$.

Example 21

N-cyclopropyl-3-[2-(6-methyl-7-oxo-6,7-dihydro-1H-pyrrolo[2,3-c]pyridin-4-yl)-4-(methyl sulfonyl)phenoxy]benzamide

Example 21a (3-bromo-4-fluorophenyl)(methyl)sulfane

A solution of 3-bromo-4-fluorobenzenethiol (CAS 942473-85-0) (10 g, 48.3 mmol) in methanol (105 mL) was stirred at 0° C. as 5M sodium hydroxide solution (10 mL, 50.0 mmol) was added. After 10 min at 0° C., iodomethane (3.6 mL, 57.6 mmol) was added and the reaction mixture was stirred at ambient temperature overnight. The reaction mixture was concentrated under reduced pressure and 500 mL ethyl acetate was added to the residue. The solution was washed with water, saturated aqueous sodium chloride, dried (anhydrous sodium sulfate), filtered, and concentrated to provide the title compound (10.75 g, 48.6 mmol, 100% yield).

Example 21b 2-bromo-1-fluoro-4-(methylsulfonyl)benzene

3-Chlorobenzoperoxoic acid (26.3 g, 152 mmol) was added portionwise to a solution of Example 21a (10.75 g, 48.6 mmol) in dichloromethane (500 mL). The reaction mixture was stirred at ambient temperature for 6 hours. The solid was filtered and was rinsed with dichloromethane. The combined filtrate was washed with 10% aqueous NaOH, saturated sodium bicarbonate solution, and saturated aqueous sodium chloride sequentially, dried (anhydrous sodium sulfate), filtered, and concentrated to afford 11.6 g white solid. The crude product was purified by flash chromatography (silica gel, eluting with heptanes containing a gradient of ethyl acetate, 5-45%) to provide the title compound (11.09 g, 43.8 mmol, 90% yield).

Example 21c methyl 3-(2-bromo-4-(methyl sulfonyl)phenoxy)benzoate

A mixture of Example 21b (50 mg, 0.198 mmol), methyl 3-hydroxybenzoate (CAS 19438-10-9, 36 mg, 0.237 mmol), cesium carbonate (92 mg, 0.282 mmol) and dimethylsulfoxide (0.8 mL) was heated in a sealed tube at 120° C. for 45 minutes. The reaction mixture was cooled to ambient temperature and water (50 mL) was added with rapid stirring to obtain a finely dispersed white solid. The mixture was extracted with ethyl acetate. The organic layer was washed with water, saturated aqueous sodium chloride, dried (anhydrous magnesium sulfate), filtered, and concentrated to provide the title compound (40 mg, 0.104 mmol, 53% yield)

Example 21d

3-[2-(6-methyl-7-oxo-6,7-dihydro-1H-pyrrolo[2,3-c]pyridin-4-yl)-4-(methylsulfonyl)phenoxy]benzoic acid A nitrogen degassed solution of Example 21c (690 mg, 1.791 mmol), Example 1f (767 mg, 1.791 mmol), cesium fluoride (812 mg, 5.35 mmol), (tetrakistriphenylphosphine)palladium(0) (106 mg, 0.092 mmol), dimethoxyethane (8.5 mL) and methanol (4.1 mL) was heated in the microwave at 120° C. for 40 minutes. Water (50 mL) was added and the mixture was extracted with ethyl acetate. The organic layer was washed with saturated aqueous sodium chloride, dried (anhydrous magnesium sulfate), filtered, and concentrated to afford 1.1 g of yellow foam. The crude product was absorbed onto silica gel and purified by flash chromatography (silica gel, eluting with dichloromethane containing a gradient with methanol, 1% to 8%) to provide a 1:1 mixture of tosylated and non-tosylated products. The mixture of products was stirred at reflux for 6 hours with sodium hydroxide (80 mg, 2.000 mmol), ethanol (8.0 mL) and water (0.3 mL). The reaction mixture was cooled to 0° and water (20 mL) was added slowly with stirring, followed by the addition of 5% aqueous citric acid to about pH5. After stirring at 0° for 30 minutes the aqueous slurry was filtered, rinsed with water, and dried (in-vacuo) to provide the title compound.

Example 21e

N-cyclopropyl-3-[2-(6-methyl-7-oxo-6,7-dihydro-1H-pyrrolo[2,3-c]pyridin-4-yl)-4-(methyl sulfonyl)phenoxy]benzamide A solution of Example 21d (88 mg, 0.201 mmol), cyclopropanamine (0.014 mL, 0.201 mmol), 1H-benzo[d][1,2,3]triazol-1-ol hydrate (36 mg, 0.235 mmol) and dimethylformamide (1.9 mL) was stirred at ambient temperature. After adding N1-((ethylimino)methylene)-N3,N3-dimethylpropane-1,3-diamine hydrochloride (46 mg, 0.240 mmol) and N-ethyl-N-isopropylpropan-2-amine (0.087 mL, 0.498 mmol) the reaction mixture was stirred at ambient temperature overnight. The reaction mixture was cooled to 0° C. and ice water (20 mL) was added slowly with rapid stirring. The resulting solid was filtered, rinsed with water and was dried (in vacuo) to provide the title compound (70 mg, 0.147 mmol, 73% yield). $^1$H NMR (300 MHz, DMSO-d$_6$) δ 12.24-11.86 (m, 1H), 8.52-8.35 (m, 1H), 8.05-7.96 (m, 1H), 7.94-7.80 (m, 1H), 7.74-7.59 (m, 1H), 7.55-7.51 (m, 1H), 7.51-7.44 (m, 1H), 7.44-7.40 (m, 1H), 7.29 (t, J=2.8 Hz, 1H), 7.28-7.23 (m, 1H), 7.12-6.91 (m, 1H), 6.35-5.80 (m, 1H), 3.62-3.50 (m, 3H), 3.25 (d, J=7.9 Hz, 3H), 2.87-2.76 (m, 1H), 0.72-0.61 (m, 2H), 0.59-0.45 (m, 2H). MS (ESI+) m/z 478.1 (M+H)$^+$.

Example 22

6-methyl-4-[2-{3-[(4-methylpiperazin-1-yl)carbonyl]phenoxy}-5-(methyl sulfonyl)phenyl]-1,6-dihydro-7H-pyrrolo[2,3-c]pyridin-7-one A stock solution of Example 21d and DIPEA (0.19 M and 0.54 M in DMA, respectively, 181 μL, 0.034 mmol Example 21d (1.0 equivalent) and 0.102 mmol DIPEA (3.0 equivalents)), HATU (0.28 M in DMA, 181 μL, 0.051 mmol, 1.5 equivalents), and 1-methylpiperazine (0.40 M in DMA, 103 μL, 0.041 mmol, 1.2 equivalents) were aspirated from their respective source vials, mixed through a perfluoroalkoxy mixing tube (0.2 mm inner diameter), and loaded into an injection loop. The reaction segment was injected into the flow reactor (Hastelloy coil, 0.75 mm inner diameter, 1.8 mL internal volume) set at 100° C., and passed through the reactor at 180 μL min$^{-1}$ (10 minute residence time). Upon exiting the reactor, the reaction mixture was loaded directly into an injection loop and was purified by preparative HPLC on a Phenomenex Luna C8(2) 5 m 100 Å AXIA column (50 mm×21.2 mm). A gradient of acetonitrile (A) and 0.1% trifluoroacetic acid in water (B) was used, at a flow rate of 30 mL/minutes (0-0.5 minutes 5% A, 0.5-6.5 minutes linear gradient 5-100% A, 6.5-8.5 minutes 100% A, 8.5-9.0 minutes linear gradient 100-5% A, 9.0-10 minutes 5% A). A sample volume of 1.0 mL was injected directly from the flow reactor stream to the HPLC system. A custom purification system was used, consisting of the following modules: Gilson 305 and 306 pumps; Gilson 806 Manometric module; Gilson UV/Vis 155 detector; Gilson 506C interface box; Gilson FC204 fraction collector; Agilent G1968D Active Splitter; Thermo MSQ Plus mass spectrometer. The system was controlled through a combination of Thermo Xcalibur 2.0.7 software and a custom application written in-house using Microsoft Visual Basic 6.0. to provide the TFA salt of the title compound (14.71 mg, 68% yield). $^1$H NMR (400 MHz, DMSO-d$_6$/D$_2$O) δ 8.01 (d, J=2.4 Hz, 1H), 7.93 (dd, J=8.6, 2.4 Hz, 1H), 7.43 (t, J=7.9 Hz, 1H), 7.30 (d, J=1.6 Hz, 2H), 7.24 (d, J=8.6 Hz, 1H), 7.18 (d, J=7.7 Hz, 1H), 7.09 (dd, J=8.2, 2.5 Hz, 1H), 7.01 (d, J=1.5 Hz, 1H), 6.25 (d, J=2.9 Hz, 1H), 3.65 (s, 2H), 3.53 (d, J=12.5 Hz, 3H), 3.25-3.16 (m, 7H), 2.84 (s, 3H). MS (APCI+) m/z 621.2 (M+H)$^+$.

Example 23

4-{2-[3-({4-[2-(1H-imidazol-1-yl)ethyl]piperazin-1-yl}carbonyl)phenoxy]-5-(methylsulfonyl)phenyl}-6-methyl-1,6-dihydro-7H-pyrrolo[2,3-c]pyridin-7-one The TFA salt of the title compound was prepared using the procedure described for Example 22, substituting 1-(2-(1H-imidazol-1-yl)ethyl)piperazine for 1-methylpiperazine and purified by preparative HPLC on a Phenomenex Luna C8(2) 5 μm 100 Å AXIA column (50 mm×21.2 mm) as described. A gradient of acetonitrile (A) and 0.1% trifluoroacetic acid in water (B) was used, at a flow rate of 30 mL/minutes (0-0.5 minutes 5% A, 0.5-6.5 minutes linear gradient 5-60% A, 6.5-7.0 minutes linear gradient 60-100% A, 7.0-8.9 minutes 100% A, 8.9-9.0 minutes linear gradient 100-5% A, 9.0-10 minutes 5% A). A sample volume of 1.0 mL was injected directly from the flow reactor stream to the HPLC system. A custom purification system was used, consisting of the following modules: Gilson 305 and 306 pumps; Gilson 806 Manometric module; Gilson UV/Vis 155 detector; Gilson 506C interface box; Gilson FC204 fraction collector; Agilent G1968D Active Splitter; Thermo MSQ Plus mass spectrometer. The system was controlled through a combination of Thermo Xcalibur 2.0.7 software and a custom application written in-house using Microsoft Visual Basic 6.0. $^1$H NMR (400 MHz, DMSO-d$_6$/D$_2$O) δ 8.95 (s, 1H), 8.01 (d, J=2.4 Hz, 1H), 7.93 (dd, J=8.6, 2.4 Hz, 1H), 7.68 (s, 1H), 7.57 (s, 1H), 7.40 (t, J=7.9 Hz, 1H), 7.29 (d, J=2.8 Hz, 2H), 7.24 (d, J=8.6 Hz, 1H), 7.10 (d, J=7.6 Hz, 1H), 7.04 (dd, J=8.3, 2.4 Hz, 1H), 6.90 (s, 1H), 6.24 (d, J=2.8 Hz, 1H), 4.38 (t, J=6.1 Hz, 2H), 3.54 (s, 3H), 3.42 (s, 4H), 3.22 (s, 3H), 2.97 (t, J=6.2 Hz, 2H), 2.62 (s, 4H). MS (APCI+) m/z 602.1 (M+H)$^+$.

Example 24

6-methyl-4-[5-(methylsulfonyl)-2-(3-{[4-(pyrrolidin-1-yl)piperidin-1-yl]carbonyl}phenoxy)phenyl]-1,6-dihydro-7H-pyrrolo[2,3-c]pyridin-7-one The trifluoroacetic acid salt of the title compound was prepared using the procedure described for Example 22, substituting 4-(pyrrolidin-1-yl)piperidine for 1-methylpiperazine and purified using method described in Example 23. $^1$H NMR (400 MHz, DMSO-d$_6$/D$_2$O) δ 8.01 (d, J=2.4 Hz, 1H), 7.93 (dd, J=8.6, 2.4 Hz, 1H), 7.41 (t, J=7.9 Hz, 1H), 7.30 (d, J=2.7 Hz, 2H), 7.24 (t, J=9.5 Hz, 1H), 7.11 (d, J=7.6 Hz, 1H), 7.05 (dd, J=8.2, 2.5 Hz, 1H), 6.92 (d, J=1.5 Hz, 1H), 6.24 (d, J=2.8 Hz, 1H), 4.02 (d, J=38.8 Hz, 2H), 3.54 (s, 4H), 3.50 (s, 1H), 3.39 (t, J=11.4 Hz, 1H), 3.23 (s, 3H), 3.15 (s, 1H), 2.91 (t, J=12.5 Hz, 2H), 2.07 (d, J=12.3 Hz, 3H), 1.96 (s, 4H), 1.51 (dt, J=11.9, 7.7 Hz, 2H). MS (APCI$^+$) m/z 575.2 (M+H)$^+$.

Example 25

N-cyclohexyl-3-[2-(6-methyl-7-oxo-6,7-dihydro-1H-pyrrolo[2,3-c]pyridin-4-yl)-4-(methyl sulfonyl)phenoxy]benzamide The trifluoroacetic acid salt of the title compound was prepared using the procedure described for Example 22, substituting cyclohexanamine for 1-methylpiperazine, and purified by the method described in Example 23. $^1$H NMR (400 MHz, DMSO-d$_6$/D$_2$O) δ 8.00 (d, J=2.4 Hz, 1H), 7.90 (dd, J=8.6, 2.4 Hz, 1H), 7.60 (d, J=7.7 Hz, 1H), 7.42 (dd, J=10.4, 5.4 Hz, 2H), 7.36-7.27 (m, 2H), 7.14 (dd, J=8.3, 3.8 Hz, 2H), 6.26 (d, J=2.8 Hz, 1H), 3.73 (s, 1H), 3.58-3.48 (m, 3H), 3.22 (d, J=4.3 Hz, 3H), 1.80 (s, 2H), 1.73 (s, 2H), 1.59 (d, J=11.6 Hz, 1H), 1.40-1.23 (m, 4H), 1.15 (d, J=8.0 Hz, 1H). MS (APCI+) m/z 519.8 (M+H)$^+$.

Example 26

4-[2-(3-{[4-(2-hydroxyethyl)piperazin-1-yl]carbonyl}phenoxy)-5-(methylsulfonyl)phenyl]-6-methyl-1,6-dihydro-7H-pyrrolo[2,3-c]pyridin-7-one The trifluoroacetic acid salt of the title compound was prepared using the procedure described for Example 22, substituting 2-(piperazin-1-yl)ethanol for 1-methylpiperazine, and purified by the method described in Example 23. $^1$H NMR (400 MHz, DMSO-d$_6$/D$_2$O) δ 8.01 (d, J=2.4 Hz, 1H), 7.93 (dd, J=8.6, 2.4 Hz, 1H), 7.43 (t, J=7.9 Hz, 1H), 7.30 (d, J=2.7 Hz, 2H), 7.24 (d, J=8.6 Hz, 1H), 7.18 (d, J=7.6 Hz, 1H), 7.09 (dd, J=8.2, 2.5 Hz, 1H), 7.02 (d, J=1.5 Hz, 1H), 6.25 (d, J=2.9 Hz, 1H), 3.81-3.76 (m, 2H), 3.69 (s, 4H), 3.55 (s, 3H), 3.23 (d, J=8.4 Hz, 6H). MS (APCI+) m/z 551.1 (M+H)$^+$.

Example 27

3-[2-(6-methyl-7-oxo-6,7-dihydro-1H-pyrrolo[2,3-c]pyridin-4-yl)-4-(methyl sulfonyl)phenoxy]-N-[3-(2-oxopyrrolidin-1-yl)propyl]benzamide The trifluoroacetic acid salt of the title compound was prepared using the procedure described for Example 22, substituting 1-(3-aminopropyl)pyrrolidin-2-one for 1-methylpiperazine, and purified by the method described in Example 23. $^1$H NMR (400 MHz, DMSO-d$_6$/D$_2$O) δ 8.00 (d, J=2.4 Hz, 1H), 7.91 (dt, J=8.7, 4.5 Hz, 1H), 7.58 (t, J=12.6 Hz, 1H), 7.43 (t, J=7.9 Hz, 2H), 7.33-7.27 (m, 2H), 7.15 (dd, J=12.9, 5.6 Hz, 2H), 6.26 (dd, J=6.2, 2.8 Hz, 1H), 3.54 (d, J=5.2 Hz, 3H), 3.39-3.31 (m, 2H), 3.25-3.18 (m, 7H), 2.22 (t, J=8.1 Hz, 2H), 1.99-1.85 (m, 2H), 1.72 (p, J=7.0 Hz, 2H). MS (APCI+) m/z 563.2 (M+H)$^+$.

Example 28

4-[2-{3-[(4-cyclopentylpiperazin-1-yl)carbonyl]phenoxy}-5-(methylsulfonyl)phenyl]-6-methyl-1,6-dihydro-7H-pyrrolo[2,3-c]pyridin-7-one The trifluoroacetic acid salt of the title compound was prepared using the procedure described for Example 22, substituting 1-cyclopentylpiperazine for 1-methylpiperazine, and purified by the method described in Example 23. $^1$H NMR (400 MHz, DMSO-d$_6$/D$_2$O) δ 8.01 (d, J=2.4 Hz, 1H), 7.93 (dd, J=8.6, 2.4 Hz, 1H), 7.43 (t, J=7.9 Hz, 1H), 7.30 (d, J=2.9 Hz, 2H), 7.24 (d, J=8.6 Hz, 1H), 7.19 (d, J=7.6 Hz, 1H), 7.09 (dd, J=8.2, 2.4 Hz, 1H), 7.03 (d, J=1.5 Hz, 1H), 6.25 (d, J=2.8 Hz, 1H), 3.59 (d, J=6.4 Hz, 4H), 3.59-3.52 (m, 5H), 3.25-3.13 (m, 5H), 2.05 (d, J=8.0 Hz, 2H), 1.65 (dd, J=45.4, 8.2 Hz, 7H). MS (APCI+) m/z 575.2 (M+H)$^+$.

Example 29

4-{2-[3-({4-[2-(dimethylamino)ethyl]piperazin-1-yl}carbonyl)phenoxy]-5-(methyl sulfonyl)phenyl}-6-methyl-1,6-dihydro-7H-pyrrolo[2,3-c]pyridin-7-one The trifluoroacetic acid salt of the title compound was prepared using the procedure described for Example 22, substituting N,N-dimethyl-2-(piperazin-1-yl)ethanamine for 1-methylpiperazine, and purified by the method described in Example 23. $^1$H NMR (400 MHz, DMSO-d$_6$/D$_2$O) δ 8.01 (d, J=2.4 Hz, 1H), 7.93 (dd, J=8.6, 2.4 Hz, 1H), 7.41 (t, J=7.9 Hz, 1H), 7.30 (d, J=2.6 Hz, 2H), 7.24 (d, J=8.6 Hz, 1H), 7.11 (d, J=7.7 Hz, 1H), 7.05 (dd, J=8.3, 2.4 Hz, 1H), 6.91 (d, J=1.5 Hz, 1H), 6.25 (d, J=2.9 Hz, 1H), 3.54 (s, 3H), 3.44 (s, 4H), 3.26-3.20 (m, 5H), 2.83 (s, 6H), 2.77 (t, J=6.2 Hz, 2H), 2.54 (dd, J=9.6, 3.7 Hz, 4H). MS (APCI+) m/z 578.2 (M+H)$^+$.

Example 30

4-[2-{3-[(4-acetylpiperazin-1-yl)carbonyl]phenoxy}-5-(methylsulfonyl)phenyl]-6-methyl-1,6-dihydro-7H-pyrrolo[2,3-c]pyridin-7-one The trifluoroacetic acid salt of the title compound was prepared using the procedure described for Example 22, substituting 1-(piperazin-1-yl)ethanone for 1-methylpiperazine, and purified by the method described in Example 23. $^1$H NMR (400 MHz, DMSO-d$_6$/D$_2$O) δ 8.00 (d, J=2.4 Hz, 1H), 7.93 (dd, J=8.6, 2.4 Hz, 1H), 7.40 (t, J=7.9 Hz, 1H), 7.30 (d, J=4.0 Hz, 2H), 7.23 (t, J=10.1 Hz, 1H), 7.13 (d, J=7.6 Hz, 1H), 7.04 (dd, J=8.2, 2.5 Hz, 1H), 6.94 (d, J=1.5 Hz, 1H), 6.25 (d, J=2.8 Hz, 1H), 3.54 (s, 3H), 3.46 (dd, J=11.7, 8.4 Hz, 4H), 3.41 (s, 4H), 3.22 (s, 3H), 2.02 (s, 3H). MS (APCI+) m/z 549.2 (M+H)$^+$.

Example 31

6-methyl-4-[5-(methylsulfonyl)-2-(3-{[4-(trifluoromethyl)piperidin-1-yl]carbonyl}phenoxy)phenyl]-1,6-dihydro-7H-pyrrolo[2,3-c]pyridin-7-one The trifluoroacetic acid salt of the title compound was prepared using the procedure described for Example 22, substituting 4-(trifluoromethyl)piperidine for 1-methylpiperazine, and purified by the method described in Example 23. $^1$H NMR (400 MHz, DMSO-d$_6$/D$_2$O) δ 8.00 (d, J=2.4 Hz, 1H), 7.92 (dd, J=8.6, 2.4 Hz, 1H), 7.40 (t, J=7.9 Hz, 1H), 7.34-7.26 (m, 2H), 7.24 (d, J=8.6 Hz, 1H), 7.11 (d, J=7.6 Hz, 1H), 7.04 (dd, J=8.2, 2.4 Hz, 1H), 6.92 (d, J=1.5 Hz, 1H), 6.25 (d, J=2.8 Hz, 1H), 4.02 (d, J=36.4 Hz, 2H), 3.54 (s, 3H), 3.21 (d, J=7.5 Hz, 3H), 2.92 (t, J=12.1 Hz, 2H), 2.55 (d, J=5.7 Hz, 1H), 1.83 (d, J=11.8 Hz, 2H), 1.38 (qd, J=12.4, 4.4 Hz, 2H). MS (APCI+) m/z 574.1 (M+H)$^+$.

Example 32

N-(cyanomethyl)-N-methyl-3-[2-(6-methyl-7-oxo-6,7-dihydro-1H-pyrrolo[2,3-c]pyridin-4-yl)-4-(methylsulfonyl)phenoxy]benzamide The trifluoroacetic acid salt of the title compound was prepared using the procedure described for Example 22, substituting 2-(methylamino)acetonitrile for 1-methylpiperazine, and purified by the method described in Example 23. $^1$H NMR (400 MHz, DMSO-d$_6$/D$_2$O) δ 8.00 (d, J=2.4 Hz, 1H), 7.92 (dd, J=8.6, 2.4 Hz, 1H), 7.43 (t, J=7.9 Hz, 1H), 7.34-7.28 (m, 2H), 7.25 (d, J=8.6 Hz, 1H), 7.17 (d, J=7.7 Hz, 1H), 7.09 (dd, J=8.2, 2.5 Hz, 1H), 6.99 (d, J=1.6 Hz, 1H), 6.25 (d, J=2.8 Hz, 1H), 4.40 (s, 2H), 3.54 (s, 3H), 3.22 (s, 3H), 2.93 (s, 3H). MS (APCI+) m/z 491.2 (M+H)$^+$.

Example 33

N-[2-(dimethylamino)ethyl]-3-[2-(6-methyl-7-oxo-6,7-dihydro-1H-pyrrolo[2,3-c]pyridin-4-yl)-4-(methylsulfonyl)phenoxy]benzamide The trifluoroacetic acid salt of the title compound was prepared using the procedure described for Example 22, substituting N1,N1-dimethylethane-1,2-diamine for 1-methylpiperazine, and purified by the method described in Example 23. $^1$H NMR (400 MHz, DMSO-d$_6$/D$_2$O) δ 8.02 (d, J=2.4 Hz, 1H), 7.92 (dd, J=8.6, 2.4 Hz, 1H), 7.62 (d, J=7.7 Hz, 1H), 7.47 (t, J=7.9 Hz, 1H), 7.44-7.42 (m, 1H), 7.31 (s, 1H), 7.29 (d, J=2.8 Hz, 1H), 7.22-7.18 (m, 1H), 7.17 (d, J=8.7 Hz, 1H), 6.25 (d, J=2.9 Hz, 1H), 3.61 (t, J=6.1 Hz, 2H), 3.55 (s, 3H), 3.30-3.27 (m, 2H), 3.22 (s, 3H), 2.85 (s, 6H). MS (APCI+) m/z 509.2 (M+H)$^+$.

Example 34

3-[2-(6-methyl-7-oxo-6,7-dihydro-1H-pyrrolo[2,3-c]pyridin-4-yl)-4-(methylsulfonyl)phenoxy]-N-[(2R)-tetrahydrofuran-2-ylmethyl]benzamide The trifluoroacetic acid salt of the title compound was prepared using the procedure described for Example 22, substituting (R)-(tetrahydrofuran-2-yl)methanamine for 1-methylpiperazine, and purified by the method described in Example 23. $^1$H NMR (400 MHz, DMSO-d$_6$/D$_2$O) δ 8.00 (d, J=2.4 Hz, 1H), 7.90 (dd, J=8.7, 2.4 Hz, 1H), 7.60 (d, J=7.7 Hz, 1H), 7.44 (dd, J=3.9, 1.9 Hz, 1H), 7.42 (d, J=7.9

Hz, 1H), 7.32 (s, 1H), 7.29 (d, J=2.9 Hz, 1H), 7.16 (d, J=8.6 Hz, 1H), 7.16-7.13 (m, 1H), 6.26 (d, J=2.8 Hz, 1H), 3.97 (p, J=6.4 Hz, 1H), 3.80-3.69 (m, 1H), 3.63 (dd, J=14.4, 7.5 Hz, 1H), 3.55 (s, 3H), 3.31 (d, J=5.9 Hz, 2H), 3.22 (s, 3H), 1.98-1.85 (m, 1H), 1.81 (dt, J=15.0, 5.1 Hz, 2H), 1.63-1.50 (m, 1H). MS (APCI+) m/z 522.2 (M+H)$^+$.

Example 35

3-[2-(6-methyl-7-oxo-6,7-dihydro-1H-pyrrolo[2,3-c] pyridin-4-yl)-4-(methylsulfonyl)phenoxy]-N-[2-(pyrrolidin-1-yl)ethyl]benzamide The trifluoroacetic acid salt of the title compound was prepared using the procedure described for Example 22, substituting 2-(pyrrolidin-1-yl)ethanamine for 1-methylpiperazine, and purified by the method described in Example 23. $^1$H NMR (400 MHz, DMSO-d$_6$/D$_2$O) δ 8.02 (d, J=2.4 Hz, 1H), 7.92 (dd, J=8.6, 2.4 Hz, 1H), 7.62 (d, J=7.9 Hz, 1H), 7.51-7.45 (m, 1H), 7.44 (d, J=2.1 Hz, 1H), 7.31 (s, 1H), 7.29 (d, J=2.9 Hz, 1H), 7.22-7.18 (m, 1H), 7.17 (d, J=8.7 Hz, 1H), 6.25 (d, J=2.8 Hz, 1H), 3.60 (t, J=6.1 Hz, 3H), 3.55 (s, 3H), 3.33 (t, J=6.1 Hz, 2H), 3.22 (s, 3H), 3.15 (s, 1H), 1.96 (s, 4H). MS (APCI+) m/z 535.1 (M+H)$^+$.

Example 36

N-(3,5-difluorobenzyl)-3-[2-(6-methyl-7-oxo-6,7-dihydro-1H-pyrrolo[2,3-c]pyridin-4-yl)-4-(methylsulfonyl)phenoxy]benzamide The trifluoroacetic acid salt of the title compound was prepared using the procedure described for Example 22, substituting (3,5-difluorophenyl)methanamine for 1-methylpiperazine, and purified by the method described in Example 23. $^1$H NMR (400 MHz, DMSO-d$_6$/D$_2$O) δ 8.00 (d, J=2.4 Hz, 1H), 7.91 (dd, J=8.7, 2.4 Hz, 1H), 7.65 (d, J=7.8 Hz, 1H), 7.49-7.47 (m, 1H), 7.48-7.42 (m, 1H), 7.31 (s, 1H), 7.29 (t, J=3.2 Hz, 1H), 7.17 (dd, J=8.4, 3.6 Hz, 2H), 6.95 (dd, J=14.9, 4.7 Hz, 3H), 6.25 (dd, J=9.3, 2.9 Hz, 1H), 4.46 (s, 2H), 3.54 (s, 3H), 3.24-3.18 (m, 3H). MS (APCI+) m/z 564.1 (M+H)$^+$.

Example 37

N-(2,4-difluorobenzyl)-3-[2-(6-methyl-7-oxo-6,7-dihydro-1H-pyrrolo[2,3-c]pyridin-4-yl)-4-(methylsulfonyl)phenoxy]benzamide The trifluoroacetic acid salt of the title compound was prepared using the procedure described for Example 22, substituting (2,4-difluorophenyl)methanamine for 1-methylpiperazine, and purified by the method described in Example 23. $^1$H NMR (400 MHz, DMSO-d$_6$/D$_2$O) δ 8.00 (d, J=2.4 Hz, 1H), 7.90 (dd, J=8.6, 2.4 Hz, 1H), 7.64 (d, J=7.7 Hz, 1H), 7.49-7.45 (m, 1H), 7.43 (d, J=7.8 Hz, 1H), 7.41-7.35 (m, 1H), 7.31 (s, 1H), 7.28 (d, J=2.8 Hz, 1H), 7.16 (dd, J=8.3, 3.2 Hz, 2H), 7.10-7.03 (m, 1H), 6.99 (dd, J=9.8, 7.3 Hz, 1H), 6.25 (d, J=2.8 Hz, 1H), 4.46 (s, 2H), 3.54 (s, 3H), 3.24-3.18 (m, 3H). MS (APCI+) m/z 564.1 (M+H)$^+$.

Example 38

N-{3-[2-(6-methyl-7-oxo-6,7-dihydro-1H-pyrrolo[2,3-c]pyridin-4-yl)-4-(methylsulfonyl)phenoxy]phenyl}-1-phenylmethanesulfonamide Example 38a 3-(2-bromo-4-(methyl sulfonyl)phenoxy)aniline A mixture of Example 21b (1.0 g, 3.95 mmol), 3-aminophenol (0.516 g, 4.73 mmol), cesium carbonate (1.84 g, 5.65 mmol) and dimethylsulfoxide (16 mL) was heated at 120° C. in a sealed tube for 1 hour. The reaction mixture was cooled to ambient temperature and water (100 mL) was added. The mixture was extracted with ethyl acetate. The ethyl acetate layer was washed with water, saturated aqueous sodium chloride, dried (anhydrous magnesium sulfate), filtered, and concentrated to afford 1.4 g oil. The crude product was flash chromatographed (Biotage 50g HP Snap Cartridge, eluting with heptanes containing a gradient with ethyl acetate, 10% to 75%) to provide the title compound (1.35 g, 3.94 mmol, 100% yield)

Example 38b 4-(2-(3-aminophenoxy)-5-(methylsulfonyl)phenyl)-6-methyl-1H-pyrrolo[2,3-c]pyridin-7(6H)-one Using the procedure described for Example 1j and substituting Example 38a for Example 1i provided the title compound.

Example 38c

N-{3-[2-(6-methyl-7-oxo-6,7-dihydro-1H-pyrrolo[2,3-c]pyridin-4-yl)-4-(methylsulfonyl)phenoxy]phenyl}-1-phenylmethanesulfonamide A 4 mL vial was charged with Example 38b (24 mg, 0.061 mmol), phenyl methane sulfonyl chloride (14 mg, 0.07 mmol), and diisopropylethyl amine (30 μL, 0.18 mmol). The reaction mixture was allowed to stir at ambient temperature overnight. The reaction mixture was concentrated and the residue was purified by reverse phase HPLC (C18, CH$_3$CN/water (0.1% TFA), 0-100% gradient) to provide the title compound. $^1$H NMR (400 MHz, DMSO-d$_6$/D$_2$O) δ 8.03-7.91 (m, 2H), 7.41 (s, 1H), 7.37-7.25 (m, 5H), 7.23-7.17 (m, 2H), 7.14 (d, J=8.6 Hz, 1H), 6.97 (d, J=7.1 Hz, 1H), 6.80-6.74 (m, 2H), 6.27 (d, J=2.8 Hz, 1H), 4.42 (s, 2H), 3.58 (s, 3H), 3.27 (s, 3H). MS (ESI+) m/z 564 (M+H)$^+$.

Example 39

4-methoxy-N-{3-[2-(6-methyl-7-oxo-6,7-dihydro-1H-pyrrolo[2,3-c]pyridin-4-yl)-4-(methylsulfonyl)phenoxy]phenyl}benzenesulfonamide Example 39 was prepared according to the procedure used for the preparation of Example 38c, substituting 4-methoxybenzene-1-sulfonyl chloride for phenyl methane sulfonyl chloride to provide the title compound. $^1$H NMR (400 MHz, DMSO-d$_6$/D$_2$O) δ 8.00 (d, J=2.4 Hz, 1H), 7.88 (dd, J=8.7, 2.4 Hz, 1H), 7.75-7.54 (m, 2H), 7.39-7.28 (m, 2H), 7.28-7.12 (m, 1H), 7.10-6.98 (m, 2H), 6.93 (d, J=8.7 Hz, 1H), 6.90-6.84 (m, 1H), 6.72 (dd, J=8.7, 1.5 Hz, 2H), 6.20 (d, J=2.8 Hz, 1H), 3.83 (d, J=19.5 Hz, 3H), 3.55 (s, 3H), 3.27 (s, 3H), 3.18 (s, 1H), 1.31-1.12 (m, 1H). MS (ESI+) m/z 580 (M+H)$^+$.

Example 40

3-fluoro-N-{3-[2-(6-methyl-7-oxo-6,7-dihydro-1H-pyrrolo[2,3-c]pyridin-4-yl)-4-(methyl sulfonyl)phenoxy]phenyl}benzenesulfonamide Example 40 was prepared according to the procedure used for the preparation of Example 38c, substituting 3-fluorobenzene-1-sulfonyl chloride for phenyl methane sulfonyl chloride. $^1$H NMR (400 MHz, DMSO-d$_6$/D$_2$O) δ 7.99 (d, J=2.4 Hz, 1H), 7.88 (dd, J=8.6, 2.4 Hz, 1H), 7.68-7.55 (m, 1H), 7.55-7.46 (m, 3H), 7.35 (s, 1H), 7.31 (d, J=2.8 Hz, 1H), 7.27 (t, J=8.1 Hz, 2H), 6.98-6.86 (m, 2H), 6.77 (dd, J=8.1, 2.4 Hz, 1H), 6.73 (t, J=2.2 Hz, 1H), 6.19 (d, J=2.8 Hz, 1H), 3.55 (s, 3H), 3.27 (s, 3H). MS (ESI+) m/z 568 (M+H)$^+$.

Example 41

4-fluoro-N-{3-[2-(6-methyl-7-oxo-6,7-dihydro-1H-pyrrolo[2,3-c]pyridin-4-yl)-4-(methylsulfonyl)phenoxy]phenyl}benzenesulfonamide Example 41 was prepared according to the procedure used for the preparation of Example 38c, substituting 4-fluorobenzene-1-sulfonyl chloride for phenyl methane sulfonyl chloride. $^1$H NMR (400 MHz, DMSO-d$_6$/D$_2$O) δ 8.00 (d, J=2.4 Hz, 1H), 7.90 (dd, J=8.6, 2.4 Hz, 1H), 7.78-7.70 (m, 2H), 7.42-7.34 (m, 3H), 7.32 (d, J=2.8 Hz, 1H), 7.26 (t, J=8.1 Hz, 1H), 6.96 (d, J=8.6 Hz, 1H), 6.87 (dd, J=8.0, 2.0 Hz, 1H), 6.75 (dd, J=8.1, 2.4 Hz, 1H), 6.71 (t, J=2.2 Hz, 1H), 6.20 (d, J=2.8 Hz, 1H), 3.56 (s, 3H), 3.27 (s, 3H). MS (ESI+) m/z 568 (M+H)$^+$.

Example 42

3-methoxy-N-{3-[2-(6-methyl-7-oxo-6,7-dihydro-1H-pyrrolo[2,3-c]pyridin-4-yl)-4-(methylsulfonyl)phenoxy]phenyl}benzenesulfonamide Example 42 was prepared according to the procedure used for the preparation of Example 38c, substituting 3-methoxybenzene-1-sulfonyl chloride for phenyl methane sulfonyl chloride. $^1$H NMR (400 MHz, DMSO-d$_6$/D$_2$O) δ 8.07-7.92 (m, 1H), 7.87 (dd, J=8.7, 2.4 Hz, 1H), 7.49-7.44 (m, 1H), 7.34 (s, 1H), 7.31 (d, J=2.8 Hz, 1H), 7.25 (dd, J=8.3, 4.7 Hz, 2H), 7.22-7.19 (m, 2H), 7.05-6.86 (m, 2H), 6.75 (dd, J=4.1, 1.9 Hz, 2H), 6.33-6.15 (m, 1H), 3.54 (d, J=8.1 Hz, 3H), 3.28 (d, J=6.3 Hz, 3H). MS (ESI+) m/z 580 (M+H)$^+$.

Example 43

N-{3-[2-(6-methyl-7-oxo-6,7-dihydro-1H-pyrrolo[2,3-c]pyridin-4-yl)-4-(methyl sulfonyl)phenoxy]phenyl}-4-nitrobenzenesulfonamide Example 43 was prepared according to the procedure used for the preparation of Example 38c, substituting 4-nitrobenzene-1-sulfonyl chloride for phenyl methane sulfonyl chloride. $^1$H NMR (400 MHz, DMSO-d$_6$/D$_2$O) δ 8.52-8.31 (m, 2H), 8.00 (d, J=2.4 Hz, 1H), 7.96-7.91 (m, 2H), 7.89 (dd, J=8.7, 2.4 Hz, 1H), 7.37 (s, 1H), 7.32 (d, J=2.8 Hz, 1H), 7.28 (t, J=8.2 Hz, 1H), 6.99 (d, J=8.6 Hz, 1H), 6.90 (dd, J=8.0, 1.7 Hz, 1H), 6.84-6.69 (m, 2H), 6.21 (d, J=2.8 Hz, 1H), 3.55 (s, 3H), 3.27 (s, 3H). MS (ESI+) m/z 595 (M+H)$^+$.

Example 44

4-acetyl-N-{3-[2-(6-methyl-7-oxo-6,7-dihydro-1H-pyrrolo[2,3-c]pyridin-4-yl)-4-(methylsulfonyl)phenoxy]phenyl}benzenesulfonamide Example 44 was prepared according to the procedure used for the preparation of Example 38c, substituting 4-acetylbenzene-1-sulfonyl chloride for phenyl methane sulfonyl chloride. $^1$H NMR (400 MHz, DMSO-d$_6$/D$_2$O) δ 8.07 (d, J=8.5 Hz, 2H), 7.99 (d, J=2.4 Hz, 1H), 7.87 (dd, J=8.6, 2.4 Hz, 1H), 7.81 (d, J=8.4 Hz, 2H), 7.35 (s, 1H), 7.31 (d, J=2.8 Hz, 1H), 7.26 (t, J=8.1 Hz, 1H), 6.95 (d, J=8.6 Hz, 1H), 6.89 (dd, J=8.0, 1.6 Hz, 1H), 6.81-6.68 (m, 2H), 6.20 (d, J=2.8 Hz, 1H), 3.55 (s, 3H), 3.27 (s, 3H), 2.61 (s, 3H). MS (ESI+) m/z 592 (M+H)$^+$.

Example 45

5-(dimethylamino)-N-{3-[2-(6-methyl-7-oxo-6,7-dihydro-1H-pyrrolo[2,3-c]pyridin-4-yl)-4-(methylsulfonyl)phenoxy]phenyl}naphthalene-1-sulfonamide Example 45 was prepared according to the procedure used for the preparation of Example 38c, substituting 5-(dimethylamino) naphthalene-1-sulfonyl chloride for phenyl methane sulfonyl chloride. $^1$H NMR (400 MHz, DMSO-d$_6$/D$_2$O) δ 8.46 (d, J=8.5 Hz, 1H), 8.31 (d, J=8.6 Hz, 1H), 8.09 (dd, J=7.3, 1.2 Hz, 1H), 7.97 (d, J=2.4 Hz, 1H), 7.85 (dd, J=8.6, 2.4 Hz, 1H), 7.67-7.54 (m, 2H), 7.36-7.12 (m, 4H), 6.87-6.79 (m, 2H), 6.64-6.59 (m, 2H), 6.10 (d, J=2.8 Hz, 1H), 3.48 (s, 3H), 3.28 (s, 3H), 2.84 (s, 6H). MS (ESI+) m/z 643.1 (M+H)$^+$.

Example 46

N-{3-[2-(6-methyl-7-oxo-6,7-dihydro-1H-pyrrolo[2,3-c]pyridin-4-yl)-4-(methyl sulfonyl)phenoxy]phenyl}-4-(propan-2-yl)benzenesulfonamide Example 46 was prepared according to the procedure used for the preparation of Example 38c, substituting 4-isopropylbenzene-1-sulfonyl chloride for phenyl methane sulfonyl chloride. $^1$H NMR (400 MHz, DMSO-d$_6$/D$_2$O) δ 8.00 (d, J=2.4 Hz, 1H), 7.89 (dd, J=8.7, 2.4 Hz, 1H), 7.60 (d, J=8.4 Hz, 2H), 7.40 (d, J=8.4 Hz, 2H), 7.32 (d, J=3.0 Hz, 2H), 7.29-7.22 (m, 1H), 6.97 (d, J=8.6 Hz, 1H), 6.88 (dd, J=7.6, 1.3 Hz, 1H), 6.74-6.68 (m, 2H), 6.19 (d, J=2.8 Hz, 1H), 3.55 (d, J=4.9 Hz, 3H), 3.27 (s, 3H), 2.94 (hept, J=7.0 Hz, 1H), 1.17 (d, J=6.9 Hz, 6H). MS (ESI+) m/z 592.1 (M+H)$^+$.

Example 47

2,4-difluoro-N-{3-[2-(6-methyl-7-oxo-6,7-dihydro-1H-pyrrolo[2,3-c]pyridin-4-yl)-4-(methyl sulfonyl)phenoxy]phenyl}benzenesulfonamide Example 47 was prepared according to the procedure used for the preparation of Example 38c, substituting 2,4-difluorobenzene-1-sulfonyl chloride for phenyl methane sulfonyl chloride. $^1$H NMR (400 MHz, DMSO-d$_6$/D$_2$O) δ 8.00 (d, J=2.4 Hz, 1H), 7.90 (dd, J=8.6, 2.4 Hz, 1H), 7.81 (td, J=8.6, 6.2 Hz, 1H), 7.55-7.43 (m, 1H), 7.32 (dd, J=14.3, 11.5 Hz, 2H), 7.29-7.17 (m, 2H), 6.97 (d, J=8.6 Hz, 1H), 6.89 (dd, J=8.1, 1.4 Hz, 1H), 6.82-6.70 (m, 2H), 6.20 (d, J=2.8 Hz, 1H), 3.56 (s, 3H), 3.27 (s, 3H). MS (ESI+) m/z 586 (M+H)$^+$.

Example 48

3-(difluoromethoxy)-N-{3-[2-(6-methyl-7-oxo-6,7-dihydro-1H-pyrrolo[2,3-c]pyridin-4-yl)-4-(methylsulfonyl)phenoxy]phenyl}benzenesulfonamide Example 48 was prepared according to the procedure used for the preparation of Example 38c, substituting 3-(difluoromethoxy) benzene-1-sulfonyl chloride for phenyl methane sulfonyl chloride. $^1$H NMR (400 MHz, DMSO-d$_6$/D$_2$O) δ 7.99 (d, J=2.4 Hz, 1H), 7.87 (dd, J=8.6, 2.4 Hz, 1H), 7.66-7.58 (m, 1H), 7.57-7.51 (m, 1H), 7.49-7.43 (m, 2H), 7.43-7.19 (m, 4H), 6.92 (t, J=8.7 Hz, 2H), 6.81-6.72 (m, 2H), 6.20 (d, J=2.8 Hz, 1H), 3.55 (s, 3H), 3.26 (s, 3H). MS (ESI+) m/z 616 (M+H)$^+$.

Example 49

N-{3-[2-(6-methyl-7-oxo-6,7-dihydro-1H-pyrrolo[2,3-c]pyridin-4-yl)-4-(methyl sulfonyl)phenoxy]phenyl}cyclopropanesulfonamide Example 49 was prepared according to the procedure used for the preparation of Example 38c, substituting cyclopropane sulfonyl chloride for phenyl methane sulfonyl chloride. $^1$H NMR (400 MHz, DMSO-d$_6$/D$_2$O) δ 8.00 (d, J=2.4 Hz, 1H), 7.93 (dd, J=8.6, 2.4 Hz, 1H), 7.42-7.32 (m, 3H), 7.32 (d, J=4.7 Hz, 2H), 7.16 (d, J=8.6 Hz, 1H), 7.02 (dd, J=8.0, 2.1 Hz, 1H), 6.88 (t, J=2.2 Hz, 1H), 6.80 (dd, J=8.1, 2.4 Hz, 1H), 6.26 (d, J=2.8 Hz, 1H), 3.57 (s, 3H), 3.26 (s, 3H), 0.97-0.83 (m, 4H). MS (ESI+) m/z 514 (M+H)$^+$.

Example 50

3-methyl-N-{3-[2-(6-methyl-7-oxo-6,7-dihydro-1H-pyrrolo[2,3-c]pyridin-4-yl)-4-(methylsulfonyl)phenoxy]phenyl}benzenesulfonamide Example 50 was prepared according to the procedure used for the preparation of Example 38c, substituting 3-methylbenzene-1-sulfonyl chloride for phenyl methane sulfonyl chloride. $^1$H NMR (400 MHz, DMSO-d$_6$/D$_2$O) δ 7.99 (d, J=2.4 Hz, 1H), 7.87 (dd, J=8.6, 2.4 Hz, 1H), 7.53 (s, 1H), 7.50-7.39 (m, 3H), 7.31 (d, J=2.8 Hz, 1H), 7.29-7.21 (m, 1H), 6.96-6.85 (m, 2H), 6.76-6.71 (m, 2H), 6.19 (d, J=2.8 Hz, 1H), 3.55 (s, 3H), 3.27 (s, 3H), 2.31 (s, 3H). MS (ESI+) m/z 564 (M+H)$^+$.

Example 51

N-{3-[2-(6-methyl-7-oxo-6,7-dihydro-1H-pyrrolo[2,3-c]pyridin-4-yl)-4-(methylsulfonyl)phenoxy]phenyl}-3-nitrobenzenesulfonamide Example 51 was prepared according to the procedure used for the preparation of Example 38c, substituting 3-nitrobenzene-1-sulfonyl chloride for phenyl methane sulfonyl chloride. $^1$H NMR (400 MHz, DMSO-d$_6$/D$_2$O) δ 8.50-8.38 (m, 2H), 8.09-8.03 (m, 1H), 7.99 (d, J=2.4 Hz, 1H), 7.90-7.82 (m, 2H), 7.36 (s, 1H), 7.30 (d, J=2.8 Hz, 2H), 7.29 (t, J=8.1 Hz, 2H), 6.97-6.88 (m, 2H), 6.80 (dd, J=8.1, 2.4 Hz, 1H), 6.76 (t, J=2.2 Hz, 1H), 6.19 (d, J=2.8 Hz, 1H), 3.55 (s, 3H), 3.27 (s, 3H). MS (ESI+) m/z 595 (M+H)$^+$.

Example 52

4-fluoro-2-methyl-N-{3-[2-(6-methyl-7-oxo-6,7-dihydro-1H-pyrrolo[2,3-c]pyridin-4-yl)-4-(methyl sulfonyl)phenoxy]phenyl}benzenesulfonamide Example 52 was prepared according to the procedure used for the preparation of Example 38c, substituting 4-fluoro-2-methylbenzene-1-sulfonyl chloride for phenyl methane sulfonyl chloride. $^1$H NMR (400 MHz, DMSO-d$_6$/D$_2$O) δ 8.00 (d, J=2.4 Hz, 1H), 7.90 (dd, J=8.6, 2.4 Hz, 1H), 7.81 (dd, J=8.8, 5.7 Hz, 1H), 7.35-7.26 (m, 3H), 7.28-7.23 (m, 1H), 7.22 (d, J=8.1 Hz, 1H), 7.15 (td, J=8.5, 2.7 Hz, 1H), 6.97 (d, J=8.6 Hz, 1H), 6.84 (dd, J=8.1, 2.0 Hz, 1H), 6.69 (dd, J=8.1, 2.4 Hz, 1H), 6.65 (t, J=2.2 Hz, 1H), 6.18 (d, J=2.8 Hz, 1H), 3.55 (s, 3H), 3.28 (s, 3H). MS (ESI+) m/z 582 (M+H)$^+$.

Example 53

3,4-dimethoxy-N-{3-[2-(6-methyl-7-oxo-6,7-dihydro-1H-pyrrolo[2,3-c]pyridin-4-yl)-4-(methyl sulfonyl)phenoxy]phenyl})benzenesulfonamide Example 53 was prepared according to the procedure used for the preparation of Example 38c, substituting 3,4-dimethoxybenzene-1-sulfonyl chloride for phenyl methane sulfonyl chloride. $^1$H NMR (400 MHz, DMSO-d$_6$/D$_2$O) δ 7.99 (d, J=2.4 Hz, 1H), 7.85 (dd, J=8.7, 2.4 Hz, 1H), 7.33 (d, J=10.9 Hz, 1H), 7.30 (dd, J=12.0, 5.6 Hz, 1H), 7.27-7.18 (m, 2H), 7.03 (d, J=8.5 Hz, 1H), 6.95-6.90 (m, 1H), 6.87 (d, J=8.6 Hz, 1H), 6.75 (dd, J=8.8, 1.4 Hz, 2H), 6.19 (d, J=2.8 Hz, 1H), 3.81 (s, 3H), 3.68 (s, 3H), 3.55 (s, 3H), 3.23 (d, J=35.1 Hz, 3H). MS (ESI+) m/z 610 (M+H)$^+$.

Example 54

N-{3-[2-(6-methyl-7-oxo-6,7-dihydro-1H-pyrrolo[2,3-c]pyridin-4-yl)-4-(methylsulfonyl)phenoxy]phenyl}-4-(methyl sulfonyl)benzenesulfonamide Example 54 was prepared according to the procedure used for the preparation of Example 38c, substituting 4-(methylsulfonyl) benzene-1-sulfonyl chloride for phenyl methane sulfonyl chloride. $^1$H NMR (400 MHz, DMSO-d$_6$/D$_2$O) δ 8.13-8.08 (m, 2H), 8.01-7.85 (m, 4H), 7.36 (s, 1H), 7.32 (d, J=2.8 Hz, 1H), 7.28 (t, J=8.1 Hz, 2H), 6.96 (d, J=8.6 Hz, 1H), 6.90 (dd, J=8.0, 2.1 Hz, 1H), 6.78 (dd, J=8.1, 2.4 Hz, 1H), 6.74 (t, J=2.2 Hz, 1H), 6.21 (d, J=2.8 Hz, 1H), 3.55 (s, 3H), 3.26 (d, J=1.4 Hz, 6H). MS (ESI+) m/z 627.9 (M+H)$^+$.

Example 55

2-cyano-N-{3-[2-(6-methyl-7-oxo-6,7-dihydro-1H-pyrrolo[2,3-c]pyridin-4-yl)-4-(methylsulfonyl)phenoxy]phenyl}benzenesulfonamide Example 55 was prepared according to the procedure used for the preparation of Example 38c, substituting 2-cyanobenzene-1-sulfonyl chloride for phenyl methane sulfonyl chloride. $^1$H NMR (400 MHz, DMSO-d$_6$/D$_2$O) δ 8.06 (dd, J=7.3, 1.7 Hz, 1H), 8.00-7.94 (m, 2H), 7.90-7.81 (m, 3H), 7.34 (s, 1H), 7.33-7.28 (m, 1H), 7.26 (d, J=8.2 Hz, 1H), 7.01 (d, J=8.6 Hz, 1H), 6.87 (dd, J=8.0, 1.8 Hz, 1H), 6.78 (dd, J=8.1, 2.2 Hz, 1H), 6.71 (t, J=2.2 Hz, 1H), 6.19 (d, J=2.8 Hz, 1H), 3.55 (s, 3H), 3.27 (s, 3H). MS (ESI+) m/z 575.0 (M+H)+.

Example 56

4-cyano-N-{3-[2-(6-methyl-7-oxo-6,7-dihydro-1H-pyrrolo[2,3-c]pyridin-4-yl)-4-(methylsulfonyl)phenoxy]phenyl}benzenesulfonamide Example 56 was prepared according to the procedure used for the preparation of Example 38c, substituting 4-cyanobenzene-1-sulfonyl chloride for phenyl methane sulfonyl chloride. $^1$H NMR (400 MHz, DMSO-d$_6$/D$_2$O) δ 8.08-7.98 (m, 3H), 7.91 (dt, J=8.2, 4.1 Hz, 1H), 7.89-7.80 (m, 2H), 7.36 (s, 1H), 7.33 (d, J=2.8 Hz, 1H), 7.27 (t, J=8.2 Hz, 1H), 6.99 (d, J=8.6 Hz, 1H), 6.86 (dd, J=8.0, 1.7 Hz, 1H), 6.78 (dd, J=8.1, 2.2 Hz, 1H), 6.72 (t, J=2.2 Hz, 1H), 6.21 (d, J=2.8 Hz, 1H), 3.55 (s, 3H), 3.27 (s, 3H). MS (ESI+) m/z 575.0 (M+H)+.

Example 57

3-cyano-N-{3-[2-(6-methyl-7-oxo-6,7-dihydro-1H-pyrrolo[2,3-c]pyridin-4-yl)-4-(methyl sulfonyl)phenoxy]phenyl}benzenesulfonamide Example 57 was prepared according to the procedure used for the preparation of Example 38c, substituting 3-cyanobenzene-1-sulfonyl chloride for phenyl methane sulfonyl chloride. $^1$H NMR (400 MHz, DMSO-d$_6$/D$_2$O) δ 8.34-8.05 (m, 2H), 8.04-7.84 (m, 3H), 7.83-7.70 (m, 1H), 7.41-7.20 (m, 3H), 7.00-6.85 (m, 2H), 6.85-6.70 (m, 2H), 6.21 (dd, J=8.0, 2.8 Hz, 1H), 3.55 (d, J=3.9 Hz, 3H), 3.28 (d, J=10.6 Hz, 3H). MS (ESI+) m/z 575 (M+H)+.

Example 58

2-chloro-4-fluoro-N-{3-[2-(6-methyl-7-oxo-6,7-dihydro-1H-pyrrolo[2,3-c]pyridin-4-yl)-4-(methylsulfonyl)phenoxy]phenyl}benzenesulfonamide Example 58 was prepared according to the procedure used for the preparation of Example 38c, substituting 2-chloro-4-fluorobenzene-1-sulfonyl chloride for phenyl methane sulfonyl chloride. $^1$H NMR (400 MHz, DMSO-d$_6$/D$_2$O) δ 8.03-7.96 (m, 2H), 7.89 (dd, J=8.6, 2.4 Hz, 1H), 7.66 (dd, J=8.5, 2.5 Hz, 1H), 7.47-7.27 (m, 3H), 7.25 (t, J=8.0 Hz, 1H), 6.96 (d, J=8.6 Hz, 1H), 6.91-6.85 (m, 1H), 6.75-6.68 (m, 2H), 6.19 (d, J=2.8 Hz, 1H), 3.55 (s, 3H), 3.27 (s, 3H). MS (ESI+) m/z 602 (M+H)+.

Example 59

1-methyl-N-{3-[2-(6-methyl-7-oxo-6,7-dihydro-1H-pyrrolo[2,3-c]pyridin-4-yl)-4-(methylsulfonyl)phenoxy]phenyl}-1H-imidazole-4-sulfonamide Example 59 was prepared according to the procedure used for the preparation of Example 38c, substituting 1-methyl-1H-imidazole-4-sulfonyl chloride for phenyl methane sulfonyl chloride. $^1$H NMR (500 MHz, DMSO-d$_6$/D$_2$O) δ 7.95 (d, J=2.4 Hz, 1H), 7.86 (dd, J=8.7, 2.4 Hz, 1H), 7.74-7.62 (m, 2H), 7.34 (s, 1H), 7.29 (d, J=2.8 Hz, 1H), 7.21 (t, J=8.2 Hz, 1H), 6.96 (d, J=8.7 Hz, 1H), 6.91 (dd, J=8.2, 1.3 Hz, 1H), 6.81 (t, J=2.1 Hz, 1H), 6.67 (dd, J=8.2, 1.8 Hz, 1H), 6.19 (d, J=2.8 Hz, 1H), 3.60 (s, 3H), 3.53 (s, 3H), 3.22 (s, 3H). MS (ESI+) m/z 554.1 (M+H)+.

Example 60

3-[({3-[2-(6-methyl-7-oxo-6,7-dihydro-1H-pyrrolo[2,3-c]pyridin-4-yl)-4-(methyl sulfonyl)phenoxy]phenyl}amino)methyl]benzonitrile A 4 mL vial was charged with a solution of Example 38b (21 mg, 0.05 mmol) in 1M solution of ammonium acetate/acetic acid buffer in methanol (pH=4) (1.0 mL), a solution of 3-formylbenzonitrile (10 mg, 0.08 mmol) dissolved in the above buffer solution (0.3 mL), followed by 60 mg of MP-Cyanoborohydride resin (0.88 mmol/g). The resulting reaction mixture was shaken at 40° C. for overnight. The reaction mixture was filtered and purification by reverse phase HPLC (C18, CH$_3$CN/water (0.1% TFA), 0-100% gradient) provided the TFA salt of the title compound (12 mg, 36% yield). $^1$H NMR (400 MHz, DMSO-d$_6$/D$_2$O) δ 7.94 (d, J=2.4 Hz, 1H), 7.83 (dd, J=8.7, 2.4 Hz, 1H), 7.73 (s, 1H), 7.67 (dd, J=17.7, 7.8 Hz, 2H), 7.53 (t, J=7.7 Hz, 1H), 7.36 (s, 1H), 7.30 (d, J=2.8 Hz, 1H), 7.09 (t, J=8.1 Hz, 1H), 6.97 (d, J=8.7 Hz, 1H), 6.44 (dd, J=8.1, 1.9 Hz, 1H), 6.28-6.23 (m, 1H), 6.22 (t, J=2.5 Hz, 2H), 4.31 (s, 2H), 3.57 (d, J=4.7 Hz, 3H), 3.26-3.20 (m, 3H). MS (ESI+) m/z 525 (M+H)+.

Example 61

4-[({3-[2-(6-methyl-7-oxo-6,7-dihydro-1H-pyrrolo[2,3-c]pyridin-4-yl)-4-(methyl sulfonyl)phenoxy]phenyl}amino)methyl]benzonitrile Using the procedure described for Example 60 and substituting 4-formylbenzonitrile for 3-formylbenzonitrile provided the TFA salt of the title compound. $^1$H NMR (400 MHz, DMSO-d$_6$/D$_2$O) δ 7.93 (d, J=2.4 Hz, 1H), 7.84 (dd, J=8.7, 2.4 Hz, 1H), 7.76 (d, J=8.3 Hz, 2H), 7.48 (d, J=8.3 Hz, 2H), 7.35 (s, 1H), 7.30 (d, J=2.8 Hz, 1H), 7.07 (t, J=8.1 Hz, 1H), 7.00 (d, J=8.7 Hz, 1H), 6.40 (d, J=10.0 Hz, 1H), 6.24 (d, J=7.9 Hz, 1H), 6.20 (d, J=2.8 Hz, 1H), 6.17 (d, J=2.1 Hz, 1H), 4.33 (s, 2H), 3.57 (s, 3H), 3.23 (s, 3H). MS (ESI+) m/z 525 (M+H)+.

Example 62

4-[2-{3-[(4-fluorobenzyl)amino]phenoxy}-5-(methylsulfonyl)phenyl]-6-methyl-1,6-dihydro-7H-pyrrolo[2,3-c]pyridin-7-one Using the procedure described for Example 60 and substituting 4-fluorobenzaldehyde for 3-formylbenzonitrile provided the TFA salt of the title compound. $^1$H NMR (400 MHz, DMSO-d$_6$/D$_2$O) δ 7.94 (d, J=2.4 Hz, 1H), 7.84 (dd, J=8.7, 2.4 Hz, 1H), 7.36-7.30 (m, 4H), 7.15-7.05 (m, 3H), 7.00 (d, J=8.7 Hz, 1H), 6.44 (dd, J=8.1, 1.8 Hz, 1H), 6.23 (dq, J=6.9, 2.1 Hz, 3H), 4.21 (s, 2H), 3.57 (s, 3H), 3.23 (s, 3H); MS (ESI+) m/z 518 (M+H)+.

Example 63

4-{2-[(2,2-difluorocyclopropyl)methoxy]-5-(ethylsulfonyl)phenyl}-2-[3-(dimethylamino)prop-1-yn-1-yl]-6-methyl-1,6-dihydro-7H-pyrrolo[2,3-c]pyridin-7-one

Example 63a 4-bromo-2-iodo-7-methoxy-1-tosyl-1H-pyrrolo[2,3-c]pyridine

To a solution of n-BuLi (2.5 M, 36 mL, 90 mmol) in anhydrous tetrahydrofuran (200 mL) was added diisopropylamine (7.33 g, 72.4 mmol) dropwise at −70° C. and the reaction mixture was then stirred at from about −70° C. to about −50° C. for 45 minutes. To the solution of Example 1c (23.0 g, 60.3 mmol) in anhydrous tetrahydrofuran (400 mL) was added the above lithium diisopropylamide solution dropwise at −70° C. and the mixture was stirred for 1.5 hours. Then a solution of diiodine (35.2 g, 139 mmol) in anhydrous tetrahydrofuran (300 mL) was added dropwise to the above mixture at −70° C. The reaction mixture was stirred for another 3 hours and poured into aqueous $Na_2S_2O_3$ solution. The suspension was filtered. The filter cake was washed with dichloromethane and then dried to give the title compound (16 g, 31.5 mmol, 52.3% yield).

Example 63b 4-bromo-2-iodo-1-tosyl-1H-pyrrolo[2,3-c]pyridin-7(6H)-one

Example 63b was prepared according to the procedure used for the preparation of Example 1d, substituting Example 63a for Example 1c.

Example 63c

Example 63c was prepared according to the procedure used for the preparation of Example 1e, substituting Example 63b for Example 1d.

Example 63d 4-bromo-2-(3-(dimethylamino)prop-1-yn-1-yl)-6-methyl-1-tosyl-1H-pyrrolo[2,3-c]pyridin-7(6H)-one To a round bottom flask equipped with a reflux condenser were added Example 63c (500 mg, 0.986 mmol), N,N-dimethylprop-2-yn-1-amine (164 mg, 1.972 mmol), $PdCl_2(PPh_3)_2$ (69.2 mg, 0.099 mmol), CuI (37.6 mg, 0.197 mmol), triethylamine (2.75 mL, 19.72 mmol) and dimethylformamide (10 mL). The suspension was heated at 70° C. for 2 hours. The reaction mixture was cooled to ambient temperature, filtered through Celite, and washed with ethyl acetate several times. The residue was partitioned between water (100 mL) and ethyl acetate (100 mL). The organic layer was separated and the aqueous layer was extracted with ethyl acetate again (50 mL twice). The combined organic layers were dried over anhydrous sodium sulfate, filtered, and concentrated. The residue was purified by a flash chromatography (silica gel, ethyl acetate/petroleum ether, 1/10 to 1/3 gradient) to afford the title compound (350 mg, 49% yield).

Example 63e 2-(5-(ethylsulfonyl)-2-fluorophenyl)-4,4,5,5-tetramethyl-1,3,2-dioxaborolane 4,4,4',4',5,5,5',5'-Octamethyl-2,2'-bi(1,3,2-dioxaborolane) (13.31 g, 52.4 mmol), Example 16i (10 g, 37.4 mmol), potassium acetate (7.35 g, 74.9 mmol), and $PdCl_2(dppf)$ (0.822 g, 1.123 mmol) were combined in dioxane (100 mL) and DMSO (3 mL). The reaction mixture was sparged with $N_2$ for 30 minutes and heated at 90° C. under $N_2$ for 16 hours. After cooling, the reaction mixture was partitioned between ethyl acetate and water and filtered through a plug of Celite to remove elemental palladium. The layers were separated and the organic layer was washed with saturated aqueous sodium chloride, dried over anhydrous sodium sulfate, treated with mercaptopropyl silica gel for 15 minutes, filtered, and concentrated. The crude product was recrystallized in heptane/ethyl acetate (4:1) to afford the title compound as amber crystals (10 g, 30.0 mmol, 80% yield).

Example 63f 2-(3-(dimethylamino)prop-1-yn-1-yl)-4-(5-(ethylsulfonyl)-2-fluorophenyl)-6-methyl-1-tosyl-1H-pyrrolo[2,3-c]pyridin-7(6H)-one To a 10 mL microwave tube was added Example 63d (10 mg, 0.022 mmol), Example 63e (10.19 mg, 0.032 mmol), $PdCl_2(dppf)$ dichloromethane adduct (0.950 mg, 1.30 µmol), $Na_2CO_3$ (6.88 mg, 0.065 mmol), dioxane (1 mL) and water (0.250 mL). The reaction mixture was heated to 130° C. in a microwave reactor for 50 minutes. The reaction mixture was filtered through Celite and washed with ethyl acetate several times. The solvent was evaporated and the residue was partitioned between water (20 mL) and ethyl acetate (20 mL). The organic layer was separated and the aqueous layer was extracted with ethyl acetate again (15 mL twice). The combined organic layers were dried under anhydrous sodium sulfate, filtered, and concentrated. The crude product was used directly without purification.

Example 63g

4-{2-[(2,2-difluorocyclopropyl)methoxy]-5-(ethylsulfonyl)phenyl}-2-[3-(dimethylamino)prop-1-yn-1-yl]-6-methyl-1,6-dihydro-7H-pyrrolo[2,3-c]pyridin-7-one NaH (35.1 mg, 0.878 mmol) was added to Example 63f (100 mg, 0.176 mmol) in dimethylformamide (10 mL), and the mixture was stirred for 10 minutes. (2,2-Difluorocyclopropyl)methanol (56.9 mg, 0.527 mmol) was added, and the mixture was stirred for 3 hours at ambient temperature. The residue was partitioned between water (10 mL) and ethyl acetate (20 mL). The organic layer was separated, and the aqueous layer was extracted with additional ethyl acetate twice (20 mL). The combined organic layers were washed with saturated aqueous sodium bicarbonate (10 mL), followed by saturated aqueous sodium chloride (100 mL), dried over anhydrous magnesium sulfate, filtered, and concentrated. The crude material was purified by reverse phase Prep HPLC (C18, 30-40% acetonitrile in 0.1% $NH_4HCO_3$/water) to afford the title compound (25 mg, 28% yield). $^1$H NMR (400 MHz, $CDCl_3$) δ 10.91 (s, 1H), 7.96-7.84 (m, 2H), 7.13-7.04 (m, 2H), 6.37 (d, J=1.0 Hz, 1H), 4.23-4.08 (m, 2H), 3.71 (s, 3H), 3.52 (s, 2H), 3.14 (q, J=7.4 Hz, 2H), 2.38

(s, 6H), 2.05-1.97 (m, 1H), 1.53 (dd, J=8.0, 4.6 Hz, 1H), 1.31 (t, J=7.4 Hz, 3H), 1.28-1.18 (m, 1H). MS (ESI+) m/z 504.2 (M+H)⁺.

Example 64

4-[2-{3-[(2-methoxyethyl)amino]phenoxy}-5-(methylsulfonyl)phenyl]-6-methyl-1,6-dihydro-7H-pyrrolo[2,3-c]pyridin-7-one Using the procedure described for Example 60 and substituting 2-methoxyacetaldehyde for 3-formylbenzonitrile provided the TFA salt of the title compound. $^1$H NMR (400 MHz, DMSO-$d_6$/$D_2$O) δ 7.95 (d, J=2.4 Hz, 1H), 7.87 (dd, J=8.7, 2.4 Hz, 1H), 7.40 (s, 1H), 7.33 (d, J=2.8 Hz, 1H), 7.10-7.01 (m, 2H), 6.48 (dd, J=8.2, 1.9 Hz, 1H), 6.33 (t, J=2.2 Hz, 1H), 6.29 (d, J=2.8 Hz, 1H), 6.19 (dd, J=7.9, 2.1 Hz, 1H), 3.59 (s, 3H), 3.22 (d, J=8.7 Hz, 3H), 2.76 (s, 2H), 0.91 (s, 9H); MS (ESI+) m/z 468 (M+H)⁺.

Example 65

6-methyl-4-[5-(methylsulfonyl)-2-{3-[(tetrahydrofuran-2-ylmethyl)amino]phenoxy}phenyl]-1,6-dihydro-7H-pyrrolo[2,3-c]pyridin-7-one Using the procedure described for Example 60 and substituting tetrahydrofuran-2-carbaldehyde for 3-formylbenzonitrile provided the title compound. $^1$H NMR (400 MHz, DMSO-$d_6$/$D_2$O) δ 7.95 (d, J=2.4 Hz, 1H), 7.88 (dd, J=8.7, 2.4 Hz, 1H), 7.40 (s, 1H), 7.33 (d, J=2.8 Hz, 1H), 7.14-7.04 (m, 2H), 6.49 (dd, J=8.1, 1.9 Hz, 1H), 6.35 (t, J=2.1 Hz, 1H), 6.28 (dd, J=8.3, 2.4 Hz, 2H), 3.92 (dd, J=11.7, 6.7 Hz, 1H), 3.75 (dd, J=11.8, 9.5 Hz, 54H), 3.62 (dd, J=14.3, 7.6 Hz, 1H), 3.58 (s, 3H), 3.24 (s, 3H), 3.04 (qd, J=13.2, 5.7 Hz, 2H), 2.02-1.87 (m, 1H), 1.87-1.73 (m, 2H), 1.54 (dt, J=15.1, 6.9 Hz, 1H); MS (ESI+) m/z 494 (M+H)⁺.

Example 66

4-[2-{3-[(3-methoxybenzyl)amino]phenoxy}-5-(methylsulfonyl)phenyl]-6-methyl-1,6-dihydro-7H-pyrrolo[2,3-c]pyridin-7-one Using the procedure described for Example 60 and substituting 3-methoxybenzaldehyde for 3-formylbenzonitrile provided the TFA salt of the title compound. $^1$H NMR (400 MHz, DMSO-$d_6$/$D_2$O) δ 7.93 (d, J=2.4 Hz, 1H), 7.83 (dd, J=8.7, 2.4 Hz, 1H), 7.35 (s, 1H), 7.30 (d, J=2.8 Hz, 1H), 7.23 (t, J=8.1 Hz, 1H), 7.08 (t, J=8.3 Hz, 1H), 6.98 (d, J=8.7 Hz, 1H), 6.87 (d, J=6.9 Hz, 2H), 6.81-6.76 (m, 1H), 6.47-6.42 (m, 1H), 6.22 (dd, J=7.4, 4.7 Hz, 3H), 4.20 (s, 2H), 3.70 (s, 3H), 3.56 (s, 3H), 3.23 (s, 3H); MS (ESI+) m/z 530 (M+H)⁺.

Example 67

4-[2-{3-[(2-fluorobenzyl)amino]phenoxy}-5-(methylsulfonyl)phenyl]-6-methyl-1,6-dihydro-7H-pyrrolo[2,3-c]pyridin-7-one Using the procedure described for Example 60 and substituting 2-fluorobenzaldehyde for 3 formylbenzonitrile provided the TFA salt of the title compound. $^1$H NMR (400 MHz, DMSO-$d_6$/$D_2$O) δ 7.94 (d, J=2.4 Hz, 1H), 7.84 (dd, J=8.7, 2.4 Hz, 1H), 7.38-7.26 (m, 4H), 7.18-7.06 (m, 3H), 7.01 (d, J=8.7 Hz, 1H), 6.47-6.42 (m, 1H), 6.24 (dd, J=10.4, 2.4 Hz, 3H), 4.26 (s, 2H), 3.56 (s, 3H), 3.24 (d, J=6.8 Hz, 3H); MS (ESI+) m/z 518 (M+H)⁺.

Example 68

4-[2-{3-[(3-fluorobenzyl)amino]phenoxy}-5-(methylsulfonyl)phenyl]-6-methyl-1,6-dihydro-7H-pyrrolo[2,3-c]pyridin-7-one Using the procedure described for Example 60 and substituting 3-fluorobenzaldehyde for 3-formylbenzonitrile provided the TFA salt of the title compound. $^1$H NMR (400 MHz, DMSO-$d_6$/$D_2$O) δ 7.93 (d, J=2.4 Hz, 1H), 7.83 (dd, J=8.7, 2.4 Hz, 1H), 7.38-7.32 (m, 2H), 7.29 (d, J=2.8 Hz, 1H), 7.09 (ddd, J=25.6, 16.8, 8.0 Hz, 4H), 6.98 (d, J=8.7 Hz, 1H), 6.46-6.41 (m, 1H), 6.22 (dd, J=7.8, 5.4 Hz, 3H), 4.26 (s, 2H), 3.56 (s, 3H), 3.23 (s, 3H); MS (ESI+) m/z 518 (M+H)⁺.

Example 69

6-methyl-4-[5-(methylsulfonyl)-2-(3-{[3-(trifluoromethoxy)benzyl]amino}phenoxy)phenyl]-1,6-dihydro-7H-pyrrolo[2,3-c]pyridin-7-one Using the procedure described for Example 60 and substituting 3-(trifluoromethoxy)benzaldehyde for 3-formylbenzonitrile provided the TFA salt of the title compound. $^1$H NMR (400 MHz, DMSO-$d_6$/$D_2$O) δ 7.93 (d, J=2.4 Hz, 1H), 7.81 (dd, J=8.7, 2.4 Hz, 1H), 7.45 (t, J=7.9 Hz, 1H), 7.38-7.32 (m, 2H), 7.29 (d, J=2.8 Hz, 1H), 7.26 (s, 1H), 7.20 (d, J=8.2 Hz, 1H), 7.09 (t, J=8.1 Hz, 1H), 6.95 (d, J=8.7 Hz, 1H), 6.45 (dd, J=8.2, 1.9 Hz, 1H), 6.27-6.23 (m, 1H), 6.22 (t, J=2.9 Hz, 2H), 4.30 (s, 2H), 3.56 (s, 3H), 3.23 (s, 3H); MS (ESI+) m/z 584 (M+H)⁺.

Example 70

4-[2-{3-[(2,4-dimethylbenzyl)amino]phenoxy}-5-(methylsulfonyl)phenyl]-6-methyl-1,6-dihydro-7H-pyrrolo[2,3-c]pyridin-7-one Using the procedure described for Example 60 and substituting 2,4-dimethylbenzaldehyde for 3-formylbenzonitrile provided the TFA salt of the title compound. $^1$H NMR (400 MHz, DMSO-$d_6$/$D_2$O) δ 7.93 (d, J=2.4 Hz, 1H), 7.85 (dd, J=8.7, 2.4 Hz, 1H), 7.34 (s, 1H), 7.30 (d, J=2.8 Hz, 1H), 7.11-7.05 (m, 2H), 7.03 (d, J=8.7 Hz, 1H), 6.97 (s, 1H), 6.92 (d, J=7.7 Hz, 1H), 6.43 (dd, J=8.1, 1.9 Hz, 1H), 6.23 (dd, J=8.2, 2.4 Hz, 2H), 6.19 (t, J=2.1 Hz, 1H), 4.11 (s, 2H), 3.56 (s, 3H), 3.23 (s, 3H), 2.23 (d, J=3.3 Hz, 6H); MS (ESI+) m/z 528 (M+H)⁺.

Example 71

2-[({3-[2-(6-methyl-7-oxo-6,7-dihydro-1H-pyrrolo[2,3-c]pyridin-4-yl)-4-(methyl sulfonyl)phenoxy]phenyl}amino)methyl]benzonitrile Using the procedure described for Example 60 and substituting 2-formylbenzonitrile for 3-formylbenzonitrile provided the TFA salt of the title compound. $^1$H NMR (400 MHz, DMSO-$d_6$/$D_2$O) δ 8.26 (d, J=7.9 Hz, 1H), 8.02 (d, J=2.4 Hz, 1H), 7.93 (dd, J=8.7, 2.4 Hz, 1H), 7.87 (t, J=7.7 Hz, 1H), 7.80 (d, J=7.6 Hz, 1H), 7.72 (t, J=7.5 Hz, 1H), 7.65 (t, J=8.1 Hz, 1H), 7.48-7.44 (m, 1H), 7.43-7.41 (m, 2H), 7.34 (dd, J=5.7, 2.9 Hz, 2H), 7.29 (dd, J=8.3, 2.1 Hz, 1H), 6.32 (d, J=2.8 Hz, 1H), 5.19 (s, 2H), 3.58 (s, 3H), 3.26 (s, 3H); MS (ESI+) m/z 525 (M+H)+.

Example 72

4-[2-{3-[(2-chloro-4-fluorobenzyl)amino]phenoxy}-5-(methylsulfonyl)phenyl]-6-methyl-1,6-dihydro-7H-pyrrolo[2,3-c]pyridin-7-one Using the procedure described for Example 60 and substituting 2-chloro-4-fluorobenzaldehyde for 3-formylbenzonitrile provided the TFA salt of the title compound. $^1$H NMR (400 MHz, DMSO-$d_6$/$D_2O$) δ 7.95 (t, J=5.9 Hz, 1H), 7.85 (dd, J=8.7, 2.4 Hz, 1H), 7.41-7.35 (m, 2H), 7.34 (s, 1H), 7.30 (d, J=2.8 Hz, 1H), 7.17 (td, J=8.5, 2.6 Hz, 1H), 7.09 (t, J=8.1 Hz, 1H), 7.02 (d, J=8.7 Hz, 1H), 6.40 (dd, J=8.1, 1.9 Hz, 1H), 6.31-6.16 (m, 2H), 6.14 (t, J=2.2 Hz, 1H), 4.25 (s, 2H), 3.56 (s, 3H), 3.24 (s, 3H); MS (ESI+) m/z 552 (M+H)+.

Example 73

4-[2-{3-[(3,5-difluorobenzyl)amino]phenoxy}-5-(methylsulfonyl)phenyl]-6-methyl-1,6-dihydro-7H-pyrrolo[2,3-c]pyridin-7-one Using the procedure described for Example 60 and substituting 3,5-difluorobenzaldehyde for 3-formylbenzonitrile provided the TFA salt of the title compound. $^1$H NMR (400 MHz, DMSO-$d_6$/$D_2O$) δ 7.94 (d, J=2.4 Hz, 1H), 7.83 (dd, J=8.7, 2.4 Hz, 1H), 7.36 (s, 1H), 7.29 (d, J=2.8 Hz, 1H), 7.10 (t, J=8.1 Hz, 1H), 7.02 (ddd, J=19.8, 11.0, 5.5 Hz, 4H), 6.44 (dd, J=8.1, 2.0 Hz, 1H), 6.31-6.17 (m, 3H), 4.28 (s, 2H), 3.57 (s, 3H), 3.23 (s, 3H); MS (ESI+) m/z 536 (M+H)+.

Example 74

4-{2-[3-({4-[3-(dimethylamino)propoxy]benzyl}amino)phenoxy]-5-(methyl sulfonyl)phenyl}-6-methyl-1,6-dihydro-7H-pyrrolo[2,3-c]pyridin-7-one Using the procedure described for Example 60 and substituting 4-(3-(dimethylamino)propoxy)benzaldehyde for 3-formylbenzonitrile provided the TFA salt of the title compound. $^1$H NMR (400 MHz, DMSO-$d_6$/$D_2O$) δ 7.94 (d, J=2.4 Hz, 1H), 7.83 (dd, J=8.7, 2.4 Hz, 1H), 7.35 (s, 1H), 7.31 (d, J=2.8 Hz, 1H), 7.22 (d, J=8.6 Hz, 2H), 7.15-7.04 (m, 2H), 6.97 (d, J=8.7 Hz, 1H), 6.88-6.84 (m, 2H), 6.45 (dd, J=8.2, 1.8 Hz, 1H), 6.23-6.17 (m, 2H), 4.16 (s, 2H), 4.01 (t, J=5.9 Hz, 2H), 3.56 (s, 3H), 3.24 (s, 3H), 3.23-3.17 (m, 2H), 2.82 (s, 6H), 2.12-2.05 (m, 2H); MS (ESI+) m/z 601 (M+H)+.

Example 75

4-[2-(3-{[3-(dimethylamino)benzyl]amino}phenoxy)-5-(methylsulfonyl)phenyl]-6-methyl-1,6-dihydro-7H-pyrrolo[2,3-c]pyridin-7-one Using the procedure described for Example 60 and substituting 3-(dimethylamino)benzaldehyde for 3-formylbenzonitrile provided the TFA salt of the title compound. $^1$H NMR (400 MHz, DMSO-$d_6$/$D_2O$) δ 7.94 (d, J=2.4 Hz, 1H), 7.84 (dd, J=8.7, 2.4 Hz, 1H), 7.39-7.33 (m, 2H), 7.30 (d, J=2.8 Hz, 1H), 7.21 (s, 1H), 7.11 (dd, J=16.8, 8.7 Hz, 3H), 6.99 (d, J=8.7 Hz, 1H), 6.49-6.41 (m, 1H), 6.27 (dd, J=10.8, 2.2 Hz, 2H), 6.22 (d, J=2.8 Hz, 1H), 4.25 (s, 2H), 3.57 (s, 3H), 3.23 (s, 3H), 3.02 (s, 6H); MS (ESI+) m/z 543 (M+H)+

Example 76

4-[2-{3-[(2,3-dihydro-1,4-benzodioxin-6-ylmethyl)amino]phenoxy}-5-(methylsulfonyl)phenyl]-6-methyl-1,6-dihydro-7H-pyrrolo[2,3-c]pyridin-7-one Using the procedure described for Example 60 and substituting 2,3-dihydrobenzo[b][1,4]dioxine-6-carbaldehyde for 3-formylbenzonitrile provided the TFA salt of the title compound. $^1$H NMR (400 MHz, DMSO-$d_6$/$D_2O$) δ 7.93 (d, J=2.4 Hz, 1H), 7.84 (dd, J=8.7, 2.4 Hz, 1H), 7.35 (s, 1H), 7.31 (d, J=2.8 Hz, 1H), 7.08 (dd, J=9.7, 6.2 Hz, 1H), 6.99 (d, J=8.7 Hz, 1H), 6.79-6.72 (m, 3H), 6.44 (d, J=7.2 Hz, 1H), 6.22 (dd, J=4.2, 2.0 Hz, 3H), 4.19 (s, 4H), 4.10 (s, 2H), 3.57 (s, 3H), 3.23 (s, 3H); MS (ESI+) m/z 558 (M+H)+.

Example 77

6-methyl-4-[5-(methylsulfonyl)-2-{3-[(tetrahydrofuran-3-ylmethyl)amino]phenoxy}phenyl]-1,6-dihydro-7H-pyrrolo[2,3-c]pyridin-7-one Using the procedure described for Example 60 and substituting tetrahydrofuran-3-carbaldehyde for 3-formylbenzonitrile provided the TFA salt of the title compound. $^1$H NMR (400 MHz, DMSO-$d_6$/$D_2O$) δ 7.96 (d, J=2.4 Hz, 1H), 7.88 (dd, J=8.7, 2.4 Hz, 1H), 7.40 (s, 1H), 7.34 (d, J=2.8 Hz, 1H), 7.15-7.10 (m, 1H), 7.08 (d, J=8.7 Hz, 1H), 6.48-6.44 (m, 1H), 6.27 (dd, J=11.2, 2.4 Hz, 3H), 3.73-3.69 (m, 2H), 3.66-3.60 (m, 1H), 3.58 (s, 3H), 3.41 (dd, J=8.5, 5.6 Hz, 1H), 3.24 (s, 3H), 2.94 (d, J=7.3 Hz, 2H), 2.46-2.34 (m, 1H), 1.97 (dtd, J=13.3, 7.9, 5.5 Hz, 1H), 1.56 (dt, J=12.7, 6.8 Hz, 1H); MS (ESI+) m/z 494 (M+H)+.

Example 78

N-{4-[({3-[2-(6-methyl-7-oxo-6,7-dihydro-1H-pyrrolo[2,3-c]pyridin-4-yl)-4-(methyl sulfonyl)phenoxy]phenyl}amino)methyl]phenyl}acetamide Using the procedure described for Example 60 and substituting N-(4-formylphenyl)acetamide for 3-formylbenzonitrile provided the TFA salt of the title compound. $^1$H NMR (400 MHz, DMSO-$d_6$/$D_2O$) δ 7.93 (d, J=2.4 Hz, 1H), 7.83 (dd, J=8.7, 2.4 Hz, 1H), 7.49 (d, J=8.5 Hz, 2H), 7.36 (s, 1H), 7.30 (d, J=2.8 Hz, 1H), 7.22 (d, J=8.5 Hz, 2H), 7.13-7.08 (m, 1H), 6.96 (d, J=8.7 Hz, 1H), 6.50 (dd, J=8.2, 1.6 Hz, 1H), 6.31-6.24 (m, 2H), 6.27 (dd, J=6.5, 2.0 Hz, 1H), 6.22 (d, J=2.8 Hz, 1H), 4.19 (s, 2H), 3.57 (s, 3H), 3.23 (s, 3H), 2.04 (s, 3H); MS (ESI+) m/z 557 (M+H)+.

Example 79

4-[2-{3-[(4-methoxybenzyl)amino]phenoxy}-5-(methylsulfonyl)phenyl]-6-methyl-1,6-dihydro-7H-pyrrolo[2,3-c]pyridin-7-one Using the procedure described for Example 60 and substituting 4-methoxybenzaldehyde for 3-formylbenzonitrile provided the TFA salt of the title compound. $^1$H NMR (400 MHz, DMSO-$d_6$/$D_2O$) δ 7.92 (t, J=8.2 Hz, 1H), 7.84 (dd, J=8.7, 2.4 Hz, 1H), 7.35 (s, 1H), 7.31 (d, J=2.8 Hz, 1H), 7.21 (d, J=8.6 Hz, 2H), 7.08 (t, J=8.0 Hz, 1H), 6.99 (d, J=8.7 Hz, 1H), 6.87 (d, J=8.6 Hz, 2H), 6.51-6.40 (m, 1H), 6.26-6.17 (m, 3H), 4.15 (s, 2H), 3.72 (s, 3H), 3.56 (s, 3H), 3.23 (s, 3H); MS (ESI+) m/z 530 (M+H)$^+$.

Example 80

4-[2-{3-[(cyclopropylmethyl)amino]phenoxy}-5-(methylsulfonyl)phenyl]-6-methyl-1,6-dihydro-7H-pyrrolo[2,3-c]pyridin-7-one Using the procedure described for Example 60 and substituting cyclopropanecarbaldehyde for 3-formylbenzonitrile provided the TFA salt of the title compound. $^1$H NMR (400 MHz, DMSO-d$_6$/D$_2$O) δ 7.97 (d, J=2.4 Hz, 1H), 7.90 (dd, J=8.7, 2.4 Hz, 1H), 7.40 (d, J=2.1 Hz, 1H), 7.33 (d, J=2.8 Hz, 1H), 7.21 (t, J=7.9 Hz, 1H), 7.12 (d, J=8.7 Hz, 1H), 6.66-6.61 (m, 1H), 6.52-6.40 (m, 2H), 6.28 (d, J=2.9 Hz, 1H), 3.58 (s, 3H), 3.25 (s, 3H), 2.91 (d, J=6.8 Hz, 2H), 0.95 (td, J=7.6, 3.7 Hz, 1H), 0.49-0.43 (m, 2H), 0.21-0.17 (m, 2H); MS (ESI+) m/z 464 (M+H)$^+$.

Example 81

4-[2-{3-[(2-cyclopentylethyl)amino]phenoxy}-5-(methylsulfonyl)phenyl]-6-methyl-1,6-dihydro-7H-pyrrolo[2,3-c]pyridin-7-one Using the procedure described for Example 60 and substituting cyclopentylacetaldehyde for 3-formylbenzonitrile provided the TFA salt of the title compound. $^1$H NMR (400 MHz, DMSO-d$_6$/D$_2$O) δ 7.97 (d, J=2.4 Hz, 1H), 7.89 (dd, J=8.7, 2.4 Hz, 1H), 7.40 (s, 1H), 7.33 (d, J=2.8 Hz, 1H), 7.15 (t, J=8.4 Hz, 1H), 7.09 (d, J=8.7 Hz, 1H), 6.50 (d, J=7.5 Hz, 1H), 6.34-6.31 (m, 2H), 6.28 (d, J=2.8 Hz, 1H), 3.58 (s, 3H), 3.24 (s, 3H), 3.04-2.92 (m, 2H), 1.86-1.67 (m, 3H), 1.61-1.41 (m, 6H), 1.07 (td, J=14.9, 7.2 Hz, 2H); MS (ESI+) m/z 506 (M+H)$^+$.

Example 82

4-[2-{4-chloro-2-[3-(morpholin-4-yl)prop-1-yn-1-yl]phenoxy}-5-(ethylsulfonyl)phenyl]-6-methyl-1,6-dihydro-7H-pyrrolo[2,3-c]pyridin-7-one Example 82a 4-(5-(ethylsulfonyl)-2-fluorophenyl)-6-methyl-1-tosyl-1H-pyrrolo[2,3-c]pyridin-7(6H)-one Example 82a was prepared according to the procedure used for the preparation of Example 16j, substituting Example 1f for Example 16f.

Example 82b 4-(2-(4-chloro-2-iodophenoxy)-5-(ethylsulfonyl)phenyl)-6-methyl-1H-pyrrolo[2,3-c]pyridin-7(6H)-one A mixture of Example 82a (0.51 g, 1.047 mmol), 4-chloro-2-iodophenol (0.293 g, 1.151 mmol), and cesium carbonate (0.409 g, 1.256 mmol) in dimethylsulfoxide (5 mL) was heated at 95° C. overnight. After cooling to ambient temperature, the reaction mixture was partitioned between water and ethyl acetate. The organic layer was separated, and the aqueous layer was extracted with additional ethyl acetate twice. The combined organic layers were washed with saturated aqueous sodium chloride, dried over anhydrous magnesium sulfate, filtered, and concentrated. The residue was purified by flash column chromatography (silica gel, 1:1 ethyl acetate/hexanes) to afford the title compound (0.22 g, 0.387 mmol, 37% yield).

Example 82c

4-[2-{4-chloro-2-[3-(morpholin-4-yl)prop-1-yn-1-yl]phenoxy}-5-(ethylsulfonyl)phenyl]-6-methyl-1,6-dihydro-7H-pyrrolo[2,3-c]pyridin-7-one A mixture of Example 82b (0.100 g, 0.176 mmol), 4-(prop-2-yn-1-yl)morpholine (0.044 g, 0.35 mmol), copper (I) iodide (6.70 mg, 0.035 mmol), triethylamine (0.503 mL, 3.52 mmol), and bis(triphenylphosphine)palladium(II) chloride (0.012 g, 0.018 mmol) in dimethylformamide (1 mL) was heated at 80° C. for 2 hours. After cooling to ambient temperature, the reaction mixture was partitioned between water and ethyl acetate. The aqueous layer was extracted with additional ethyl acetate twice. The combined organic layers were washed with saturated aqueous sodium chloride, dried over anhydrous magnesium sulfate, filtered, and concentrated. The residue was purified by reverse phase Prep HPLC (C18, 10-100% acetonitrile in 0.1% TFA/water) to afford the title compound as TFA salt (0.075 g, 0.110 mmol, 62.7% yield). $^1$H NMR (400 MHz, DMSO-d$_6$) δ 12.12 (s, 1H), 7.98 (d, J=2.44 Hz, 1H), 7.84 (dd, J=8.54, 2.44 Hz, 1H), 7.73 (d, J=2.44 Hz, 1H), 7.53 (dd, J=8.85, 2.75 Hz, 1H), 7.44 (s, 1H), 7.33 (t, J=2.75 Hz, 1H), 7.23 (d, J=8.85 Hz, 1H), 7.07 (d, J=8.54 Hz, 1H), 6.31 (t, J=2.29 Hz, 1H), 4.09 (br s, 2H), 3.62 (br s, 4H), 3.57 (s, 3H), 3.32-3.38 (m, 2H), 2.92 (br s, 4H), 1.15 (t, J=7.32 Hz, 3H). MS (ESI+) m/z 566.1 (M+H)$^+$.

Example 83

4-[2-{4-chloro-2-[3-(morpholin-4-yl)propyl]phenoxy}-5-(ethylsulfonyl)phenyl]-6-methyl-1,6-dihydro-7H-pyrrolo[2,3-c]pyridin-7-one Example 82c (60 mg, 0.106 mmol) and tetrahydrofuran (10 mL) were added to 5% Pt/C (about 50% water) (30 mg, 0.063 mmol) in a 50 mL pressure bottle. The reaction mixture was stirred at 30 psi of hydrogen and ambient temperature for 2 hours. The mixture was filtered through a nylon membrane and concentrated. The residue was purified by reverse phase Prep HPLC (C18, 10-100% acetonitrile in 0.1% TFA/water) to afford the title compound as TFA salt (0.045 g, 0.066 mmol, 62.1% yield). $^1$H NMR (400 MHz, DMSO-d$_6$) δ 12.15 (s, 1H), 9.64 (s, 1H), 7.96 (d, J=2.44 Hz, 1H), 7.86 (dd, J=8.7, 2.29 Hz, 1H), 7.45 (d, J=2.44 Hz, 1H), 7.42 (s, 1H), 7.31-7.35 (m, 1H), 7.09 (d, J=5.49 Hz, 1H), 7.06 (d, J=8.54 Hz, 1H), 6.25 (t, J=2.29 Hz, 1H), 3.91-3.94 (m, 2H), 3.57 (s, 3H), 3.32-3.38 (m, 2H), 3.21-3.24 (m, 2H), 2.90 (br s, 4H), 2.46-2.52 (m, 4H), 1.71-1.79 (m, 2H), 1.16 (t, J=7.32 Hz, 3H). MS (ESI+) m/z 570.2 (M+H)$^+$.

Example 84

6-methyl-4-[5-(methylsulfonyl)-2-{[1-(phenylsulfonyl)piperidin-4-yl]amino}phenyl]-1,6-dihydro-7H-pyrrolo[2,3-c]pyridin-7-one Example 84a tert-butyl 4-((2-bromo-4-(methyl sulfonyl)phenyl)amino)piperidine-1-carboxylate A solution of Example 21b (2.71 g, 10.71 mmol), N,N-diisopropylethylamine (2.15 mL, 12.31 mmol), and tert-butyl 4-aminopiperidine-1-carboxylate (2.43 g, 11.78 mmol) in dimethylsulfoxide (20 mL) was stirred at 100° C. for 4 hours. To the cooled mixture was added dilute ammonium chloride solution and extracted twice with diethylether. The combined organic layers were dried with anhydrous magnesium sulfate, filtered, and concentrated. The residue was purified by chromatography (silica gel, 40-66% ethyl acetate in heptane) to afford 3.21 g (62%) of the title compound.

Example 84b tert-butyl 4-{[2-(6-methyl-7-oxo-6,7-dihydro-1H-pyrrolo[2,3-c]pyridin-4-yl)-4-(methylsulfonyl)phenyl]amino}piperidine-1-carboxylate Example 84a (3.19 g, 7.36 mmol), Example 1f (3.31 g, 7.73 mmol), tetrakis(triphenylphosphine)palladium (0) (0.851 g, 0.736 mmol), and cesium fluoride (3.35 g, 22.08 mmol) were combined and sparged with argon for 10 minutes, followed by the addition of dimethoxyethane (70 mL) and methanol (35 mL), and bubbled argon through the mixture for 15 minutes. Reaction mixture was stirred at 75° C. for 2 hours. To the cooled reaction mixture was added 5N sodium hydroxide aqueous solution (100 mL) and stirred for 2 hours at ambient temperature. To the resulting mixture was added dilute ammonium chloride solution and extracted twice with ethyl acetate. The combined organic layers were dried with anhydrous magnesium sulfate, filtered, and concentrated. The residue was purified by chromatography (silica gel, 80% ethyl acetate in heptane) to afford 1.80 g (49%) of the title compound.

Example 84c 6-methyl-4-[5-(methylsulfonyl)-2-(piperidin-4-ylamino)phenyl]-1,6-dihydro-7H-pyrrolo[2,3-c]pyridin-7-one A solution of Example 84b (1.53 g, 3.06 mmol) in dichloromethane (14 mL) was stirred at ambient temperature. To this solution was added excess trifluoroacetic acid (2 mL) and stirred 4 hours at ambient temperature. The mixture was neutralized slowly with sodium carbonate solution until pH was about 10, and extracted twice with dichloromethane. The combined organic layers were dried with anhydrous magnesium sulfate, filtered, and concentrated. The solid residue was triturated with warm ethyl acetate, filtered, and dried to afford 1.01 g (82%) of title compound.

Example 84d 6-methyl-4-[5-(methylsulfonyl)-2-{[1-(phenylsulfonyl)piperidin-4-yl]amino}phenyl]-1,6-dihydro-7H-pyrrolo[2,3-c]pyridin-7-one A solution of Example 84c (0.039 g, 0.097 mmol) and 4-methylmorpholine (0.015 mL, 0.136 mmol) in dimethylformamide (4.0 mL) was stirred at ambient temperature. To this solution was added benzenesulfonyl chloride (0.014 mL, 0.107 mmol) and stirred for 1.5 hours at ambient temperature. Dilute aqueous sodium chloride solution was added to the reaction mixture and extracted twice with ethyl acetate. The combined organic layers were dried with anhydrous magnesium sulfate, filtered, and concentrated. The solid residue was triturated with ethyl acetate, filtered, and dried to afford 0.043 g (82%) of the title compound. $^1$H NMR (400 MHz, DMSO-d$_6$) δ 12.11 (s, 1H), 7.77-7.70 (m, 3H), 7.66 (dd, J=10.1, 4.9 Hz, 2H), 7.60 (dd, J=8.7, 2.3 Hz, 1H), 7.49 (d, J=2.3 Hz, 1H), 7.23 (dd, J=5.5, 2.8 Hz, 2H), 6.88 (d, J=9.0 Hz, 1H), 5.95 (t, J=2.3 Hz, 1H), 5.05 (d, J=8.1 Hz, 1H), 3.58-3.42 (m, 6H), 3.09 (s, 3H), 2.43 (dd, J=11.5, 9.9 Hz, 2H), 1.89 (d, J=10.7 Hz, 2H), 1.40 (td, J=14.3, 3.8 Hz, 2H). MS (ESI+) m/z 541.1 (M+H)$^+$.

Example 85

4-[2-({1-[(dimethylamino)acetyl]piperidin-4-yl}amino)-5-(methylsulfonyl)phenyl]-6-methyl-1,6-dihydro-7H-pyrrolo[2,3-c]pyridin-7-one A solution of Example 84c (0.028 g, 0.070 mmol) and 4-methylmorpholine (0.009 mL, 0.083 mmol) in dimethylformamide (4.0 mL) was stirred at ambient temperature. To this solution was added 2-(dimethylamino)acetyl chloride, hydrochloride (0.012 g, 0.076 mmol) and stirred for 2 hours at ambient temperature. Dilute aqueous sodium chloride and dilute sodium bicarbonate solution was added to reaction mixture until pH was about 9, and extracted twice with ethyl acetate. The combined organic layers were dried with anhydrous magnesium sulfate, filtered, and concentrated. The residue was triturated with ethyl acetate, filtered, and dried to afford 0.019 g (56%) of the title compound. $^1$H NMR (400 MHz, DMSO-d$_6$) δ 12.11 (s, 1H), 7.67 (dd, J=8.7, 2.3 Hz, 1H), 7.52 (d, J=2.3 Hz, 1H), 7.27 (dd, J=7.1, 4.4 Hz, 2H), 6.95 (d, J=9.0 Hz, 1H), 6.00 (s, 1H), 5.07 (d, J=8.1 Hz, 1H), 4.22 (d, J=13.0 Hz, 1H), 3.95 (d, J=13.4 Hz, 1H), 3.77-3.63 (m, 1H), 3.55 (s, 3H), 3.16-2.90 (m, 6H), 2.70 (t, J=11.5 Hz, 1H), 2.13 (s, 6H), 1.92-1.78 (m, 2H), 1.28 (dd, J=20.4, 10.9 Hz, 1H), 1.14 (dd, J=20.5, 10.8 Hz, 1H). MS (ESI+) m/z 486.2 (M+H)$^+$.

Example 86

6-methyl-4-[2-({1-[3-(methylsulfanyl)propyl]piperidin-4-yl}amino)-5-(methylsulfonyl)phenyl]-1,6-dihydro-7H-pyrrolo[2,3-c]pyridin-7-one A 4 mL vial was charged with Example 84c (25 mg, 0.063 mmol), 3-(methylthio)propanal (10 mg, 0.095 mmol), in a buffer solution of 1M sodium acetate/acetic acid in methanol with pH 4 (1.5 mL), followed by the addition of Silica-cyanoborohydride (150 mg, loading 0.89 mmol/g). The reaction mixture was allowed to stir at ambient temperature overnight. The reaction mixture was concentrated and the residue was purified by reverse phase HPLC (C18, CH$_3$CN/water (0.1% TFA), 0-100% gradient) to afford the TFA salt of the title compound. $^1$H NMR (400 MHz, PYRIDINE-d$_5$) δ 13.66 (s, 1H), 8.17 (dd, J=8.7, 2.3 Hz, 1H), 8.09 (d, J=2.3 Hz, 1H), 7.59 (d, J=2.7 Hz, 1H), 7.03 (d, J=8.9 Hz, 1H), 6.96 (s, 1H), 6.41-6.31 (m, 1H), 3.71 (t, J=19.0 Hz, 1H), 3.49 (s, 3H), 3.31 (s, 3H), 3.14 (s, 2H), 2.74 (d, J=6.9 Hz, 2H), 2.53 (d, J=24.4 Hz, 2H), 2.47 (t, J=7.1 Hz, 2H), 2.35-2.10 (m, 2H), 1.99 (s, 3H), 1.96-1.66 (m, 4H) MS (ESI+) m/z 489.1 (M+H)$^+$.

Example 87

N-{4-[(4-{[2-(6-methyl-7-oxo-6,7-dihydro-1H-pyrrolo[2,3-c]pyridin-4-yl)-4-(methylsulfonyl)phenyl]amino}piperidin-1-yl)methyl]phenyl}acetamide The TFA salt of Example 87 was prepared according to the procedure used for the preparation of Example 86, substituting N-(4-formylphenyl) acetamide for 3-(methylthio)propanal. $^1$H NMR (400 MHz, PYRIDINE-$d_5$) δ 13.64 (s, 1H), 10.85 (s, 1H), 8.17 (dd, J=8.7, 2.3 Hz, 1H), 8.06 (t, J=13.4 Hz, 1H), 7.99 (d, J=8.4 Hz, 2H), 7.59 (d, J=2.7 Hz, 1H), 7.44 (d, J=8.5 Hz, 2H), 7.03 (d, J=8.9 Hz, 1H), 6.95 (s, 1H), 6.35 (t, J=2.3 Hz, 1H), 5.76 (d, J=7.3 Hz, 1H), 3.81 (d, J=1.7 Hz, 2H), 3.69 (s, 1H), 3.48 (s, 3H), 3.30 (s, 3H), 3.11 (d, J=11.9 Hz, 2H), 2.52 (t, J=10.2 Hz, 2H), 2.18 (s, 3H), 2.12 (d, J=12.5 Hz, 2H), 1.85 (d, J=10.8 Hz, 2H). MS (ESI+) m/z 548.2 (M+H)$^+$.

Example 88

6-methyl-4-[5-(methylsulfonyl)-2-{[1-(3,4,5-trimethoxybenzyl)piperidin-4-yl]amino}phenyl]-1,6-dihydro-7H-pyrrolo[2,3-c]pyridin-7-one The TFA salt of Example 88 was prepared according to the procedure used for the preparation of Example 86, substituting 3,4,5-trimethoxybenzaldehyde for 3-(methylthio)propanal. $^1$H NMR (400 MHz, PYRIDINE-$d_5$) δ 13.65 (s, 1H), 8.17 (dd, J=8.7, 2.3 Hz, 1H), 8.09 (d, J=2.3 Hz, 1H), 7.59 (d, J=4.7, 2.0 Hz, 1H), 7.04 (d, J=8.9 Hz, 2H), 6.95 (s, 1H), 6.89 (s, 2H), 6.41-6.31 (m, 1H), 5.82 (d, J=7.1 Hz, 1H), 3.91 (d, J=5.3 Hz, 5H), 3.76 (s, 6H), 3.48 (s, 3H), 3.31 (s, 3H), 3.19 (t, J=20.3 Hz, 2H), 2.66 (t, J=10.5 Hz, 2H), 2.18 (d, J=12.5 Hz, 2H), 1.94 (d, J=10.1 Hz, 2H) MS (ESI+) m/z 581.1 (M+H)$^+$.

Example 89

6-methyl-4-[5-(methylsulfonyl)-2-{[1-(thiophen-2-ylmethyl)piperidin-4-yl]amino}phenyl]-1,6-dihydro-7H-pyrrolo[2,3-c]pyridin-7-one The trifluoroacetic acid salt of Example 89 was prepared according to the procedure used for the preparation of Example 86, substituting thiophene-2-carbaldehyde for 3-(methylthio)propanal. $^1$H NMR (400 MHz, PYRIDINE-$d_5$) δ 13.68 (s, 1H), 8.17 (dd, J=8.7, 2.3 Hz, 1H), 8.08 (d, J=2.3 Hz, 1H), 7.40 (dd, J=4.9, 1.3 Hz, 1H), 7.02 (td, J=5.6, 3.3 Hz, 3H), 6.96 (s, 1H), 6.35 (t, J=2.4 Hz, 1H), 5.58 (d, J=7.4 Hz, 1H), 3.82 (d, J=2.8 Hz, 2H), 3.72-3.60 (m, 1H), 3.54 (d, J=31.4 Hz, 4H), 3.30 (s, 3H), 3.00 (t, J=39.6 Hz, 2H), 2.28 (t, J=10.6 Hz, 2H), 1.93 (t, J=62.3 Hz, 2H), 1.67 (d, J=10.7 Hz, 2H) MS (ESI+) m/z 497.2 (M+H)$^+$.

Example 90

4-{2-[(1-{4-[3-(dimethylamino)propoxy]benzyl}piperidin-4-yl)amino]-5-(methylsulfonyl)phenyl}-6-methyl-1,6-dihydro-7H-pyrrolo[2,3-c]pyridin-7-one The trifluoroacetic acid salt of Example 90 was prepared according to the procedure used for the preparation of Example 86, substituting 4-(3-(dimethylamino)propoxy)benzaldehyde for 3-(methylthio)propanal. $^1$H NMR (400 MHz, PYRIDINE-$d_5$) δ 13.65 (s, 1H), 8.17 (dd, J=8.7, 2.3 Hz, 1H), 8.09 (d, J=2.3 Hz, 1H), 7.59 (dd, J=4.7, 2.0 Hz, 1H), 7.04 (d, J=8.9 Hz, 2H), 6.95 (s, 1H), 6.89 (s, 2H), 6.41-6.31 (m, 1H), 5.82 (d, J=7.1 Hz, 1H), 3.91 (d, J=5.3 Hz, 5H), 3.76 (s, 6H), 3.48 (s, 3H), 3.31 (s, 3H), 3.19 (t, J=20.3 Hz, 2H), 2.66 (t, J=10.5 Hz, 2H), 2.18 (d, J=12.5 Hz, 2H), 1.94 (d, J=10.1 Hz, 2H). MS (ESI+) m/z 592.2 (M+H)$^+$.

Example 91

6-methyl-4-[2-({1-[(methylsulfanyl)acetyl]piperidin-4-yl}amino)-5-(methylsulfonyl)phenyl]-1,6-dihydro-7H-pyrrolo[2,3-c]pyridin-7-one A 4 mL vial was charged with 2-(methylthio) acetic acid (11 mg, 0.10 mmol), O-(7-azabenzotriazol-1-yl)-N,N,N',N'-tetramethyluronium hexafluorophosphate (40 mg, 0.10 mmol) followed by the addition of diisopropyl ethyl amine (61 μL, 0.35 mmol) and Example 84c (28 mg, 0.07 mmol) in 1.5 mL of dimethyl acetamide. The reaction mixture was allowed to stir at ambient temperature overnight. The reaction mixture was concentrated and the residue was purified by reverse phase HPLC (C18, CH$_3$CN/water (0.1% TFA), 0-100% gradient) to afford the TFA salt of the title compound. $^1$H NMR (400 MHz, DMSO-$d_6$/D$_2$O) δ 7.70 (dd, J=8.8, 2.4 Hz, 1H), 7.54 (d, J=2.4 Hz, 1H), 7.29 (d, J=2.8 Hz, 1H), 7.18 (s, 1H), 6.97 (d, J=8.9 Hz, 1H), 6.02 (d, J=2.8 Hz, 1H), 3.78-3.64 (m, 2H), 3.57 (s, 3H), 3.31 (d, J=8.5 Hz, 2H), 3.20 (s, 2H), 3.07 (s, 3H), 2.07 (s, 3H), 2.01-1.85 (m, 2H), 1.28 (s, 2H). MS (ESI+) m/z 489.1 (M+H)$^+$.

Example 92

6-methyl-4-[5-(methylsulfonyl)-2-({1-[3-(2,3,4-trimethoxyphenyl)propanoyl]piperidin-4-yl}amino)phenyl]-1,6-dihydro-7H-pyrrolo[2,3-c]pyridin-7-one The trifluoroacetic acid salt of Example 92 was prepared according to the procedure used for the preparation of Example 91, substituting 3-(2,3,4-trimethoxyphenyl)propanoic acid for 2-(methylthio) acetic acid. $^1$H NMR (400 MHz, DMSO-$d_6$/D$_2$O) δ 7.70 (dd, J=8.7, 2.4 Hz, 1H), 7.53 (d, J=2.3 Hz, 1H), 7.29 (d, J=2.8 Hz, 1H), 7.18 (s, 1H), 6.96 (d, J=8.9 Hz, 1H), 6.81 (d, J=8.5 Hz, 1H), 6.64 (d, J=8.5 Hz, 1H), 6.01 (d, J=2.8 Hz, 1H), 3.76 (d, J=3.7 Hz, 3H), 3.72 (d, J=6.2 Hz, 6H), 3.68 (dd, J=9.0, 5.0 Hz, 2H), 3.57 (s, 3H), 3.07 (s, 3H), 2.76-2.66 (m, 2H), 2.47 (d, J=7.2 Hz, 2H), 1.94-1.82 (m, 2H), 1.17 (td, J=14.1, 4.2 Hz, 2H). MS (ESI+) m/z 623.2 (M+H)$^+$.

Example 93

1-[(4-{[2-(6-methyl-7-oxo-6,7-dihydro-1H-pyrrolo[2,3-c]pyridin-4-yl)-4-(methylsulfonyl)phenyl]amino}piperidin-1-yl)carbonyl]cyclopropanecarboxamide The trifluoroacetic acid salt of Example 93 was prepared according to the procedure used for the preparation of Example 91, substituting 1-carbamoylcyclopropanecarboxylic acid for 2-(methylthio) acetic acid. $^1$H NMR (400 MHz, DMSO-$d_6$/D$_2$O) δ 7.70 (dd, J=8.7, 2.4 Hz, 1H), 7.54 (d, J=2.4 Hz, 1H), 7.40-7.25 (m, 1H), 7.18 (s, 1H), 6.97 (d, J=8.9 Hz, 1H), 6.02 (d, J=2.8 Hz, 1H), 3.96 (d, J=10.8 Hz, 2H), 3.82-3.63 (m, 1H), 3.58 (s, 3H), 3.07 (s, 3H), 3.02 (d, J=12.1 Hz, 2H), 1.96-1.84 (m, 2H), 1.29 (td, J=14.3, 4.1 Hz, 2H), 1.20 (dd, J=7.2, 4.1 Hz, 2H), 1.04 (dd, J=7.2, 4.1 Hz, 2H). MS (ESI+) m/z 512.1 (M+H)$^+$.

Example 94

4-[2-({1-[(4-methoxycyclohexyl)carbonyl]piperidin-4-yl}amino)-5-(methylsulfonyl)phenyl]-6-methyl-1,6-dihydro-7H-pyrrolo[2,3-c]pyridin-7-one The trifluoroacetic acid salt of Example 94 was prepared according to the procedure used for the preparation of Example 91, substituting 4-methoxycyclohexanecarboxylic acid for 2-(methylthio) acetic acid. $^1$H NMR (400 MHz, DMSO-d$_6$/D$_2$O) δ 7.70 (dd, J=8.7, 2.4 Hz, 1H), 7.53 (d, J=2.4 Hz, 1H), 7.29 (d, J=2.8 Hz, 1H), 7.17 (s, 1H), 6.96 (d, J=8.9 Hz, 1H), 6.01 (d, J=2.8 Hz, 1H), 3.98 (s, 3H), 3.70 (qd, J=9.7, 4.6 Hz, 1H), 3.57 (s, 3H), 3.36 (d, J=6.3 Hz, 1H), 3.20 (d, J=2.0 Hz, 3H), 3.07 (s, 3H), 2.96 (t, J=23.7 Hz, 2H), 2.57 (ddd, J=14.4, 7.2, 3.7 Hz, 2H), 1.85 (ddd, J=13.1, 10.4, 3.2 Hz, 4H), 1.68-1.53 (m, 2H), 1.49-1.29 (m, 4H), 1.21 (dd, J=20.4, 9.8 Hz, 2H). MS (ESI+) m/z 541.2 (M+H)$^+$.

Example 95

4-[2-{[1-(methoxyacetyl)piperidin-4-yl]amino}-5-(methylsulfonyl)phenyl]-6-methyl-1,6-dihydro-7H-pyrrolo[2,3-c]pyridin-7-one The trifluoroacetic acid salt of Example 95 was prepared according to the procedure used for the preparation of Example 91, substituting 2-methoxyacetic acid for 2-(methylthio) acetic acid. $^1$H NMR (400 MHz, DMSO-d$_6$/D$_2$O) δ 7.70 (dd, J=8.8, 2.4 Hz, 1H), 7.54 (d, J=2.3 Hz, 1H), 7.44-7.25 (m, 1H), 7.18 (s, 1H), 6.97 (d, J=8.9 Hz, 1H), 6.02 (d, J=2.8 Hz, 1H), 3.99 (d, J=12.9 Hz, 3H), 3.92 (s, 1H), 3.70 (ddt, J=18.1, 12.2, 6.2 Hz, 2H), 3.57 (s, 3H), 3.27 (s, 3H), 3.07 (s, 3H), 2.94 (d, J=31.1 Hz, 2H), 2.01-1.84 (m, 2H), 1.24 (dd, J=20.7, 9.9 Hz, 2H). MS (ESI+) m/z 473.2 (M+H)$^+$.

Example 96

6-methyl-4-[2-({1-[(4-methylpiperazin-1-yl)acetyl]piperidin-4-yl}amino)-5-(methylsulfonyl)phenyl]-1,6-dihydro-7H-pyrrolo[2,3-c]pyridin-7-one The trifluoroacetic acid salt of Example 96 was prepared according to the procedure used for the preparation of Example 91, substituting 2-(4-methylpiperazin-1-yl) acetic acid for 2-(methylthio) acetic acid. $^1$H NMR (400 MHz, DMSO-d$_6$/D$_2$O) δ 7.71 (dd, J=8.7, 2.3 Hz, 1H), 7.55 (d, J=2.3 Hz, 1H), 7.30 (d, J=2.8 Hz, 1H), 7.19 (s, 1H), 6.97 (d, J=8.7 Hz, 1H), 6.03 (d, J=2.8 Hz, 1H), 3.96-3.59 (m, 2H), 3.58 (s, 3H), 3.54 (bs, 2H), 3.25-3.19 (m, 4H), 3.08 (s, 3H), 3.06-2.85 (m, 5H), 2.77 (s, 3H), 1.99-1.87 (m, 2H), 1.41-1.19 (m, 2H). MS (ESI+) m/z 541.2 (M+H)$^+$.

Example 97

6-methyl-4-[5-(methylsulfonyl)-2-{[1-(pyrrolidin-1-ylacetyl)piperidin-4-yl]amino}phenyl]-1,6-dihydro-7H-pyrrolo[2,3-c]pyridin-7-one The trifluoroacetic acid salt of Example 97 was prepared according to the procedure used for the preparation of Example 91, substituting 2-(pyrrolidin-1-yl) acetic acid for 2-(methylthio) acetic acid. $^1$H NMR (400 MHz, DMSO-d$_6$/D$_2$O) δ 7.72 (dd, J=8.7, 2.3 Hz, 1H), 7.55 (d, J=2.3 Hz, 1H), 7.30 (d, J=2.8 Hz, 1H), 7.19 (s, 1H), 6.99 (d, J=8.7 Hz, 1H), 6.03 (d, J=2.8 Hz, 1H), 4.23 (s, 2H), 3.84-3.61 (m, 2H), 3.58 (s, 3H), 3.56-3.38 (m, 2H), 3.08 (s, 4H), 2.14-1.88 (m, 6H), 1.39-1.20 (m, 2H). MS (ESI+) m/z 512.2 (M+H)$^+$.

Example 98

4-[2-({1-[(2-methoxyethoxy)acetyl]piperidin-4-yl}amino)-5-(methyl sulfonyl)phenyl]-6-methyl-1,6-dihydro-7H-pyrrolo[2,3-c]pyridin-7-one The trifluoroacetic acid salt of Example 98 was prepared according to the procedure used for the preparation of Example 91, substituting 2-(2-methoxyethoxy) acetic acid for 2-(methylthio) acetic acid. $^1$H NMR (400 MHz, DMSO-d$_6$/D$_2$O) δ 7.70 (dd, J=8.7, 2.4 Hz, 1H), 7.54 (d, J=2.3 Hz, 1H), 7.29 (d, J=2.8 Hz, 1H), 7.18 (s, 1H), 6.97 (d, J=8.9 Hz, 1H), 6.01 (d, J=2.9 Hz, 1H), 4.08 (s, 2H), 3.94 (d, J=26.7 Hz, 2H), 3.78-3.64 (m, 1H), 3.57 (s, 3H), 3.56-3.49 (m, 2H), 3.49-3.41 (m, 2H), 3.21 (d, J=8.8 Hz, 3H), 3.07 (s, 3H), 2.94 (d, J=33.7 Hz, 2H), 1.91 (dt, J=8.1, 7.4 Hz, 2H), 1.23 (dd, J=15.3, 8.3 Hz, 2H). MS (ESI+) m/z 517.1 (M+H)$^+$.

Example 99

6-methyl-4-[5-(methylsulfonyl)-2-({1-[3-(morpholin-4-yl)propanoyl]piperidin-4-yl}amino)phenyl]-1,6-dihydro-7H-pyrrolo[2,3-c]pyridin-7-one The trifluoroacetic acid salt of Example 99 was prepared according to the procedure used for the preparation of Example 91, substituting 3-morpholinopropanoic acid for 2-(methylthio) acetic acid. $^1$H NMR (400 MHz, DMSO-d$_6$/D$_2$O) δ 7.72 (dd, J=8.8, 2.4 Hz, 1H), 7.55 (d, J=2.3 Hz, 1H), 7.30 (d, J=2.8 Hz, 1H), 7.19 (s, 1H), 6.98 (d, J=8.9 Hz, 1H), 6.02 (d, J=2.8 Hz, 1H), 3.83 (s, 4H), 3.75 (td, J=10.1, 5.0 Hz, 2H), 3.58 (s, 3H), 3.34 (t, J=6.9 Hz, 2H), 3.27-3.22 (m, 4H), 3.08 (s, 3H), 2.78 (dd, J=23.9, 16.9 Hz, 2H), 2.02-1.83 (m, 2H), 1.25 (s, 2H). MS (ESI+) m/z 542.2 (M+H)$^+$.

Example 100

6-methyl-4-[2-({1-[(4-methylphenyl)acetyl]piperidin-4-yl}amino)-5-(methylsulfonyl)phenyl]-1,6-dihydro-7H-pyrrolo[2,3-c]pyridin-7-one Example 100 was prepared according to the procedure used for the preparation of Example 91, substituting 2-(p-tolyl) acetic acid for 2-(methylthio) acetic acid. 1H NMR (500 MHz, DMSO-d$_6$) δ 12.12 (s, 1H), 7.66 (dd, J=8.8, 2.3 Hz, 1H), 7.51 (d, J=2.3 Hz, 1H), 7.27 (dd, J=13.4, 10.6 Hz, 2H), 7.07 (s, 4H), 6.93 (d, J=9.0 Hz, 1H), 5.97 (t, J=2.3 Hz, 1H), 5.00 (d, J=7.9 Hz, 1H), 4.25 (d, J=12.9 Hz, 1H), 3.85 (d, J=13.7 Hz, 1H), 3.72-3.60 (m, 3H), 3.55 (s, 3H), 3.14-3.02 (m, 4H), 2.71 (t, J=11.4 Hz, 1H), 2.26 (d, J=13.3 Hz, 3H), 1.80 (dd, J=35.6, 11.4 Hz, 2H), 1.11 (ddd, J=25.7, 17.1, 7.2 Hz, 2H). MS (ESI+) m/z 533.2 (M+H)$^+$.

Example 101

4-[2-{[1-(benzylsulfonyl)piperidin-4-yl]amino}-5-(methylsulfonyl)phenyl]-6-methyl-1,6-dihydro-7H-pyrrolo[2,3-c]pyridin-7-one A 4 mL vial was charged with Example 84c (23 mg, 0.06 mmol) in 1.5 mL of dichloromethane, followed by the addition of phenyl methane sulfonyl chloride (13 mg, 0.07 mmol), and diisopropyl ethyl amine (30 μL, 0.18 mmol). The reaction mixture was allowed to stir at ambient temperature overnight. The reaction mixture was concentrated and the residue was purified by reverse phase HPLC (C18, CH$_3$CN/water (0.1% TFA), 0-100% gradient) to afford the TFA salt of the title compound. $^1$H NMR (400 MHz, DMSO-d$_6$/D$_2$O) δ 7.69 (dd, J=8.7, 2.4 Hz, 1H), 7.54 (d, J=2.3 Hz, 1H), 7.41-7.28 (m, 5H), 7.18 (s, 1H), 6.93 (d, J=8.7 Hz, 1H), 6.01 (d, J=2.8 Hz, 1H), 4.29 (s, 2H), 3.58 (s, 3H), 3.47-3.36 (m, 2H), 3.07 (s, 3H), 2.95-2.85 (m, 2H), 1.92-1.83 (m, 2H), 1.34-1.20 (m, 2H). MS (ESI+) m/z 555.1 (M+H)$^+$.

Example 102

6-methyl-4-{5-(methyl sulfonyl)-2-[(1-{[(E)-2-phenylethenyl]sulfonyl}piperidin-4-yl)amino]phenyl})-1,6-dihydro-7H-pyrrolo[2,3-c]pyridin-7-one The trifluoroacetic acid salt of Example 102 was prepared according to the procedure used for the preparation of Example 101, substituting (E)-2-phenylethenesulfonyl chloride for phenyl methane sulfonyl chloride. $^1$H NMR (400 MHz, DMSO-$d_6$/D$_2$O) δ 7.71-7.59 (m, 3H), 7.53 (d, J=2.3 Hz, 1H), 7.48-7.43 (m, 3H), 7.41-7.33 (m, 1H), 7.25 (d, J=2.8 Hz, 1H), 7.17 (s, 1H), 7.11-7.02 (m, 1H), 6.93 (d, J=8.7 Hz, 1H), 6.00 (d, J=2.8 Hz, 1H), 3.65-3.55 (m, 2H), 3.55 (s, 4H), 3.51 (d, J=3.4 Hz, 1H), 3.06 (s, 3H), 2.97-2.86 (m, 2H), 2.03-1.91 (m, 2H), 1.47-1.34 (m, 2H). MS (ESI+) m/z 567.1 (M+H)$^+$.

Example 103

N-{4-[(4-{[2-(6-methyl-7-oxo-6,7-dihydro-1H-pyrrolo[2,3-c]pyridin-4-yl)-4-(methyl sulfonyl)phenyl]amino}piperidin-1-yl)sulfonyl]phenyl}acetamide The trifluoroacetic acid salt of Example 103 was prepared according to the procedure used for the preparation of Example 101, substituting 4-acetamidobenzene-1-sulfonyl chloride for phenyl methane sulfonyl chloride. $^1$H NMR (400 MHz, DMSO-$d_6$/D$_2$O) δ 7.82-7.71 (m, 2H), 7.70-7.59 (m, 3H), 7.56-7.46 (m, 1H), 7.30-7.20 (m, 1H), 7.14 (d, J=3.9 Hz, 1H), 6.93-6.82 (m, 1H), 6.01-5.92 (m, 1H), 3.59-3.40 (m, 6H), 3.05 (s, 3H), 2.67-2.54 (m, 2H), 2.12 (s, 3H), 1.98-1.86 (m, 2H), 1.46-1.28 (m, 2H), 1.12-1.02 (m, 1H). MS (ESI+) m/z 598 (M+H)$^+$.

Example 104

4-[2-({1-[(4-methoxyphenyl)sulfonyl]piperidin-4-yl}amino)-5-(methylsulfonyl)phenyl]-6-methyl-1,6-dihydro-7H-pyrrolo[2,3-c]pyridin-7-one Example 104 was prepared according to the procedure used for the preparation of Example 101, substituting 4-methoxybenzene-1-sulfonyl chloride for phenyl methane sulfonyl chloride to provide the TFA salt of the title compound. $^1$H NMR (400 MHz, DMSO-$d_6$/D$_2$O) δ 7.71-7.59 (m, 3H), 7.56-7.47 (m, 1H), 7.30-7.21 (m, 1H), 7.18-7.07 (m, 3H), 6.93-6.82 (m, 1H), 6.02-5.92 (m, 1H), 3.87 (s, 3H), 3.55 (s, 3H), 3.51-3.37 (m, 3H), 3.05 (s, 3H), 2.65-2.54 (m, 2H), 2.01-1.86 (m, 2H), 1.46-1.28 (m, 2H). MS (ESI+) m/z 571.1 (M+H)$^+$.

Example 105

3-[(4-{[2-(6-methyl-7-oxo-6,7-dihydro-1H-pyrrolo[2,3-c]pyridin-4-yl)-4-(methylsulfonyl)phenyl]amino}piperidin-1-yl)sulfonyl]benzonitrile The trifluoroacetic acid salt of Example 105 was prepared according to the procedure used for the preparation of Example 101, substituting 3-cyanobenzene-1-sulfonyl chloride for phenyl methane sulfonyl chloride. $^1$H NMR (400 MHz, DMSO-$d_6$/D$_2$O) δ 8.16-8.05 (m, 2H), 8.05-7.96 (m, 1H), 7.90-7.77 (m, 1H), 7.71-7.60 (m, 1H), 7.51 (d, J=2.4 Hz, 1H), 7.25 (t, J=3.2 Hz, 1H), 7.14 (s, 1H), 6.93-6.83 (m, 1H), 5.96 (t, J=2.5 Hz, 1H), 3.60-3.53 (m, 4H), 3.53-3.44 (m, 3H), 3.05 (s, 3H), 2.78-2.63 (m, 2H), 1.99-1.87 (m, 2H), 1.46-1.19 (m, 2H). MS (ESI+) m/z 566.1 (M+H)$^+$.

Example 106

6-methyl-4-[5-(methylsulfonyl)-2-{[1-(thiophen-2-ylsulfonyl)piperidin-4-yl]amino}phenyl]-1,6-dihydro-7H-pyrrolo[2,3-c]pyridin-7-one The trifluoroacetic acid salt of Example 106 was prepared according to the procedure used for the preparation of Example 101, substituting thiophene-2-sulfonyl chloride for phenyl methane sulfonyl chloride. $^1$H NMR (400 MHz, DMSO-$d_6$/D$_2$O) δ 7.95 (dd, J=6.8, 2.9 Hz, 1H), 7.72-7.61 (m, 1H), 7.61-7.48 (m, 2H), 7.25 (dd, J=8.4, 3.8 Hz, 2H), 7.15 (s, 1H), 6.90 (d, J=8.8 Hz, 1H), 5.97 (d, J=2.8 Hz, 1H), 3.66-3.48 (m, 4H), 3.46-3.33 (m, 2H), 3.06 (s, 3H), 2.73 (ddd, J=12.6, 7.0, 3.9 Hz, 2H), 1.94 (ddd, J=9.4, 5.2, 2.3 Hz, 2H), 1.52-1.34 (m, 2H) MS (ESI+) m/z 546.9 (M+H)$^+$.

Example 107

6-methyl-4-[5-(methylsulfonyl)-2-({trans-4-[(thiophen-2-ylmethyl)amino]cyclohexyl}amino)phenyl]-1,6-dihydro-7H-pyrrolo[2,3-c]pyridin-7-one

Example 107a tert-butyl (trans-4-((2-bromo-4-(methyl sulfonyl)phenyl)amino)cyclohexyl)carbamate A solution of Example 21b (0.403 g, 1.592 mmol), N,N-diisopropylethylamine (0.320 mL, 1.831 mmol), and tert-butyl (trans-4-aminocyclohexyl)carbamate (0.352 g, 1.592 mmol) in dimethylsulfoxide (12 mL) was stirred at 100° C. for 4 hours. To the cooled mixture was added dilute ammonium chloride solution and the mixture was extracted twice with diethylether. The combined organic layers were dried with anhydrous magnesium sulfate, filtered, and concentrated. The residue was purified by chromatography (silica gel, 25% ethyl acetate in heptane) to afford 0.39 g (55%) of the title compound.

Example 107b tert-butyl (trans-4-{[2-(6-methyl-7-oxo-6,7-dihydro-1H-pyrrolo[2,3-c]pyridin-4-yl)-4-(methyl sulfonyl)phenyl]amino}cyclohexyl)carbamate Example 107a (0.380 g, 0.849 mmol), Example 1f (0.382 g, 0.892 mmol), tetrakis(triphenylphosphine)palladium (0) (0.098 g, 0.085 mmol), and cesium fluoride (0.387 g, 2.550 mmol) were combined and sparged with argon for 10 minutes. Dimethoxyethane (20 mL) and methanol (10 mL) were added and and argon was bubbled through mixture for 15 min. The reaction mixture was stirred at 80° C. for 2 hours. To 25 mL of cooled reaction mixture was added 5N sodium hydroxide aqueous solution (2.0 mL) and the mixture was stirred for 2 hours at room temperature. To the resulting mixture was added dilute ammonium chloride solution and extracted twice with ethyl acetate. The combined organic layers were dried with anhydrous magnesium sulfate, filtered, and concentrated. The residue was purified by chromatography (silica gel, 2% methanol in dichloromethane) to afford 0.24 g (63%) of the title compound.

Example 107c

4-{2-[(trans-4-aminocyclohexyl)amino]-5-(methylsulfonyl)phenyl}-6-methyl-1,6-dihydro-7H-pyrrolo[2,3-c]pyridin-7-one A solution of Example 107b (0.025 g, 0.049 mmol) in dichloromethane (2.0 mL) was stirred at room temperature. To this solution was added excess trifluoroacetic acid (0.2 mL) and the mixture was stirred 2 hours at room temperature. The mixture was neutralized slowly with sodium carbonate solution until pH was about 10, and then extracted twice with dichloromethane. The combined organic layers were dried with anhydrous magnesium sulfate, filtered, and concentrated. The solid residue was triturated with warm ethyl acetate, filtered, and dried to afford 0.020 g (99%) of title compound.

Example 107d 6-methyl-4-[5-(methylsulfonyl)-2-({trans-4-[(thiophen-2-ylmethyl)amino]cyclohexyl}amino)phenyl]-1,6-dihydro-7H-pyrrolo[2,3-c]pyridin-7-one A 4 mL vial was charged Example 107c (20 mg, 0.05 mmol), in 1.5 mL of 1:1 dichloromethane:methanol to which was added thiophene-2-carbaldehyde (6 mg, 0.08 mmol), and di-isopropyl ethyl amine (21 μL, 0.12 mmol). The reaction mixture was allowed to stir at ambient temperature for 30 minutes after which was added Silica-cyanoborohydride (150 mg, loading 0.89 mmol/g), and the mixture was allowed to stir overnight. The reaction mixture was concentrated and the residue was purified by reverse phase HPLC (C18, $CH_3CN$/water (0.1% TFA), 0-100% gradient) to afford the TFA salt of the title compound. $^1$H NMR (400 MHz, DMSO-$d_6$/$D_2O$) δ 7.69 (dd, J=8.8, 2.3 Hz, 1H), 7.51 (d, J=2.3 Hz, 1H), 7.34 (d, J=2.8 Hz, 1H), 7.26 (s, 1H), 6.90 (d, J=9.0 Hz, 1H), 6.02 (d, J=2.8 Hz, 1H), 3.57 (s, 3H), 3.43 (dd, J=32.4, 21.5 Hz, 1H), 3.10 (s, 3H), 2.50 (d, J=6.9 Hz, 2H), 1.93 (d, J=10.4 Hz, 4H), 1.80-1.68 (m, 1H), 1.31 (dd, J=23.1, 11.3 Hz, 2H), 1.08 (dt, J=13.9, 8.9 Hz, 2H), 0.89 (d, J=6.7 Hz, 6H). MS (ESI+) m/z 511.1 (M+H)$^+$.

Example 108

N-(4-{[(trans-4-{[2-(6-methyl-7-oxo-6,7-dihydro-1H-pyrrolo[2,3-c]pyridin-4-yl)-4-(methylsulfonyl)phenyl]amino}cyclohexyl)amino]methyl}phenyl)acetamide The trifluoroacetic acid salt of Example 108 was prepared according to the procedure used for the preparation Example 107d substituting N-(4-formylphenyl) acetamide for thiophene-2-carbaldehyde. $^1$H NMR (400 MHz, DMSO-$d_6$/$D_2O$) δ 7.76 (ddd, J=21.3, 11.1, 5.5 Hz, 1H), 7.50 (dd, J=5.4, 3.0 Hz, 3H), 7.38-7.14 (m, 4H), 6.90 (d, J=9.0 Hz, 1H), 6.01 (d, J=2.8 Hz, 1H), 3.57 (s, 3H), 3.42 (dd, J=25.7, 14.7 Hz, 1H), 3.10 (s, 3H), 2.48-2.36 (m, 1H), 2.04 (s, 3H), 1.92 (d, J=10.6 Hz, 4H), 1.27 (dd, J=23.5, 11.1 Hz, 2H), 1.06 (dd, J=23.1, 11.5 Hz, 2H). MS (ESI+) m/z 562.1 (M+H)$^+$.

Example 109

4-[2-({trans-4-[(2,4-difluorobenzyl)amino]cyclohexyl}amino)-5-(methylsulfonyl)phenyl]-6-methyl-1,6-dihydro-7H-pyrrolo[2,3-c]pyridin-7-one The trifluoroacetic acid salt of Example 109 was prepared according to the procedure used for the preparation of Example 107d, substituting 2,4-difluorobenzaldehyde for thiophene-2-carbaldehyde. $^1$H NMR (400 MHz, DMSO-$d_6$/$D_2O$) δ 7.68 (dd, J=8.7, 2.4 Hz, 1H), 7.53-7.44 (m, 2H), 7.33 (d, J=2.8 Hz, 1H), 7.25 (s, 1H), 7.12 (td, J=9.8, 2.6 Hz, 1H), 7.03 (td, J=8.6, 2.7 Hz, 1H), 6.89 (d, J=8.8 Hz, 1H), 6.01 (d, J=2.8 Hz, 1H), 3.57 (s, 3H), 3.45-3.34 (m, 1H), 3.10 (s, 3H), 2.35-2.25 (m, 1H), 1.94-1.83 (m, 6H), 1.29-1.12 (m, 2H), 1.14-0.98 (m, 2H). MS (ESI+) m/z 541.1 (M+H)$^+$.

Example 110

6-methyl-4-[5-(methylsulfonyl)-2-({trans-4-[(naphthalen-2-ylmethyl)amino]cyclohexyl}amino)phenyl]-1,6-dihydro-7H-pyrrolo[2,3-c]pyridin-7-one The trifluoroacetic acid salt of Example 110 was prepared according to the procedure used for the preparation of Example 107d, substituting 2-naphthaldehyde for thiophene-2-carbaldehyde. $^1$H NMR (400 MHz, DMSO-$d_6$/$D_2O$) δ 7.87 (dd, J=17.8, 9.4 Hz, 4H), 7.68 (dd, J=8.8, 2.3 Hz, 1H), 7.58-7.42 (m, 4H), 7.32 (d, J=2.8 Hz, 1H), 7.24 (s, 1H), 6.90 (d, J=9.0 Hz, 1H), 6.00 (d, J=2.8 Hz, 1H), 3.93 (s, 2H), 3.56 (s, 3H), 3.41 (t, J=11.1 Hz, 1H), 3.10 (s, 3H), 2.42 (d, J=10.8 Hz, 1H), 1.93 (t, J=12.8 Hz, 4H), 1.28 (dd, J=23.5, 11.0 Hz, 2H), 1.06 (dd, J=22.6, 11.0 Hz, 2H). MS (ESI+) m/z 555.1 (M+H)$^+$.

Example 111

4-[2-({trans-4-[(2-methoxyethyl)amino]cyclohexyl}amino)-5-(methylsulfonyl)phenyl]-6-methyl-1,6-dihydro-7H-pyrrolo[2,3-c]pyridin-7-one The trifluoroacetic acid salt of Example 111 was prepared according to the procedure used for the preparation of Example 107d, substituting 2-methoxyacetaldehyde for thiophene-2-carbaldehyde. $^1$H NMR (400 MHz, DMSO-$d_6$/$D_2O$) δ 7.69 (dd, J=8.8, 2.3 Hz, 1H), 7.51 (d, J=2.3 Hz, 1H), 7.34 (d, J=2.8 Hz, 1H), 7.26 (s, 1H), 6.90 (d, J=9.0 Hz, 1H), 6.02 (d, J=2.8 Hz, 1H), 3.57 (s, 3H), 3.41 (dt, J=16.0, 8.0 Hz, 3H), 3.33-3.19 (m, 4H), 3.10 (s, 3H), 2.77 (t, J=5.5 Hz, 2H), 1.90 (t, J=12.4 Hz, 4H), 1.29-1.14 (m, 2H), 1.15-1.02 (m, 2H). MS (ESI+) m/z 473.2 (M+H)$^+$.

Example 112

6-methyl-4-{2-[(trans-4-{[3-(methyl sulfanyl)propyl]amino}cyclohexyl)amino]-5-(methyl sulfonyl)phenyl}-1, 6-dihydro-7H-pyrrolo[2,3-c]pyridin-7-one The trifluoroacetic acid salt of Example 112 as prepared according to the procedure used for the preparation of Example 107d, substituting 3-(methylthio)propanal for thiophene-2-carbaldehyde. $^1$H NMR (400 MHz, DMSO-$d_6$/$D_2O$) δ 7.72-7.64 (m, 1H), 7.58-7.47 (m, 1H), 7.38-7.29 (m, 1H), 7.29-7.21 (m, 1H), 6.94-6.86 (m, 1H), 6.02 (d, J=2.8 Hz, 1H), 3.57 (s, 3H), 3.50-3.30 (m, 1H), 3.10 (s, 3H), 2.73-2.60 (m, 2H), 2.50 (d, J=7.2 Hz, 2H), 2.03 (s, 3H), 1.98-1.83 (m, 4H), 1.74-1.61 (m, 2H), 1.34-1.15 (m, 2H), 1.15-0.97 (m, 2H) MS (ESI+) m/z 503.1 (M+H)$^+$.

Example 113

4-[2-({trans-4-[(4-chlorobenzyl)amino]cyclohexyl}amino)-5-(methylsulfonyl)phenyl]-6-methyl-1,6-dihydro-7H-pyrrolo[2,3-c]pyridin-7-one The trifluoroacetic acid salt of Example 113 was prepared according to the procedure used for the preparation of Example 107d, substituting 4-chlorobenzaldehyde for thiophene-2-carbaldehyde. $^1$H NMR (400 MHz, DMSO-$d_6$/$D_2O$) δ 7.68 (dd, J=8.8, 2.3 Hz, 1H), 7.50 (d, J=2.3 Hz, 1H), 7.42-7.27 (m, 5H), 7.24 (s, 1H), 6.89 (d, J=9.0 Hz, 1H), 6.01 (d, J=2.8 Hz, 1H), 3.56 (s, 3H), 3.39 (t, J=10.9 Hz, 1H), 3.10 (s, 3H), 2.33 (d, J=10.3 Hz, 1H), 1.89 (s, 6H), 1.22 (dd, J=23.8, 10.7 Hz, 2H), 1.05 (dd, J=23.2, 10.9 Hz, 2H). MS (ESI+) m/z 539.1 (M+H)$^+$.

Example 114

4-[2-(2,4-difluorophenoxy)-5-(methylsulfonyl)phenyl]-6-methyl-2-{[4-(1,3-thiazol-2-yl)piperazin-1-yl]methyl}-1,6-dihydro-7H-pyrrolo[2,3-c]pyridin-7-one Example 114a ethyl 4-bromo-7-methoxy-1-tosyl-1H-pyrrolo[2,3-c]pyridine-2-carboxylate To a solution of Example 1c (10.5 g, 27.5 mmol) in tetrahydrofuran (170 mL) was added dropwise lithium diisopropylamide (20.7 mL, 41.4 mmol) at −70° C. and then stirred between −70° C. and −50° C. for 45 min. After that, to the stirred resulting mixture at −70° C. was added ethyl carbonochloridate (4.48 g, 41.3 mmol) dropwise. The mixture was stirred at −70° C. for 1.5 hours. After the reaction was complete, the reaction mixture was quenched with 20% aqueous ammonium chloride, extracted with ethyl acetate (150 mL). The combined organic layer was dried over anhydrous $Na_2SO_4$, concentrated in vacuum to give the crude product, which was washed with dichloromethane to give the title compound (10 g, 80%) as a white solid.

Example 114b ethyl 4-bromo-7-oxo-1-tosyl-6,7-dihydro-1H-pyrrolo[2,3-c]pyridine-2-carboxylate To a mixture of Example 114a (32.5 g, 71.7 mmol) and sodium iodide (16.12 g, 108 mmol) in acetonitrile (554 mL) was added chlorotrimethylsilane (11.68 g, 108 mmol) dropwise at ambient temperature. The resulting mixture was stirred at ambient temperature for 1 hour. Then water (0.685 g, 38.0 mmol) was added dropwise to the reaction mixture and stirred at 65° C. for 3 hours. The reaction mixture was cooled to ambient temperature and filtered. The precipitate was dissolved in dichloromethane. The mixture was filtered again and the combined filtrate was concentrated under reduced pressure to give a brown solid which was washed with petroleum and dichloromethane to afford the title compound (23 g, 52.4 mmol, 73.0% yield) as light yellow solid.

Example 114c ethyl 4-bromo-6-methyl-7-oxo-1-tosyl-6,7-dihydro-1H-pyrrolo[2,3-c]pyridine-2-carboxylate To a solution of Example 114b (7.5 g, 17.07 mmol) in tetrahydrofuran (100 mL) was added sodium hydride (0.520 g, 21.68 mmol) in portions at 0° C. and stirred for 30 minutes. Iodomethane (3.64 g, 25.6 mmol) was added dropwise to the above mixture at 0° C. The resulting mixture was stirred at ambient temperature for 3 hours and another portion of iodomethane (3.64 g, 25.6 mmol) was added at 0° C. The reaction mixture was stirred at ambient temperature for 12 hours. The reaction mixture was quenched with 20% aqueous ammonium chloride and extracted with ethyl acetate three times. The combined organic extracts were dried over anhydrous $Na_2SO_4$ and concentrated in vacuo. The resulting crude product was purified by column chromatography on silica gel (hexane/ethyl acetate gradient) to provide a yellow crude product which was washed with methanol to give the title compound (15.3 g, 80% yield) as white solid.

Example 114d ethyl 6-methyl-7-oxo-4-(4,4,5,5-tetramethyl-1,3,2-dioxaborolan-2-yl)-1-tosyl-6,7-dihydro-1H-pyrrolo[2,3-c]pyridine-2-carboxylate Example 114d was prepared according to the procedure used for the preparation of Example 1f, substituting Example 114c for Example 1e.

Example 114e ethyl 4-(2-fluoro-5-(methyl sulfonyl)phenyl)-6-methyl-7-oxo-1-tosyl-6,7-dihydro-1H-pyrrolo[2,3-c]pyridine-2-carboxylate Example 114e was prepared according to the procedure used for the preparation of Example 16j, substituting Example 114d for Example 16f, and Example 21b for Example 16i, respectively.

Example 114f ethyl 4-(2-(2,4-difluorophenoxy)-5-(methyl sulfonyl)phenyl)-6-methyl-7-oxo-6,7-dihydro-1H-pyrrolo[2,3-c]pyridine-2-carboxylate A mixture of Example 114e (0.405 g, 1.032 mmol), 2,4-difluorophenol (0.161 g, 1.239 mmol), and cesium carbonate (0.404 g, 1.239 mmol) in DMSO (5 mL) was heated at 110° C. overnight. The reaction mixture was partitioned between water and ethyl acetate. The aqueous layer was extracted with additional ethyl acetate three times. The combined organic layers were washed with brine, dried over anhydrous $MgSO_4$, filtered, and concentrated. The residue was purified by flash chromatography on silica gel eluting with 1:100 methanol/ethyl acetate to give the title compound (0.44 g, 0.876 mmol, 85% yield).

Example 114g

4-[2-(2,4-difluorophenoxy)-5-(methylsulfonyl)phenyl]-2-(hydroxymethyl)-6-methyl-1,6-dihydro-7H-pyrrolo[2,3-c]pyridin-7-one To a suspension of Example 114f (0.20 g, 0.40 mmol) in tetrahydrofuran (5 mL) stirring at 0° C. was added lithium aluminum hydride (1M in tetrahydrofuran, 0.398 mL, 0.398 mmol) and the mixture was stirred at 0° C. for two hours. The solvent was evaporated under reduced pressure and the residue was partitioned between ethyl acetate (30 mL) and water (20 mL). The mixture was filtered to remove the undissolved materials. The aqueous layer was extracted with ethyl acetate (2×30 mL). The combined organic layers were dried over anhydrous sodium sulfate, filtered, and concentrated. The residue was triturated with dichloromethane and the resulting solid was filtered and dried to provide the title compound (0.10 g, 55% yield).

Example 114h 4-(2-(2,4-difluorophenoxy)-5-(methylsulfonyl)phenyl)-6-methyl-7-oxo-6,7-dihydro-1H-pyrrolo[2,3-c]pyridine-2-carbaldehyde To the solution of Example 114g (1.0 g, 2.2 mmol) in dichloromethane (50 mL) at 0° C. was added Dess-Martin Periodinane (1.84 g, 4.34 mmol) and the reaction mixture was stirred at 0° C. for 30 minutes. The reaction mixture was then stirred at ambient temperature for three hours. A solution of sodium bisulfite (0.9 g, 9 mmol) in saturated aqueous sodium bicarbonate (5 mL) was added, and the reaction mixture was stirred for 15 minutes and extracted with ethyl acetate. The organic layer was dried (anhydrous sodium sulfate), filtered, and concentrated to provide the title compound (0.80 g, 70% yield).

Example 114i

4-[2-(2,4-difluorophenoxy)-5-(methylsulfonyl)phenyl]-6-methyl-2-{[4-(1,3-thiazol-2-yl)piperazin-1-yl]methyl}-1,6-dihydro-7H-pyrrolo[2,3-c]pyridin-7-one Example 114i was prepared according to the procedure used for the preparation of Example 16o, substituting 2-(piperazin-1-yl)thiazole for 1-(pyridin-4-yl)piperazine, and Example 114h for Example 16n, respectively. $^1$H NMR (400 MHz, DMSO-$d_6$) δ 12.02 (s, 1H), 7.99 (d, J=2.4 Hz, 1H), 7.87 (dd, J=8.7, 2.4 Hz, 1H), 7.54-7.50 (m, 1H), 7.47-7.38 (m, 2H), 7.21-7.08 (m, 2H), 6.99 (d, J=8.2 Hz, 1H), 6.81 (d, J=3.6 Hz, 1H), 6.19 (s, 1H), 3.65 (s, 2H), 3.58 (s, 3H), 3.33-3.28 (m, 4H), 3.26 (s, 3H), 2.48-2.40 (m, 4H). MS (ESI+) m/z 612.2 (M+H)$^+$.

Example 115

2-[(4-cyclopropylpiperazin-1-yl)methyl]-4-[2-(2,4-difluorophenoxy)-5-(methylsulfonyl)phenyl]-6-methyl-1,6-dihydro-7H-pyrrolo[2,3-c]pyridin-7-one Example 115 was prepared according to the procedure used for the preparation of Example 16o, substituting 1-cyclopropylpiperazine for 1-(pyridin-4-yl)piperazine, and Example 114h for Example 16n, respectively. $^1$H NMR (400 MHz, DMSO-$d_6$) δ 11.95 (s, 1H), 7.98 (d, J=2.4 Hz, 1H), 7.87 (dd, J=8.7, 2.4 Hz, 1H), 7.56-7.50 (m, 1H), 7.46-7.37 (m, 2H), 7.16 (dd, J=11.8, 5.5 Hz, 1H), 7.00 (d, J=8.6 Hz, 1H), 6.12 (s, 1H), 3.58 (s, 3H), 3.54 (s, 2H), 3.26 (s, 3H), 2.46-2.13 (m, 8H), 1.55-1.48 (m, 1H), 0.38-0.30 (m, 2H), 0.19-0.16 (m, 2H). MS (ESI+) m/z 569.2 (M+H)$^+$.

Example 116

4-[2-(2,4-difluorophenoxy)-5-(methylsulfonyl)phenyl]-6-methyl-2-{[4-(tetrahydro-2H-pyran-4-yl)piperazin-1-yl]methyl}-1,6-dihydro-7H-pyrrolo[2,3-c]pyridin-7-one Example 116 was prepared according to the procedure used for the preparation of Example 16o, substituting 1-(tetrahydro-2H-pyran-4-yl)piperazine for 1-(pyridin-4-yl)piperazine, and Example 114h for Example 16n, respectively. $^1$H NMR (400 MHz, CD$_3$OD) δ 8.07 (d, J=2.3 Hz, 1H), 7.94 (dd, J=8.7, 2.4 Hz, 1H), 7.38 (s, 1H), 7.27-7.15 (m, 2H), 7.07-6.96 (m, 2H), 6.30 (s, 1H), 4.03-3.94 (m, 2H), 3.75-3.66 (m, 5H), 3.39 (t, J=11.3 Hz, 2H), 3.21 (s, 3H), 2.76-2.33 (m, 9H), 1.82 (d, J=10.9 Hz, 2H), 1.56-1.40 (m, 2H). MS (ESI+) m/z 613.2 (M+H)$^+$.

Example 117

4-[2-(2,4-difluorophenoxy)-5-(ethylsulfonyl)phenyl]-6-methyl-2-(1-phenyl-1H-pyrazol-5-yl)-1,6-dihydro-7H-pyrrolo[2,3-c]pyridin-7-one

Example 117a 4-bromo-6-methyl-2-(1-phenyl-1H-pyrazol-5-yl)-1-tosyl-1H-pyrrolo[2,3-c]pyridin-7(6H)-one Example 117a was prepared according to the procedure used for the preparation of Example 16j, substituting (1-phenyl-1H-pyrazol-5-yl)boronic acid for Example 16f, and Example 63c for Example 16i, respectively.

Example 117b 4-(5-(ethylsulfonyl)-2-fluorophenyl)-6-methyl-2-(1-phenyl-1H-pyrazol-5-yl)-1-tosyl-1H-pyrrolo[2,3-c]pyridin-7(6H)-one Example 117b was prepared according to the procedure used for the preparation of Example 16j, substituting Example 63e for Example 16f, and Example 117a for Example 16i, respectively.

Example 117c

4-[2-(2,4-difluorophenoxy)-5-(ethylsulfonyl)phenyl]-6-methyl-2-(1-phenyl-1H-pyrazol-5-yl)-1,6-dihydro-7H-pyrrolo[2,3-c]pyridin-7-one Example 117c was prepared according to the procedure used for the preparation of Example 114f, substituting Example 117b for Example 114e. $^1$H NMR (400 MHz, CD$_3$OD) δ 7.88 (d, J=2.3 Hz, 1H), 7.84 (dd, J=8.6, 2.4 Hz, 1H), 7.78 (d, J=2.0 Hz, 1H), 7.44-7.33 (m, 6H), 7.18-7.11 (m, 1H), 7.10-7.03 (m, 1H), 7.02-6.95 (m, 2H), 6.87 (d, J=2.0 Hz, 1H), 5.92 (s, 1H), 3.69 (s, 3H), 3.23 (q, J=7.4 Hz, 2H), 1.25 (t, J=7.4 Hz, 3H). MS (ESI+) m/z 587.0 (M+H)$^+$.

Example 118

4-[2-(2,4-difluorophenoxy)-5-(ethyl sulfonyl)phenyl]-6-methyl-2-[2-(morpholin-4-yl)pyridin-3-yl]-1,6-dihydro-7H-pyrrolo[2,3-c]pyridin-7-one

Example 118a 4-bromo-2-(2-fluoropyridin-3-yl)-6-methyl-1-tosyl-1H-pyrrolo[2,3-c]pyridin-7(6H)-one Example 118a was prepared according to the procedure used for the preparation of Example 16j, substituting (2-fluoropyridin-3-yl)boronic acid for Example 16f, and Example 63c for Example 16i, respectively.

Example 118b 4-bromo-6-methyl-2-(2-morpholinopyridin-3-yl)-1H-pyrrolo[2,3-c]pyridin-7(6H)-one Cesium carbonate (0.103 g, 0.315 mmol), morpholine (0.091 g, 1.050 mmol), and Example 118a (0.05 g, 0.105 mmol) were combined in DMSO (1 mL) and heated at 120° C. for 18 hours in sealed tube. The mixture was partitioned between ethyl acetate and water. The combined organics were washed with brine, dried (anhydrous $MgSO_4$), filtered, and concentrated to a tan oil that was purified by Prep HPLC (C18, 0-100% acetonitrile/water (0.1% TFA) gradient) to give the title compound (0.027 g, 0.070 mmol, 67% yield).

Example 118c 4-(5-(ethylsulfonyl)-2-fluorophenyl)-6-methyl-2-(2-morpholinopyridin-3-yl)-1H-pyrrolo[2,3-c]pyridin-7(6H)-one Example 118c was prepared according to the procedure used for the preparation of Example 16j, substituting Example 63e for Example 16f, and Example 118b for Example 16i, respectively.

Example 118d

4-[2-(2,4-difluorophenoxy)-5-(ethyl sulfonyl)phenyl]-6-methyl-2-[2-(morpholin-4-yl)pyridin-3-yl]-1,6-dihydro-7H-pyrrolo[2,3-c]pyridin-7-one Example 118d was prepared according to the procedure used for the preparation of Example 114f, substituting Example 118c for Example 114e. $^1$H NMR (400 MHz, $CD_3OD$) δ 8.25 (dd, J=4.9, 1.8 Hz, 1H), 8.07 (d, J=2.3 Hz, 1H), 7.92 (dd, J=8.7, 2.4 Hz, 1H), 7.86 (dd, J=7.6, 1.8 Hz, 1H), 7.43 (s, 1H), 7.27-7.14 (m, 2H), 7.12-7.06 (m, 2H), 7.00 (m, 1H), 6.69 (s, 1H), 3.78-3.74 (m, 4H), 3.74 (s, 3H), 3.28 (q, J=7.4 Hz, 2H), 3.10-3.05 (m, 4H), 1.29 (t, J=7.4 Hz, 3H). MS (ESI+) m/z 606.1 $(M+H)^+$

Example 119

4-[2-{2-[(cyclopropylmethyl)amino]-6-methylphenoxy}-5-(ethylsulfonyl)phenyl]-N-ethyl-6-methyl-7-oxo-6,7-dihydro-1H-pyrrolo[2,3-c]pyridine-2-carboxamide

Example 119a ethyl 4-(5-(ethylsulfonyl)-2-fluorophenyl)-6-methyl-7-oxo-1-tosyl-6,7-dihydro-1H-pyrrolo[2,3-c]pyridine-2-carboxylate Example 119a was prepared according to the procedure used for the preparation of Example 16j, substituting Example 114d for Example 16f.

Example 119b 4-(5-(ethylsulfonyl)-2-fluorophenyl)-6-methyl-7-oxo-6,7-dihydro-1H-pyrrolo[2,3-c]pyridine-2-carboxylic acid A mixture of Example 119a (2.05 g, 3.66 mmol), and 2.0 N sodium hydroxide (7.31 mL, 14.63 mmol) in dioxane (15 mL) was heated at 90° C. for 2 hours. The reaction mixture was partially concentrated, then quenched with 0.1 N HCl. The resulting solid was collected by filtration and dried to give the title compound (1.32 g, 3.49 mmol, 95% yield).

Example 119c

N-ethyl-4-(5-(ethylsulfonyl)-2-fluorophenyl)-6-methyl-7-oxo-6,7-dihydro-1H-pyrrolo[2,3-c]pyridine-2-carboxamide A mixture of Example 119b (0.74 g, 1.956 mmol), oxalyl chloride (0.514 mL, 5.87 mmol), and dimethylformamide (0.151 mL, 1.956 mmol) in dichloromethane (30 mL) was stirred for 2 hours. The solvent was removed, and the residue was treated with tetrahydrofuran (10 mL) and dimethylformamide (5 mL). To this solution was added 1.0 N ethanamine in tetrahydrofuran (15.65 mL, 15.65 mmol). The reaction mixture was stirred at ambient temperature for 3 hours, tetrahydrofuran was removed under reduced pressure, and the residue was partitioned between water and ethyl acetate. The aqueous layer was extracted with additional ethyl acetate three times. The combined organic layers were washed with brine, dried over anhydrous $MgSO_4$, filtered, and concentrated. The residue was purified by flash column chromatography on silica gel eluting with 5% methanol in ethyl acetate to give the title compound (0.7 g, 1.727 mmol, 88% yield).

Example 119d 4-(2-(2-amino-6-methylphenoxy)-5-(ethylsulfonyl)phenyl)-N-ethyl-6-methyl-7-oxo-6,7-dihydro-1H-pyrrolo[2,3-c]pyridine-2-carboxamide A mixture of Example 119c (0.081 g, 0.2 mmol), 2-amino-6-methylphenol (0.049 g, 0.400 mmol), and cesium carbonate (0.130 g, 0.400 mmol) in DMSO (2 mL) was heated at 110° C. for 16 hours. The reaction mixture was diluted with ethyl acetate. The solid was removed by filtration. The filtrate was concentrated. The residue was purified by Prep HPLC (C18, 0-100% acetonitrile/water (0.1% TFA) gradient) to give the title compound as trifluroacetic acid salt. (0.055 g, 0.088 mmol, 44.2% yield).

Example 119e

4-[2-{2-[(cyclopropylmethyl)amino]-6-methylphenoxy}-5-(ethylsulfonyl)phenyl]-N-ethyl-6-methyl-7-oxo-6,7-dihydro-1H-pyrrolo[2,3-c]pyridine-2-carboxamide A mixture of Example 119d (0.02 g, 0.032 mmol), cyclopropanecarbaldehyde (2.93 mg, 0.042 mmol) and sodium cyanotrihydroborate (2.62 mg, 0.042 mmol) in 1,2-dichloroethane (1 mL) was stirred at ambient temperature for 16 hours. Solvent was removed under reduced pressure, and the residue was purified by Prep HPLC (C18, 0-100% acetonitrile/water (0.1% TFA) gradient) to afford the title compound as the trifluoroacetic acid salt (0.019 g, 0.028 mmol, 87% yield). $^1$H NMR (400 MHz, DMSO-$d_6$) δ 12.35 (d, J=2.4 Hz, 1H), 8.35 (t, J=5.3 Hz, 1H), 7.91 (d, J=2.4 Hz, 1H), 7.82 (dd, J=8.8, 2.4 Hz, 1H), 7.60 (s, 1H), 7.00 (t, J=7.8 Hz, 1H), 6.85 (d, J=2.1 Hz, 1H), 6.70 (dd, J=27.9, 8.3 Hz, 2H), 6.51 (d, J=7.5 Hz, 1H), 3.61 (s, 3H), 3.36-3.21 (m, 4H), 2.92 (s, 2H), 1.89 (s, 3H), 1.18-1.07 (m, 6H), 0.95 (tt, J=9.7, 3.5 Hz, 1H), 0.32 (dt, J=8.2, 3.0 Hz, 2H), 0.06 (d, J=3.7 Hz, 1H). MS (ESI+) m/z 613.2 (M+H)+.

Example 120

4-[2-(2-chloro-6-methylphenoxy)-5-(ethylsulfonyl)phenyl]-N-(cyanomethyl)-6-methyl-7-oxo-6,7-dihydro-1H-pyrrolo[2,3-c]pyridine-2-carboxamide Example 120a 2-(2-bromo-4-(ethylsulfonyl)phenoxy)-1-chloro-3-methylbenzene Example 120a was prepared according to the procedure used for the preparation of Example 114f, substituting Example 16i for Example 114e, and 2-chloro-6-methylphenol for 2,4-difluorophenol, respectively.

Example 120b ethyl 4-(2-(2-chloro-6-methylphenoxy)-5-(ethylsulfonyl)phenyl)-6-methyl-7-oxo-1-tosyl-6,7-dihydro-1H-pyrrolo[2,3-c]pyridine-2-carboxylate Example 120b was prepared according to the procedure used for the preparation of Example 16j, substituting Example 120a for Example 16i, and substituting Example 114d for Example 16f.

Example 120c 4-(2-(2-chloro-6-methylphenoxy)-5-(ethylsulfonyl)phenyl)-6-methyl-7-oxo-6,7-dihydro-1H-pyrrolo[2,3-c]pyridine-2-carboxylic acid Example 120c was prepared according to the procedure used for the preparation of Example 119b, substituting Example 120b for Example 119a.

Example 120d

4-[2-(2-chloro-6-methylphenoxy)-5-(ethylsulfonyl)phenyl]-N-(cyanomethyl)-6-methyl-7-oxo-6,7-dihydro-1H-pyrrolo[2,3-c]pyridine-2-carboxamide In a 4 mL vial a solution of Example 120c (15 mg, 0.03 mmol) in dimethylacetamide (0.3 mL) was added, followed by a solution of O-(7-azabenzotriazol-1-yl)-N,N,N',N'-tetramethyluronium hexafluorophosphate (14 mg, 0.04 mmol) in dimethylacetamide (0.3 mL). Then a solution of 2-aminoacetonitrile (0.04 mmol) in dimethylacetamide (0.09 mL) was added followed by diisopropylethylamine (16 μL, 0.06 mmol). The reaction mixture was shaken at 100° C. for 10 minutes. The reaction mixture was then purified by Prep HPLC (C18, 0-100% acetonitrile/water (0.1% TFA) gradient) to give the title product. $^1$H NMR (DMSO-$d_6$) δ: 7.94 (d, J=2.4 Hz, 1H), 7.81 (dd, J=8.7, 2.4 Hz, 1H), 7.50 (s, 1H), 7.47 (d, J=7.9 Hz, 1H), 7.36 (d, J=7.6 Hz, 1H), 7.27 (t, J=7.9 Hz, 1H), 6.80 (s, 1H), 6.66 (d, J=8.7 Hz, 1H), 6.58 (s, 2H), 3.60 (s, 3H), 3.30-3.34 (m, 4H), 2.11 (s, 3H), 1.14 (t, J=7.3 Hz, 3H). MS (ESI+) m/z 540.1 (M+H)+.

Example 121

4-[2-(2-chloro-6-methylphenoxy)-5-(ethyl sulfonyl)phenyl]-6-methyl-N-[1-(methylamino)-1-oxopropan-2-yl]-7-oxo-6,7-dihydro-1H-pyrrolo[2,3-c]pyridine-2-carboxamide Example 121 was prepared according to the procedure used for the preparation of Example 120d, substituting 2-amino-N-methylpropanamide for 2-aminoacetonitrile. $^1$H NMR (DMSO-$d_6$) δ: 7.93 (d, J=2.4 Hz, 1H); 7.80 (dd, J=8.7, 2.4 Hz, 1H), 7.43 (s, 1H), 7.41 (dd, J=8.1, 1.6 Hz, 1H), 7.30-7.33 (m, 1H), 7.21-7.26 (m, 1H), 6.94 (s, 1H), 6.68 (d, J=8.7 Hz, 1H), 4.44 (q, J=7.1 Hz, 1H), 3.63 (s, 3H), 3.24-3.29 (m, 2H), 2.62 (s, 3H), 2.11 (s, 3H), 1.33 (d, J=7.1 Hz, 3H), 1.19 (t, J=7.3 Hz, 3H), MS (ESI+) m/z 585 (M+H)+.

Example 122

4-[2-(2-chloro-6-methylphenoxy)-5-(ethylsulfonyl)phenyl]-6-methyl-7-oxo-N-[2-oxo-2-(piperidin-1-yl)ethyl]-6,7-dihydro-1H-pyrrolo[2,3-c]pyridine-2-carboxamide Example 122 was prepared according to the procedure used for the preparation of Example 120d, substituting 2-amino-1-(piperidin-1-yl)ethanone for 2-aminoacetonitrile. $^1$H NMR (DMSO-$d_6$) δ: 7.93 (d, J=2.3 Hz, 1H), 7.81 (dd, J=8.7, 2.4 Hz, 1H), 7.43 (s, 1H), 7.38-7.42 (m, 1H), 7.29-7.34 (m, 1H), 7.20-7.26 (m, 1H), 6.92 (s, 1H), 6.68 (d, J=8.7 Hz, 1H), 4.13 (s, 2H), 3.62 (s, 3H), 3.40-3.47 (m, 4H), 3.24-3.28 (m, 2H), 2.11 (s, 3H), 1.46-1.65 (m, 6H), 1.18 (t, J=7.4 Hz, 3H). MS (ESI+) m/z 625 (M+H)+.

Example 123

4-[2-(2-chloro-6-methylphenoxy)-5-(ethylsulfonyl)phenyl]-N-(2-cyanoethyl)-6-methyl-7-oxo-6,7-dihydro-1H-pyrrolo[2,3-c]pyridine-2-carboxamide Example 123 was prepared according to the procedure used for the preparation of Example 120d, substituting 3-aminopropanenitrile for 2-aminoacetonitrile. $^1$H NMR (DMSO-$d_6$) δ: 7.93 (d, J=2.4 Hz, 1H), 7.81 (dd, J=8.7, 2.4 Hz, 1H), 7.42 (s, 1H), 7.38-7.42 (m, 1H), 7.29-7.33 (m, 1H), 7.23 (t, J=7.8 Hz, 1H), 6.92 (s, 1H), 6.69 (d, J=8.7 Hz, 1H), 3.62 (s, 3H), 3.52 (t, J=6.5 Hz, 2H), 3.25-3.29 (m, 2H), 2.74 (t, J=6.5 Hz, 2H), 2.11 (s, 3H), 1.19 (t, J=7.4 Hz, 3H). MS (ESI+) m/z 553 (M+H)+.

Example 124

4-[2-(2-chloro-6-methylphenoxy)-5-(ethylsulfonyl)phenyl]-6-methyl-N-[2-(methylamino)-2-oxoethyl]-7-oxo-6,7-dihydro-1H-pyrrolo[2,3-c]pyridine-2-carboxamide Example 124 was prepared according to the procedure used for the preparation of Example 120d, substituting 2-amino-N-methylacetamide for 2-aminoacetonitrile. $^1$H NMR (DMSO-$d_6$) δ: 7.93 (d, J=2.4 Hz, 1H), 7.81 (dd, J=8.7, 2.4 Hz, 1H), 7.43 (s, 1H), 7.39-7.42 (m, 1H), 7.29-7.33 (m, 1H), 6.92 (s, 1H), 7.21-7.26 (m, 1H), 6.69 (d, J=8.7 Hz, 1H), 3.88 (s, 2H), 3.62 (s, 3H), 3.25-3.29 (m, 2H), 2.64 (s, 3H), 2.11 (s, 3H), 1.19 (t, J=7.5 Hz, 3H). MS (ESI+) m/z 571 (M+H)+.

Example 125

4-[2-(2,4-difluorophenoxy)-5-(methylsulfonyl)phenyl]-6-methyl-2-{[4-(1-methylpiperidin-4-yl)piperazin-1-yl]methyl}-1,6-dihydro-7H-pyrrolo[2,3-c]pyridin-7-one In a 4 mL vial was added the Example 114h (10 mg, 0.02 mmol) in 1M solution of ammonium acetate/acetic acid buffer in methanol(pH=4) (1.0 mL) followed by the addition of 1-(1-methylpiperidin-4-yl)piperazine (0.02) mmol) in the buffer solution (0.06 mL). After that, 75 mg of MP-Cyanoborohydride resin (0.89 mmol/g) was added and the resulting mixture was shaken at 60° C. overnight. The solid was filtered off, and the filtrate was concentrated. The residue was purified by Prep-HPLC (C18, 0-100% acetonitrile/water (0.1% TFA) gradient) to give the title compound. $^1$H NMR (DMSO-$d_6$) δ: 7.99 (d, J=2.4 Hz, 1H), 7.93 (dd, J=8.7, 2.4 Hz, 1H), 7.41 (s, 1H), 7.25-7.38 (m, 2H), 7.05-7.18 (m, 2H), 6.38 (s, 1H), 4.19 (s, 2H), 3.61 (s, 3H), 3.39-3.56 (m, 2H), 3.24 (s, 3H), 2.84-3.09 (m, 11H), 2.80 (s, 3H), 2.07 (s, 2H), 1.75 (s, 2H). MS (ESI+) m/z 626 (M+H)$^+$.

Example 126

4-[2-(2,4-difluorophenoxy)-5-(methyl sulfonyl)phenyl]-6-methyl-2-{[4-(pyridin-2-yl)-1,4-diazepan-1-yl]methyl}-1,6-dihydro-7H-pyrrolo[2,3-c]pyridin-7-one Example 126 was prepared according to the procedure used for the preparation of Example 125, substituting 1-(pyridin-2-yl)-1,4-diazepane for 1-(1-methylpiperidin-4-yl)piperazine. $^1$H NMR (DMSO-$d_6$) δ: 8.03-8.14 (m, 1H), 7.98-8.03 (m, 1H), 7.94 (dd, J=8.6, 2.4 Hz, 1H), 7.61-7.74 (m, 1H), 7.42 (s, 1H), 7.25-7.36 (m, 2H), 7.05-7.15 (m, 2H), 6.81 (d, J=8.7 Hz, 1H), 6.74 (dd, J=7.2, 5.4 Hz, 1H), 6.50 (s, 1H), 4.48 (s, 2H), 3.96 (s, 2H), 3.62 (d, J=6.5 Hz, 5H), 3.39 (d, J=5.1 Hz, 4H), 3.24 (s, 3H), 2.11-2.24 (m, 2H). MS (ESI+) m/z 620 (M+H)$^+$.

Example 127

4-[2-(2,4-difluorophenoxy)-5-(methylsulfonyl)phenyl]-2-{[3-(furan-2-yl)morpholin-4-yl]methyl}-6-methyl-1,6-dihydro-7H-pyrrolo[2,3-c]pyridin-7-one Example 127 was prepared according to the procedure used for the preparation of Example 125, substituting 3-(furan-2-yl)morpholine for 1-(1-methylpiperidin-4-yl)piperazine, to provide the title compound. $^1$H NMR (DMSO-$d_6$) δ: 7.96-8.05 (m, 1H), 7.86-7.96 (m, 1H), 7.59-7.70 (m, 1H), 7.38 (s, 1H), 7.25-7.37 (m, 2H), 7.03-7.12 (m, 2H), 6.57-6.64 (m, 1H), 6.46-6.53 (m, 1H), 6.23 (s, 1H), 4.04-4.12 (m, 1H), 3.66-4.01 (m, 6H), 3.60 (s, 3H), 3.24 (s, 3H), 2.96-3.02 (m, 1H), 2.64-2.72 (m, 1H). MS (ESI+) m/z 596 (M+H)$^+$.

Example 128

4-[2-(2,4-difluorophenoxy)-5-(methylsulfonyl)phenyl]-2-{[4-(3,5-dimethyl-4H-1,2,4-triazol-4-yl)piperidin-1-yl]methyl}-6-methyl-1,6-dihydro-7H-pyrrolo[2,3-c]pyridin-7-one Example 128 was prepared according to the procedure used for the preparation of Example 125, substituting 4-(3,5-dimethyl-4H-1,2,4-triazol-4-yl)piperidine for 1-(1-methylpiperidin-4-yl)piperazine. $^1$H NMR (DMSO-$d_6$) δ: 7.98-8.04 (m, 1H), 7.94 (dd, J=8.7, 2.4 Hz, 1H), 7.44 (s, 1H), 7.26-7.37 (m, 2H), 7.06-7.14 (m, 2H), 6.53 (s, 1H), 4.50-4.57 (m, 1H), 4.48 (s, 2H), 3.63 (s, 3H), 3.50-3.59 (m, 2H), 3.24 (s, 3H), 3.19 (t, J=12.3 Hz, 2H), 2.38 (s, 3H), 2.22-2.31 (m, 2H), 2.20 (s, 3H), 2.06-2.16 (m, 2H). MS (ESI+) m/z 623 (M+H)$^+$.

Example 129

4-[2-(2,4-difluorophenoxy)-5-(methylsulfonyl)phenyl]-2-{[3-(3,5-dimethyl-1H-pyrazol-1-yl)azetidin-1-yl]methyl}-6-methyl-1, 6-dihydro-7H-pyrrolo[2,3-c]pyridin-7-one Example 129 was prepared according to the procedure used for the preparation of Example 125, substituting 1-(azetidin-3-yl)-3,5-dimethyl-1H-pyrazole for 1-(1-methylpiperidin-4-yl)piperazine. $^1$H NMR (DMSO-$d_6$) δ: 7.98-8.01 (m, 1H), 7.93 (dd, J=8.7, 2.4 Hz, 1H), 7.42 (s, 1H), 7.25-7.33 (m, 2H), 7.02-7.11 (m, 2H), 6.50 (s, 1H), 5.88 (s, 1H), 5.12-5.27 (m, 1H), 4.65 (s, 2H), 4.44-4.59 (m, 4H), 3.62 (s, 3H), 3.23 (s, 3H), 2.15 (d, J=8.9 Hz, 6H). MS (ESI+) m/z 594 (M+H)$^+$.

Example 130

4-[2-(2,4-difluorophenoxy)-5-(methylsulfonyl)phenyl]-6-methyl-2-{[4-(morpholin-4-yl)piperidin-1-yl]methyl}-1,6-dihydro-7H-pyrrolo[2,3-c]pyridin-7-one Example 130 was prepared according to the procedure used for the preparation of Example 125, substituting 4-(piperidin-4-yl)morpholine for 1-(1-methylpiperidin-4-yl)piperazine. $^1$H NMR (DMSO-$d_6$) δ: 8.00 (d, J=2.4 Hz, 1H), 7.94 (dd, J=8.7, 2.4 Hz, 1H), 7.43 (s, 1H), 7.25-7.38 (m, 2H), 7.03-7.16 (m, 2H), 6.47 (s, 1H), 4.37 (s, 2H), 3.80-3.89 (m, 4H), 3.62 (s, 3H), 3.50 (d, J=12.9 Hz, 2H), 3.27-3.32 (m, 1H), 3.24 (s, 3H), 3.14-3.21 (m, 4H), 2.89-3.01 (m, 2H), 2.17-2.30 (m, 2H), 1.81-1.99 (m, 2H). MS (ESI+) m/z 613 (M+H)$^+$.

Example 131

4-[2-(2,4-difluorophenoxy)-5-(methyl sulfonyl)phenyl]-6-methyl-2-{[2-(3-methyl-1,2,4-oxadiazol-5-yl)pyrrolidin-1-yl]methyl}-1,6-dihydro-7H-pyrrolo[2,3-c]pyridin-7-one Example 131 was prepared according to the procedure used for the preparation of Example 125, substituting 3-methyl-5-(pyrrolidin-2-yl)-1,2,4-oxadiazole for 1-(1-methylpiperidin-4-yl)piperazine. $^1$H NMR (DMSO-$d_6$) δ: 7.94-8.02 (m, 1H), 7.91 (dd, J=8.7, 2.4 Hz, 1H), 7.36 (s, 1H), 7.25-7.35 (m, 2H), 7.02-7.13 (m, 2H), 6.20 (s, 1H), 4.35-4.44 (m, 1H), 4.02-4.24 (m, 2H), 3.60 (s, 3H), 3.23 (s, 3H), 3.17-3.23 (m, 1H), 2.83-2.92 (m, 1H), 2.29-2.41 (m, 1H), 2.27 (s, 3H), 2.03-2.13 (m, 1H), 1.85-2.02 (m, 2H). MS (ESI+) m/z 596 (M+H)$^+$.

Example 132

4-[2-(2,4-difluorophenoxy)-5-(methylsulfonyl)phenyl]-6-methyl-2-{[4-(pyridin-2-yl)piperazin-1-yl]methyl}-1,6-dihydro-7H-pyrrolo[2,3-c]pyridin-7-one Example 132 was prepared according to the procedure used for the preparation of Example 125, substituting 1-(pyridin-2-yl)piperazine for 1-(1-methylpiperidin-4-yl)piperazine. $^1$H NMR (DMSO-d$_6$) δ: 8.10-8.18 (m, 1H), 7.97-8.05 (m, 1H), 7.94 (dd, J=8.7, 2.4 Hz, 1H), 7.61-7.72 (m, 1H), 7.43 (s, 1H), 7.24-7.37 (m, 2H), 7.04-7.13 (m, 2H), 6.92 (d, J=8.6 Hz, 1H), 3.24 (s, 3H), 6.76-6.83 (m, 1H), 6.51 (s, 1H), 4.48 (s, 2H), 3.65-3.88 (m, 4H), 3.62 (s, 3H), 3.24-3.29 (m, 4H). MS (ESI+) m/z 606 (M+H)$^+$.

Example 133

N-ethyl-4-[5-(ethylsulfonyl)-2-{2-methyl-6-[(tetrahydrofuran-3-ylmethyl)amino]phenoxy}phenyl]-6-methyl-7-oxo-6,7-dihydro-1H-pyrrolo[2,3-c]pyridine-2-carboxamide Example 119d (30.5 mg, 0.060 mmol), 50% tetrahydrofuran-3-carbaldehyde in water (0.015 mL, 0.078 mmol), and sodium cyanoborohydride (4.9 mg, 0.078 mmol) were combined in 1,2-dichloroethane (1 mL). The reaction mixture was stirred at ambient temperature for 3 hours. To this reaction mixture was added 50% tetrahydrofuran-3-carbaldehyde in water (0.015 mL, 0.078 mmol) and sodium cyanoborohydride (4.9 mg, 0.078 mmol). The reaction mixture was stirred at ambient temperature for another 3 hours. To this reaction mixture was added 50% tetrahydrofuran-3-carbaldehyde in water (0.015 mL, 0.078 mmol) and sodium cyanoborohydride (4.9 mg, 0.078 mmol). The reaction mixture was stirred at ambient temperature for another 16 hours, and partitioned with ethyl acetate and water. The organic layer was washed with saturated aqueous sodium chloride, dried with anhydrous sodium sulfate, filtered, and concentrated. The residue was purified by reverse phase HPLC (C18, 50-100% acetonitrile in 0.1% TFA/water) to provide the title compound (3.6 mg, 10%). $^1$H NMR (400 MHz, DMSO-d$_6$) δ 12.35 (s, 1H), 8.33 (t, J=5.3 Hz, 1H), 7.91 (d, J=2.4 Hz, 1H), 7.80 (dd, J=8.7, 2.4 Hz, 1H), 7.64 (s, 1H), 6.99 (dd, J=10.3, 5.4 Hz, 1H), 6.86 (d, J=2.2 Hz, 1H), 6.71 (d, J=8.7 Hz, 1H), 6.65 (d, J=7.9 Hz, 1H), 6.49 (d, J=7.3 Hz, 1H), 4.83 (s, br, 1H), 3.69-3.61 (m, 2H), 3.59 (s, 3H), 3.58-3.51 (m, 2H), 3.32-3.25 (m, 4H), 3.08-2.99 (m, 2H), 2.46-2.38 (m, 1H), 1.85 (s, 3H), 1.83-1.76 (m, 1H), 1.45-1.38 (m, 1H), 1.17-1.10 (m, 6H). (ESI+) m/z 593 (M+H)$^+$.

Example 134

(2E)-3-{4-[2-(2,6-dimethylphenoxy)-5-(ethylsulfonyl)phenyl]-6-methyl-7-oxo-6,7-dihydro-1H-pyrrolo[2,3-c]pyridin-2-yl}-N-ethylprop-2-enamide Example 134a (E)-ethyl 3-(4-bromo-6-methyl-7-oxo-1-tosyl-6,7-dihydro-1H-pyrrolo[2,3-c]pyridin-2-yl)acrylate A mixture of Example 63c (1.5 g, 2.96 mmol), PdCl$_2$(dppf)-CH$_2$Cl$_2$ Adduct (0.242 g, 0.296 mmol), ethyl acrylate (0.592 g, 5.92 mmol), and triethylamine (2.061 mL, 14.79 mmol) in dimethylformamide (15 mL) was heated at 100° C. for 1 hour. After cooling, the reaction mixture was partitioned between water and ethyl acetate. The aqueous layer was extracted with ethyl acetate two more times. The combined organic layers were dried over anhydrous MgSO$_4$, filtered, and concentrated. The residue was purified by flash chromatography on silica gel to afford the title compound (1 g, 1.460 mmol, 49.4% yield).

Example 134b (E)-ethyl 3-(4-(5-(ethylsulfonyl)-2-fluorophenyl)-6-methyl-7-oxo-1-tosyl-6,7-dihydro-1H-pyrrolo[2,3-c]pyridin-2-yl)acrylate Example 134b was prepared according to the procedure used for the preparation of Example 16j, substituting Example 63e for Example 16f, and Example 134a for Example 16i, respectively.

Example 134c (E)-ethyl 3-(4-(2-(2,6-dimethylphenoxy)-5-(ethylsulfonyl)phenyl)-6-methyl-7-oxo-6,7-dihydro-1H-pyrrolo[2,3-c]pyridin-2-yl)acrylate Example 134c was prepared according to the procedure used for the preparation of Example 114f, substituting Example 134b for Example 114e, and 2,6-dimethylphenol for 2,4-difluorophenol, respectively.

Example 134d

Example 134d was prepared according to the procedure used for the preparation of Example 119b, substituting Example 134c for Example 119a.

Example 134e (2E)-3-{4-[2-(2,6-dimethylphenoxy)-5-(ethylsulfonyl)phenyl]-6-methyl-7-oxo-6,7-dihydro-1H-pyrrolo[2,3-c]pyridin-2-yl}-N-ethylprop-2-enamide Example 134e was prepared according to the procedure used for the preparation of Example 119c, substituting Example 134d for Example 119b. $^1$H NMR (400 MHz, CD$_3$OD) δ 8.03 (d, J=2.3 Hz, 1H), 7.81 (dd, J=8.7, 2.4 Hz, 1H), 7.53 (d, J=15.8 Hz, 1H), 7.45 (s, 1H), 7.20-7.07 (m, 3H), 6.68 (d, J=8.7 Hz, 1H), 6.66-6.57 (m, 2H), 3.75 (s, 3H), 3.37 (q, J=7.6 Hz, 2H), 3.27 (q, J=7.4 Hz, 2H), 2.10 (s, 6H), 1.29 (t, J=7.4 Hz, 3H), 1.21 (t, J=7.3 Hz, 3H). MS (ESI+) m/z 534.2 (M+H)$^+$.

Example 135

2-(3-cyclopropyl-1,2,4-oxadiazol-5-yl)-4-[2-(2,6-dimethylphenoxy)-5-(methylsulfonyl)phenyl]-6-methyl-1,6-dihydro-7H-pyrrolo[2,3-c]pyridin-7-one Example 135a 2-(2-bromo-4-(methylsulfonyl)phenoxy)-1,3-dimethylbenzene To a mixture of Example 21b (3.027 g, 11.96 mmol), 2,6-dimethylphenol (1.534 g, 12.56 mmol) and cesium carbonate (4.68 g, 14.35 mmol) was added dimethyl sulfoxide (60 mL). The reaction mixture was heated at 80° C. for 1 hour, cooled to ambient temperature and acidified with 2 N aqueous hydrochloric acid. The solid was collected by filtration, washed with water and then triturated with methanol. The filtrates were combined and concentrated to remove methanol. A second crop precipitated out of solution. The solid was collected by filtration, washed with water and then triturated with methanol. The two portions were dried overnight in a vacuum oven at 70° C. to provide the title compound (3.486 g, 82%).

Example 135b ethyl 4-(2-(2,6-dimethylphenoxy)-5-(methylsulfonyl)phenyl)-6-methyl-7-oxo-1-tosyl-6,7-dihydro-1H-pyrrolo[2,3-c]pyridine-2-carboxylate Example 114d (4 g, 8 mmol), Example 135a (3.41 g, 9.6 mmol), tris(dibenzylideneacetone)dipalladium(0) (0.366 g, 0.4 mmol), 1,3,5,7-tetramethyl-8-phenyl-2,4,6-trioxa-8-phosphaadamantane (0.351 g, 1.2 mmol) and sodium carbonate (3.65 g, 34.4 mmol) were combined and sparged with nitrogen for 30 minutes. To this were added nitrogen-sparged 1,4-dioxane (40 mL) and water (10 mL) via syringe. The reaction mixture was stirred at 60° C. for 5 hours. The reaction mixture was cooled to ambient temperature and partitioned between ethyl acetate and water. The organic layer was washed with brine, treated with 3-mercaptopropyl-functionalized silica gel for 20 minutes, dried over anhydrous magnesium sulfate, filtered through a plug of Celite and concentrated. The residue was purified by flash chromatography (silica gel, 0 to 80% ethyl acetate in heptanes) to provide the title compound as an impure mixture. The material was further purified by flash chromatography (silica gel, 0-25% ethyl acetate in dichloromethane) to give the title compound (3.73 g, 72%).

Example 135c 4-(2-(2,6-dimethylphenoxy)-5-(methylsulfonyl)phenyl)-6-methyl-7-oxo-6,7-dihydro-1H-pyrrolo[2,3-c]pyridine-2-carboxylic acid To a solution of Example 135b (4.2 g, 6.47 mmol) in 1,4-dioxane (42 mL) was added lithium hydroxide (0.775 g, 32.4 mmol) and water (14 mL). The reaction mixture was heated at 75° C. for 5 hours, cooled to ambient temperature and acidified with 2 N aqueous hydrochloric acid. The solid was collected by filtration, washed with water and dried overnight in a vacuum oven at 70° C. to afford the title compound with 28 mole % 1,4-dioxane as an excipient (3.08 g, 97%).

Example 135d 2-(3-cyclopropyl-1,2,4-oxadiazol-5-yl)-4-[2-(2,6-dimethylphenoxy)-5-(methylsulfonyl)phenyl]-6-methyl-1, 6-dihydro-7H-pyrrolo[2,3-c]pyridin-7-one Example 135c (0.12 M in DMSO, 300 µL, 0.036 mmol), 1-ethyl-3-[3-(dimethylamino)propyl]-carbodiimide hydrochloride (0.15 M in DMSO, 300 µL, 0.044 mmol, 1.2 equivalents), 1-hydroxybenzotriazole hydrate (0.15 M in DMSO, 300 µL, 0.044 mmol, 1.2 equivalents) and N'-hydroxycyclopropanecarboximidamide (0.40 M in DMSO, 137 µL, 0.055 mmol, 1.5 equivalents) were combined in a 4 mL vial, passed through a perfluoroalkoxy mixing tube (0.2 mm inner diameter), and loaded into an injection loop. The reaction segment was injected into a flow reactor (Hastelloy coil, 0.75 mm inner diameter, 1.8 mL internal volume) set at 175° C., and passed through the reactor at 180 µL min$^{-1}$ (10 minute residence time). Upon exiting the reactor, the reaction mixture was loaded directly into an injection loop and purified by preparative HPLC on a Phenomenex Luna C8(2) 5 µm 100 Å AXIA column (50 mm×21.2 mm). A gradient of acetonitrile (A) and 0.1% trifluoroacetic acid in water (B) was used, at a flow rate of 30 mL/min (0-0.5 min 5% A, 0.5-6.5 min linear gradient 5-100% A, 6.5-8.5 min 100% A, 8.5-9.0 min linear gradient 100-5% A, 9.0-10 min 5% A) to yield the title compound (8.72 mg, 45.2% yield). $^1$H NMR (400 MHz, DMSO-d$_6$-D$_2$O) δ 7.99 (d, J=2.4 Hz, 1H), 7.86 (dd, J=8.7, 2.4 Hz, 1H), 7.56 (s, 1H), 7.18 (d, J=6.6 Hz, 2H), 7.13 (dd, J=8.7, 6.0 Hz, 1H), 7.05 (s, 1H), 6.62 (d, J=8.7 Hz, 1H), 3.65 (s, 3H), 3.24 (s, 3H), 2.18 (ddd, J=13.2, 8.3, 4.9 Hz, 1H), 2.04 (s, 6H), 1.12 (dt, J=8.1, 3.2 Hz, 2H), 0.98 (dt, J=6.9, 4.0 Hz, 2H). MS (APCI+) m/z 563.0 (M+MeOH+H)$^+$.

Example 136

2-(3-cyclohexyl-1,2,4-oxadiazol-5-yl)-4-[2-(2,6-dimethylphenoxy)-5-(methylsulfonyl)phenyl]-6-methyl-1, 6-dihydro-7H-pyrrolo[2,3-c]pyridin-7-one Example 136 (9.58 mg, 46.0%) was prepared using the procedure described in Example 135d substituting N'-hydroxycyclohexanecarboximidamide for N'-hydroxycyclopropanecarboximidamide. $^1$H NMR (400 MHz, DMSO-d$_6$-D$_2$O) δ 8.00 (d, J=2.4 Hz, 1H), 7.87 (dd, J=8.7, 2.4 Hz, 1H), 7.57 (s, 1H), 7.18 (m, 2H), 7.13 (m, 1H), 7.08 (s, 1H), 6.63 (d, J=8.7 Hz, 1H), 3.65 (s, 3H), 3.24 (s, 3H), 2.86 (tt, J=11.0, 3.6 Hz, 1H), 2.05 (s, 6H), 1.98 (m, 2H), 1.77 (dt, J=11.7, 3.1 Hz, 2H), 1.68 (m, 1H), 1.54 (qd, J=12.4, 2.9 Hz, 2H), 1.40 (qt, J=12.3, 3.0 Hz, 2H), 1.26 (m, 1H). MS (APCI+) m/z 605.1 (M+MeOH+H)$^+$.

Example 137

4-[2-(2,6-dimethylphenoxy)-5-(methylsulfonyl)phenyl]-6-methyl-2-(3-phenyl-1,2,4-oxadiazol-5-yl)-1, 6-dihydro-7H-pyrrolo[2,3-c]pyridin-7-one Example 137 (14.0 mg, 76.8%) was prepared using the procedure described in Example 135d substituting N'-hydroxybenzimidamide for N'-hydroxycyclopropanecarboximidamide. $^1$H NMR (400 MHz, DMSO-d$_6$-D$_2$O) δ 8.09 (m, 2H), 8.03 (d, J=2.4 Hz, 1H), 7.88 (dd, J=8.7, 2.4 Hz, 1H), 7.63 (m, 3H), 7.59 (s, 1H), 7.19 (m, 3H), 7.12 (m, 1H), 6.65 (d, J=8.7 Hz, 1H), 3.67 (s, 3H), 3.26 (s, 3H), 2.08 (s, 6H). MS (APCI+) m/z 599.1 (M+MeOH+H)$^+$.

Example 138

4-[2-(2,6-dimethylphenoxy)-5-(methylsulfonyl)phenyl]-6-methyl-2-[3-(pyridin-3-yl)-1,2,4-oxadiazol-5-yl]-1,6-dihydro-7H-pyrrolo[2,3-c]pyridin-7-one Example 135c (0.21 M in DMSO, 200 µL, 0.043 mmol), 1-ethyl-3-[3-(dimethylamino)propyl]-carbodiimide hydrochloride (0.28 M in DMSO, 200 µL, 0.056 mmol, 1.3 equivalents), 1-hydroxybenzotriazole hydrate (0.28 M in DMSO, 200 µL, 0.056 mmol, 1.3 equivalents) and N'-hydroxynicotinimidamide (0.40 M in DMSO, 139 µL, 0.055 mmol, 1.3 equivalents) were combined in a 4 mL vial, passed through a perfluoroalkoxy mixing tube (0.2 mm inner diameter), and loaded into an injection loop. The reaction segment was injected into a flow reactor (Hastelloy coil, 0.75 mm inner diameter, 1.8 mL internal volume) set at 175° C., and passed through the reactor at 180 µL min$^{-1}$ (10 minute residence time). Upon exiting the reactor, the reaction mixture was loaded directly into an injection loop and and purified by preparative HPLC on a Phenomenex Luna C8(2) 5 μm 100 Å AXIA column (50 mm×21.2 mm). A gradient of acetonitrile (A) and 0.1% trifluoroacetic acid in water (B) was used, at a flow rate of 30 mL/min (0-0.5 min 5% A, 0.5-6.5 min linear gradient 5-100% A, 6.5-8.5 min 100% A, 8.5-9.0 min linear gradient 100-5% A, 9.0-10 min 5% A) to yield the title compound (6.33 mg, 21.7% yield). $^1$H NMR (400 MHz, DMSO-d$_6$-D$_2$O) δ 9.23 (dd, J=2.1, 0.7 Hz, 1H), 8.79 (dd, J=4.9, 1.7 Hz, 1H), 8.42 (dt, J=8.0, 2.0 Hz, 1H), 8.01 (d, J=2.4 Hz, 1H), 7.85 (dd, J=8.7, 2.4 Hz, 1H), 7.63 (m, 1H), 7.50 (s, 1H), 7.16 (m, 3H), 7.10 (m, 1H), 6.65 (d, J=8.7 Hz, 1H), 3.67 (s, 3H), 3.21 (s, 3H), 2.07 (s, 6H). MS (APCI+) m/z 600.0 (M+MeOH+H)$^+$.

Example 139

4-[2-(2,6-dimethylphenoxy)-5-(methylsulfonyl)phenyl]-6-methyl-2-[3-(pyridin-2-yl)-1,2,4-oxadiazol-5-yl]-1,6-dihydro-7H-pyrrolo[2,3-c]pyridin-7-one Example 139 (5.89 mg, 20.1%) was prepared using the procedure described in Example 138 substituting N'-hydroxypicolinimidamide for N'-hydroxynicotinimidamide. $^1$H NMR (400 MHz, DMSO-d$_6$-D$_2$O) δ 8.77 (ddd, J=4.7, 1.6, 0.9 Hz, 1H), 8.15 (m, 1H), 8.04 (td, J=7.8, 1.7 Hz, 1H), 8.01 (d, J=2.4 Hz, 1H), 7.85 (dd, J=8.7, 2.4 Hz, 1H), 7.61 (ddd, J=7.6, 4.8, 1.1 Hz, 1H), 7.50 (s, 1H), 7.16 (m, 3H), 7.10 (m, 1H), 6.65 (d, J=8.7 Hz, 1H), 3.66 (s, 3H), 3.21 (s, 3H), 2.07 (s, 6H). MS (APCI+) m/z 600.0 (M+MeOH+H)$^+$.

Example 140

4-[2-(2,6-dimethylphenoxy)-5-(methylsulfonyl)phenyl]-6-methyl-2-[3-(pyrazin-2-yl)-1,2,4-oxadiazol-5-yl]-1,6-dihydro-7H-pyrrolo[2,3-c]pyridin-7-one Example 140 (2.58 mg, 8.8%) was prepared using the procedure described in Example 138 substituting N'-hydroxypyrazine-2-carboximidamide for N'-hydroxynicotinimidamide. $^1$H NMR (400 MHz, DMSO-d$_6$-D$_2$O) δ 9.31 (d, J=1.0 Hz, 1H), 8.85 (m, 2H), 8.01 (d, J=2.3 Hz, 1H), 7.85 (dd, J=8.7, 2.3 Hz, 1H), 7.50 (s, 1H), 7.19 (s, 1H), 7.16 (m, 2H), 7.11 (m, 1H), 6.65 (d, J=8.7 Hz, 1H), 3.67 (s, 3H), 3.21 (s, 3H), 2.07 (s, 6H). MS (APCI+) m/z 601.0 (M+MeOH+H)$^+$.

Example 141

4-[2-(2,6-dimethylphenoxy)-5-(methylsulfonyl)phenyl]-6-methyl-2-[3-(tetrahydro-2H-pyran-4-yl)-1,2,4-oxadiazol-5-yl]-1,6-dihydro-7H-pyrrolo[2,3-c]pyridin-7-one Example 141 (7.2 mg, 24.3%) was prepared using the procedure described in Example 138, substituting N'-hydroxytetrahydro-2H-pyran-4-carboximidamide for N'-hydroxynicotinimidamide. $^1$H NMR (400 MHz, DMSO-d$_6$-D$_2$O) δ 7.99 (d, J=2.4 Hz, 1H), 7.84 (dd, J=8.7, 2.4 Hz, 1H), 7.47 (s, 1H), 7.16 (m, 2H), 7.11 (m, 1H), 7.05 (s, 1H), 6.63 (d, J=8.7 Hz, 1H), 3.91 (dt, J=11.4, 3.7 Hz, 2H), 3.65 (s, 3H), 3.51 (td, J=11.3, 2.5 Hz, 2H), 3.20 (s, 3H), 3.15 (m, 1H), 2.05 (s, 6H), 1.96 (m, 2H), 1.81 (m, 2H). MS (APCI+) m/z 607.1 (M+MeOH+H)$^+$.

Example 142

4-[2-(2,6-dimethylphenoxy)-5-(methylsulfonyl)phenyl]-6-methyl-2-[3-(1,3-thiazol-4-yl)-1,2,4-oxadiazol-5-yl]-1,6-dihydro-7H-pyrrolo[2,3-c]pyridin-7-one Example 142 (5.5 mg, 18.6%) was prepared using the procedure described in Example 138 substituting N'-hydroxythiazole-4-carboximidamide for N'-hydroxynicotinimidamide. $^1$H NMR (400 MHz, DMSO-d$_6$-D$_2$O) δ 9.26 (d, J=2.0 Hz, 1H), 8.46 (d, J=2.0 Hz, 1H), 8.01 (d, J=2.4 Hz, 1H), 7.85 (dd, J=8.7, 2.4 Hz, 1H), 7.49 (s, 1H), 7.15 (m, 3H), 7.11 (m, 1H), 6.65 (d, J=8.7 Hz, 1H), 3.66 (s, 3H), 3.21 (s, 3H), 2.06 (s, 6H). MS (APCI+) m/z 606.0 (M+MeOH+H)$^+$.

Example 143

N-[2-(diethylamino)-2-methylpropyl]-4-[2-(2,6-dimethylphenoxy)-5-(methylsulfonyl)phenyl]-6-methyl-7-oxo-6,7-dihydro-1H-pyrrolo[2,3-c]pyridine-2-carboxamide To a solution of Example 135c (74.5 mg, 0.160 mmol) in dichloromethane (4 mL) at 0° C. was added 1-chloro-N,N,2-trimethyl-1-propenylamine (Ghosez's reagent) (55 μL, 0.416 mmol). The mixture was stirred for 60 minutes. 2-(Diethylamino)-2-methylpropylamine dihydrochloride (108.06 mg, 0.547 mmol) in pyridine (0.5 mL, 6.18 mmol)/tetrahydrofuran (2 mL) was added, and the mixture stirred at ambient temperature overnight. The mixture was diluted with dichloromethane and extracted with pH 7 buffer. After filtration and solvent removal, the crude product was purified by preparative HPLC on a Phenomenex Luna C8(2) 5 μm 100 Å AXIA column (30 mm×75 mm). A gradient of acetonitrile (A) and 0.1% trifluoroacetic acid in water (B) was used, at a flow rate of 30 mL/minutes (0-0.5 minutes 5% A, 0.5-6.5 minutes linear gradient 5-100% A, 6.5-8.5 minutes 100% A, 8.5-9.0 minutes linear gradient 100-5% A, 9.0-10 minutes 5% A). Samples were injected in 1.5 mL DMSO:methanol (1:1). A custom purification system was used, consisting of the following modules: Waters LC4000 preparative pump; Waters 996 diode-array detector; Waters 717+ autosampler; Waters SAT/IN module, Alltech Varex III evaporative light-scattering detector; Gilson 506C interface box; and two Gilson FC204 fraction collectors. The system was controlled using Waters Millennium32 software, automated using an Abbott developed Visual Basic application for fraction collector control and fraction tracking. Fractions were collected based upon UV signal threshold and selected fractions subsequently analyzed by flow injection analysis mass spectrometry using positive APCI ionization on a Finnigan LCQ using 70:30 methanol: 10 mM NH$_4$OH(aq) at a flow rate of 0.8 mL/minutes. Loop-injection mass spectra were acquired using a Finnigan LCQ running LCQ Navigator 1.2 software and a Gilson 215 liquid handler for fraction injection controlled by an Abbott developed Visual Basic application. Purification as described provided the title compound as a trifluoroacetic acid salt. $^1$H NMR (400 MHz, DMSO-d$_6$) δ 7.96 (d, J=2.4 Hz, 1H), 7.84 (dd, J=8.7, 2.4 Hz, 1H), 7.43 (s, 1H), 7.25-7.05 (m, 3H), 6.94 (s, 1H), 6.63 (d, J=8.6 Hz, 1H), 3.66 (s, 2H), 3.64 (s, 3H), 3.48 (m, 4H), 3.20 (s, 3H), 2.03 (s, 6H), 1.40 (s, 6H), 1.33 (t, J=7.3 Hz, 6H). MS (APCI+) m/z 592.1 (M+H)$^+$.

Example 144

N-[4-(diethylamino)butyl]-4-[2-(2,6-dimethylphenoxy)-5-(methylsulfonyl)phenyl]-6-methyl-7-oxo-6,7-dihydro-1H-pyrrolo[2,3-c]pyridine-2-carboxamide The trifluoroacetic acid salt of Example 144 was prepared according to the procedure used for the preparation of Example 143, substituting 4-(diethylamino)butylamine for 2-(diethylamino)-2-methylpropylamine dihydrochloride. $^1$H NMR (400 MHz, DMSO-$d_6$) δ 7.96 (d, J=2.4 Hz, 1H), 7.83 (dd, J=8.8, 2.4 Hz, 1H), 7.42 (s, 1H), 7.19-7.07 (m, 3H), 6.87 (s, 1H), 6.63 (d, J=8.7 Hz, 1H), 3.63 (s, 3H), 3.32 (m, 2H), 3.19 (s, 3H), 3.15-3.03 (m, 6H), 2.03 (s, 6H), 1.76-1.55 (m, 4H), 1.22 (t, J=7.3 Hz, 6H). MS (APCI+) m/z 592.1 (M+H)$^+$.

Example 145

N-ethyl-4-{5-(ethylsulfonyl)-2-[2-methyl-6-(1H-pyrazol-1-ylmethyl)phenoxy]phenyl}-6-methyl-7-oxo-6,7-dihydro-1H-pyrrolo[2,3-c]pyridine-2-carboxamide

Example 145a 2-(2-bromo-4-(ethylsulfonyl)phenoxy)-3-methylbenzaldehyde

A mixture of 2-bromo-4-(ethylsulfonyl)-1-fluorobenzene (1.20 g, 4.5 mmol), 2-hydroxy-3-methylbenzaldehyde (1.225 g, 9.00 mmol), and cesium carbonate (2.93 g, 9.00 mmol) in DMSO (10 mL) was heated at 110° C. overnight. Aqueous workup followed by flash chromatography (silica gel, heptane/ethyl acetate gradient) afforded the title compound (1.62 g, 4.23 mmol, 94% yield)

Example 145b (2-(2-bromo-4-(ethylsulfonyl)phenoxy)-3-methylphenyl)methanol

To a solution of Example 145a (3 g, 7.83 mmol) in tetrahydrofuran (30 mL) was added sodium borohydride (0.444 g, 11.7 mmol) portionwise. The mixture was stirred at ambient temperature overnight. The reaction mixture was then quenched with water and extracted with ethyl acetate. The organic phase was dried over anhydrous sodium sulfate, filtered, and concentrated under vacuum. Purification of the residue by flash chromatography (silica gel, 0-50% (ethyl acetate/petroleum ether) afforded the title compound (2.5 g, 6.49 mmol, 83% yield).

Example 145c 2-(2-bromo-4-(ethylsulfonyl)phenoxy)-1-(bromomethyl)-3-methylbenzene To a solution of Example 145b (700 mg, 1.817 mmol) in dichloromethane (5 mL) was added phosphorus tribromide (0.188 mL, 1.999 mmol). The mixture was stirred at ambient temperature overnight. The mixture was then concentrated under vacuum to afford the crude product, which was used directly in next step without purification.

Example 145d 1-(2-(2-bromo-4-(ethylsulfonyl)phenoxy)-3-methylbenzyl)-1H-pyrazole Example 145c (150 mg, 0.335 mmol), 1H-pyrazole (68.4 mg, 1.004 mmol), and dimethylformamide (3 mL) were placed in a 5 mL vial. The mixture was stirred at 50° C. overnight. The mixture was cooled to ambient temperature and concentrated under reduced pressure. The residue was purified by flash chromatography (silica gel, 0-50% ethyl acetate/petroleum ether) to afford the title compound (120 mg, 0.276 mmol, 82% yield).

Example 145e 4-bromo-6-methyl-7-oxo-6,7-dihydro-1H-pyrrolo[2,3-c]pyridine-2-carboxylic acid Example 114c (7.25 g, 24.24 mmol) in tetrahydrofuran (70 mL) and ethanol (140 mL was heated at 75° C. to dissolution and then cooled to 35° C. To this solution was added 1M LiOH solution (97 mL). The reaction mixture was heated at 75° C. for 2 hours, start. The reaction mixture was cooled to ambient temperature, and 1N HCl (100 mL) was added followed by water (300 mL). The resulting suspension was allowed to stir at ambient temperature overnight. The resulting precipitate was collected by vacuum filtration, rinsed with water, and dried in vacuo at 50° C. for 24 hours to provide the title compound (6.41 g, 98% yield).

Example 145f 4-bromo-N-ethyl-6-methyl-7-oxo-6,7-dihydro-1H-pyrrolo[2,3-c]pyridine-2-carboxamide A mixture of Example 145e (5.4 g, 20 mmol) in dimethyl sulfoxide (100 mL) was treated with 2-(3H-[1,2,3]triazolo[4,5-b]pyridin-3-yl)-1,1,3,3-tetramethylisouronium hexafluorophosphate(V) (8.33 g, 21.91 mmol) and N-ethyl-N-isopropylpropan-2-amine (10.5 mL, 60.1 mmol) and stirred for 5 minutes. Ethylamine solution (2 M in tetrahydrofuran) (11 mL, 22.00 mmol) was added and stirring was continued at ambient temperature for 6 hours and 40 minutes. The reaction mixture was then diluted with 600 mL of water and stirred overnight at ambient temperature. The solid was collected by vacuum filtration and rinsed with 1 L of water. The solid was dried by pulling air through for an hour and then further dried in a vacuum oven at 70° C. to give the title compound (5.54 g, 93% yield).

Example 145g

N-ethyl-6-methyl-7-oxo-4-(4,4,5,5-tetramethyl-1,3,2-dioxaborolan-2-yl)-6,7-dihydro-1H-pyrrolo[2,3-c]pyridine-2-carboxamide A mixture of Example 145f (2.504 g, 8.4 mmol), 4,4,4',4',5,5,5',5'-octamethyl-2,2'-bi(1,3,2-dioxaborolane) (3.41 g, 13.44 mmol), 2-(dicyclohexylphosphino)-2',4',6'-triisopropylbiphenyl (0.521 g, 1.092 mmol), tris(dibenzylideneacetone)dipalladium(0) (0.308 g, 0.336 mmol) and potassium acetate (2.473 g, 25.2 mmol) was purged with nitrogen for 15 minutes. Dioxane (42 mL, thoroughly degassed with nitrogen) was transferred into the flask and the mixture was purged with nitrogen for another 5 minutes. The reaction mixture was stirred at 80° C. for 16 hours. The reaction mixture was then partitioned with ethyl acetate and water. The organic layer was washed with saturated aqueous sodium chloride, dried with anhydrous sodium sulfate, treated with 3-mercaptopropyl functionalized silica gel, filtered and evaporated. The residue was purified by flash chromatography (silica gel, 0%-100% ethyl acetate in dichloromethane) to give a solid. This solid was triturated with heptanes to give the title compound (1.89 g, 65% yield).

Example 145h

N-ethyl-4-{5-(ethyl sulfonyl)-2-[2-methyl-6-(1H-pyrazol-1-ylmethyl)phenoxy]phenyl}-6-methyl-7-oxo-6,7-dihydro-1H-pyrrolo[2,3-c]pyridine-2-carboxamide A mixture of Example 145d 1 (20 mg, 0.046 mmol), Example 145g (17.45 mg, 0.051 mmol), sodium carbonate (19.48 mg, 0.184 mmol), tris(dibenzylideneacetone)dipalladium(0) (4.21 mg, 4.59 µmol), 1,3,5,7-tetramethyl-8-phenyl-2,4,6-trioxa-8-phosphaadamantane (1.343 mg, 4.59 µmol), and tetrahydrofuran (4 mL) and water, (1 mL) was degassed thoroughly under nitrogen, and then was stirred at 60° C. overnight. The reaction mixture was cooled to ambient temperature and the solvent removed under reduced pressure. The residue was purified by reverse phase HPLC (C18, 5-95% acetonitrile in 0.05% TFA/water) to provide the title compound. $^1$H NMR (300 MHz, CD$_3$OD) δ 8.32 (d, J=2.4 Hz, 1H), 8.05 (dd, J=8.7, 2.4 Hz, 1H), 7.80 (s, 1H), 7.70 (s, 1H), 7.64 (d, J=2.5 Hz, 2H), 7.54 (t, J=7.5 Hz, 1H), 7.40 (d, J=7.5 Hz, 1H), 7.29 (s, 1H), 6.92 (d, J=8.7 Hz, 1H), 6.46 (s, 1H), 5.53 (d, J=11.2 Hz, 2H), 4.03 (s, 3H), 3.70 (q, J=7.3 Hz, 1H), 3.61-3.51 (m, 5H), 2.37 (s, 3H), 1.58 (t, J=7.3 Hz, 3H), 1.50 (t, J=7.3 Hz, 3H). MS (ESI+) m/z 574.3 (M+H)$^+$.

Example 146

N-ethyl-4-{5-(ethylsulfonyl)-2-[2-methyl-6-(morpholin-4-ylmethyl)phenoxy]phenyl}-6-methyl-7-oxo-6,7-dihydro-1H-pyrrolo[2,3-c]pyridine-2-carboxamide Example 146a N-ethyl-4-(5-(ethylsulfonyl)-2-(2-formyl-6-methylphenoxy)phenyl)-6-methyl-7-oxo-6,7-dihydro-1H-pyrrolo[2,3-c]pyridine-2-carboxamide Example 145g (500 mg, 1.304 mmol), tris(dibenzylideneacetone)dipalladium(0) (119 mg, 0.130 mmol), sodium carbonate (553 mg, 5.21 mmol), 1,3,5,7-tetramethyl-8-phenyl-2,4,6-trioxa-8-phosphaadamantane (38.1 mg, 0.130 mmol), and Example 145a (555 mg, 1.30 mmol) were combined and sparged with argon for 15 minutes. Meanwhile a solution of tetrahydrofuran (20 mL) and water (5 mL) was sparged with nitrogen for 15 minutes and transferred by syringe into the reaction vessel under argon. The mixture was stirred for 4 hours under argon at 60° C., cooled to ambient temperature, and partitioned between ethyl acetate and water. The organic layer was washed with saturated aqueous sodium chloride, dried over anhydrous sodium sulfate, treated with 3-mercaptopropyl functionalized silica gel, filtered and concentrated. Purification by chromatography (silica gel, 20-70% 3:1 ethyl acetate/ethanol in heptanes) provided the title compound (530 mg, 74% yield).

Example 146b

N-ethyl-4-{5-(ethylsulfonyl)-2-[2-methyl-6-(morpholin-4-ylmethyl)phenoxy]phenyl}-6-methyl-7-oxo-6,7-dihydro-1H-pyrrolo[2,3-c]pyridine-2-carboxamide A mixture of Example 146a (140 mg, 0.228 mmol), sodium triacetoxyhydroborate (145 mg, 0.684 mmol), morpholine (0.060 g, 0.68 mmol), and two drops of acetic acid in 1,2 dichloroethane (20 mL) was stirred at ambient temperature overnight. The solvent was removed under reduced pressure, and the residue was purified by reverse phase HPLC (C18, 0-100% acetonitrile in 0.1% TFA/water) to provide the title compound (54.5 mg, 40% yield). $^1$H NMR (300 MHz, DMSO-d$_6$) δ 12.4 (bs, 1H), 8.35 (bs, 1H), 7.91 (d, J=2.4 Hz, 1H), 7.78 (dd, J=8.8, 2.4 Hz, 1H), 7.46 (s, 1H), 7.28 (d, J=7.6 Hz, 2H), 7.19 (dd, J=8.0, 6.8 Hz, 1H), 6.81 (s, 1H), 6.58 (d, J=8.8 Hz, 1H), 3.61 (s, 3H), 3.30 (m, 8H), 3.25 (d, J=7.2 Hz, 1H), 2.14 (bs, 4H), 2.06 (s, 3H), 1.14 (t, J=7.2 Hz, 3H), 1.12 (t, J=7.2 Hz, 3H). MS (ESI+) m/z 593.3 (M+H)$^+$.

Example 147

N-ethyl-4-{5-(ethyl sulfonyl)-2-[2-methyl-6-(piperidin-1-ylmethyl)phenoxy]phenyl}-6-methyl-7-oxo-6,7-dihydro-1H-pyrrolo[2,3-c]pyridine-2-carboxamide Example 147 was prepared according to the procedure described for the preparation of Example 146b, substituting peperidine for morpholine. $^1$H NMR (400 MHz, DMSO) δ 12.32 (s, 1H), 8.35 (t, J=5.2 Hz, 1H), 7.90 (d, J=2.4 Hz, 1H), 7.77 (dd, J=8.7, 2.4 Hz, 1H), 7.45 (s, 1H), 7.26 (d, J=7.6 Hz, 2H), 7.21-7.15 (m, 1H), 6.81 (s, 1H), 6.57 (d, J=8.7 Hz, 1H), 3.61 (s, 4H), 3.32 (s, 5H), 3.32-3.20 (m, 6H), 3.03 (d, J=13.0 Hz, 1H), 2.08 (s, 3H), 2.06 (s, 5H), 1.21 (s, 7H), 1.13 (dd, J=13.5, 7.2 Hz, 8H). MS (ESI+) m/z 591.4 (M+H)$^+$.

Example 148

N-ethyl-4-{5-(ethylsulfonyl)-2-[2-methyl-6-(2-phenylethyl)phenoxy]phenyl}-6-methyl-7-oxo-6, 7-dihydro-1H-pyrrolo[2,3-c]pyridine-2-carboxamide Example 148a ethyl 4-(5-(ethylsulfonyl)-2-(2-formyl-6-methylphenoxy)phenyl)-6-methyl-7-oxo-1-tosyl-6,7-dihydro-1H-pyrrolo[2,3-c]pyridine-2-carboxylate To a degassed solution of Example 114d (914 mg, 1.826 mmol) in 1,4-dioxane (8 mL) and water (2 mL) was added Example 145a (700 mg, 1.826 mmol), tris(dibenzylideneacetone)dipalladium(0) (50.2 mg, 0.055 mmol), 1,3,5,7-tetramethyl-8-phenyl-2,4,6-trioxa-8-phosphaadamantane (53.4 mg, 0.183 mmol), and potassium phosphate (1163 mg, 5.48 mmol). The mixture was stirred for 4 hours under nitrogen at 60° C. The mixture was cooled and partitioned between ethyl acetate and water. The organic layer was washed with saturated aqueous sodium chloride, dried over anhydrous sodium sulfate, treated with Celite, filtered and concentrated. The residue was purified by chromatography (silica gel, 0-100% ethyl acetate in heptanes) to provide the title compound (350 mg, 0.517 mmol, 28.3% yield).

Example 148b ethyl 4-(5-(ethylsulfonyl)-2-(2-methyl-6-styrylphenoxy)phenyl)-6-methyl-7-oxo-1-tosyl-6,7-dihydro-1H-pyrrolo[2,3-c]pyridine-2-carboxylate (E/Z mixture)

Under nitrogen to a solution of benzyltriphenylphosphonium chloride (345 mg, 0.887 mmol) in tetrahydrofuran (6 mL) was added sodium bis(trimethylsilyl)amide (0.975 mL, 0.975 mmol) dropwise at −30° C. The mixture was stirred for 1 hour at 20° C. A solution of Example 148a (300 mg, 0.443 mmol) in tetrahydrofuran (0.5 mL) was added dropwise to the mixture at −78° C. The mixture was allowed to warm to 20° C. and stirred for 2 hours. The mixture was partitioned between ethyl acetate and water. The organic layer was washed with saturated aqueous sodium chloride, dried over anhydrous sodium sulfate, filtered and concentrated. The residue was purified by chromatography (silica gel, 0-50% ethyl acetate in heptane gradient) to provide the title compound (310 mg, 0.407 mmol, 92% yield).

Example 148c 4-(5-(ethylsulfonyl)-2-(2-methyl-6-styrylphenoxy)phenyl)-6-methyl-7-oxo-6,7-dihydro-1H-pyrrolo[2,3-c]pyridine-2-carboxylic acid (E/Z mixture)

To a solution of Example 148b (300 mg, 0.400 mmol) in a mixture of 1,4-dioxane (4 mL) and water (3 mL) was added lithium hydroxide hydrate (168 mg, 4.00 mmol). The reaction mixture was heated at 85° C. for 1.5 hours, cooled, diluted with ethyl acetate and the pH was adjusted to 2 by addition of concentrated hydrochloric acid. The mixture was extracted with ethyl acetate. The organic layer was washed with saturated sodium chloride solution, dried over anhydrous sodium sulfate, filtered and concentrated to afford the title compound (185 mg, 0.325 mmol, 81% yield).

Example 148d

N-ethyl-4-(5-(ethylsulfonyl)-2-(2-methyl-6-styrylphenoxy)phenyl)-6-methyl-7-oxo-6,7-dihydro-1H-pyrrolo[2,3-c]pyridine-2-carboxamide (E/Z mixture)

Under nitrogen, to a solution of Example 148c (180 mg, 0.317 mmol) in DMSO (10 mL) was added O-(7-azabenzotriazol-1-yl)-N,N,N',N'-tetramethyluronium hexafluorophosphate (144 mg, 0.380 mmol), ethanamine (0.317 mL, 0.633 mmol) and diisopropylethylamine (0.111 mL, 0.633 mmol). The mixture was stirred for 12 hours at 25° C. The mixture was partitioned between ethyl acetate and water. The organic layer was washed with saturated brine, dried over anhydrous sodium sulfate, filtered and concentrated. The crude product was purified by Prep-HPLC with the following conditions: Column:Waters HSS C18, 2.1*50 mm, 1.8 μm; Mobile Phase A:Water/0.05% TFA, Mobile Phase B: acetonitrile/0.05% TFA, Flow rate: 0.7 mL/min; Gradient:5% B to 95% B in 2.0 min, hold 0.6 min; 254 nm to provide (Z)—N-ethyl-4-(5-(ethylsulfonyl)-2-(2-methyl-6-styrylphenoxy)phenyl)-6-methyl-7-oxo-6,7-dihydro-1H-pyrrolo[2,3-c]pyridine-2-carboxamide (58.3 mg, 0.098 mmol, 31% yield) and (E)-N-ethyl-4-(5-(ethylsulfonyl)-2-(2-methyl-6-styrylphenoxy)phenyl)-6-methyl-7-oxo-6,7-dihydro-1H-pyrrolo[2,3-c]pyridine-2-carboxamide (2.6 mg, 4.36 mol, 1.4% yield).

Example 148e

N-ethyl-4-{5-(ethylsulfonyl)-2-[2-methyl-6-(2-phenylethyl)phenoxy]phenyl}-6-methyl-7-oxo-6,7-dihydro-1H-pyrrolo[2,3-c]pyridine-2-carboxamide Under nitrogen, to a solution of Example 148d (5 mg, 8.39 μmol) in methanol (1 mL) was added 10% Pd/C (0.179 mg, 1.679 μmol). The mixture was charged with hydrogen. The mixture was stirred for 1 hour at 20° C. under hydrogen (2 atmosphere). The solids were removed by filtration. The filtrate was concentrated under reduced pressure to obtain the title compound (5 mg, 100% yield) as a light-yellow solid. $^{1}$H NMR (300 MHz, CD$_3$OD) δ 8.32 (d, J=2.4 Hz, 1H), 8.05 (dd, J=8.7, 2.4 Hz, 1H), 7.80 (s, 1H), 7.70 (s, 1H), 7.64 (d, J=2.5 Hz, 2H), 7.54 (t, J=7.5 Hz, 1H), 7.40 (d, J=7.5 Hz, 1H), 7.29 (s, 1H), 6.92 (d, J=8.7 Hz, 1H), 6.46 (s, 1H), 5.53 (d, J=11.2 Hz, 2H), 4.03 (s, 3H), 3.70 (q, J=7.3 Hz, 1H), 3.61-3.51 (m, 5H), 2.37 (s, 3H), 2.04-2.04 (m, 1H), 2.02-2.01 (m, 1H), 1.58 (t, J=7.3 Hz, 3H), 1.50 (t, J=7.3 Hz, 4H). MS (ESI+) m/z 598.2 (M+H)$^{+}$.

Example 149

4-[2-(cyclohexyloxy)-5-(ethylsulfonyl)phenyl]-6-methyl-2-[1-(piperidin-4-yl)-1H-pyrazol-4-yl]-1,6-dihydro-7H-pyrrolo[2,3-c]pyridin-7-one Example 149a tert-butyl 4-(4-(4-bromo-6-methyl-7-oxo-1-tosyl-6,7-dihydro-1H-pyrrolo[2,3-c]pyridin-2-yl)-1H-pyrazol-1-yl)piperidine-1-carboxylate Example 63c (1.32 g, 2.60 mmol), sodium carbonate (0.964 g, 9.10 mmol), tris(dibenzylideneacetone)dipalladium (0.071 g, 0.078 mmol) and 1,3,5,7-tetramethyl-6-phenyl-2,4,8-trioxa-6-phosphaadamantane (0.068 g, 0.23 mmol) were combined and purged with nitrogen for 15 minutes. A mixture of tetrahydrofuran (16 mL) and water (4 mL) was purged with nitrogen for 15 minutes and transferred to the reaction vessel. To this reaction mixture was added tert-butyl 4-(4-(4,4,5,5-tetramethyl-1,3,2-dioxaborolan-2-yl)-1H-pyrazol-1-yl)piperidine-1-carboxylate (0.981 g, 2.60 mmol) in tetrahydrofuran (4 mL). The reaction mixture was purged with nitrogen for another 5 minutes, heated at 35° C. for 20 hours, cooled to ambient temperature, and partitioned with ethyl acetate and water. The organic layer was washed with saturated aqueous sodium chloride, dried with anhydrous sodium sulfate, treated with 3-mercaptopropyl functionalized silica gel, filtered, and concentrated. The residue was purified by flash chromatography (silica gel, 1-2% methanol in dichloromethane) and followed by trituration with heptanes to give the title compound (1.29 g, 79%).

Example 149b tert-butyl 4-(4-(6-methyl-7-oxo-4-(4,4,5,5-tetramethyl-1,3,2-dioxaborolan-2-yl)-1-tosyl-6,7-dihydro-1H-pyrrolo[2,3-c]pyridin-2-yl)-1H-pyrazol-1-yl)piperidine-1-carboxylate Example 149a (1.26 g, 2.00 mmol), 4,4,4',4',5,5,5',5'-octamethyl-2,2'-bi(1,3,2-dioxaborolane) (1.52 g, 6.00 mmol), 2-(dicyclohexylphosphino)-2',4',6'-triisopropylbiphenyl (86 mg, 0.18 mmol), tris(dibenzylideneacetone)dipalladium (55 mg, 0.060 mmol) and potassium acetate (589 mg, 6.00 mmol) were combined and purged with nitrogen for 15 minutes. Dioxane (20 mL) was purged with nitrogen for 15 minutes and transferred to the reaction vessel. The reaction mixture was heated at 70° C. for 16 hours, cooled to ambient temperature, and partitioned with ethyl acetate and water. The organic layer was washed with saturated aqueous sodium chloride, dried with anhydrous sodium sulfate, treated with 3-mercaptopropyl functionalized silica gel, filtered, and concentrated. The residue was purified by flash chromatography (silica gel, 20-40% 3:1 ethyl acetate/ethanol in heptanes) and followed by trituration with heptanes to give the title compound (545 mg, 40%).

Example 149c 2-bromo-1-(cyclohexyloxy)-4-(ethylsulfonyl)benzene

To a solution of cyclohexanol (3.00 g, 30.0 mmol) in tetrahydrofuran (60 mL) was added 60% sodium hydride (1.32 g, 33.0 mmol) portionwise. The reaction mixture was stirred at ambient temperature for 10 minutes. To this reaction mixture was added Example 16i (4.01 g, 15.0 mmol). The reaction mixture was heated at 60° C. for 6 hours, cooled to ambient temperature, and partitioned with ethyl acetate and water. The organic layer was washed with saturated aqueous sodium chloride, dried with anhydrous sodium sulfate, filtered and concentrated. The residue was purified by flash chromatography (silica gel, 20-40% ethyl acetate in heptanes) and dried by vacuum to give the title compound (5.21 g, 100%).

Example 149d tert-butyl 4-(4-(4-(2-(cyclohexyloxy)-5-(ethylsulfonyl)phenyl)-6-methyl-7-oxo-1-tosyl-6,7-dihydro-1H-pyrrolo[2,3-c]pyridin-2-yl)-1H-pyrazol-1-yl)piperidine-1-carboxylate Example 149b (500 mg, 0.738 mmol), Example 149c (256 mg, 0.738 mmol), sodium carbonate (274 mg, 2.58 mmol), tris(dibenzylideneacetone)dipalladium (20 mg, 0.022 mmol) and 1,3,5,7-tetramethyl-6-phenyl-2,4,8-trioxa-6-phosphaadamantane (19.4 mg, 0.066 mmol) were combined and purged with nitrogen for 15 minutes. A mixture of tetrahydrofuran (6 mL) and water (1.5 mL) was purged with nitrogen for 15 minutes and transferred to the reaction vessel. The reaction mixture was heated at 60° C. for 3 hours, cooled to ambient temperature, and partitioned with ethyl acetate and water. The organic layer was washed with saturated aqueous sodium chloride, dried with anhydrous sodium sulfate, treated with 3-mercaptopropyl functionalized silica gel, filtered, and concentrated. The residue was purified by flash chromatography (silica gel, 20-50% 3:1 ethyl acetate/ethanol in heptanes) and followed by trituration with heptanes to give the title compound (480 mg, 80%).

Example 149e tert-butyl 4-(4-(4-(2-(cyclohexyloxy)-5-(ethylsulfonyl)phenyl)-6-methyl-7-oxo-6,7-dihydro-1H-pyrrolo[2,3-c]pyridin-2-yl)-1H-pyrazol-1-yl)piperidine-1-carboxylate Example 149d (478 mg, 0.584 mmol) and lithium hydroxide (140 mg, 5.84 mmol) were combined in the mixture of dioxane (12 mL) and water (4 mL). The reaction mixture was heated at 70° C. for 16 hours, cooled to ambient temperature, diluted with water, filtered, washed with water and dried to give the title compound (318 mg, 82%).

Example 149f

4-[2-(cyclohexyloxy)-5-(ethylsulfonyl)phenyl]-6-methyl-2-[1-(piperidin-4-yl)-1H-pyrazol-4-yl]-1,6-dihydro-7H-pyrrolo[2,3-c]pyridin-7-one To a solution of Example 149e (309 mg, 0.465 mmol) in dichloromethane (3.0 mL) was added trifluoroacetic acid (3.0 mL, 39 mmol). The reaction mixture was stirred at ambient temperature for 30 minutes, concentrated, azeotroped with dichloromethane twice, and triturated with ethyl ether to give the title compound (315 mg, 100%) as the trifluoroacetic acid salt. $^1$H NMR (400 MHz, DMSO-d$_6$) δ 12.11 (s, 1H), 8.78-8.64 (m, 1H), 8.52-8.38 (m, 1H), 8.32 (s, 1H), 8.01 (s, 1H), 7.80 (dd, J=8.6, 2.2 Hz, 1H), 7.76 (d, J=2.1 Hz, 1H), 7.38 (d, J=8.8 Hz, 1H), 7.29 (s, 1H), 6.29 (d, J=1.8 Hz, 1H), 4.67-4.41 (m, 2H), 3.56 (s, 3H), 3.44-3.36 (m, 2H), 3.27 (q, J=7.3 Hz, 2H), 3.15-3.03 (m, 2H), 2.26-2.17 (m, 2H), 2.14-2.01 (m, 2H), 1.91-1.79 (m, 2H), 1.58-1.47 (m, 2H), 1.45-1.26 (m, 5H), 1.22-1.08 (m, 4H). (ESI+) m/z 564 (M+H)$^+$.

Example 150

N-ethyl-4-{5-(ethylsulfonyl)-2-[2-(1H-imidazol-1-ylmethyl)-6-methylphenoxy]phenyl}-6-methyl-7-oxo-6,7-dihydro-1H-pyrrolo[2,3-c]pyridine-2-carboxamide Example 150a 1-(2-(2-bromo-4-(ethylsulfonyl)phenoxy)-3-methylbenzyl)-1H-imidazole Example 150a was prepared according to the procedure described for the preparation of Example 145d, substituting 1H-imidazole for 1H-pyrazole.

Example 150b

N-ethyl-4-{5-(ethylsulfonyl)-2-[2-(1H-imidazol-1-ylmethyl)-6-methylphenoxy]phenyl}-6-methyl-7-oxo-6,7-dihydro-1H-pyrrolo[2,3-c]pyridine-2-carboxamide Example 150b was prepared according to the procedure described for the preparation of Example 145h, substituting Example 150a for Example 145d. $^1$H NMR (400 MHz, CD$_3$OD) δ 8.31 (d, J=2.3 Hz, 1H), 8.03 (dd, J=8.7, 2.3 Hz, 1H), 7.73 (s, 1H), 7.67 (m, 2H), 7.56 (t, J=7.5 Hz, 1H), 7.51 (d, J=6.0 Hz, 1H), 7.22 (s, 1H), 7.08 (d, J=6.0 Hz, 2H), 6.87 (d, J=8.7 Hz, 1H), 5.35 (m, 2H), 4.00 (s, 3H), 3.68 (dd, J=14.7, 7.3 Hz, 3H), 3.55 (q, J=7.4 Hz, 3H), 2.41 (s, 3H), 1.58 (t, J=7.4 Hz, 3H), 1.49 (t, J=7.3 Hz, 3H).). MS (ESI+) m/z 575.2 (M+H)$^+$.

Example 151

N-ethyl-4-[5-(ethylsulfonyl)-2-{2-methyl-6-[(2-oxopyrrolidin-1-yl)methyl]phenoxy}phenyl]-6-methyl-7-oxo-6,7-dihydro-1H-pyrrolo[2,3-c]pyridine-2-carboxamide

Example 151a 1-(2-(2-bromo-4-(ethylsulfonyl)phenoxy)-3-methylbenzyl)pyrrolidin-2-one To a solution of Example 145c (300 mg, 0.669 mmol) and pyrrolidin-2-one (171 mg, 2.008 mmol) in tetrahydrofuran (10 mL) at 0° C. was added sodium hydride (56.2 mg, 2.343 mmol). The mixture was stirred at ambient temperature overnight. The reaction mixture was partitioned between ethyl acetate and water, and the organic layer separated and dried over anhydrous sodium sulfate, filtered, and concentrated. The residue was purified by flash chromatography (silica gel, 0-10% methanol/dichloromethane gradient) to provide the title compound (150 mg, 49.5% yield).

Example 151b

N-ethyl-4-[5-(ethylsulfonyl)-2-{2-methyl-6-[(2-oxopyrrolidin-1-yl)methyl]phenoxy}phenyl]-6-methyl-7-oxo-6,7-dihydro-1H-pyrrolo[2,3-c]pyridine-2-carboxamide Example 151b was prepared according to the procedure described for the preparation of Example 145h, substituting Example 151a for Example 145d. $^1$H NMR (400 MHz, CD$_3$OD) δ 8.32 (d, J=2.3 Hz, 1H), 8.13 (dd, J=8.6, 2.3 Hz, 1H), 7.95 (s, 1H), 7.56 (m, 3H), 7.29 (s, 1H), 6.96 (d, J=8.8 Hz, 1H), 5.07 (m, 2H), 4.05 (s, 3H), 3.71 (q, J=7.2 Hz, 3H), 3.57 (q, J=7.4 Hz, 3H), 3.45 (t, J=7.1 Hz, 2H), 2.52 (m, 1H), 2.33 (s, 3H), 2.16 (m, 2H), 1.58 (t, J=7.4 Hz, 4H), 1.53 (t, J=7.3 Hz, 3H). MS (ESI+) m/z 562.2 (M−28)$^+$.

Example 152

4-[2-{2-[(1,1-dioxido-1,2-thiazolidin-2-yl)methyl]-6-methylphenoxy}-5-(ethylsulfonyl)phenyl]-N-ethyl-6-methyl-7-oxo-6,7-dihydro-1H-pyrrolo[2,3-c]pyridine-2-carboxamide

Example 152a 2-(2-(2-bromo-4-(ethyl sulfonyl)phenoxy)-3-methylbenzyl)isothiazolidine 1,1-dioxide Example 152a was prepared according to the procedure described for the preparation of Example 151a, substituting isothiazolidine 1,1-dioxide for pyrrolidin-2-one.

Example 152b

4-[2-{2-[(1,1-dioxido-1,2-thiazolidin-2-yl)methyl]-6-methylphenoxy}-5-(ethylsulfonyl)phenyl]-N-ethyl-6-methyl-7-oxo-6,7-dihydro-1H-pyrrolo[2,3-c]pyridine-2-carboxamide Example 152b was prepared according to the procedure described for the preparation of Example 145h, substituting Example 152a for Example 145d. $^1$H NMR (400 MHz, CD$_3$OD) δ 8.28 (d, J=2.3 Hz, 1H), 8.09 (dd, J=8.7, 2.4 Hz, 1H), 7.83 (s, 1H), 7.61 (d, J=7.7 Hz, 1H), 7.57 (d, J=6.2 Hz, 1H), 7.50 (t, J=7.6 Hz, 1H), 7.24 (s, 1H), 6.96 (d, J=8.7 Hz, 1H), 4.48 (m, 1H), 4.09 (m, 1H), 4.01 (s, 3H), 3.69 (m, 2H), 3.53 (q, J=7.4 Hz, 2H), 3.25 (m, 4H), 2.42 (m, 2H), 2.30 (s, 3H), 1.54 (t, J=7.4 Hz, 3H), 1.50 (t, J=7.3 Hz, 3H). MS (ESI+) m/z 627.4 (M+H)$^+$.

Example 153

4-[2-(2, 6-dimethylphenoxy)-4-{[2-(methylamino)-2-oxoethyl](pyridin-2-ylmethyl)carbamoyl}phenyl]-N-ethyl-6-methyl-7-oxo-6,7-dihydro-1H-pyrrolo[2,3-c]pyridine-2-carboxamide

Example 153a

Methyl 3-(2,6-dimethylphenoxy)-4-nitrobenzoate

A mixture of methyl 3-fluoro-4-nitrobenzoate (70 g, 352 mmol), 2,6-dimethylphenol (42.9 g, 352 mmol) and potassium carbonate (58.3 g, 422 mmol) in dimethylsulfoxide (500 mL) was heated at 120° C. for 4 hours. The reaction mixture was quenched with water and extracted twice with ethyl acetate. The combined organic layers were washed with brine, dried with anhydrous magnesium sulfate, filtered and concentrated. The residue was purified by flash chromatography (silica gel, 0-100% ethyl acetate in heptane) to afford 73 g (69%) of the title compound.

Example 153b

Methyl 4-amino-3-(2,6-dimethylphenoxy)benzoate

To Example 153a (30 g, 100 mmol) in tetrahydrofuran (800 mL) was added palladium on carbon (5.30 g, 49.8 mmol). The reaction mixture was stirred for 40 hours at 60 psi hydrogen atmosphere and 40° C. The mixture was filtered through a nylon membrane, and the filtrate was concentrated to afford 25 g (93%) of the title compound.

Example 153c

Methyl 3-(2,6-dimethylphenoxy)-4-iodobenzoate

Example 153b (25 g, 92 mmol) in tetrahydrofuran (200 mL) was treated with concentrated hydrochloric acid (140 mL, 1694 mmol) at 0° C. The reaction mixture was stirred at 0° C. for 10 minutes. To this solution was added a solution sodium nitrite (7.63 g, 111 mmol) in water (20 mL). The reaction mixture was stirred at 0° C. for 1 hour. To this solution was added a solution of potassium iodide (30.6 g, 184 mmol) in water (50 mL). The reaction mixture was stirred for 2 hours at 10° C. The reaction mixture was partitioned between water and ethyl acetate. The aqueous layer was extracted twice with ethyl acetate. The combined organic layers were washed with brine, dried with anhydrous magnesium sulfate, filtered and concentrated. The residue was purified by flash chromatography (10:1 petroleum ether: ethyl acetate) to afford 18 g (51%) of the title compound.

Example 153d

Methyl 3-(2,6-dimethylphenoxy)-4-(2-(ethylcarbamoyl)-6-methyl-7-oxo-6,7-dihydro-1H-pyrrolo[2,3-c]pyridin-4-yl)benzoate Example 153c (1.843 g, 4.82 mmol), Example 145g (1.5137 g, 4.38 mmol), sodium carbonate (1.627 g, 15.35 mmol), tris(dibenzylideneacetone)dipalladium(0) (0.201 g, 0.219 mmol), and 1,3,5,7-tetramethyl-6-phenyl-2,4,6-trioxa-6-phosphaadamantane (0.218 g, 0.745 mmol) were flow purged with nitrogen for 90 min. Degassed tetrahydrofuran (35.1 mL) and water (8.77 mL) were added. The reaction mixture was heated to 60° C. for 3 hours. The reaction mixture was cooled to ambient temperature and partitioned between ethyl acetate and water. The organic layer was washed with brine, dried with anhydrous magnesium sulfate, filtered and concentrated. The residue was purified by flash chromatography (10:1 petroleum ether:ethyl acetate) to afford 2.0084 g (97%) of the title compound.

Example 153e 3-(2,6-dimethylphenoxy)-4-(2-(ethylcarbamoyl)-6-methyl-7-oxo-6,7-dihydro-1H-pyrrolo[2,3-c]pyridin-4-yl)benzoic acid To a solution of Example 153d (1.1175 g, 2.360 mmol) in tetrahydrofuran (17.70 mL) and water (5.90 mL) was added lithium hydroxide monohydrate (0.990 g, 23.60 mmol). The reaction mixture was stirred at ambient temperature over 2 nights. The reaction mixture was quenched with 1N hydrochloric acid. The resulting suspension was filtered, and the solid was rinsed with water and dried to afford 1.0213 g (94%) of the title compound.

Example 153f 4-(2-(2,6-dimethylphenoxy)-4-((2-(methylamino)-2-oxoethyl)(pyridin-2-ylmethyl)carbamoyl)phenyl)-N-ethyl-6-methyl-7-oxo-6,7-dihydro-1H-pyrrolo[2,3-c]pyridine-2-carboxamide A solution of Example 153e and diisopropylethyl amine (0.13 M and 0.39 M in N,N-dimethylacetamide, respectively, 300 μL, 0.039 mmol Example 153e (1.0 equivalent) and 0.11 mmol diisopropylethyl amine (3.0 equivalents)), O-(7-azabenzotriazol-1-yl)-N,N,N',N'-tetramethyluronium hexafluorophosphate (0.16 M in N,N-dimethylacetamide, 300 μL, 0.048 mmol, 1.2 equivalents), and N-methyl-2-((pyridin-2-ylmethyl)amino)acetamide (0.40 M in N,N-dimethylacetamide, 147 μL, 0.059 mmol, 1.5 equivalents) were stirred until complete. The reaction mixture was purified by reverse phase preparative HPLC (C8, 5-100% acetonitrile in 0.1% trifluoroacetic acid/water) to afford 18.5 mg of the title compound (64%). $^1$H NMR (400 MHz, DMSO-$d_6$) δ 8.49 (s, 1H), 7.92 (s, 1H), 7.52 (d, J=7.7 Hz, 1H), 7.46 (d, J=7.5 Hz, 2H), 7.32 (s, 1H), 7.20 (dd, J=7.6, 1.5 Hz, 1H), 7.05 (s, 3H), 6.86 (s, 1H), 6.49 (s, 1H), 4.68 (s, 2H), 3.93-4.00 (m, 2H), 3.60 (s, 3H), 3.31 (d, J=7.2 Hz, 2H), 2.60 (s, 3H), 1.93 (s, 6H), 1.14 (t, J=7.2 Hz, 3H). MS (APCI+) m/z 621.6 (M+H)$^+$.

Example 154

4-[2-(2,6-dimethylphenoxy)-4-{methyl[1-(propanoyloxy)piperidin-4-yl]carbamoyl}phenyl]-N-ethyl-6-methyl-7-oxo-6,7-dihydro-1H-pyrrolo[2,3-c]pyridine-2-carboxamide Example 154 was prepared according to the procedure used for the preparation of Example 153f, substituting 4-(methylamino)piperidin-1-yl propionate for N-methyl-2-((pyridin-2-ylmethyl)amino)acetamide. $^1$H NMR (400 MHz, DMSO-$d_6$) δ 7.55 (d, J=7.7 Hz, 1H), 7.36 (s, 1H), 7.02-7.18 (m, 4H), 6.90 (s, 1H), 6.31 (d, J=1.5 Hz, 1H), 4.05 (q, J=7.1 Hz, 4H), 3.61 (s, 3H), 3.30 (q, J=7.2 Hz, 2H), 2.73 (s, 3H), 2.64 (t, J=12.9 Hz, 2H), 2.03 (s, 6H), 1.56-1.69 (m, 2H), 1.47 (d, J=12.4 Hz, 2H), 1.17 (dt, J=18.0, 7.1 Hz, 6H). MS (APCI+) m/z 628.6 (M+H)$^+$.

Example 155

1-({4-[2-(2,4-difluorophenoxy)-5-(methylsulfonyl)phenyl]-6-methyl-7-oxo-6,7-dihydro-1H-pyrrolo[2,3-c]pyridin-2-yl}methyl)-N,N-dimethyl-4-(2-oxopyrrolidin-1-yl)piperidine-4-carboxamide Example 155a 1-(2,4-difluorophenoxy)-4-(methylsulfonyl)-2-nitrobenzene A mixture of 1-fluoro-4-(methylsulfonyl)-2-nitrobenzene (20 g, 91 mmol), 2,4-difluorophenol (11.87 g, 91 mmol) and potassium carbonate (12.6 g, 91 mmol) in DMSO (90 mL) was heated at 120° C. for 2 hours. The reaction mixture was quenched with water and extracted with ethyl acetate. The combined organic layers were washed with saturated aqueous sodium chloride, dried over anhydrous magnesium sulfate, filtered, and concentrated. The residue was purified by flash chromatography (silica gel, 1:1 ethyl acetate/hexanes) to provide the title compound (28 g, 89% yield).

Example 155b 2-(2,4-difluorophenoxy)-5-(methylsulfonyl)aniline

A solution of Example 155a (10.0 g, 30.4 mmol) in tetrahydrofuran (150 mL) was added to 10% Pd/C (1.616 g, 15.18 mmol) in a 250 mL bottle and the mixture was stirred for 24 hour under a 30 psi hydrogen atmosphere at 40° C. The mixture was filtered through a nylon membrane and concentrated. The residue was purified flash chromatography (silica gel, 70:30 ethyl acetate/hexanes) to provide the title compound (8.6 g, 55% yield).

Example 155c 1-(2,4-difluorophenoxy)-2-iodo-4-(methylsulfonyl)benzene

Example 155b (5.00 g, 16.7 mmol) in dioxane (30 mL) was treated with concentrated HCl (150 mL) at 0° C. The reaction mixture was stirred at 0° C. for 10 minutes. To this solution was added sodium nitrite (1.383 g, 20.05 mmol) in water (6 mL). The reaction mixture was stirred at 0° C. for one hour. To this solution was added potassium iodide (5.55 g, 33.4 mmol) in water (20 mL). The reaction mixture was stirred for two hours at 10° C. The reaction mixture was then partitioned between water and ethyl acetate. The organic layer was extracted with additional ethyl acetate twice. The combined organic layer was washed with saturated aqueous sodium chloride, dried (anhydrous magnesium sulfate), filtered, and concentrated. The residue was purified by flash chromatography (silica gel, 2:3 ethyl acetate/hexanes) to provide the title compound (8.9 g, 89% yield)

Example 155d ethyl 1-benzyl-4-(2-(2,4-difluorophenoxy)-5-(methylsulfonyl)phenyl)-6-methyl-7-oxo-6,7-dihydro-1H-pyrrolo[2,3-c]pyridine-2-carboxylate Example 16f (2.3 g, 5.27 mmol), Example 155c (2.270 g, 5.54 mmol), 1,3,5,7-tetramethyl-6-phenyl-2,4, 8-trioxa-6-phosphaadamantane (0.154 g, 0.527 mmol), tris(dibenzylideneacetone)dipalladium(0) (0.121 g, 0.132 mmol) and potassium phosphate (1.119 g, 5.27 mmol) were combined and sparged with argon for 30 minutes. A mixture of degassed dioxane (30 mL) and water (7.5 mL) was added and the reaction mixture was stirred at 60° C. for 16 hours. The reaction mixture was cooled to ambient temperature and partitioned between ethyl acetate and water. The organic layer was washed with saturated aqueous sodium chloride, dried (anhydrous sodium sulfate), filtered, and concentrated. The residue was purified by flash chromatography (silica gel, 20-100% ethyl acetate in petroleum ether) to afford the title compound (1.77 g, 33.4% yield).

Example 155e ethyl 4-(2-(2,4-difluorophenoxy)-5-(methylsulfonyl)phenyl)-6-methyl-7-oxo-6,7-dihydro-1H-pyrrolo[2,3-c]pyridine-2-carboxylate A mixture of Example 155d, anisole (1.585 mL, 14.51 mmol) and concentrated sulfuric acid (4.3 mL, 81 mmol) in trifluoroacetic acid (20 mL, 260 mmol) was heated at 90° C. for 4 hours. Excess trifluoroacetic acid was removed under reduced pressure, and the residue was partitioned between water (100 mL) and ethyl acetate (200 mL). The organic layer was separated, and the aqueous layer was extracted with additional ethyl acetate (2×200 mL). The combined organic layers were washed with saturated aqueous sodium bicarbonate (100 mL), followed by saturated aqueous sodium chloride (100 mL), dried over anhydrous magnesium sulfate, filtered, and concentrated. The crude material was taken into methanol (50 mL) and the resulting solid was filtered, rinsed with methanol, and dried to provide the title compound (3.1 g, 63% yield).

Example 155f

4-[2-(2,4-difluorophenoxy)-5-(methylsulfonyl)phenyl]-2-(hydroxymethyl)-6-methyl-1,6-dihydro-7H-pyrrolo[2,3-c]pyridin-7-one To a suspension of Example 155e (0.20 g, 0.40 mmol) in tetrahydrofuran (5 mL) stirring at 0° C. was added lithium aluminum hydride (1M in tetrahydrofuran, 0.398 mL, 0.398 mmol) and the mixture was stirred at 0° C. for two hours. The solvent was evaporated under reduced pressure and the residue was partitioned between ethyl acetate (30 mL) and water (20 mL). The mixture was filtered to remove the undissolved materials. The aqueous layer was extracted with ethyl acetate (2×30 mL). The combined organic layers were dried over anhydrous sodium sulfate, filtered, and concentrated. The residue was triturated with dichloromethane and the resulting solid was filtered and dried to provide the title compound (0.10 g, 55% yield).

Example 155g 4-(2-(2,4-difluorophenoxy)-5-(methylsulfonyl)phenyl)-6-methyl-7-oxo-6,7-dihydro-1H-pyrrolo[2,3-c]pyridine-2-carbaldehyde To a solution of Example 155f (1.0 g, 2.2 mmol) in dichloromethane (50 mL) at 0° C. was added Dess-Martin Periodinane (1.84 g, 4.34 mmol) and the reaction mixture was stirred at 0° C. for 30 minutes. The reaction mixture was then stirred at ambient temperature for three hours. A solution of sodium bisulfite (0.9 g, 9 mmol) in saturated aqueous sodium bicarbonate (5 mL) was added, and the reaction mixture was stirred for 15 minutes and extracted with ethyl acetate. The organic layer was dried (anhydrous sodium sulfate), filtered, and concentrated to provide the title compound (0.80 g, 70% yield).

Example 155h 1-({4-[2-(2,4-difluorophenoxy)-5-(methylsulfonyl)phenyl]-6-methyl-7-oxo-6,7-dihydro-1H-pyrrolo[2,3-c]pyridin-2-yl}methyl)-N,N-dimethyl-4-(2-oxopyrrolidin-1-yl)piperidine-4-carboxamide Example 155h was prepared according to the procedure used for the preparation of Example 16o, substituting Example 155g for Example 16n and N,N-dimethyl-4-(2-oxopyrrolidin-1-yl)piperidine-4-carboxamide for 1-(pyridin-4-yl)piperazine. The reaction mixture was concentrated and the crude material was purified by reverse phase Prep HPLC (C18, 10-50% acetonitrile in 0.1% trifluoroacetic acid/water) to provide the trifluoroacetic acid salt of the title compound. $^1$H NMR (400 MHz, Pyridine-$d_5$) δ 13.59 (d, J=2.3 Hz, 1H), 8.47 (d, J=2.4 Hz, 1H), 8.22 (dd, J=8.7, 2.4 Hz, 1H), 7.41 (td, J=9.1, 5.5 Hz, 1H), 7.31-7.23 (m, 2H), 7.15 (dd, J=8.6, 1.1 Hz, 1H), 7.04 (dddd, J=11.8, 7.3, 3.6, 2.1 Hz, 1H), 6.66 (d, J=1.9 Hz, 1H), 4.01 (s, 2H), 3.63 (s, 3H), 3.42 (s, 3H), 3.34 (t, J=6.9 Hz, 2H), 3.09-2.93 (m, 4H), 2.89 (s, 6H), 2.48 (d, J=14.8 Hz, 2H), 2.27 (t, J=8.1 Hz, 2H), 2.14 (dt, J=14.1, 7.7 Hz, 2H), 1.78 (p, J=7.5 Hz, 2H). MS (APCI+) m/z 681.9 (M+H)$^+$.

Example 156

4-[2-(2,4-difluorophenoxy)-5-(methylsulfonyl)phenyl]-6-methyl-2-{[3-(1H-1,2,4-triazol-1-yl)azetidin-1-yl]methyl}-1,6-dihydro-7H-pyrrolo[2,3-c]pyridin-7-one Example 156 was prepared according to the procedure used for the preparation of Example 16o, substituting Example 155g for Example 16n and 1-(azetidin-3-yl)-1H-1,2,4-triazole for 1-(pyridin-4-yl)piperazine. The reaction mixture was concentrated and the crude material was purified by reverse phase Prep HPLC (C18, 10-50% acetonitrile in 0.1% trifluoroacetic acid/water) to provide the trifluoroacetic acid salt of the title compound. $^1$H NMR (400 MHz, Pyridine-$d_5$) δ 13.76 (s, 1H), 8.95 (s, 1H), 8.47 (d, J=2.4 Hz, 1H), 3.85-3.68 (m, 3H), 8.34 (s, 1H), 8.21 (dd, J=8.7, 2.5 Hz, 1H), 7.45-7.29 (m, 2H), 7.14 (d, J=8.7 Hz, 1H), 7.06-6.95 (m, 2H), 6.59 (d, J=2.0 Hz, 1H), 3.99 (s, 2H), 3.80 (t, J=7.4

Hz, 2H), 3.73 (dd, J=7.9, 6.2 Hz, 2H), 3.63 (s, 3H), 3.42 (s, 4H), 2.50 (m, 1H). MS (APCI+) m/z 566.8 (M+H)+.

Example 157

N-ethyl-4-[5-(ethylsulfonyl)-2-{2-methyl-6-[(2-oxoazetidin-1-yl)methyl]phenoxy}phenyl]-6-methyl-7-oxo-6,7-dihydro-1H-pyrrolo[2,3-c]pyridine-2-carboxamide

Example 157a 1-(2-(2-bromo-4-(ethylsulfonyl)phenoxy)-3-methylbenzyl)azetidin-2-one A mixture of Example 145c (300 mg, 0.669 mmol), azetidin-2-one (71.4 mg, 1.004 mmol), potassium carbonate (463 mg, 3.35 mmol), and tetrabutylammonium bromide (21.6 mg, 0.067 mmol) in acetonitrile (10 mL) was heated at 90° C. for two days. The mixture was cooled to ambient temperature and partitioned with ethyl acetate and water. The organic phase was separated, dried over anhydrous sodium sulfate, filtered, and evaporated under reduced pressure. The residue was purified by flash chromatography (silica gel, 0-100% ethyl acetate/petroleum ether gradient), to provide the title compound (0.070 g, 24% yield).

Example 157b

N-ethyl-4-[5-(ethylsulfonyl)-2-{2-methyl-6-[(2-oxoazetidin-1-yl)methyl]phenoxy}phenyl]-6-methyl-7-oxo-6,7-dihydro-1H-pyrrolo[2,3-c]pyridine-2-carboxamide Example 157b was prepared according to the procedure described for the preparation of Example 145h, substituting Example 157a for Example 145d. $^1$H NMR (400 MHz, CD$_3$OD) δ 8.31 (d, J=2.3 Hz, 1H), 8.13 (dd, J=8.7, 2.3 Hz, 1H), 7.88 (s, 1H), 7.57 (m, 3H), 7.29 (s, 1H), 6.97 (d, J=8.7 Hz, 1H), 4.84 (m, 1H), 4.35 (m, 1H), 4.04 (s, 3H), 3.71 (q, J=7.3 Hz, 3H), 3.56 (q, J=7.4 Hz, 1H), 3.27 (t, J=3.9 Hz, 2H), 2.96 (m, 2H), 2.34 (s, 3H), 1.57 (t, J=7.4 Hz, 3H), 1.52 (t, J=7.3 Hz, 3H). MS (ESI+) m/z (M+H)+.

Example 158

N-ethyl-4-[5-(ethylsulfonyl)-2-{2-methyl-6-[(2-oxopyridin-1(2H)-yl)methyl]phenoxy}phenyl]-6-methyl-7-oxo-6,7-dihydro-1H-pyrrolo[2,3-c]pyridine-2-carboxamide

Example 158a 1-(2-(2-bromo-4-(ethylsulfonyl)phenoxy)-3-methylbenzyl)pyridin-2(1H)-one Example 158a was prepared according to the procedure described for the preparation of Example 151a, substituting pyridin-2(1H)-one for pyrrolidin-2-one. The crude mixture was purified by flash column chromatography on silica gel, eluting with 20-100% methanol in dichloromethane to provide the title compound.

Example 158b

N-ethyl-4-[5-(ethylsulfonyl)-2-{2-methyl-6-[(2-oxopyridin-1(2H)-yl)methyl]phenoxy}phenyl]-6-methyl-7-oxo-6,7-dihydro-1H-pyrrolo[2,3-c]pyridine-2-carboxamide Example 158b was prepared according to the procedure described for the preparation of Example 145h, substituting Example 158a for Example 145d. $^1$H NMR (300 MHz, CDCl$_3$) δ 10.92 (s, 1H), 7.94 (d, J=2.2 Hz, 1H), 7.77 (m, 1H), 7.63 (dd, J=8.6, 2.3 Hz, 1H), 7.22 (m, 3H), 7.12 (d, J=7.0 Hz, 1H), 7.01 (s, 1H), 6.44 (dd, J=8.8, 5.5 Hz, 2H), 6.07 (t, J=6.6 Hz, 1H), 5.55 (d, J=14.5 Hz, 1H), 4.63 (d, J=14.6 Hz, 1H), 3.74 (s, 3H), 3.50 (m, 2H), 3.13 (q, J=7.3 Hz, 2H), 1.96 (s, 3H), 1.30 (t, J=7.4 Hz, 3H), 1.24 (t, J=7.2 Hz, 2H). MS (ESI+) m/z (M+H)+.

Example 159

3-[({4-[2-(2,4-difluorophenoxy)-5-(methylsulfonyl)phenyl]-6-methyl-7-oxo-6,7-dihydro-1H-pyrrolo[2,3-c]pyridin-2-yl}methyl)amino]propanamide Example 159 was prepared according to the procedure used for the preparation of Example 16o, substituting Example 155g for Example 16n and 3-aminopropanamide for 1-(pyridin-4-yl)piperazine. $^1$H NMR (400 MHz, DMSO-d$_6$) δ 11.85 (s, 1H), 7.98 (d, J=2.3 Hz, 1H), 7.87 (dd, J=8.7, 2.4 Hz, 1H), 7.56-7.46 (m, 1H), 7.46-7.37 (m, 2H), 7.33 (s, 1H), 7.21-7.12 (m, 1H), 6.98 (d, J=8.6 Hz, 1H), 6.73 (s, 1H), 6.16 (s, 1H), 3.73 (s, 2H), 3.58 (s, 3H), 3.26 (s, 3H), 2.60 (t, 2H), 2.17 (t, J=6.7 Hz, 2H). MS (APCI+) m/z 531.2 (M+H)+.

Example 160 methyl 3-[{3-(2,6-dimethylphenoxy)-4-[2-(ethylcarbamoyl)-6-methyl-7-oxo-6,7-dihydro-1H-pyrrolo[2,3-c]pyridin-4-yl]benzoyl}(phenyl)amino]propanoate A solution of Example 153e (0.11 M in pyridine, 200 μL, 0.022 mmoL), 1-ethyl-3-[3-(dimethylamino)propyl]-carbodiimide hydrochloride (6.42 mg 0.041 mmol, 1.0 equivalent), and methyl 3-(phenylamino)propanoate (0.40 M in N,N-dimethylacetamide, 76.2 μL, 0.030 mmol, 1.4 equivalents) were combined and stirred overnight at 40° C. The reaction mixture was purified by reverse phase preparative HPLC (C8, 5-100% acetonitrile in 0.1% trifluoroacetic acid/water) to afford 10.9 mg of the title compound (81%). $^1$H NMR (400 MHz, DMSO-d$_6$) δ 7.36 (d, J=7.8 Hz, 1H), 7.17-7.25 (m, 4H), 7.14 (dd, J=7.8, 1.7 Hz, 1H), 7.07 (s, 3H), 6.86-6.97 (m, 2H), 6.76 (s, 1H), 6.16 (d, J=1.7 Hz, 1H), 3.98 (t, J=7.0 Hz, 2H), 3.56 (s, 3H), 3.50 (s, 3H), 3.29 (q, J=7.2 Hz, 2H), 2.50-2.57 (m, 2H), 1.79 (s, 6H), 1.14 (t, J=7.2 Hz, 3H). MS (APCI+) m/z 621.2 (M+H)+.

Example 161

4-[4-{benzyl[3-(morpholin-4-yl)propyl]carbamoyl}-2-(2,6-dimethylphenoxy)phenyl]-N-ethyl-6-methyl-7-oxo-6,7-dihydro-1H-pyrrolo[2,3-c]pyridine-2-carboxamide Example 161 was prepared according to the procedure used for the preparation of Example 160, substituting N-benzyl-3-morpholinopropan-1-amine for methyl 3-(phenylamino)propanoate. $^1$H NMR (400 MHz, DMSO-$d_6$) δ 7.55 (d, J=7.8 Hz, 1H), 7.28-7.34 (m, 4H), 7.19 (dd, J=7.8, 1.6 Hz, 1H), 7.04-7.11 (m, 4H), 6.85 (s, 1H), 6.38 (d, J=1.5 Hz, 1H), 4.52 (s, 2H), 3.81 (s, 4H), 3.60 (s, 3H), 3.31-3.38 (m, 2H), 3.26-3.32 (m, 2H), 3.17 (s, 4H), 2.99-3.08 (m, 2H), 1.87-1.97 (m, 8H), 1.14 (t, J=7.2 Hz, 3H). MS (APCI+) m/z 676.3 (M+H)$^+$.

Example 162

4-[4-{(3,4-dichlorophenyl)[2-(thiomorpholin-4-yl)ethyl]carbamoyl}-2-(2,6-dimethylphenoxy)phenyl]-N-ethyl-6-methyl-7-oxo-6,7-dihydro-1H-pyrrolo[2,3-c]pyridine-2-carboxamide Example 162a 3-(2,6-dimethylphenoxy)-4-(2-(ethylcarbamoyl)-6-methyl-7-oxo-6,7-dihydro-1H-pyrrolo[2,3-c]pyridin-4-yl)benzoyl chloride Example 153e (30 mg, 0.065 mmol) was suspended in dichloromethane (1 mL). Oxalyl chloride (12 μL, 0.13 mmol, 2 equivalents) was added, followed by a drop of N,N-dimethylformamide. The reaction mixture was stirred at ambient temperature until complete consumption of Example 153e. The reaction mixture was dried under a stream of nitrogen, dissolved in dichloromethane (2 mL) and dried again under nitrogen.

Example 162b 4-(4-((3,4-dichlorophenyl)(2-thiomorpholinoethyl)carbamoyl)-2-(2,6-dimethylphenoxy)phenyl)-N-ethyl-6-methyl-7-oxo-6,7-dihydro-1H-pyrrolo[2,3-c]pyridine-2-carboxamide To Example 162a (10 mg, 0.021 mmol) in tetrahydrofuran (300 uL) was added 3,4-dichloro-N-(2-thiomorpholinoethyl)aniline (0.40 M in N,N-dimethylacetamide, 163 μL, 0.065 mmol, 3.0 equivalents) and the reaction mixture was allowed to stir overnight at ambient temperature. The reaction mixture was purified by reverse phase preparative HPLC (C8, 5-100% acetonitrile in 0.1% trifluoroacetic acid/water) to afford 8.9 mg of the title compound (48%). $^1$H NMR (400 MHz, DMSO-$d_6$) δ 7.48 (d, J=7.8 Hz, 1H), 7.41 (d, J=8.6 Hz, 1H), 7.24-7.35 (m, 3H), 7.07 (s, 3H), 6.99 (dd, J=8.6, 2.6 Hz, 1H), 6.77 (s, 1H), 6.11 (s, 1H), 4.06 (t, J=7.0 Hz, 2H), 3.58 (s, 3H), 3.26-3.35 (m, 4H), 3.14 (t, J=7.0 Hz, 2H), 2.84 (t, J=5.2 Hz, 4H), 1.81 (s, 6H), 1.14 (t, J=7.2 Hz, 3H). MS (APCI+) m/z 732.6 (M+H)$^+$.

Example 163

N-{4-(2,4-difluorophenoxy)-3-[2-(3-methoxyprop-1-yn-1-yl)-6-methyl-7-oxo-6,7-dihydro-1H-pyrrolo[2,3-c]pyridin-4-yl]phenyl}ethanesulfonamide Example 163a 2-bromo-1-(2,4-difluorophenoxy)-4-nitrobenzene 2-Bromo-1-fluoro-4-nitrobenzene (15 g, 68.2 mmol), 2,4-difluorophenol (7.82 mL, 82 mmol), and cesium carbonate (26.7 g, 82 mmol) were combined in DMSO (75 mL) then heated to 110° C. for 1 hour. After cooling, the reaction mixture was partitioned between water and ethyl acetate. The aqueous layer was extracted with additional ethyl acetate twice. The combined organic layers were washed with saturated aqueous sodium chloride, dried over anhydrous magnesium sulfate, filtered, and concentrated to give the title compound (22.51 g, 68.2 mmol, 100%).

Example 163b 3-bromo-4-(2,4-difluorophenoxy)aniline

A mixture of Example 163a (42 g, 127 mmol), iron (35.5 g, 636 mmol), and ammonium chloride (13.61 g, 254 mmol) in tetrahydrofuran (234 mL), ethanol (234 mL), and water (78 mL) was heated under reflux at 100° C. for 2 hours. The mixture was cooled to just below reflux and filtered through Celite. The filter cake was washed with warm methanol. The resulting combined filtrate solution was concentrated under reduced pressure to remove organics, and then neutralized to a pH of about 8 with saturated NaHCO$_3$. The resulting aqueous solution was extracted with ethyl acetate three times. The combined organics were washed with saturated aqueous sodium chloride, dried over anhydrous magnesium sulfate, filtered, concentrated to provide the title compound (38 g, 127 mmol, 100% yield).

Example 163c 4-(2,4-difluorophenoxy)-3-(4,4,5,5-tetramethyl-1,3,2-dioxaborolan-2-yl)aniline Example 163b (15.04 g, 50.1 mmol), 4,4,4',4',5,5,5',5'-octamethyl-2,2'-bi(1,3,2-dioxaborolane) (25.5 g, 100 mmol), potassium acetate (10.82 g, 110 mmol), 1,3,5,7-tetramethyl-6-phenyl-2,4,8-trioxa-6-phosphaadamantane (1.465 g, 5.01 mmol), and tris(dibenzylideneacetone)dipalladium(0) (1.377 g, 1.504 mmol) were degassed under argon for 30 minutes. Dioxane (200 mL), degassed with argon for 30 minutes, was then cannulated and the mixture heated at 80° C. for 22 hours. The cooled mixture was filtered through Celite, rinsed with ethyl acetate (100 mL), washed with brine (150 mL) and water (150 mL), and partitioned. The aqueous was extracted with ethyl acetate (3×150 mL). The combined organics were washed with brine, dried (anhydrous MgSO$_4$), filtered, and concentrated to an amber oil. Purification by flash chromatography (ethyl acetate/Hexanes, 0:25% gradient) afforded the title compound (12.4 g, 71% yield).

Example 163d 4-bromo-2-iodo-7-methoxy-1-tosyl-1H-pyrrolo[2,3-c]pyridine

In a 1 L round-bottomed flask charged with tetrahydrofuran (200 ml) cooled to −78° C. was added butyllithium (36.7 ml, 92 mmol) followed by diisopropylamine (9.29 g, 92 mmol) added dropwise. The resulting mixture was stirred at −78° C. for 45 minutes. To a mixture of Example 1c (25 g, 65.6 mmol) in tetrahydrofuran (200 ml) stirred at −78° C. was added dropwise the lithium diisopropylamide solution generated as described above. The mixture was stirred at −78° C. for 1.5 hours. To the resulting mixture stirred at −78° C. was added dropwise the solution of diiodine (38.3 g, 151 mmol) in tetrahydrofuran (100 mL) and the mixture stirred at −78° C. for 2 hours. The reaction mixture was quenched with Na$_2$S$_2$O$_3$ solution, extracted with ethyl acetate (2×1000 mL) followed by dichloromethane (4×1000 mL), and the organic phase was dried over anhydrous sodium sulfate, filtered, and concentrated in vacuo. The residue was triturated with dichloromethane. The solid was collected and dried in vacuo to give the title compound (19.95 g, 39.3 mmol, 60% yield).

Example 163e 4-bromo-2-iodo-1-tosyl-1H-pyrrolo[2,3-c]pyridin-7 (6H)-one

To a mixture of Example 163d (14 g, 27.6 mmol) in acetonitrile (260 mL) was added sodium iodide (6.62 g, 44.2 mmol) followed by chlorotrimethylsilane (4.80 g, 44.2 mmol) added dropwise. The resulting mixture was stirred at room temperature for 30 minutes and then water (0.249 g, 13.80 mmol) was added. The resulting mixture was stirred at 65° C. for 3 hours, cooled to ambient temperature, and filtered. The resulting solid was collected, suspended in dichloromethane, and filtered. The eluent was dried over anhydrous sodium sulfate and concentrated in vacuo to give the desired product. The filtrate was concentrated in vacuo, purified by column chromatography (silica gel, dichloromethane/methanol, 20:1) to give additional desired product. The combined yield as 12 g (88% yield).

Example 163f 4-bromo-2-iodo-6-methyl-1-tosyl-1H-pyrrolo[2,3-c] pyridin-7(6H)-one To a solution of Example 163e (11 g, 22.31 mmol) in DMF (130 ml) was added sodium hydride (1.160 g, 29.0 mmol) in portions at 0° C., and the mixture was stirred for 30 minutes. Then iodomethane (4.12 g, 29.0 mmol) was added dropwise to the above mixture. The resulting mixture was stirred at room temperature for 3 hours. The reaction mixture was quenched with aqueous ammonium chloride solution. The resulting suspension was filtered and the filter cake was dissolved in dichloromethane, dried over anhydrous sodium sulfate, filtered and concentrated under reduced pressure. The residue was dissolved in dichloromethane, and methanol was added. The suspension was filtered and the filter cake was dried to the title compound (5.0 g, 44% yield).

Example 163g 4-bromo-2-(3-methoxyprop-1-yn-1-yl)-6-methyl-1-tosyl-1H-pyrrolo[2,3-c]pyridin-7(6H)-one A mixture of Example 163f (51 mg, 0.101 mmol), 3-methoxyprop-1-yne (10.6 mg, 0.151 mmol), copper(I) iodide (3.83 mg, 0.020 mmol), bis(triphenylphosphine)palladium(II) chloride (7.1 mg), and triethylamine (204 mg, 2.01 mmol) in dimethylformamide (2 mL) was degassed and heated at 80° C. under argon for 3 hours. The mixture was cooled to ambient temperature and combined with the contents of an identical reaction mixture. The mixture was partitioned between ethyl acetate and ammonium chloride solution, and the organic layer separated, dried over anhydrous magnesium sulfate, filtered, and concentrated under reduced pressure. The residue was purified by flash chromatography (silica gel, 0-2% methanol/dichloromethane gradient) and followed by trituration with diethyl ether to afford the title compound (55.7 mg, 61% yield from combined reactions).

Example 163h 4-(5-amino-2-(2,4-difluorophenoxy)phenyl)-2-(3-methoxyprop-1-yn-1-yl)-6-methyl-1-tosyl-1H-pyrrolo[2,3-c]pyridin-7(6H)-one A mixture of Example 163g (55.6 mg, 0.124 mmol), Example 163c (86 mg, 0.247 mmol), cesium fluoride (56.4 mg, 0.371 mmol), and tetrakis(triphenylphosphine)palladium(0) (14.3 mg, 0.012 mmol) was sparged under argon for 15 minutes. To this mixture was added degassed 1,2-dimethoxyethane (5 mL) and degassed methanol (2.5 mL), and the mixture was heated at 100° C. for 50 minutes. The reaction mixture was cooled to ambient temperature, and partitioned between ethyl acetate and saturated aqueous ammonium chloride. The organic layer was dried over anhydrous magnesium sulfate, filtered, and evaporated under reduced pressure. The residue was purified by flash chromatography (silica gel, 3:2 ethyl acetate/heptane) to provide the title compound (18 mg).

Example 163i

N-{4-(2,4-difluorophenoxy)-3-[2-(3-methoxyprop-1-yn-1-yl)-6-methyl-7-oxo-6, 7-dihydro-1H-pyrrolo[2, 3-c]pyridin-4-yl]phenyl}ethanesulfonamide To Example 163h (18 mg, 0.031 mmol) in dichloromethane (8 mL) at 0° C. was added triethylamine (0.017 ml, 0.122 mmol) followed by the dropwise addition of ethanesulfonyl chloride (8.68 µL, 0.092 mmol). The reaction mixture was stirred at ambient temperature for 1 hour, and additional ethanesulfonyl chloride (20 µL, 0.21 mmol) was added twice. The reaction mixture was heated at 45° C. for 2 hours and then at ambient temperature for 18 hours. The mixture was partitioned between dichloromethane and saturated aqueous ammonium chloride and the organic layer dried over anhydrous magnesium sulfate, filtered, and concentrated under reduced pressure. The residue was dissolved in dioxane (2.5 mL) and 5N aqueous sodium hydroxide (1 mL) and the mixture heated at 90° C. for 1.5 hours. The mixture was cooled to ambient temperature, and partitioned between ethyl acetate and saturated aqueous sodium chloride. The pH was adjusted to pH=2 by the addition of 1 N HCl, and the mixture further extracted with ethyl acetate. The combined organic layers were dried over anhydrous magnesium sulfate, filtered, and evaporated. The residue was triturated with ethyl acetate/hexane to provide the title compound (6 mg, 37% yield). $^1$H NMR (400 MHz, DMSO-d$_6$) δ 12.65 (s, 1H), 9.78 (s, 1H), 7.37 (m, 3H), 7.20 (dd, J=8.8, 2.7 Hz, 1H), 7.08 (td, J=9.1, 5.6 Hz, 1H), 6.99 (m, 1H), 6.92 (d, J=8.8 Hz, 1H), 6.46 (s, 1H), 4.33 (s, 2H), 3.52 (s, 3H), 3.11 (q, J=7.3 Hz, 3H), 1.23 (m, 3H).). MS (APCI+) m/z 528.3 (M+H)$^+$.

Example 164

4-{2-[2-(2-cyclopentylethyl)-6-methylphenoxy]-5-(ethylsulfonyl)phenyl}-N-ethyl-6-methyl-7-oxo-6,7-dihydro-1H-pyrrolo[2,3-c]pyridine-2-carboxamide Example 164a 2-(2-(2-cyclopentylvinyl)-4-(ethylsulfonyl)phenoxy)-3-methylbenzaldehyde To a solution of (cyclopentylmethyl)triphenylphosphonium iodide (2.465 g, 5.22 mmol) in tetrahydrofuran (40 mL) was added 2.5 M n-butyllithium (2.296 mL in hexanes, 5.74 mmol) at −50° C. The mixture was stirred for 1 hour at 0° C. A solution of Example 145a (1 g, 2.61 mmol) in tetrahydrofuran (10 mL) was added dropwise to the mixture at −78° C. The mixture was allowed to warm to 15° C. slowly and stirred for 2 hours. The mixture was partitioned between ethyl acetate and water. The organic layer was washed with saturated aqueous sodium chloride, dried over anhydrous sodium sulfate, filtered and concentrated. The residue was purified by flash chromatography (silica gel, 0-50% ethyl acetate in petroleum ether) to provide the title compound (1.1 g, 90% yield).

Example 164b (Z)-4-(2-(2-(2-cyclopentylvinyl)-6-methylphenoxy)-5-(ethylsulfonyl)phenyl)-N-ethyl-6-methyl-7-oxo-6,7-dihydro-1H-pyrrolo[2,3-c]pyridine-2-carboxamide To a solution of Example 145g (300 mg, 0.869 mmol) in 1,4-dioxane (8 mL) and water (2 mL) was added Example 164a (449 mg, 0.999 mmol),), tris(dibenzylideneacetone)-dipalladium(0) (39.8 mg, 0.043 mmol), 1,3,5,7-tetramethyl-8-phenyl-2,4,6-trioxa-8-phosphaadamantane (25.4 mg, 0.087 mmol) and potassium phosphate (553 mg, 2.61 mmol). The reaction mixture was stirred for 2 hours under nitrogen at 60° C. The mixture was cooled to ambient temperature and partitioned between ethyl acetate and water. The organic layer was washed with saturated aqueous sodium chloride, dried over anhydrous sodium sulfate, treated with Celite, filtered, and concentrated. The residue was purified by flash chromatography (silica gel, 0-100% ethyl acetate in petroleum ether). The crude product was purified by Prep-HPLC (C18, Mobile Phase A: Water/0.05% TFA, Mobile Phase B: acetonitrile/0.05% TFA; Gradient: 5% B to 95% B) to provide the title compound (145.5 mg, 0.207 mmol, 24% yield).

Example 164c 4-(2-(2-(2-cyclopentylethyl)-6-methylphenoxy)-5-(ethyl sulfonyl)phenyl)-N-ethyl-6-methyl-7-oxo-6,7-dihydro-1H-pyrrolo[2,3-c]pyridine-2-carboxamide To a solution of Example 164b (80 mg, 0.114 mmol) in methanol (5 mL) was added acetic acid (0.5 mL) and 10% Pd—C (2.426 mg, 0.023 mmol). The mixture was charged with hydrogen. The mixture was stirred for 4 hour at 20° C. under hydrogen (3 atmosphere). The mixture was diluted with ethyl acetate (15 mL) and filtered through a Celite pad. The mixture was concentrated under reduced pressure. The residue was treated with ammonium hydroxide and washed with water. The crude product was purified by recrystallization from acetonitrile to obtain the title compound (40.1 mg, 0.068 mmol, 59.6% yield). $^1$H NMR (400 MHz, DMSO-d$_6$) δ 12.34 (s, 1H), 8.35 (m, 1H), 7.92 (d, J=2.1 Hz, 1H), 7.80 (dd, J=8.7, 2.2 Hz, 1H), 7.46 (s, 1H), 7.25-7.08 (m, 3H), 6.81 (s, 1H), 6.61 (d, J=8.7 Hz, 1H), 3.60 (s, 3H), 3.31-3.14 (m, 4H), 2.24 (t, J=7.8 Hz, 2H), 2.12 (s, 3H), 1.57-1.21 (m, 9H), 1.12 (m, 6H), 0.75 (bs, 2H). MS (ESI$^+$) m/z 590 (M+H)$^+$.

Example 165

4-[2-(2,6-dimethylphenoxy)-4-{(1-phenylpropan-2-yl)[3-(pyrrolidin-1-yl)propyl]carbamoyl}phenyl]-N-ethyl-6-methyl-7-oxo-6,7-dihydro-1H-pyrrolo[2,3-c]pyridine-2-carboxamide The trifluoroacetic acid salt of Example 165 was prepared according to the procedure used for the preparation of Example 162b, substituting N-(1-phenylpropan-2-yl)-3-(pyrrolidin-1-yl)propan-1-amine for 3,4-dichloro-N-(2-thiomorpholinoethyl)aniline. $^1$H NMR (400 MHz, DMSO-d$_6$) δ 7.50 (d, J=7.7 Hz, 1H), 7.36 (s, 1H), 7.07-7.24 (m, 6H), 6.95 (d, J=6.9 Hz, 2H), 6.89 (s, 1H), 6.82 (d, J=7.8 Hz, 1H), 6.18 (s, 1H), 3.97-4.10 (m, 1H), 3.64 (s, 3H), 3.55 (s, 3H), 3.33 (s, 2H), 3.14 (t, J=7.7 Hz, 2H), 3.01 (s, 2H), 2.67-2.88 (m, 2H), 2.03 (s, 6H), 1.94 (s, 4H). MS (APCI+) m/z 688.7 (M+H)$^+$.

Example 166

4-{4-[(cyanomethyl)(1-phenylpropan-2-yl)carbamoyl]-2-(2,6-dimethylphenoxy)phenyl}-N-ethyl-6-methyl-7-oxo-6,7-dihydro-1H-pyrrolo[2,3-c]pyridine-2-carboxamide Example 166 was prepared according to the procedure used for the preparation of Example 162b, substituting 2-((1-phenylpropan-2-yl)amino)acetonitrile for 3,4-dichloro-N-(2-thiomorpholinoethyl)aniline. $^1$H NMR (400 MHz, DMSO-d$_6$) δ 7.49 (d, J=7.7 Hz, 1H), 7.35 (s, 1H), 7.03-7.24 (m, 7H), 6.96 (d, J=6.8 Hz, 2H), 6.88 (s, 1H), 6.76 (d, J=7.9 Hz, 1H), 6.19 (s, 1H), 4.32 (s, 2H), 4.13 (s, 1H), 3.62 (s, 3H), 3.27-3.36 (m, 2H), 2.78 (t, J=6.7 Hz, 2H), 2.00 (s, 6H), 1.15 (t, J=7.0 Hz, 7H). MS (APCI+) m/z 616.6 (M+H)$^+$.

Example 167

4-{4-[(cyanomethyl)(2-phenylpropyl)carbamoyl]-2-(2,6-dimethylphenoxy)phenyl}-N-ethyl-6-methyl-7-oxo-6,7-dihydro-1H-pyrrolo[2,3-c]pyridine-2-carboxamide Example 167 was prepared according to the procedure used for the preparation of Example 162b, substituting 2-((2-phenylpropyl)amino)acetonitrile for 3,4-dichloro-N-(2-thiomorpholinoethyl)aniline. $^1$H NMR (400 MHz, DMSO-d$_6$) δ 7.53 (d, J=7.7 Hz, 1H), 7.37 (s, 1H), 7.02-7.28 (m, 9H), 6.97 (dd, J=7.8, 1.6 Hz, 1H), 6.89 (s, 1H), 6.29 (d, J=1.6 Hz, 1H), 4.31 (d, J=17.5 Hz, 1H), 4.20 (d, J=17.6 Hz, 1H), 3.62 (s, 3H), 3.52 (dd, J=7.7, 6.0 Hz, 2H), 3.31 (q, J=7.2 Hz, 2H), 2.98-3.09 (m, 1H), 2.02 (s, 6H), 1.15 (t, J=7.2 Hz, 3H), 1.09 (d, J=6.9 Hz, 3H). MS (APCI+) m/z 616.6 (M+H)$^+$.

Example 168

4-{4-[(3-chlorophenyl)(cyanomethyl)carbamoyl]-2-(2,6-dimethylphenoxy)phenyl}-N-ethyl-6-methyl-7-oxo-6,7-dihydro-1H-pyrrolo[2,3-c]pyridine-2-carboxamide Example 168 was prepared according to the procedure used for the preparation of Example 162b, substituting 2-((3-chlorophenyl)amino)acetonitrile for 3,4-dichloro-N-(2-thiomorpholinoethyl)aniline. $^1$H NMR (400 MHz, DMSO-d$_6$) δ 7.47 (d, J=7.8 Hz, 1H), 7.24-7.38 (m, 4H), 7.05-7.16 (m, 4H), 6.97-7.01 (m, 1H), 6.78 (s, 1H), 6.19 (d, J=1.7 Hz, 1H), 4.78 (s, 2H), 3.57 (s, 3H), 3.26-3.35 (m, 2H), 1.81 (s, 6H), 1.14 (t, J=7.2 Hz, 3H). MS (APCI+) m/z 608.5 (M+H)$^+$.

Example 169

4-{4-[(4-chlorophenyl)(cyanomethyl)carbamoyl]-2-(2,6-dimethylphenoxy)phenyl}-N-ethyl-6-methyl-7-oxo-6,7-dihydro-1H-pyrrolo[2,3-c]pyridine-2-carboxamide Example 169 was prepared according to the procedure used for the preparation of Example 162b, substituting 2-((4-chlorophenyl)amino)acetonitrile for 3,4-dichloro-N-(2-thiomorpholinoethyl)aniline. $^1$H NMR (400 MHz, DMSO-d$_6$) δ 7.48 (d, J=7.8 Hz, 1H), 7.25-7.36 (m, 4H), 7.08 (s, 3H), 6.96-7.05 (m, 2H), 6.80 (s, 1H), 6.17 (d, J=1.6 Hz, 1H), 4.75 (s, 2H), 3.57 (s, 3H), 3.31 (d, J=7.3 Hz, 2H), 1.80 (s, 6H), 1.14 (t, J=7.2 Hz, 3H). MS (APCI+) m/z 608.5 (M+H)$^+$.

Example 170

4-[4-{[2-(diethylamino)ethyl](2-methylphenyl)carbamoyl}-2-(2,6-dimethylphenoxy)phenyl]-N-ethyl-6-methyl-7-oxo-6,7-dihydro-1H-pyrrolo[2,3-c]pyridine-2-carboxamide The trifluoroacetic acid salt of Example 170 was prepared according to the procedure used for the preparation of Example 162b, substituting N$^1$,N-diethyl-N$^2$-(o-tolyl)ethane-1,2-diamine for 3,4-dichloro-N-(2-thiomorpholinoethyl)aniline. $^1$H NMR (400 MHz, DMSO-d$_6$) δ 7.43 (d, J=7.9 Hz, 1H), 7.20-7.30 (m, 3H), 7.05-7.19 (m, 5H), 6.97 (d, J=7.8 Hz, 1H), 6.77 (s, 1H), 6.14 (s, 1H), 4.31 (ddd, J=14.5, 9.6, 5.7 Hz, 2H), 3.58 (s, 4H), 3.32-3.45 (m, 2H), 3.21 (q, J=7.3 Hz, 4H), 1.95 (s, 3H), 1.79 (s, 6H), 1.23 (t, J=7.3 Hz, 6H), 1.16 (t, J=7.2 Hz, 3H). MS (APCI+) m/z 648.6 (M+H)$^+$.

Example 171

4-[4-{(cyanomethyl)[3-(trifluoromethyl)phenyl]carbamoyl}-2-(2,6-dimethylphenoxy)phenyl]-N-ethyl-6-methyl-7-oxo-6,7-dihydro-1H-pyrrolo[2,3-c]pyridine-2-carboxamide Example 171 was prepared according to the procedure used for the preparation of Example 162b, substituting 2-((3-(trifluoromethyl)phenyl)amino)acetonitrile for 3,4-dichloro-N-(2-thiomorpholinoethyl)aniline. $^1$H NMR (400 MHz, DMSO-d$_6$) δ 7.63 (d, J=7.8 Hz, 1H), 7.53 (t, J=7.9 Hz, 1H), 7.45 (d, J=7.9 Hz, 1H), 7.36 (d, J=7.8 Hz, 2H), 7.22-7.28 (m, 2H), 7.04 (s, 3H), 6.75 (s, 1H), 6.19 (s, 1H), 4.85 (s, 2H), 3.57 (s, 3H), 3.31 (d, J=7.4 Hz, 2H), 1.78 (s, 6H), 1.14 (t, J=7.3 Hz, 3H). MS (APCI+) m/z 642.4 (M+H)$^+$.

Example 172

4-[4-{cyclohexyl[3-(dimethylamino)propyl]carbamoyl}-2-(2,6-dimethylphenoxy)phenyl]-N-ethyl-6-methyl-7-oxo-6,7-dihydro-1H-pyrrolo[2,3-c]pyridine-2-carboxamide The trifluoroacetic acid salt of Example 172 was prepared according to the procedure used for the preparation of Example 162b, substituting N$^1$-cyclohexyl-N$^3$,N$^3$-dimethylpropane-1,3-diamine for 3,4-dichloro-N-(2-thiomorpholinoethyl)aniline. $^1$H NMR (400 MHz, DMSO-d$_6$) δ 7.59 (d, J=7.8 Hz, 1H), 7.39 (s, 1H), 7.05-7.18 (m, 4H), 6.91 (s, 1H), 6.29 (s, 1H), 3.64 (s, 3H), 3.42 (d, J=13.3 Hz, 2H), 3.35 (d, J=7.4 Hz, 1H), 3.04-3.13 (m, 2H), 2.81 (s, 6H), 2.06 (s, 6H), 1.91 (p, J=7.9 Hz, 2H), 1.73 (d, J=11.9 Hz, 3H), 1.45-1.57 (m, 6H), 1.17 (t, J=7.2 Hz, 3H), 1.03 (t, J=10.2 Hz, 4H). MS (APCI+) m/z 626.6 (M+H)$^+$.

Example 173

4-{4-[benzyl(4-chlorobenzyl)carbamoyl]-2-(2, 6-dimethylphenoxy)phenyl}-N-ethyl-6-methyl-7-oxo-6,7-dihydro-1H-pyrrolo[2,3-c]pyridine-2-carboxamide Example 173 was prepared according to the procedure used for the preparation of Example 162b, substituting N-benzyl-1-(4-chlorophenyl)methanamine for 3,4-dichloro-N-(2-thiomorpholinoethyl)aniline. $^1$H NMR (400 MHz, DMSO-d$_6$) δ 7.57 (d, J=7.7 Hz, 1H), 7.20-7.38 (m, 7H), 7.01-7.15 (m, 7H), 6.89 (s, 1H), 6.40 (s, 1H), 4.50 (s, 2H), 4.47 (s, 2H), 3.61 (s, 3H), 3.33 (d, J=7.3 Hz, 2H), 1.90 (s, 6H), 1.16 (t, J=7.2 Hz, 3H). MS (APCI+) m/z 673.3 (M+H)$^+$.

Example 174

4-[4-{[2-(dimethylamino)ethyl](pyrimidin-2-yl)carbamoyl}-2-(2,6-dimethylphenoxy)phenyl]-N-ethyl-6-methyl-7-oxo-6,7-dihydro-1H-pyrrolo[2,3-c]pyridine-2-carboxamide The trifluoroacetic acid salt of Example 174 was prepared according to the procedure used for the preparation of Example 162b, substituting N$^1$,N-dimethyl-N2-(pyrimidin-2-yl)ethane-1,2-diamine for 3,4-dichloro-N-(2-thiomorpholinoethyl)aniline. $^1$H NMR (400 MHz, DMSO-d$_6$) δ 8.54 (d, J=4.9 Hz, 2H), 7.48 (d, J=7.9 Hz, 1H), 7.33 (s, 1H), 7.28 (t, J=4.9 Hz, 1H), 7.23 (dd, J=7.9, 1.7 Hz, 1H), 7.07 (s, 3H), 6.83 (s, 1H), 6.20 (t, J=1.8 Hz, 1H), 4.34 (t, J=6.5 Hz, 2H), 3.61 (s, 3H), 3.38 (t, J=6.5 Hz, 3H), 3.31 (s, 2H), 2.90 (s, 6H), 1.89 (s, 6H), 1.17 (t, J=7.3 Hz, 3H). MS (APCI+) m/z 608.6 (M+H)$^+$.

Example 175

4-{4-[(3-chlorophenyl)(2-cyanoethyl)carbamoyl]-2-(2,6-dimethylphenoxy)phenyl}-N-ethyl-6-methyl-7-oxo-6,7-dihydro-1H-pyrrolo[2,3-c]pyridine-2-carboxamide Example 175 was prepared according to the procedure used for the preparation of Example 162b, substituting 3-((3-chlorophenyl)amino)propanenitrile for 3,4-dichloro-N-(2-thiomorpholinoethyl)aniline. $^1$H NMR (400 MHz, DMSO-d$_6$) δ 7.45 (d, J=7.8 Hz, 1H), 7.19-7.34 (m, 4H), 7.12 (t, J=2.0 Hz, 4H), 7.09 (s, 3H), 6.99 (dt, J=7.6, 1.6 Hz, 1H), 6.80 (s, 1H), 6.20 (d, J=1.6 Hz, 1H), 4.03 (t, J=6.6 Hz, 2H), 3.60 (s, 3H), 3.33 (d, J=7.2 Hz, 2H), 2.78 (t, J=6.6 Hz, 2H), 1.84 (s, 6H), 1.16 (t, J=7.2 Hz, 3H). MS (APCI+) m/z 622.5 (M+H)$^+$.

Example 176

4-{4-[(2-cyanoethyl)(cyclohexyl)carbamoyl]-2-(2,6-dimethylphenoxy)phenyl}-N-ethyl-6-methyl-7-oxo-6,7-dihydro-1H-pyrrolo[2,3-c]pyridine-2-carboxamide Example 176 was prepared according to the procedure used for the preparation of Example 162b, substituting 3-(cyclohexylamino)propanenitrile for 3,4-dichloro-N-(2-thiomorpholinoethyl)aniline. $^1$H NMR (400 MHz, DMSO-$d_6$) δ 7.59 (d, J=7.7 Hz, 1H), 7.40 (s, 1H), 7.04-7.18 (m, 4H), 6.92 (s, 1H), 6.37 (d, J=1.5 Hz, 1H), 3.64 (s, 3H), 3.52 (t, J=6.8 Hz, 2H), 3.44 (s, 1H), 3.32 (d, J=7.1 Hz, 2H), 2.75 (t, J=6.8 Hz, 2H), 2.06 (s, 6H), 1.72 (d, J=12.1 Hz, 2H), 1.50 (t, J=8.1 Hz, 4H), 1.17 (t, J=7.2 Hz, 3H), 1.02 (s, 2H). MS (APCI+) m/z 594.5 (M+H)$^+$.

Example 177

4-{4-[(cyanomethyl)(phenyl)carbamoyl]-2-(2,6-dimethylphenoxy)phenyl}-N-ethyl-6-methyl-7-oxo-6,7-dihydro-1H-pyrrolo[2,3-c]pyridine-2-carboxamide Example 177 was prepared according to the procedure used for the preparation of Example 162b, substituting 2-(phenylamino)acetonitrile for 3,4-dichloro-N-(2-thiomorpholinoethyl)aniline. $^1$H NMR (400 MHz, DMSO-$d_6$) δ 7.45 (d, J=7.9 Hz, 1H), 7.24-7.38 (m, 5H), 7.10 (s, 3H), 7.02 (dd, J=7.6, 2.1 Hz, 2H), 6.80 (s, 1H), 6.24 (d, J=1.6 Hz, 1H), 4.77 (s, 2H), 3.59 (s, 3H), 3.33 (d, J=7.3 Hz, 2H), 1.80 (s, 5H), 1.16 (t, J=7.2 Hz, 3H). MS (APCI+) m/z 574.5 (M+H)$^+$.

Example 178

4-[4-{[2-(diethylamino)ethyl](2-methoxyphenyl)carbamoyl}-2-(2,6-dimethylphenoxy)phenyl]-N-ethyl-6-methyl-7-oxo-6,7-dihydro-1H-pyrrolo[2,3-c]pyridine-2-carboxamide The trifluoroacetic acid salt of Example 178 was prepared according to the procedure used for the preparation of Example 162b, substituting $N^1$,N-diethyl-N2-(2-methoxyphenyl)ethane-1,2-diamine for 3,4-dichloro-N-(2-thiomorpholinoethyl)aniline. $^1$H NMR (400 MHz, DMSO-$d_6$) δ 7.41 (d, J=7.8 Hz, 1H), 7.31 (td, J=7.7, 1.7 Hz, 1H), 7.24 (s, 1H), 7.21 (dd, J=7.8, 1.6 Hz, 1H), 7.11 (s, 3H), 7.00 (dd, J=7.9, 1.7 Hz, 1H), 6.91-6.95 (m, 1H), 6.82-6.88 (m, 1H), 6.76 (s, 1H), 6.20 (d, J=1.4 Hz, 1H), 3.95 (s, 2H), 3.59 (d, J=4.3 Hz, 6H), 3.28 (d, J=6.1 Hz, 2H), 3.21 (q, J=7.2 Hz, 4H), 1.81 (s, 6H), 1.23 (t, J=7.2 Hz, 6H), 1.16 (t, J=7.2 Hz, 3H). MS (APCI+) m/z 664.6 (M+H)$^+$.

Example 179

4-[4-{[2-(dimethylamino)ethyl](phenyl)carbamoyl}-2-(2,6-dimethylphenoxy)phenyl]-N-ethyl-6-methyl-7-oxo-6,7-dihydro-1H-pyrrolo[2,3-c]pyridine-2-carboxamide The trifluoroacetic acid salt of Example 179 was prepared according to the procedure used for the preparation of Example 162b, substituting $N^1$,N-dimethyl-$N^2$-phenylethane-1,2-diamine for 3,4-dichloro-N-(2-thiomorpholinoethyl)aniline. $^1$H NMR (400 MHz, DMSO-$d_6$) δ 7.41 (d, J=7.9 Hz, 1H), 7.24-7.32 (m, 4H), 7.20 (dd, J=7.8, 1.7 Hz, 1H), 7.10 (s, 3H), 7.02-7.07 (m, 2H), 6.77 (s, 1H), 6.23 (s, 1H), 4.11 (t, J=6.8 Hz, 2H), 3.59 (s, 3H), 3.33 (d, J=7.2 Hz, 3H), 2.87 (s, 6H), 1.82 (s, 6H), 1.16 (t, J=7.2 Hz, 3H). MS (APCI+) m/z 606.6 (M+H)$^+$.

Example 180 ethyl 4-[{3-(2,6-dimethylphenoxy)-4-[2-(ethylcarbamoyl)-6-methyl-7-oxo-6,7-dihydro-1H-pyrrolo[2,3-c]pyridin-4-yl]benzoyl}(phenyl)amino]butanoate Example 180 was prepared according to the procedure used for the preparation of Example 162b, substituting ethyl 4-(phenylamino)butanoate for 3,4-dichloro-N-(2-thiomorpholinoethyl)aniline. $^1$H NMR (400 MHz, DMSO-$d_6$) δ 7.39 (d, J=7.9 Hz, 1H), 7.19-7.29 (m, 4H), 7.16 (dd, J=7.8, 1.6 Hz, 1H), 7.09 (s, 3H), 6.89-6.98 (m, 2H), 6.79 (s, 1H), 6.18 (s, 1H), 4.04 (q, J=7.1 Hz, 2H), 3.74-3.83 (m, 2H), 3.59 (s, 3H), 3.33 (d, J=7.2 Hz, 2H), 2.29 (t, J=7.4 Hz, 2H), 1.82 (s, 6H), 1.76 (q, J=7.3 Hz, 2H), 1.17 (td, J=7.1, 2.8 Hz, 6H). MS (APCI+) m/z 649.6 (M+H)$^+$.

Example 181

4-[4-{[2-(dimethylamino)ethyl](pyridin-2-yl)carbamoyl}-2-(2,6-dimethylphenoxy)phenyl]-N-ethyl-6-methyl-7-oxo-6,7-dihydro-1H-pyrrolo[2,3-c]pyridine-2-carboxamide The trifluoroacetic acid salt of Example 181 was prepared according to the procedure used for the preparation of Example 162b, substituting $N^1$,N-dimethyl-$N^2$-(pyridin-2-yl)ethane-1,2-diamine for 3,4-dichloro-N-(2-thiomorpholinoethyl)aniline. $^1$H NMR (400 MHz, DMSO-$d_6$) δ 8.32 (dd, J=5.0, 1.9 Hz, 1H), 7.69 (td, J=7.7, 1.9 Hz, 1H), 7.46 (d, J=7.9 Hz, 1H), 7.25-7.32 (m, 2H), 7.22 (dd, J=7.7, 1.7 Hz, 1H), 7.09 (s, 3H), 6.94 (d, J=8.0 Hz, 1H), 6.79 (s, 1H), 6.18 (d, J=1.6 Hz, 1H), 4.23 (t, J=6.5 Hz, 2H), 3.60 (s, 3H), 3.36 (d, J=6.5 Hz, 2H), 2.89 (s, 6H), 1.85 (s, 6H), 1.17 (t, J=7.2 Hz, 3H). MS (APCI+) m/z 607.6 (M+H)$^+$.

Example 182

4-[4-{[2-(diethylamino)ethyl](phenyl)carbamoyl}-2-(2,6-dimethylphenoxy)phenyl]-N-ethyl-6-methyl-7-oxo-6,7-dihydro-1H-pyrrolo[2,3-c]pyridine-2-carboxamide The trifluoroacetic acid salt of Example 182 was prepared according to the procedure used for the preparation of Example 162b, substituting $N^1$,N-diethyl-$N^2$-phenylethane-1,2-diamine for 3,4-dichloro-N-(2-thiomorpholinoethyl)aniline. $^1$H NMR (400 MHz, DMSO-$d_6$) δ 7.41 (d, J=7.9 Hz, 1H), 7.24-7.33 (m, 4H), 7.21 (dd, J=7.8, 1.7 Hz, 1H), 7.09 (s, 3H), 7.01-7.06 (m, 2H), 6.77 (s, 1H), 6.22 (s, 1H), 4.11 (dd, J=8.5, 6.2 Hz, 2H), 3.59 (s, 3H), 3.33 (d, J=7.2 Hz, 2H), 3.26 (d, J=7.1 Hz, 2H), 3.20 (q, J=7.3 Hz, 4H), 1.81 (s, 6H), 1.22 (t, J=7.3 Hz, 6H), 1.16 (t, J=7.2 Hz, 3H). MS (APCI+) m/z 634.6 (M+H)$^+$.

Example 183

4-{4-[(cyanomethyl)(4-methoxyphenyl)carbamoyl]-2-(2,6-dimethylphenoxy)phenyl}-N-ethyl-6-methyl-7-oxo-6,7-dihydro-1H-pyrrolo[2,3-c]pyridine-2-carboxamide Example 183 was prepared according to the procedure used for the preparation of Example 162b, substituting 2-((4-methoxyphenyl)amino)acetonitrile for 3,4-dichloro-N-(2-thiomorpholinoethyl)aniline. $^1$H NMR (400 MHz, DMSO-$d_6$) δ 7.44 (d, J=7.8 Hz, 1H), 7.24-7.31 (m, 2H), 7.02-7.12 (m, 3H), 6.86-6.95 (m, 2H), 6.76-6.84 (m, 3H), 6.20 (d, J=1.5 Hz, 1H), 4.70 (s, 2H), 3.79 (s, 3H), 3.57 (s, 3H), 3.30 (t, J=7.2 Hz, 2H), 1.79 (s, 6H), 1.14 (t, J=7.2 Hz, 3H). MS (APCI+) m/z 604.5 (M+H)$^+$.

Example 184

4-{4-[butyl(2-cyanoethyl)carbamoyl]-2-(2,6-dimethylphenoxy)phenyl}-N-ethyl-6-methyl-7-oxo-6,7-dihydro-1H-pyrrolo[2,3-c]pyridine-2-carboxamide Example 184 was prepared according to the procedure used for the preparation of Example 162b, substituting 3-(butylamino)propanenitrile for 3,4-dichloro-N-(2-thiomorpholinoethyl)aniline. $^1$H NMR (400 MHz, DMSO-d$_6$) δ 7.58 (d, J=7.7 Hz, 1H), 7.38 (s, 1H), 7.11-7.17 (m, 3H), 7.06-7.11 (m, 1H), 6.91 (s, 1H), 6.38 (d, J=1.5 Hz, 1H), 3.64 (s, 3H), 3.59 (t, J=6.7 Hz, 2H), 3.34 (d, J=7.2 Hz, 2H), 3.26 (d, J=7.2 Hz, 2H), 2.76 (t, J=6.7 Hz, 2H), 2.05 (s, 6H), 1.40 (q, J=7.6 Hz, 2H), 1.16 (q, J=7.6 Hz, 5H), 0.81 (t, J=7.3 Hz, 3H). MS (APCI+) m/z 568.6 (M+H)$^+$.

Example 185

4-[4-{[2-(dimethylamino)ethyl](2-fluoropyridin-4-yl)carbamoyl}-2-(2,6-dimethylphenoxy)phenyl]-N-ethyl-6-methyl-7-oxo-6,7-dihydro-1H-pyrrolo[2,3-c]pyridine-2-carboxamide The trifluoroacetic acid salt of Example 185 was prepared according to the procedure used for the preparation of Example 162b, substituting N$^1$-(2-fluoropyridin-4-yl)-N$^2$,N$^2$-dimethylethane-1,2-diamine for 3,4-dichloro-N-(2-thiomorpholinoethyl)aniline. $^1$H NMR (400 MHz, DMSO-d$_6$) δ 8.09 (d, J=5.5 Hz, 1H), 7.52 (d, J=7.8 Hz, 1H), 7.24-7.34 (m, 2H), 7.08 (s, 3H), 6.98 (dt, J=5.4, 1.6 Hz, 1H), 6.83-6.88 (m, 1H), 6.81 (s, 1H), 6.24 (s, 1H), 4.20 (t, J=6.8 Hz, 2H), 3.61 (s, 3H), 3.34 (d, J=7.2 Hz, 2H), 3.28 (d, J=6.7 Hz, 2H), 2.87 (s, 6H), 1.85 (s, 6H), 1.17 (t, J=7.2 Hz, 3H). MS (APCI+) m/z 625.4 (M+H)$^+$.

Example 186

4-{4-[cyclohexyl(phenyl)carbamoyl]-2-(2,6-dimethylphenoxy)phenyl}-N-ethyl-6-methyl-7-oxo-6,7-dihydro-1H-pyrrolo[2,3-c]pyridine-2-carboxamide Example 186 was prepared according to the procedure used for the preparation of Example 162b, substituting N-cyclohexylaniline for 3,4-dichloro-N-(2-thiomorpholinoethyl)aniline. $^1$H NMR (400 MHz, DMSO-d$_6$) δ 7.31 (d, J=7.7 Hz, 1H), 7.17-7.26 (m, 4H), 7.08-7.14 (m, 3H), 7.05 (dd, J=7.8, 1.6 Hz, 1H), 6.82-6.88 (m, 2H), 6.74 (s, 1H), 6.14 (d, J=1.6 Hz, 1H), 4.29-4.41 (m, 1H), 3.56 (s, 3H), 3.31 (d, J=7.3 Hz, 2H), 1.82 (s, 6H), 1.66-1.81 (m, 4H), 1.54 (d, J=13.3 Hz, 2H), 1.21-1.36 (m, 2H), 1.14 (t, J=7.2 Hz, 3H), 1.02-1.11 (m, 2H). MS (APCI+) m/z 617.6 (M+H)$^+$.

Example 187

N-{3-[cyclohexyl(methyl)amino]propyl}-4-[2-(2,6-dimethylphenoxy)-5-(methylsulfonyl)phenyl]-6-methyl-7-oxo-6,7-dihydro-1H-pyrrolo[2,3-c]pyridine-2-carboxamide Example 187 was prepared according to the procedure used for the preparation of Example 143, substituting 3-[cyclohexyl(methyl)amino]propyl amine for 2-(diethylamino)-2-methylpropylamine dihydrochloride to provide the trifluoroacetic acid salt of the title compound. $^1$H NMR (400 MHz, DMSO-d6) δ 7.95 (d, J=2.4 Hz, 1H), 7.83 (dd, J=8.7, 2.4 Hz, 1H), 7.42 (s, 1H), 7.19-7.06 (m, 3H), 6.86 (s, 1H), 6.63 (d, J=8.7 Hz, 1H), 3.63 (s, 3H), 3.37 (m, 3H), 3.19 (s, 3H), 2.71 (s, 3H), 2.03 (s, 6H), 1.96 (m, 4H), 1.82 (m, 2H), 1.61 (m, 2H), 1.51-1.20 (m, 4H), 1.19-1.04 (m, 2H). MS (APCI+) m/z 618.8 (M+H)$^+$.

Example 188

4-[2-(2,4-difluorophenoxy)-5-(methylsulfonyl)phenyl]-6-methyl-2-[(4-methyl-2-phenylpiperazin-1-yl)methyl]-1,6-dihydro-7H-pyrrolo[2,3-c]pyridin-7-one A mixture of Example 114h (0.1 g, 0.218 mmol), 1-methyl-3-phenylpiperazine (0.077 g, 0.436 mmol), sodium cyanotrihydroborate (0.027 g, 0.436 mmol), and zinc(II) chloride (0.030 g, 0.218 mmol) in methanol (5 mL) was stirred at ambient temperature for 15 hours. The reaction mixture was concentrated under reduced pressure, and the residue was purified by reverse phase HPLC (C18, CH$_3$CN/water (0.1% TFA), 0-100%)) to provide the trifluoroacetic acid salt of the title compound (0.13 g, 70%). $^1$H NMR (400 MHz, DMSO-d$_6$) δ 12.01 (d, J=2.2 Hz, 1H), 9.68 (s, 1H), 7.99 (d, J=2.3 Hz, 1H), 7.53-7.32 (m, 7H), 7.01 (d, J=8.7 Hz, 1H), 6.13 (d, J=2.0 Hz, 1H), 3.42 (dd, J=11.2, 6.1 Hz, 3H), 3.28 (s, 4H), 3.18-2.93 (m, 3H), 2.77 (s, 3H), 2.43 (s, 1H). MS (ESI$^+$) m/z 619.0 (M+H)$^+$.

Biological Examples

Bromodomain Domain Binding Assay

A time-resolved fluorescence resonance energy transfer (TR-FRET) assay was used to determine the affinities of compounds of the Examples listed in Table 1 for each bromodomain of BRD4. His-tagged first (BD1: amino acids K57-E168) and second (BD2: amino acids E352-E168) bromodomains of BRD4 were expressed and purified. An Alexa647-labeled BET-inhibitor was used as the fluorescent probe in the assay.

Synthesis of Alexa647-Labeled Bromodomain Inhibitor Compound: 2-((6S,Z)-4-(4-chlorophenyl)-2,3,9-trimethyl-6H-thieno[3,2-f][1,2,4]triazolo[4,3-a][1,4]diazepin-6-yl)acetic acid Methyl 2-((6S,Z)-4-(4-chlorophenyl)-2,3,9-trimethyl-6H-thieno[3,2-f][1,2,4]triazolo[4,3-a][1,4]diazepin-6-yl)acetate (see e.g., WO 2006129623)(100.95 mg, 0.243 mmol was suspended in 1 mL methanol to which was added a freshly prepared solution of lithium hydroxide monohydrate (0.973 mL, 0.5 M, 0.487 mmol) and shaken at ambient temperature for 3 hours. The methanol was evaporated and the pH adjusted with aqueous hydrochloric acid (1 M, 0.5 mL, 0.5 mmol) and extracted four times with ethyl acetate. The combined ethyl acetate layers were dried over magnesium sulfate and evaporated to afford 2-((6S,Z)-4-(4-chlorophenyl)-2,3,9-trimethyl-6H-thieno[3,2-f][1,2,4]triazolo[4,3-a][1,4]diazepin-6-yl)acetic acid (85.3 mg, 87.0%); ESI-MS m/z=401.1 [(M+H)$^+$] which was used directly in the next reaction.

N-(2-(2-(2-aminoethoxy)ethoxy)ethyl)-2-((6S,Z)-4-(4-chlorophenyl)-2,3,9-trimethyl-6H-thieno[3,2-f][1,2,4]triazolo[4,3-a][1,4]diazepin-6-yl)acetamide bis (2,2,2-trifluoroacetate)

2-((6S,Z)-4-(4-chlorophenyl)-2,3,9-trimethyl-6H-thieno[3,2-f][1,2,4]triazolo[4,3-a][1,4]diazepin-6-yl)acetic acid) (85.3 mg, 0.213 mmol) was combined with 2,2'-(ethane-1, 2-diylbis(oxy))diethanamine (Sigma-Aldrich, 0.315 mg, 2.13 mmol) were combined in 5 mL anhydrous dimethylformamide. (1H-benzo[d][1,2,3]triazol-1-yloxy)tripyrrolidin-1-ylphosphonium hexafluorophosphate(V) (PyBOB, CSBio, Menlo Park Calif.; 332 mg, 0.638 mmol) was added and the reaction shaken at ambient temperature for 16 hours. The reaction was diluted to 6 mL with dimethylsulfoxide:water (9:1, v:v) and purified in two injections with time collection Waters Deltapak C18 200×25 mm column eluted with a gradient of 0.1% trifluoroacetic acid (v/v) in water and acetonitrile. The fractions containing the two purified products were lyophilized to afford N-(2-(2-(2-aminoethoxy)ethoxy)ethyl)-2-((6S,Z)-4-(4-chlorophenyl)-2,3,9-trimethyl-6H-thieno[3,2-f][1,2,4]triazolo[4,3-a][1,4]diazepin-6-yl)acetamide bis(2,2,2-trifluoroacetate) (134.4 mg, 82.3%); ESI-MS m/z=531.1 [(M+H)$^+$]; 529.1 [(M−H)$^-$] and (S,Z)—N,N'-(2,2'-(ethane-1,2-diylbis(oxy))bis(ethane-2,1-diyl))bis(2-((6S,Z)-4-(4-chlorophenyl)-2,3,9-trimethyl-6H-thieno[3,2-f][1,2,4]triazolo[4,3-a][1,4]diazepin-6-yl)acetamide) bis(2,2,2-trifluoroacetate) (3.0 mg, 1.5%); ESI-MS m/z=913.2 [(M+H)$^+$]; 911.0 [(M−H)$^-$].

N-(2-(2-(2-amido-(Alexa647)-ethoxy)ethoxy)ethyl)-2-((6S,Z)-4-(4-chlorophenyl)-2,3,9-trimethyl-6H-thieno[3,2-f][1,2,4]triazolo[4,3-a][1,4]diazepin-6-yl)acetamide(2,2,2-trifluoroacetate)

N-(2-(2-(2-aminoethoxy)ethoxy)ethyl)-2-((6 S,Z)-4-(4-chlorophenyl)-2,3,9-trimethyl-6H-thieno[3,2-f][1,2,4]triazolo[4,3-a][1,4]diazepin-6-yl)acetamide bis(2,2,2-trifluoroacetate) (5.4 mg, 0.0071 mmol) was combined with Alexa Fluor® 647 carboxylic Acid, succinimidyl ester (Life Technologies, Grand Island, N.Y.; 3 mg, 0.0024 mmol) were combined in 1 mL anhydrous dimethylsulfoxide containing diisopropylethylamine (1% v/v) and shaken at ambient temperature for 16 hours. The reaction was diluted to 3 mL with dimethylsulfoxide:water (9:1, v:v) and purified in one injection with time collection Waters Deltapak C18 200×25 mm column eluted with a gradient of 0.1% trifluoroacetic acid (v/v) in water and acetonitrile. The fractions containing the purified product were lyophilized to afford N-(2-(2-(2-amido-(Alexa647)-ethoxy)ethoxy)ethyl)-2-((6S,Z)-4-(4-chlorophenyl)-2,3,9-trimethyl-6H-thieno[3,2-f][1,2,4]triazolo[4,3-a][1,4]diazepin-6-yl)acetamide(2,2,2-trifluoroacetate) (1.8 mg); MALDI-MS m/z=1371.1, 1373.1 [(M+H)$^+$] as a dark blue powder.

Assay

Compound dilution series were prepared in DMSO via a 3-fold serial dilution from 2.5 mM to 42 nM. Compounds were then diluted 6:100 in assay buffer (20 mM Sodium Phosphate, pH 6.0, 50 mM NaCl, 1 mM Ethylenediaminetetraacetic acid disodium salt dihydrate, 0.01% Triton X-100, 1 mM DL-Dithiothreitol) to yield 3× working solutions. Six microliters (µL) of the working solution was then transferred to white, low-volume assay plates (Costar #3673). A 1.5× assay mixture containing His-tagged bromodomain, Europium-conjugated anti-His antibody (Invitrogen PV5596) and the Alexa-647-conjugated probe molecule was also prepared. Twelve µL of this solution were added to the assay plate to reach a final volume of 18 µL. The final concentration of 1× assay buffer contains 2% DMSO, 50 µM-0.85 nM compound, 8 nM His-tagged bromodomain, 1 nM Europium-conjugated anti-His-tag antibody and 100 nM or 30 nM probe (for BDI or BDII, respectively). After a one-hour incubation at room temperature, TR-FRET ratios were determined using an Envision multilabel plate reader (Ex 340, Em 495/520).

TR-FRET data were normalized to the means of 24 no-compound controls ("high") and 8 controls containing 1 µM un-labeled probe ("low"). Percent inhibition was plotted as a function of compound concentration and the data were fit with the 4 parameter logistic equation to obtain $IC_{50}$s. Inhibition constants ($K_i$) were calculated from the $IC_{50}$s, probe $K_d$ and probe concentration. Typical Z' values were between 0.65 and 0.75. The minimum significant ratio was determined to evaluate assay reproducibility (Eastwood et al., (2006) J Biomol Screen, 11: 253-261). The MSR was determined to be 2.03 for BDI and 1.93 for BDII, and a moving MSR (last six run MSR overtime) for both BDI and BDII was typically <3. The $K_i$ values are reported in Table 1.

MX-1 Cell Line Proliferation Assay

The impact of compounds of the Examples on cancer cell proliferation was determined using the breast cancer cell line MX-1 (ATCC) in a 3-day proliferation assay and the data are reported in Table 1.

Method A: MX-1 cells were maintained in RPMI 1640 medium (Sigma) supplemented with 10% FBS at 37 C.° and an atmosphere of 5% $CO_2$. For compound testing, MX-1 cells were plated in 96-well black bottom plates at a density of 5000 cells/well in 90 µL of culture media and incubated at 370 overnight to allow cell adhesion and spreading. Compound dilution series were prepared in DMSO via a 3-fold serial dilution from 3 mM to 0.1 µM. The DMSO dilution series were then diluted 1:100 in phosphate buffered saline, and 10 µL of the resulted solution were added to the appropriate wells of the MX-1 cell plate. The final compound concentrations in the wells were 3, 1, 0.3, 0.1, 0.03, 0.01, 0.003, 0.001, 0.0003 and 0.0001 µM. After the addition of compounds, the cells were incubated for 72 more hours and the amounts of viable cells were determined using the Cell Titer Glo assay kit (Promega) according to manufacturer suggested protocol.

Luminescence readings from the Cell Titer Glo assay were normalized to the DMSO treated cells and analyzed using the GraphPad Prism software with sigmoidal curve fitting to obtain $EC_{50}$s. The minimum significant ratio (MSR) was determined to evaluate assay reproducibility (Eastwood et al., (2006) J Biomol Screen, 11: 253-261). The overall MSR was determined to be 2.1 and a moving MSR (last six run MSR overtime) has been <2.

Method B: MX-1 cells were maintained in RPMI 1640 medium (Sigma) supplemented with 10% FBS at 37 C.° and an atmosphere of 5% $CO_2$. For compound testing, MX-1 cells were plated in 384-well white with clear, flat bottom plates at a density of 750 cells/well in 25 µL of culture media and incubated at 370 overnight to allow cell adhesion and spreading. Ten point compound dilution series were prepared in DMSO via a 3-fold serial dilution from either 10 M or 1 µM stock and added directly to the appropriate wells of the MX-1 cell plate by an ECHO liquid handler (Labcyte). The final compound concentrations in the wells were 10, 3.25, 1, 0.25, 0.124, 0.040, 0.0124, 0.0031, 0.0015 and 0.0005 µM or 1, 0.33, 0.1, 0.025, 0.0124, 0.004, 0.0012, 0.0003, 0.00015, 0.00005 µM, depending on the concentration of the compound stock solution. After the addition of compounds, the cells were incubated for 72 more hours and the amounts of viable cells were determined using the Cell Titer Glo assay kit (Promega) according to manufacturer suggested protocol.

Luminescence readings from the Cell Titer Glo assay were normalized to the DMSO treated cells and analyzed using Accelrys Assay Explorer 3.3 software with sigmoidal curve fitting to obtain ECsos. The minimum significant ratio (MSR) was determined to evaluate assay reproducibility (Eastwood et al., (2006) J Biomol Screen, 11: 253-261). The overall MSR was determined to be 3.3 and a moving MSR (last six run MSR overtime) has averaged

TABLE 1

| Example # | TR-FRET Binding Ki: BRD4 (BDI_K57-E168) (µM) | TR-FRET Binding Ki: BRD4 (BDII_E352-M457) (µM) | Cellular proliferation: EC$_{50}$ (µM) | |
|---|---|---|---|---|
| | | | Method A | Method B |
| 1 | 0.026 | 0.055 | 0.151 | ND |
| 2 | 0.057 | 0.0040 | 0.110 | ND |
| 3 | 0.088 | 0.0028 | 0.0368 | ND |
| 4 | 0.011 | 0.0017 | 0.0163 | ND |
| 5 | 0.016 | 0.0017 | 0.0401 | ND |
| 6 | 0.014 | 0.0020 | 0.0291 | ND |
| 7 | 0.032 | 0.0069 | 0.139 | ND |
| 8 | 0.0015 | 0.0018 | 0.0449 | ND |
| 9 | 0.0017 | 0.0020 | 0.0653 | ND |
| 10 | 0.072 | 0.0083 | 0.0982 | ND |
| 11 | 0.0008 | 0.0010 | 0.452 | ND |
| 12 | 0.0018 | 0.0016 | 0.0684 | ND |
| 13 | 0.042 | 0.0074 | 0.307 | ND |
| 14 | 0.071 | 0.014 | 0.184 | ND |
| 15 | 0.0046 | 0.0026 | 0.105 | ND |
| 16 | 0.0025 | 0.030 | 0.202 | ND |
| 17 | 0.0044 | 0.060 | ND | ND |
| 18 | 0.0044 | 0.048 | ND | ND |
| 19 | 0.0061 | 0.062 | ND | ND |
| 20 | 0.0049 | 0.048 | 0.101 | ND |
| 21 | 0.033 | 0.010 | 0.487 | ND |
| 22 | 0.018 | 0.015 | >1 | ND |
| 23 | 0.011 | 0.0087 | >1 | ND |
| 24 | 0.015 | 0.012 | >1 | ND |
| 25 | 0.019 | 0.0061 | 0.134 | ND |
| 26 | 0.027 | 0.015 | ND | ND |
| 27 | 0.026 | 0.011 | 0.442 | ND |
| 28 | 0.013 | 0.011 | 0.195 | ND |
| 29 | 0.019 | 0.0091 | >1 | ND |
| 30 | 0.028 | 0.017 | >1 | ND |
| 31 | 0.021 | 0.011 | 0.443 | ND |
| 32 | 0.021 | 0.010 | ND | ND |
| 33 | 0.0081 | 0.0031 | >1 | ND |
| 34 | 0.015 | 0.0036 | 0.155 | ND |
| 35 | 0.0031 | 0.0019 | 0.406 | ND |
| 36 | 0.014 | 0.0057 | 0.255 | ND |
| 37 | 0.018 | 0.0060 | ND | ND |
| 38 | 0.0051 | 0.0019 | 0.103 | ND |
| 39 | 0.0046 | 0.0021 | 0.0974 | ND |
| 40 | 0.0054 | 0.0020 | 0.143 | ND |
| 41 | 0.011 | 0.0051 | ND | ND |
| 42 | 0.0091 | 0.0035 | 0.157 | ND |
| 43 | 0.0050 | 0.0030 | 0.451 | ND |
| 44 | 0.0049 | 0.0021 | 0.391 | ND |
| 45 | 0.016 | 0.0033 | ND | ND |
| 46 | 0.010 | 0.0018 | 0.0431 | ND |
| 47 | 0.0059 | 0.0027 | ND | ND |
| 48 | 0.0078 | 0.0024 | 0.172 | ND |
| 49 | 0.0044 | 0.0010 | 0.0738 | ND |
| 50 | 0.0034 | 0.0012 | 0.0405 | ND |
| 51 | 0.0050 | 0.0030 | >1 | ND |
| 52 | 0.0020 | 0.0011 | 0.0386 | ND |
| 53 | 0.0034 | 0.0010 | 0.144 | ND |
| 54 | 0.0032 | 0.0011 | >1 | ND |
| 55 | 0.0069 | 0.0028 | 0.393 | ND |
| 56 | 0.0088 | 0.0034 | ND | ND |
| 57 | 0.0053 | 0.0022 | >1 | ND |
| 58 | 0.0047 | 0.0024 | 0.152 | ND |
| 59 | ND | ND | ND | ND |
| 60 | 0.0079 | 0.0020 | 0.0641 | ND |
| 61 | 0.0037 | 0.0013 | 0.0430 | ND |
| 62 | 0.0031 | 0.0014 | 0.0511 | ND |
| 63 | 0.0013 | 0.0033 | 0.0094 | ND |
| 64 | 0.0052 | 0.0034 | 0.0526 | ND |
| 65 | 0.0069 | 0.0021 | 0.0400 | ND |
| 66 | 0.0038 | 0.0017 | 0.0547 | ND |
| 67 | 0.0043 | 0.0028 | 0.0506 | ND |
| 68 | 0.010 | 0.0047 | ND | ND |
| 69 | 0.0041 | 0.0016 | 0.0933 | ND |
| 70 | 0.016 | 0.0065 | ND | ND |
| 71 | 0.033 | 0.019 | ND | ND |
| 72 | 0.0074 | 0.0041 | ND | ND |
| 73 | 0.0056 | 0.0035 | 0.0624 | ND |
| 74 | 0.0043 | 0.0014 | 0.0451 | ND |
| 75 | 0.0085 | 0.0029 | 0.112 | ND |
| 76 | 0.0033 | 0.0011 | 0.0499 | ND |
| 77 | 0.011 | 0.0028 | 0.0692 | ND |
| 78 | 0.0009 | 0.0006 | 0.0140 | ND |
| 79 | 0.0078 | 0.0027 | ND | ND |
| 80 | 0.019 | 0.0046 | 0.128 | ND |
| 81 | 0.035 | 0.010 | ND | ND |
| 82 | 0.039 | 0.0085 | 0.221 | ND |
| 83 | 0.0053 | 0.0035 | 0.0899 | ND |
| 84 | 0.0047 | 0.0089 | 0.0878 | ND |
| 85 | 0.008 | 0.060 | >1 | ND |
| 86 | 0.024 | 0.075 | ND | ND |
| 87 | 0.021 | 0.034 | 0.325 | ND |
| 88 | 0.0049 | 0.023 | ND | ND |
| 89 | 0.022 | 0.044 | ND | ND |
| 90 | 0.014 | 0.025 | ND | ND |
| 91 | 0.0050 | 0.0075 | ND | ND |
| 92 | 0.015 | 0.033 | ND | ND |
| 93 | 0.019 | 0.024 | ND | ND |
| 94 | 0.030 | 0.020 | ND | ND |
| 95 | 0.022 | 0.016 | ND | ND |
| 96 | 0.017 | 0.021 | >1 | ND |
| 97 | 0.010 | 0.028 | ND | ND |
| 98 | 0.014 | 0.020 | ND | ND |
| 99 | 0.012 | 0.028 | ND | ND |
| 100 | ND | ND | ND | ND |
| 101 | 0.0060 | 0.0058 | 0.0729 | ND |
| 102 | 0.0060 | 0.0068 | 0.0673 | ND |
| 103 | 0.0041 | 0.0049 | ND | ND |
| 104 | 0.0046 | 0.0040 | 0.176 | ND |
| 105 | 0.0072 | 0.017 | ND | ND |
| 106 | 0.0079 | 0.0065 | ND | ND |
| 107 | 0.0030 | 0.0089 | 0.0235 | ND |
| 108 | 0.0034 | 0.0056 | 0.299 | ND |
| 109 | 0.0016 | 0.0083 | 0.0181 | ND |
| 110 | 0.0011 | 0.0022 | 0.0104 | ND |
| 111 | 0.0046 | 0.012 | 0.156 | ND |
| 112 | 0.0054 | 0.010 | 0.142 | ND |
| 113 | 0.0025 | 0.0070 | 0.0195 | ND |
| 114 | 0.00693 | 0.0807 | 0.762 | ND |
| 115 | 0.00522 | 0.12 | 0.411 | ND |
| 116 | 0.00333 | 0.0984 | 0.183 | ND |
| 117 | 0.00609 | 0.00339 | 0.249 | ND |
| 118 | 0.0992 | 0.367 | ND | ND |
| 119 | 1.51 | 0.00669 | 1.51 | ND |
| 120 | >0.238 | 0.158 | ND | ND |
| 121 | 0.0621 | 0.0072 | ND | ND |
| 122 | 0.0391 | 0.00758 | ND | ND |
| 123 | 0.0399 | 0.0056 | ND | ND |
| 124 | 0.0883 | 0.0101 | ND | ND |
| 125 | 0.00847 | 0.189 | 0.606 | ND |
| 126 | 0.0545 | 0.276 | ND | ND |
| 127 | 0.0158 | 0.0938 | 0.128 | ND |
| 128 | 0.0478 | 0.182 | ND | ND |
| 129 | 0.0159 | 0.087 | 0.249 | ND |
| 130 | 0.0101 | 0.108 | 0.337 | ND |
| 131 | 0.0497 | 0.165 | ND | 0.827 |
| 132 | 0.0269 | 0.128 | ND | 0.653 |
| 133 | 2.13 | 0.0203 | ND | ND |
| 134 | 0.0234 | 0.00162 | ND | 0.238 |
| 135 | 0.0549 | 0.0231 | ND | ND |
| 136 | 2.89 | 0.0822 | ND | >1 |
| 137 | >4.77 | 0.0848 | ND | >1 |
| 138 | 0.0885 | 0.00738 | ND | 0.465 |
| 139 | 0.117 | 0.00716 | ND | 0.532 |
| 140 | 0.0938 | 0.00679 | ND | 0.491 |

TABLE 1-continued

| Example # | TR-FRET Binding Ki: BRD4 (BDI_K57-E168) (μM) | TR-FRET Binding Ki: BRD4 (BDII_E352-M457) (μM) | Cellular proliferation: EC$_{50}$ (μM) | |
|---|---|---|---|---|
| | | | Method A | Method B |
| 141 | 0.0868 | 0.0086 | ND | 0.443 |
| 142 | 0.0941 | 0.00576 | ND | 0.615 |
| 143 | 0.19 | 0.015 | ND | 0.532 |
| 144 | 0.209 | 0.00234 | ND | 0.498 |
| 145 | 0.807 | 0.0087 | ND | ND |
| 146 | 3.28 | 0.0501 | ND | 9.32 |
| 147 | 0.761 | 0.0575 | ND | 6.32 |
| 148 | 5.72 | 0.00702 | ND | 1.68 |
| 149 | 0.00281 | 0.000669 | ND | 0.00118 |
| 150 | 2.68 | 0.0739 | ND | >10 |
| 151 | 0.813 | 0.00995 | ND | NV |
| 152 | 2.08 | 0.036 | ND | 8.14 |
| 153 | 1.04 | 0.00261 | ND | >10 |
| 154 | 1.04 | 0.0137 | ND | ND |
| 155 | 0.0237 | 0.364 | ND | ND |
| 156 | 0.0268 | 0.0423 | ND | 0.332 |
| 157 | 0.387 | 0.0169 | ND | ND |
| 158 | 0.883 | 0.0285 | ND | ND |
| 159 | 0.23 | 0.156 | ND | 0.599 |
| 160 | 1.71 | 0.00999 | ND | ND |
| 161 | 1.05 | 0.00316 | ND | 1.95 |
| 162 | >12.7 | 0.0886 | ND | ND |
| 163 | 0.00164 | 0.000605 | 0.0477 | ND |
| 164 | ND | 0.0151 | ND | 10.0 |
| 165 | 0.429 | 0.00448 | ND | 1.46 |
| 166 | >12.7 | 0.0175 | ND | 3.03 |
| 167 | >12.7 | 0.0344 | ND | 2.02 |
| 168 | 2.31 | 0.0223 | ND | 3.06 |
| 169 | 1.4 | 0.0278 | ND | 2.17 |
| 170 | 0.863 | 0.00422 | ND | 2.17 |
| 171 | >12.7 | 0.0383 | ND | 6.41 |
| 172 | 1.0 | 0.00666 | ND | 2.54 |
| 173 | >12.7 | 0.0643 | ND | 5.25 |
| 174 | 2.3 | 0.0133 | ND | 1.61 |
| 175 | 2.23 | 0.0175 | ND | 2.41 |
| 176 | 0.927 | 0.00865 | ND | 3.91 |
| 177 | 1.49 | 0.00921 | ND | 10.0 |
| 178 | 0.592 | 0.0025 | ND | 10.0 |
| 179 | 1.58 | 0.00824 | ND | 0.991 |
| 180 | 8.61 | 0.0308 | ND | 6.06 |
| 181 | 1.73 | 0.00918 | ND | 3.98 |
| 182 | 0.921 | 0.00606 | ND | 2.12 |
| 183 | 2.8 | 0.0141 | ND | 1.48 |
| 184 | 1.08 | 0.0111 | ND | 2.84 |
| 185 | 2.94 | 0.0143 | ND | 2.72 |
| 186 | >12.7 | 0.178 | ND | 7.65 |
| 187 | 0.0998 | 0.00252 | ND | 0.29 |
| 188 | 0.00156 | 0.151 | ND | 0.0768 |

ND = Not Determined

LPS (Lipopolysaccharide) Induced IL-6 Production Mouse Assay

Example 2 was assayed for its ability to inhibit LPS (lipopolysaccharide) induced IL-6 (Interleukin-6) production in mice. CD-1 female mice (Charles River Laboratories, 5 per group) received an intraperitoneal challenge of lipopolysaccharide (2.5 mg/kg, L2630 E. coli 0111:B4) one hour after oral administration of compound or compound vehicle. Mice were euthanized 2 hours after lipopolysaccharide injection, blood was removed by cardiac puncture, and then the serum harvested from the blood samples was frozen at −80 OC. On the day of the assay the serum samples were brought to room temperature and then diluted 1:20 in phosphate-buffered saline containing 2% bovine serum albumin. Interleukin-6 measurements were performed using a cytokine assay from Meso Scale Discovery (Gaithersburg, Md.) for mouse serum analysis according to the manufacturer's protocol and read on a SECTOR Imager 6000 (Meso Scale Discovery, Gaithersburg, Md.) instrument. Statistical analysis was performed using Prism software (version 5.0) incorporating Dunnett's one way ANOVA. The IL-6 mean and standard deviation of the group of vehicle treated animals were compared with the IL-6 mean and standard deviation of the group treated with drug. A p value <0.05 means that there is less than a 5% probability that the mean values in the two groups are equal. Example 2 showed 45% inhibition with a p value of less than 0.05.

It is understood that the foregoing detailed description and accompanying examples are merely illustrative and are not to be taken as limitations upon the scope of the invention, which is defined solely by the appended claims and their equivalents. Various changes and modifications to the disclosed embodiments will be apparent to those skilled in the art. Such changes and modifications, including without limitation those relating to the chemical structures, substituents, derivatives, intermediates, syntheses, formulations and/or methods of use of the invention, may be made without departing from the spirit and scope thereof. All publications, patents, and patent applications cited herein are hereby incorporated by reference in their entirety for all purposes.

The invention claimed is:

1. A compound or a pharmaceutically acceptable salt thereof, wherein the compound is selected from the group consisting of N-{3-[cyclohexyl(methyl)amino]propyl}-4-[2-(2,6-dimethylphenoxy)-5-(methylsulfonyl)phenyl]-6-methyl-7-oxo-6,7-dihydro-1H-pyrrolo[2,3-c]pyridine-2-carboxamide; and 4-[2-(2,4-difluorophenoxy)-5-(methylsulfonyl)phenyl]-6-methyl-2-[(4-methyl-2-phenylpiperazin-1-yl)methyl]-1,6-dihydro-7H-pyrrolo[2,3-c]pyridin-7-one.

2. A compound or a pharmaceutically acceptable salt thereof, wherein the compound is 4-{2-[2-(2-cyclopentylethyl)-6-methylphenoxy]-5-(ethylsulfonyl)phenyl}-N-ethyl-6-methyl-7-oxo-6,7-dihydro-1H-pyrrolo[2,3-c]pyridine-2-carboxamide.

3. A compound or a pharmaceutically acceptable salt thereof, wherein the compound is selected from the group consisting of 4-[2-(2,6-dimethylphenoxy)-4-{(1-phenylpropan-2-yl)[3-(pyrrolidin-1-yl)propyl]carbamoyl}phenyl]-N-ethyl-6-methyl-7-oxo-6,7-dihydro-1H-pyrrolo[2,3-c]pyridine-2-carboxamide;

4-{4-[(cyanomethyl)(1-phenylpropan-2-yl)carbamoyl]-2-(2,6-dimethylphenoxy)phenyl}-N-ethyl-6-methyl-7-oxo-6,7-dihydro-1H-pyrrolo[2,3-c]pyridine-2-carboxamide;

4-{4-[(cyanomethyl)(2-phenylpropyl)carbamoyl]-2-(2,6-dimethylphenoxy)phenyl}-N-ethyl-6-methyl-7-oxo-6,7-dihydro-1H-pyrrolo[2,3-c]pyridine-2-carboxamide;

4-{4-[(3-chlorophenyl)(cyanomethyl)carbamoyl]-2-(2,6-dimethylphenoxy)phenyl}-N-ethyl-6-methyl-7-oxo-6,7-dihydro-1H-pyrrolo[2,3-c]pyridine-2-carboxamide;

4-{4-[(4-chlorophenyl)(cyanomethyl)carbamoyl]-2-(2,6-dimethylphenoxy)phenyl}-N-ethyl-6-methyl-7-oxo-6,7-dihydro-1H-pyrrolo[2,3-c]pyridine-2-carboxamide;

4-[4-{[2-(diethylamino)ethyl](2-methylphenyl)carbamoyl}-2-(2,6-dimethylphenoxy)phenyl]-N-ethyl-6-methyl-7-oxo-6,7-dihydro-1H-pyrrolo[2,3-c]pyridine-2-carboxamide;

4-[4-{(cyanomethyl)[3-(trifluoromethyl)phenyl]carbamoyl}-2-(2,6-dimethylphenoxy)phenyl]-N-ethyl-6-methyl-7-oxo-6,7-dihydro-1H-pyrrolo[2,3-c]pyridine-2-carboxamide;

4-[4-{cyclohexyl[3-(dimethylamino)propyl]carbamoyl}-2-(2,6-dimethylphenoxy)phenyl]-N-ethyl-6-methyl-7-oxo-6,7-dihydro-1H-pyrrolo[2,3-c]pyridine-2-carboxamide;

4-{4-[benzyl(4-chlorobenzyl)carbamoyl]-2-(2,6-dimethylphenoxy)phenyl}-N-ethyl-6-methyl-7-oxo-6,7-dihydro-1H-pyrrolo[2,3-c]pyridine-2-carboxamide;

4-[4-{[2-(dimethylamino)ethyl](pyrimidin-2-yl)carbamoyl}-2-2,6-dimethylphenoxy)phenyl]-N-ethyl-6-methyl-7-oxo-6,7-dihydro-1H-pyrrolo[2,3-c]pyridine-2-carboxamide;

4-{4-[(3-chlorophenyl)(2-cyanoethyl)carbamoyl]-2-(2,6-dimethylphenoxy)phenyl}-N-ethyl-6-methyl-7-oxo-6,7-dihydro-1H-pyrrolo[2,3-c]pyridine-2-carboxamide;

4-{4-[(2-cyanoethyl)(cyclohexyl)carbamoyl]-2-(2,6-dimethylphenoxy)phenyl}-N-ethyl-6-methyl-7-oxo-6,7-dihydro-1H-pyrrolo[2,3-c]pyridine-2-carboxamide;

4-{4-[(cyanomethyl)(phenyl)carbamoyl]-2-(2,6-dimethylphenoxy)phenyl}-N-ethyl-6-methyl-7-oxo-6,7-dihydro-1H-pyrrolo[2,3-c]pyridine-2-carboxamide;

4-[4-{[2-(diethylamino)ethyl](2-methoxyphenyl)carbamoyl}-2-(2,6-dimethylphenoxy)phenyl]-N-ethyl-6-methyl-7-oxo-6,7-dihydro-1H-pyrrolo[2,3-c]pyridine-2-carboxamide;

4-[4-{[2-(dimethylamino)ethyl](phenyl)carbamoyl}-2-(2,6-dimethylphenoxy)phenyl]-N-ethyl-6-methyl-7-oxo-6,7-dihydro-1H-pyrrolo[2,3-c]pyridine-2-carboxamide;

ethyl 4-[{3-(2,6-dimethylphenoxy)-4-[2-(ethylcarbamoyl)-6-methyl-7-oxo-6,7-dihydro-1H-pyrrolo[2,3-c]pyridin-4-yl]benzoyl}(phenyl)amino]butanoate;

4-[4-{[2-(dimethylamino)ethyl](pyridin-2-yl)carbamoyl}-2-(2,6-dimethylphenoxy)phenyl]-N-ethyl-6-methyl-7-oxo-6,7-dihydro-1H-pyrrolo[2,3-c]pyridine-2-carboxamide;

4-[4-{[2-(diethylamino)ethyl](phenyl)carbamoyl}-2-(2,6-dimethylphenoxy)phenyl]-N-ethyl-6-methyl-7-oxo-6,7-dihydro-1H-pyrrolo[2,3-c]pyridine-2-carboxamide;

4-{4-[(cyanomethyl)(4-methoxyphenyl)carbamoyl]-2-(2,6-dimethylphenoxy)phenyl}-N-ethyl-6-methyl-7-oxo-6,7-dihydro-1H-pyrrolo[2,3-c]pyridine-2-carboxamide;

4-{4-[butyl(2-cyanoethyl)carbamoyl]-2-(2,6-dimethylphenoxy)phenyl}-N-ethyl-6-methyl-7-oxo-6,7-dihydro-1H-pyrrolo[2,3-c]pyridine-2-carboxamide;

4-[4-{[2-(dimethylamino)ethyl](2-fluoropyridin-4-yl)carbamoyl}-2-(2,6-dimethylphenoxy)phenyl]-N-ethyl-6-methyl-7-oxo-6,7-dihydro-1H-pyrrolo[2,3-c]pyridine-2-carboxamide; and 4-{4-[cyclohexyl(phenyl)carbamoyl]-2-(2,6-dimethylphenoxy)phenyl}-N-ethyl-6-methyl-7-oxo-6,7-dihydro-1H-pyrrolo[2,3-c]pyridine-2-carboxamide.

4. A pharmaceutical composition comprising a therapeutically effective amount of a compound according to claim 1, 2, or 3, or a pharmaceutically acceptable salt thereof, in combination with a pharmaceutically acceptable carrier.

5. A method for treating cancer in a subject comprising administering a therapeutically effective amount of a compound according to claim 1, 2, or 3, or a pharmaceutically acceptable salt thereof, to a subject in need thereof, wherein the cancer is a bromodomain-mediated hematologic or solid cancer.

* * * * *